United States Patent
Todd et al.

(10) Patent No.: US 8,962,238 B2
(45) Date of Patent: Feb. 24, 2015

(54) NUCLEIC ACID ENZYMES AND COMPLEXES AND METHODS FOR THEIR USE

(75) Inventors: Alison Velyian Todd, Glebe (AU); Elisa Mokany, Woolooware (AU); Tram Bich Doan, Fairfield West (AU); Paul Ean Young, Engadine (AU)

(73) Assignee: SpeedDx Pty Ltd, Eveleigh, NSW (AU)

( * ) Notice: Subject to any disclaimer, the term of this patent is extended or adjusted under 35 U.S.C. 154(b) by 648 days.

(21) Appl. No.: 12/594,656

(22) PCT Filed: Apr. 4, 2008

(86) PCT No.: PCT/AU2008/000492
§ 371 (c)(1),
(2), (4) Date: May 17, 2010

(87) PCT Pub. No.: WO2008/122084
PCT Pub. Date: Oct. 16, 2008

(65) Prior Publication Data
US 2011/0143338 A1  Jun. 16, 2011

Related U.S. Application Data

(63) Continuation-in-part of application No. 11/697,021, filed on Apr. 5, 2007, now abandoned.

(60) Provisional application No. 60/910,427, filed on Apr. 5, 2007.

(30) Foreign Application Priority Data

Apr. 5, 2007  (AU) ................................ 2007901833

(51) Int. Cl.
*C12Q 1/68* (2006.01)
*C07H 21/02* (2006.01)
(Continued)

(52) U.S. Cl.
CPC ............ *C12Q 1/6811* (2013.01); *C12N 15/111* (2013.01); *C12Q 1/6816* (2013.01); *C12N 2310/127* (2013.01); *C12N 2320/11* (2013.01); *G01N 2333/9005* (2013.01)
USPC ......... 435/6.1; 435/6.11; 435/91.1; 536/23.1; 536/24.3; 536/24.33

(58) Field of Classification Search
USPC ........ 435/6.1, 6.11, 91.1, 91.52, 183; 436/94, 436/501; 536/23.1, 24.3, 24.33
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| AU | PI 5911 | 12/1987 |
| AU | 199959817 B2 | 10/2000 |

(Continued)

OTHER PUBLICATIONS

U.S. Appl. No. 11/697,021, filed Apr. 5, 2007, Todd et al.
(Continued)

*Primary Examiner* — Frank Lu
(74) *Attorney, Agent, or Firm* — Alston & Bird LLP

(57) ABSTRACT

The present invention relates to methods that utilize multi-component nucleic acid complex (MNA complex) cascades. The MNA complexes may have cleavage or ligase activity. Further, the invention provides cascades which may include one or more DNAzymes. The invention also provides methods which use these cascades for the identification, detection and quantification of targets.

4 Claims, 16 Drawing Sheets

(51) Int. Cl.
C07H 21/04 (2006.01)
C12N 15/11 (2006.01)

(56) References Cited

U.S. PATENT DOCUMENTS

| | | | |
|---|---|---|---|
| 4,800,159 | A | 1/1989 | Mullis et al. |
| 4,965,188 | A | 10/1990 | Mullis et al. |
| 5,176,995 | A | 1/1993 | Sninsky et al. |
| 5,545,729 | A | 8/1996 | Goodchild et al. |
| 5,589,332 | A | 12/1996 | Shih et al. |
| 5,807,718 | A | 9/1998 | Joyce et al. |
| 5,876,924 | A * | 3/1999 | Zhang et al. ............... 435/5 |
| 6,140,055 | A | 10/2000 | Todd et al. |
| 6,201,113 | B1 | 3/2001 | Todd et al. |
| 6,326,174 | B1 | 12/2001 | Joyce et al. |
| 6,365,724 | B2 | 4/2002 | Todd et al. |
| 6,451,535 | B1 | 9/2002 | Jenne et al. |
| 6,861,223 | B2 | 3/2005 | Jenne et al. |
| 7,141,665 | B1 | 11/2006 | Joyce et al. |
| 7,553,945 | B2 | 6/2009 | Leontis |
| 2002/0102568 | A1 | 8/2002 | Usman et al. |
| 2003/0013095 | A1 | 1/2003 | Taira et al. |
| 2007/0231810 | A1 | 10/2007 | Todd et al. |
| 2010/0136536 | A1 | 6/2010 | Todd et al. |
| 2010/0221711 | A1 | 9/2010 | Nauwelaers et al. |
| 2013/0123480 | A1 | 5/2013 | Todd et al. |

FOREIGN PATENT DOCUMENTS

| | | |
|---|---|---|
| EP | 0 552 931 A1 | 7/1993 |
| EP | 1063296 A1 | 12/2000 |
| WO | WO 96/17086 A1 | 6/1996 |
| WO | WO 96/27026 | 9/1996 |
| WO | WO 98/49346 A1 | 11/1998 |
| WO | WO 99/45146 | 9/1999 |
| WO | WO 99/50452 | 10/1999 |
| WO | WO 00/58505 | 10/2000 |
| WO | WO 03/089650 A2 | 10/2003 |
| WO | WO 2005/051174 A2 | 6/2005 |
| WO | WO 2005/073405 A2 | 8/2005 |
| WO | WO 2007/041774 A1 | 4/2007 |
| WO | WO 2007/065926 A1 | 6/2007 |
| WO | WO 2008/040095 A1 | 4/2008 |
| WO | WO 2008/054834 A2 | 5/2008 |
| WO | WO 2008/122084 A1 | 10/2008 |
| WO | WO 2009/022125 A1 | 2/2009 |
| WO | WO 2010/017246 A1 | 2/2010 |

OTHER PUBLICATIONS

Achenbach et al., "Structure-switching allosteric deoxyribozymes," *Analytica Chimica Acta.*, 534(1):41-51, (2005).
Adams, "Biotin amplification of biotin and horseradish peroxidase signals in histochemical stains," *J Histochem Cytochem.*, 40(10):1457-1463, (1992).
Benenson et al., "Programmable and autonomous computing machine made of biomolecules," *Nature*, 414(6862):430-434, (2001).
Bobrow, et al., "Catalyzed reporter deposition, a novel method of signal amplification. Application to immunoassays," *J Immunol Methods*, 125:279-285, (1989).
Breaker et al., "A DNA enzyme that cleaves RNA," *Chem Biol.*, 1(4):223-229, (1994).
Breaker, "DNA enzymes," *Nature Biotech.*, 15:427-431, (1997).
Brown et al., "A lead-dependent DNAzyme with a two-step mechanism," *Biochem.*, 42(23):7152-7161, (2003).
Cairns et al., "Nucleic acid mutation analysis using catalytic DNA," *Nucl Acids Res*, 28(3):e9(i-vi), (2000).
Cairns et al., "Optimisation of the 10-23 DNAzyme-substrate pairing interactions enhanced RNA cleavage activity at purine-cytosine target sites," *Nucl Acids Res*, 31(11):2883-2889, (2003).
Carmi et al., "In vitro selection of self-cleaving DNAs," *Chem Biol*, 3(12):1039-1046, (1996).

Chehab, et al., "Detection of sickle cell anaemia and thalassaemias," *Nature*, [letter], [published erratum titled "Sickle cell detection: Erratum," 329(10):678, (1987)], 329(9):293-294, (1987).
Chen, et al., "MicroRNA quantitation by looped RT-PCR," *Applied Biosystems*, Poster, (2005).
Cheng, et al., "A versatile method for coupling of proteins to DNA: synthesis of $\alpha_2$-macroglobin-DNA conjugates," *Nucleic Acid Research*, 11(3):659-669, (1983).
Compton, "Nucleic acid sequence-based amplification," *Nature*, 350(6313):91-92, (1991).
Coppins, et al., "Rational modification of a selection strategy leads to deoxyribozymes that create native 3'-5' RNA linkages," *J. Am. Chem. Soc.*, 126(50):16426-16432, (2004).
Cruz et al., "Dinucleotide junction cleavage versatility of 8-17 deoxyribozyme," *Chem Biol*, 11:57-67, (2004).
Cuenoud et al., "A DNA metalloenzyme with DNA ligase activity," *Nature*, 375:611-614, (1995).
Eigen, et al., "Sorting single molecules: application to diagnostics and evolutionary biotechnology," *Proc Natl Acad Sci USA*, 91:5740-5747, (1994).
Elghanian et al., "Selective colorimetric detection of polynucleotides based on the distance-dependent optical properties of gold nanoparticles," *Science*, 277:1078-1081, (1997).
Emilsson et al., "Deoxyribozymes: new activities and new applications," *Cell. Mol. Life Sci*, 59:596-607, (2002).
Fahy, et al., "Self-sustained sequence replication (3SR): an isothermal transcription-based amplification system alternative to PCR," *Cold Spring Harbor Laboratory Press*, PCR Methods and Applications, 1:25-33, (1991).
Flynn-Charlebois, et al., "In vitro evolution of an RNA-cleaving DNA enzyme into an RNA ligase switches the selectivity from 3'-5' to 2'-5'," *J. Am. Chem. Soc.*, 125:5346-5350, (2003).
Hall, et al., "Sensitive detection of DNA polymorphisms by the serial invasive signal amplification reaction," *Proc Natl Acad Sci USA*, 97(15):8272-8277, (2000).
Haseloff et al., "Simple RNA enzymes with new and highly specific endoribonuclease activities," *Nature*, 334:585-591, (1988).
Hobartner, et al., "Recent advances in DNA catalysis," *Biopolymers*. 87(5-6):279:292, (2007).
Huizenga et al., "A DNA aptamer that binds adenosine and ATP," *Biochemistry*, 34:656-665, (1995).
Illangasekare et al., "Aminoacyl-RNA synthesis catalyzed by an RNA," *Science*, 267:643-647, (1995).
Impey, et al., "Factors that influence deoxyribozyme cleavage during polymerase chain reaction," *Anal Biochem.*, 286:300-303, (2000).
Jonas, et al., "Detection and identification of *Mycobacterium tuberculosis* directly from sputum sediments by amplification of rRNA," *Journal of Clinical Microbiology*, 31(9):2410-2416, (1993).
Kossen et al., "High throughput ribozyme-based assays for detection of viral nucleic acids," *Chemistry and Biology*, 11:807-815, (2004).
Kurata, et al., "MAXIZYMEs: Allosterically controllable ribozymes with biosensor functions," *Journal of Biochemistry and Molecular Biology*, 33(5):359-365, (2000).
Kuwabara, et al., "tRNA$^{Val}$-heterodimeric maxizymes with high potential as gene-inactivating agents: Simultaneous cleavage at two sites in HIV-1 tat mRNA in cultured cells," *Proc Natl Acad Sci USA*, 96:1886-1891, (1999).
Kuwubara et al., "Allosterically controllable maxizymes cleave mRNA with high efficiency and specificity," *TIBTECH*, 18:462-468, (2000).
Lee et al., "Aptamer Database," *Nucl Acids Res.*, Database Issue, 32:D95-D100, (2004).
Levy et al., "Exponential growth by cross-catalytic cleavage of deoxyribozymogens," *Proc Natl Acad Sci USA*, 100(11):6416-6421, (2003).
Li et al., "A catalytic DNA for porphyrin metallation," *Nat Struct Biol*, Correspondence, 3(9):743-747, (1996).
Li, et al., "In vitro selection and characterization of a highly efficient Zn(II)-dependent RNA-cleaving deoxyribozyme," *Nucl Acids Res*, 28(2):481-488, (2000).
Liu et al., "Adenosine-dependent assembly of aptazyme-functionalized gold nanoparticles and its application as a colorimetric biosensor," *Analytical Chemistry*, 76:1627-1632, (2004).

(56) References Cited

OTHER PUBLICATIONS

Lizardi, et al., "Mutation detection and single-molecule counting using isothermal rolling-circle amplification," *Nat Genet*, 19:225-232, (1998).
Lohse et al., "Ribozyme-catalysed amino-acid transfer reactions," *Nature*, 381:442-444, (1996).
McCall, et al., "Minimal Sequence Requirements for Ribozyme Activity," *Proc Natl Acad Sci USA*, 89:5710-5714, (1992).
Mirkin et al., "A DNA-based method for rationally assembling nanoparticles into macroscopic materials," *Nature*, 382:607-609, (1996).
Nagamine, et al., "Isolation of Single-Stranded DNA from Loop-Mediated Isothermal Amplification Products," *Biochemical and Biophysical Research Communications*, 290(4):1195-1198, (2002).
New Zealand Application No. NZ580129, Examination Report mailed Oct. 4, 2010.
Notomi, et al., "Loop-mediated isothermal amplification of DNA," *Nucl Acids Res*, 28(12): E63(i-vii), (2000).
Oshima, et al., "Maxizymes and Small Hairpin-Type RNAs That Are Driven by a tRNA Promoter Specifically Cleave a Chimeric Gene Associated with Leukemia in Vitro and in Vivo," *Cancer Res.* 63:6809-6814, (2003).
Paul et al., "Minimal self-replicating systems," *Current Opinion in Chemical Biology*, 8:634-639, (2004).
PCT International Preliminary Report on Patentability (Chapter I) for application PCT/AU08/000492 mailed Oct. 6, 2009.
Perreault et al., "Mixed deoxyribo- and ribo-oligonucleotides with catalytic activity," *Nature*, 344:565-567, (1990).
Perreault et al., "Relationship between 2'-hydroxyls and magnesium binding in the hammerhead RNA domain: a model for ribozyme catalysis," *Biochemistry*, 30:4020-4025, (1991).
Perriman, et al., "Extended target-site specificity for a hammerhead ribozyme," *Gene*, 113:157-163, (1992).
Prior et al., "Structure-function correlations derived from faster variants of a RNA ligase deoxyribozyme," *Nucleic Acids Research*, 32(3):1075-1082, (2004).
Raap, et al. "Ultra-sensitive FISH using peroxidase-mediated deposition of biotin- or fluorochrome tyramides," *Hum Mol Genet*, 4(4):529-534, (1995).
Raillard et al., "Targeting sites within HIV-1 cDNA with a DNA-cleaving ribozyme," *Biochemistry*, 35:11693-11701, (1996).
Saiki, et al., "Enzymatic amplification of β-globin genomic sequences and restriction site analysis for diagnosis of sickle cell anemia," *Science*, 230:1350-1354, (1985).
Santoro et al., "A general purpose RNA cleaving DNA enzyme," *Proc Natl Acad Sci U S A*, 94:4262-4266, (1997).
Santoro et al., "Mechanism and utility of an RNA-cleaving DNA enzyme," *Biochem*, 37:13330-13342, (1998).
Schubert et al., "Gaining target access for deoxyribozymes," *J Mol Biol*, 339:355-363, (2004).
Sidorov et al., "Sequence-specific cleavage of RNA in the absence of divalent metal ions by a DNAzyme incorporating imidazolyl and amino functionalities," *Nucl Acids Res*, 32(4):1591-1601, (2004).
Silverman, "Breaking up is easy to do (if you're a DNA enzyme that cleaves RNA)," *Chem. Biol*, 11:7-8, (2004).
Silverman, "In vitro selection and application of nucleic acid enzymes (Ribozymes and deoxyribozymes)," *Wiley Encyclopedia of Chemical Biology*, pp. 1-17, (2008).
Singapore Application No. SG200906638-2, final Examination Report mailed Jun. 16, 2011.
Singapore Application No. SG200906638-2, first Written Opinion mailed Aug. 5, 2010.
Supplementary European Search Report and European Search Opinion for application EP08733324.1 mailed Sep. 28, 2010.
Tabor et al., "Deoxyribozymes that recode sequence information," *Nucleic Acids Res*, 34(8):2166-2172, (2006).
Tarasow et al., "RNA-catalysed carbon-carbon bond formation," *Nature*, 389:54-57, (1997).
Todd et al., "DzyNA-PCR: Use of DNAzymes to detect and quantify nucleic acid sequences in a real time fluorescent format," *Clinical Chemistry*, 46(5):625-630, (2000).
Urdea, "Synthesis and characterization of branched DNA (bDNA) for direct and quantitative detection of CMV, HBV, HCV and HIV," *Clin Chem*, 39(4):725-726, (1993).
U.S. Appl. No. 11/544,926, Final Office Action mailed Nov. 24, 2010.
U.S. Appl. No. 11/544,926, Non-Final Office Action mailed Apr. 6, 2010.
Vaish et al., "Zeptomole detection of a viral nucleic acid using a target-activated ribozyme," *RNA*, 9:1058-1072, (2003).
Van Gijlswijk, et al., "Fluorochrome-labeled tyramides: use in immunocytochemistry and fluorescence in situ hybridization," *J Histochem Cytochem*, 45(3):375-382, (1997).
Walker, et al., "Strand displacement amplification—an isothermal, in vitro DNA amplification technique," *Nucl Acids Res*, 20(7):1691-1696, (1992).
Warashina et al., "Extremely high and specific activity of DNA enzymes in cells with a Philadelphia chromosome," *Chem Biol*, 6(4):237-250, (1999).
Yakimovich, et al., "Influence of DNA aptamer structure on the specificity of binding to Taq DNA polymerase," *Biochemistry* (Moscow), 68(2):228-235, (2003).
Zaborowska et al., "Sequence requirements in the catalytic core of the '10-23' DNA enzyme," *J Biol Chem*, 277(43):40617-40622, (2002).
Zhang, et al., "Aptamer-based multiplexed amplified real-time biochemical detector," *Indiana Biosensor Symposium*, Poster, (2002).
Australian application No. AU2006302729, first Examination Report mailed Jan. 5, 2010.
Australian Application No. AU2006302729, second Examination Report mailed Aug. 5, 2010.
Australian Application No. AU2007304837, first Examination Report mailed Jan. 14, 2010.
Australian Application No. AU2007304837, Notice of Acceptance mailed Sep. 15, 2011.
Australian Application No. AU2007304837, second Examination Report mailed Mar. 7, 2011.
Australian Application No. AU2007304837, third Examination Report mailed Jun. 27, 2011.
Australian Application No. AU2011202017, first Examination Report mailed Nov. 14, 2011.
Barany, "Genetic disease detection and DNA amplification using cloned thermostable ligase," *PNAS*, 88:189-193, (1991).
Benenson, et al., "An autonomous molecular computer for logical control of gene expression," *Nature*, 429:423-429, (2004).
Beyer, et al., "A modular DNA signal translator for the controlled release of a protein by an aptamer," *Nucleic Acids Research*, 34(5):1581-1587, (2006).
China Application No. 200680045926.6, first Office Action mailed Mar. 9, 2011.
China Application No. 200680045926.6, second Office Action mailed May 3, 2012.
China Application No. 200780037345.2, first Office Action mailed Jan. 18, 2012.
Cox, et al., "DNA computation," *Curr Biol*, 11(9):R336, (2001).
European Application No. EP06790343.5, first Examination Report mailed Jan. 20, 2010.
European Application No. EP06790343.5, second Examination Report mailed Aug. 11, 2010.
European Application No. EP06790343.5, Supplementary European Search Report and European Search Opinion dated Sep. 16, 2009.
European Application No. EP07815323.6, European Search Opinion mailed Jan. 31, 2011.
European Application No. EP07815323.6, European Search Report mailed Jan. 12, 2011.
European Application No. EP07815323.6, Office Action mailed Oct. 19, 2011.
European Application No. EP08733324.1, first Examination Report mailed Jun. 30, 2011.
European Application No. EP08733324.1, first Office Action mailed Feb. 9, 2010.

(56) References Cited

OTHER PUBLICATIONS

European Application No. EP08733324.1, further Examination Report mailed Jan. 31, 2012.
European Application No. EP08733324.1, second Office Action mailed Jun. 23, 2010.
Fokina et al., "Two-Component 10-23 DNA Enzymes," Nucleosides, Nucleotides & Nucleic Acids, 23(6&7):1031-1035, (2004).
Hayden et al., "Self-Assembly of a Group I Intron from Inactive Oligonucleotide Fragments,"Chemistry & Biology, 13:909-918, (2006).
Hendry et al., "Redesigned and chemically-modified hammerhead ribozymes with improved activity and serum stability," BMC Chemical Biology, 4(1):1-11, (2004).
Israel Application No. IL 201420, first Office Action dated Feb. 23, 2012.
Israel Application No. IL190501, first Office Action dated May 24, 2010.
Israel Application No. IL190501, second Office Action dated Jan. 31, 2012.
Israel Application No. IL197543, Office Action mailed Jul. 4, 2011.
Japanese Application No. JP2008-533829, first Office Action mailed Mar. 1, 2012.
Kuwabara, et al., "A Novel Allosterically tran-Activated Ribozyme, the Maxizyme, with Exceptional Specificity in Vitro and in Vivo", Mol. Cell., 2:617-627, (1998).
Mexico Application No. MX/a/08/004039, first Office Action (spanish language only) received Mar. 9, 2011.
Mexico Application No. MX/a/2009/003193, first Examination Report mailed Mar. 7, 2012.
Mokany et al. "MNAzymes, a versatile new class of nucleic acid enzymes that can function as biosensors and molecular switches," J Am Chem Soc, 132:1051-1059, (2010).
New Zealand Application No. NZ567403, first Examination report mailed Mar. 18, 2010.
New Zealand Application No. NZ567403, second Examination report mailed Aug. 18, 2010.
New Zealand Application No. NZ575802, first Examination Report mailed Sep. 27, 2010.
New Zealand Application No. NZ575802, second Examination Report mailed Nov. 17, 2011.
New Zealand Application No. NZ580129, Examination Report mailed Mar. 8, 2012.
New Zealand Application No. NZ580129, second Examination Report mailed Dec. 22, 2011.
PCT Application No. PCT/AU2006/001473, International Search Report mailed Dec. 14, 2006.
PCT Application No. PCT/AU2007/001517, International Preliminary Report on Patentability (Chapter 1) dated Apr. 7, 2009.
PCT Application No. PCT/AU2007/001517, International Search Report mailed Jan. 19, 2008.
PCT Application No. PCT/AU2007/001517, Written Opinion of the International Searching Authority, mailed Jan. 19, 2008.
PCT Application No. PCT/AU2008/000492, International Search Report mailed Jul. 4, 2008.
PCT Application No. PCT/AU2011/001504, International Search Report mailed Feb. 17, 2012.
PCT Application No. PCT/AU2011/001504, Written Opinion mailed Feb. 17, 2012.
Sando, et al., "Amplified Nucleic Acid Sensing Using Programmed Self-Cleaving DNAzyme," J. Am. Chem. Soc., 125:15720-15721, (2003).
Schweitzer, et al., "Combining nucleic acid amplification and detection," Current Opinion in Biotechnology, 12:21-27, (2001).
Singapore Application No. SG 200901779-9, first Written Opinion mailed Oct. 5, 2010.
Singapore Application No. SG 200901779-9, second Written Opinion mailed May 19, 2011.
Singapore Application No. SG200802640-3, Search and Examination Report mailed Apr. 30, 2010.
Singapore Application No. SG200802640-3, Written Opinion and Search Report mailed May 11, 2009.
Soda, et al., "A novel maxizyme vector targeting a bcr-abl fusion gene induced specific cell death in Philadelphia chromosome—positive acute lymphoblastic leukemia," Blood, 104(2):356-363, (2004).
Stojanovic, "Deoxyribozyme-Based Half-Adder," J. Am. Chem. Soc., 125(22):6673-6676, (2003).
Stojanovic, "Deoxyribozyme-Based Ligase Logic Gates and their Initial Circuits," J. Am. Chem. Soc., 127(19):6914-6915, (2005).
Stojanovic, "Deoxyribozyme-Based Logic Gates," J. Am. Chem. Soc., 124(14):3555-3561, (2002).
Stojanovic, et al., "A Deoxyribozyme-Based Molecular Automation," Nature Biotechnology, 21(9):1069-1074, (2003).
Swearingen, et al., "Immobilization of a Catalytic DNA Molecular Beacon on Au for Pb (II) Detection," Anal. Chem., 77(2):442-448, (2005).
Tanabe, et al., "Maxizymes, Novel Allosterically Controllable Ribozymes, Can Be Designed to Cleave Various Substrates," Biomacromolecules, American Chemical Society,1:108-117, (2000).
U.S. Appl. No. 11/544,926, Non-Final Office Action mailed Mar. 22, 2012.
U.S. Appl. No. 11/697,021, Final Office Action mailed Sep. 10, 2012.
U.S. Appl. No. 11/697,021, Non-Final Office Action mailed Dec. 28, 2011.
U.S. Appl. No. 11/697,021, Requirement for Restriction/Election mailed Aug. 23, 2011.
U.S. Appl. No. 12/442,275, Final Office Action mailed Jul. 19, 2012.
U.S. Appl. No. 12/442,275, Non-Final Office Action mailed Nov. 4, 2011.
U.S. Appl. No. 12/442,275, Requirement for Restriction/Election mailed May 4, 2011.
U.S. Appl. No. 11/544,926, Notice of Allowance mailed Oct. 15, 2012.
U.S. Appl. No. 11/544,926, Requirement for Restriction/Election mailed Mar. 20, 2009.
U.S. Appl. No. 11/544,926, Requirement for Restriction/Election mailed Jun. 30, 2009.
Warashina, et al., "Working at the Cutting Edge: the Creation of Allosteric Ribozymes," Structures, 8:R207-R212, (2000).
Xiao et al., "Lighting Up Biochemiluminescence by the Surface Self-Assembly of DNA—Hemin Complexes," ChemBioChem, 5:374-379 (2004).
Yang et al., "Minimum Ribonucleotide Requirement for Catalysis by the RNA Hammerhead Domains," Biochemistry, 31:5005-5009, (1992).
AU Application No. 2008235256, First Examination Report mailed Apr. 2, 2013.
CN Application No. 2008880018552.8, Second Office Action mailed Apr. 9, 2013.
EPO Application No. 08733324.1, Communication under Rule 71(3) EPC mailed Oct. 17, 2012.
JP Application No. 2001-501333, First Office Action mailed Mar. 27, 2013.
NZ Application No. 580129, Notice of Acceptance mailed May 8, 2012.
TW Application No. 097112521, First Office Action mailed Jan. 7, 2013.
U.S. Appl. No. 13/741,895, Non-Final Office Action mailed Apr. 17, 2013.

\* cited by examiner

NUCLEIC ACID ENZYMES AND COMPLEXES AND METHODS FOR THEIR USE

CROSS REFERENCE TO RELATED APPLICATIONS

This application claims priority to International Application Serial No. PCT/AU2008/000492 filed 4 Apr. 2008 under 37 C.F.R. 371(c), which claims the benefit of U.S. Provisional Patent Application No. 60/910,427 filed 5 Apr. 2007, Australian Provisional Patent Application No. 2007901833 filed 5 Apr. 2007 and is a US Continuation-in-Part of application Ser. No. 11/697,021 filed 5 Apr. 2007, all of which are incorporated herein in their entireties.

SEQUENCE LISTING

The instant application contains a Sequence Listing which has been submitted in ASCII format via EFS-Web and is hereby incorporated by reference in its entirety. Said ASCII copy, created on Feb. 18, 2011, is names 48514214.txt and is 43,107 bytes in size.

TECHNICAL FIELD

The present invention relates to methods that utilise multi-component nucleic acid (MNA) complexes. The MNA complexes may be active enzymes (e.g. MNAzymes including apta-MNAzymes) with modifying activity such as ligase or cleavage activity. Further, the invention relates to cascades which use MNAzymes and may also include one or more DNAzymes. The invention also relates to methods which use these cascades for the identification, detection and quantification of targets.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety In addition to their evolutionary optimized functions, the extraordinary physical and functional properties of nucleic acids provide the opportunity for a plethora of new bio-molecular devices and methods. Designer nucleic acids have been contemplated for therapeutic entities, biosensors, nano-scale devices and tools for molecular computation. The methods exploit the characteristics of DNA self-assembly, electro-conductivity, information elements, amplification, switching, molecular detection and catalytic activity. Further, since DNA is robust, stable and thermostable it provides an ideal material for molecular engineering of mechanical or computational devices.

Single stranded nucleic acids, such as DNA and RNA, have the ability to fold into complex three-dimensional structures that can function as highly specific receptors (e.g. aptamers) and catalysts (e.g. ribozymes, DNAzymes). Further, the requirement for complementarity between nucleic acid strands for hybridization forms the basis for a wide range of techniques, which allow target detection (e.g. microarray analysis, Northern blotting or Southern blotting), and/or target amplification (e.g. the polymerase chain reaction). Further, hybridization provides the basis for nucleic acid nano-scale construction and for DNA based computational strategies.

A wide variety of nucleic acid molecules, with enzymatic or catalytic activity, have been discovered in the last 20 years. RNA enzymes ("ribozymes") occur in nature but can be engineered to specifically recognize and modify a target RNA substrate (Haseloff and Gerlach, 1988). In vitro evolution techniques have facilitated the discovery and development of many more catalytic nucleic acids, including deoxyribo-nucleic acids often referred to as "DNA enzymes" or "DNAzymes" (reviewed Emillson and Breaker, 2002). In vitro evolved DNAzymes and/or ribozymes have been discovered which have the capacity to catalyse a broad range of reactions including, but not limited to, cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion or phosphoramidate cleavage (reviewed Silverman, 2007)

In particular, DNAzymes and ribozymes have been characterized which specifically cleave distinct nucleic acid sequences after hybridizing via Watson Crick base pairing. DNAzymes are capable of cleaving either RNA (Breaker and Joyce, 1994; Santoro and Joyce, 1997; Santoro and Joyce, 1998) or DNA (Carmi et al., 1996) molecules. Ribozymes are also able to cleave both RNA (Haseloff and Gerlach, 1988) and DNA (Raillard and Joyce, 1996) target sequences.

The "10:23" and "8:17" DNAzymes are capable of cleaving nucleic acid substrates at specific RNA phosphodiester bonds. These DNAzymes cleave native 3'-5' phosphodiester linkages to create reaction products which have 2',3'-cyclic phosphate and 5'-hydroxyl groups (Santoro and Joyce, 1997; reviewed Emilsson and Breaker, 2002).

DNAzymes which specifically ligate distinct nucleic acid sequences after hybridizing to two independent substrate nucleic acids have also been characterized. Specific deoxyribozymes (DNAzymes) can ligate 2',3'-cyclic phosphate and 5'-hydroxyl products and create non-native 2'-5' linkages. Examples of such DNAzymes include the "7Z81" and "7Z48" ligases (Prior et al, 2004) as well as the "7Q10" DNAzyme ligase (Flynn-Charlebois et al, 2003). Other DNAzymes have been described (Coppins and Silverman, 2004) which can ligate 2',3' diol and 5'-triphosphate products and create native 3'-5' linkages.

Several catalytic nucleic acids have similar basic structures with multiple domains including a conserved catalytic domain ("catalytic core") flanked by two non-conserved substrate-binding domains ("arms"), which specifically recognize and hybridise to the substrate. Examples of nucleic acids with this basic structure include, but are not limited to, the hammerhead ribozyme, the 10:23 and 8:17 DNAzymes, the "7Z81", "7Z48" and "7Q10" DNAzyme ligases, the "UV1C" thymine dimer photoreversion DNAzyme and the "DAB22" carbon-carbon bond forming DNAzyme. To date catalytic nucleic acids are typically uni-molecular although examples of catalytic nucleic acids with more than one component are known but these required extensive engineering (Tabor et al, 2006, Kurata et al, 2000).

Catalytic nucleic acids have been shown to tolerate only certain modifications in the area that forms the catalytic core (Perreault et al., 1990; Perreault et al., 1991; Zaborowska et al., 2002; Cruz et al., 2004; Silverman, 2004). Depending on the stringency of the reaction conditions, some degree of mismatch may be tolerated within the substrate arms. However, the requirement for Watson Crick base pairing is sufficiently strict so as to have enabled the development of protocols that use catalytic nucleic acids to facilitate the discrimination of closely related sequences (Cairns et al., 2000) (WO 99/50452).

Target amplification and detection technologies, such as PCR, have been widely used in research and/or in clinical diagnostics. However, despite their power, each has inherent disadvantages. They all require the use of protein enzymes (e.g. DNA polymerase, RNA polymerase, reverse transcriptase, and or ligase). The inclusion of protein enzymes increases the complexity and cost of reagent manufacture and decreases the shelf life of kits containing reagents. Other associated technical challenges include contamination by replicons (target amplicons) from previous reactions leading to false positive signal, and/or background signal caused by replication of primer sequences (primer-dimers) or background caused by target-independent ligation.

Nucleic acid enzymes and nucleic acid enzyme cascades have been considered for a range of biotechnological applications, especially in diagnostics. They could allow detection of proteins and nucleic acids for disease diagnosis by facilitating signal amplification.

Several groups have reported using catalytic nucleic acids for the detection of nucleic acid targets, and other analytes with colourimetric readouts (Elghanian et al., 1997, Mirkin et al, 1996, and Liu and Lu, 2004). Examples of signal amplification cascades, which use uni-molecular catalytic nucleic acids, are known in the art. For example, Paul and Joyce (2004) described a replication cascade mediated by a ribozyme with ligase activity. In another approach, a signal amplification cascade used two inactive, circularized 10:23 DNAzymes which were capable of activating each other by cross cleavage resulting in linearisation (Levy and Ellington, 2003).

There is an ongoing need in the art for the detection of targets, in particular detection using amplification systems such as cascades, for example, detection systems involving cascades which comprise a plurality of nucleic acid enzymes and in particular at least one multicomponent nucleic acid enzyme (MNAzyme). The present invention provides detection methods involving nucleic acid enzyme cascades which incorporate at least one nucleic acid enzyme with ligase activity. Moreover, the use of nucleic acid enzymes with ligase activity allows formation of components for nucleic acid complexes, such as assembly facilitators, partzymes, substrates, DNAzymes or components thereof.

SUMMARY OF THE INVENTION

In one aspect of the invention there is provided a method for detecting the presence of at least one target comprising (a) providing at least two or more oligonucleotide components and at least one substrate of at least a first nucleic acid complex wherein at least a first oligonucleotide component and a second oligonucleotide component are capable of self-assembly in the presence of a target to form at least a first nucleic acid enzyme which comprises a catalytically active multi-component nucleic acid enzyme with ligase activity (MNAzyme ligase), (b) contacting the two or more oligonucleotide components and at least one substrate with a sample putatively containing the at least one target under conditions permitting:
(1) the self-assembly of said at least one catalytically active MNAzyme ligase and
(2) the catalytic activity of said at least one MNAzyme ligase; and
(c) determining the presence of the catalytic activity of said at least one MNAzyme ligase, wherein the presence of the catalytic activity is indicative of the presence of said at least one target.

In another aspect of the invention there is provided a method for the detection of a target comprising a) providing a first nucleic acid complex comprising components which require association with said target to facilitate formation of a first nucleic acid enzyme, wherein said first nucleic acid complex further comprises at least one substrate, and b) providing at least one component of a second nucleic acid complex capable of associating with a product of a reaction catalysed by the first nucleic acid enzyme and forming a second nucleic acid complex capable of functioning as a second nucleic acid enzyme wherein at least one of said nucleic acid enzymes has ligase activity and at least one of said nucleic acid enzymes is an MNAzyme, and wherein said method comprises:

i) contacting a sample putatively containing a target with the first nucleic acid complex, wherein said target associates with said first nucleic acid complex to facilitate formation of said first nucleic acid enzyme, and ii) contacting a product of the reaction catalysed by the first nucleic acid enzyme with said at least one component of the second nucleic acid complex thereby permitting formation of the second nucleic acid complex which functions as said second nucleic acid enzyme, and wherein activity of at least one of the first or second nucleic acid enzymes or both is indicative of the presence of said target.

In one embodiment the method may further comprise providing at least one component of a third nucleic acid complex capable of associating with a product of a reaction catalysed by the first or second nucleic acid enzyme or both and forming a third nucleic acid complex capable of functioning as a third nucleic acid enzyme wherein said method comprises contacting a product of the reaction catalysed by the first or second nucleic acid enzyme or both with said at least one component of the third nucleic acid complex thereby permitting formation of a third nucleic acid complex which functions as said third nucleic acid enzyme, and wherein activity of the first, second, or third nucleic acid enzymes or any combination thereof is indicative of the presence of said target.

In another embodiment the method may further comprise providing at least one component of at least one additional nucleic acid complex capable of associating with a product of at least one of said first, second or third nucleic acid enzymes and forming at least one additional nucleic acid complex capable of functioning as at least one additional nucleic acid enzyme wherein said method comprises contacting a product of the reaction catalysed by at least one of said first, second or third nucleic acid enzymes with said at least one component of the at least one additional nucleic acid complex thereby permitting formation of at least one additional nucleic acid complex which functions as said at least one additional nucleic acid enzyme, and wherein activity of the first, second, third or at least one additional nucleic acid enzymes or any combination thereof is indicative of the presence of said target.

In one embodiment at least one of said nucleic acid enzymes may have cleavage activity or ligase activity. Moreover the first nucleic acid enzyme may be an MNAzyme. Further at least one of the nucleic acid enzymes may be a DNAzyme.

In another embodiment a product of a reaction catalysed by any one of the nucleic acid enzymes may be selected from the group comprising an assembly facilitator, partzyme, substrate, DNAzyme, stabiliser arm or component thereof.

In one embodiment the target may be a nucleic acid.

In one embodiment at least one of said components may further comprise at least one aptamer and wherein said method may further comprise providing at least one assembly facilitator and at least one assembly inhibitor of said first nucleic acid complex wherein said target associates with said aptamer allowing said first nucleic acid complex to function as a first nucleic acid enzyme.

In one embodiment the target is a non-nucleic acid target. The assembly facilitator may be an additional target to be detected.

In a further embodiment a product of a reaction catalysed by at least one of said nucleic acid enzymes, or any combination thereof, associates with at least one component of at least one of the preceding nucleic acid complexes thereby permitting formation of further at least one of said preceding nucleic acid complexes which functions as further said preceding nucleic acid enzyme.

In another aspect of the invention there is provided a method for the detection of a first assembly facilitator using a cascade comprising
  a) providing components for a first MNAzyme, at least a first MNAzyme substrate, a first DNAzyme ligase, a first DNAzyme ligase substrate, a second assembly facilitator, at least a second MNAzyme substrate, and a first partzyme for a second MNAzyme wherein said method comprises:
  b) associating said first assembly facilitator with said components for said first MNAzyme under conditions permitting catalytic activity of said first MNAzyme thus facilitating the catalytic activity of said first MNAzyme thereby allowing modification of said first MNAzyme substrate wherein;
    the modification of the first MNAzyme substrate results in the production of a second DNAzyme ligase substrate; and
    wherein the first DNAzyme ligase assembles with the first and second DNAzyme ligase substrates; and
    wherein catalytic activity of the DNAzyme ligase produces a second partzyme for the second MNAzyme, and wherein;
    association of said second partzyme for the second MNAzyme with said second assembly facilitator, and the first partzyme for the second MNAzyme under conditions permitting catalytic activity of the second MNAzyme facilitates the catalytic activity of said second MNAzyme thereby allowing modification of at least the second MNAzyme substrate wherein modification of any of said substrates, or a combination thereof, is indicative of the presence of said first assembly facilitator.

In another aspect of the invention there is provided a method for the detection of a first assembly facilitator using a cascade comprising
  a) providing components for a first MNAzyme, at least a first MNAzyme substrate, a DNAzyme ligase, a first DNAzyme ligase substrate, at least a second MNAzyme substrate, and first and second partzymes for a second MNAzyme and wherein said method comprises:
  b) associating said first assembly facilitator with said components for the first MNAzyme under conditions permitting catalytic activity of said first MNAzyme thus facilitating the catalytic activity of said first MNAzyme thereby allowing modification of said first MNAzyme substrate wherein;
    the modification of the first MNAzyme substrate results in the production of a second DNAzyme ligase substrate; and
    wherein the first DNAzyme ligase assembles with the first and second DNAzyme ligase substrates; and
    wherein catalytic activity of the DNAzyme ligase produces a second assembly facilitator for the second MNAzyme, and
    wherein association of said second assembly facilitator with said first and second partzymes for the second MNAzyme under conditions permitting catalytic activity of the said second MNAzyme facilitates the catalytic activity of said second MNAzyme thereby allowing modification of at least the second MNAzyme substrate wherein modification of any of said substrates, or a combination thereof, is indicative of the presence of said first assembly facilitator.

In one embodiment a product of the reaction catalysed by the second MNAzyme may be a component required to permit function of a third nucleic acid enzyme. A product of the reaction catalysed by the third nucleic acid enzyme may be a component which participates in a reaction catalysed by the second MNAzyme or the DNAzyme ligase, or both.

In another aspect of the invention there is provided a method for the detection of a first assembly facilitator using a cascade comprising
  a) providing components for a first MNAzyme, at least a first MNAzyme substrate, components for a second MNAzyme wherein said second MNAzyme has ligase activity, a second assembly facilitator for the second MNAzyme, a second MNAzyme substrate, a third assembly facilitator for a third MNAzyme, at least a third MNAzyme substrate, and a first partzyme for the third MNAzyme and wherein said method comprises:
  b) associating said first assembly facilitator with said components for said first MNAzyme under conditions permitting catalytic activity of said first MNAzyme thus facilitating the catalytic activity of said first MNAzyme thereby allowing modification of said first MNAzyme substrate wherein;
    the modification of the first MNAzyme substrate results in the production of a fourth MNAzyme substrate; and
    wherein the second MNAzyme assembly facilitator facilitates assembly of the components for a second MNAzyme with the second and fourth MNAzyme substrates; and
    wherein catalytic ligase activity of the second MNAzyme produces a second partzyme for the third MNAzyme, and wherein;
    association of said first and second partzymes for the third MNAzyme with said third assembly facilitator, under conditions permitting catalytic activity of the third MNAzyme facilitates the catalytic activity of said third MNAzyme thereby allowing modification of at least the third MNAzyme substrate wherein modification of any of said substrates, or a combination thereof, is indicative of the presence of said first assembly facilitator.

In another aspect of the invention there is provided a method for the detection of a first assembly facilitator using a cascade comprising
  a) providing components for a first MNAzyme, at least a first MNAzyme substrate, components for a second MNAzyme wherein said second MNAzyme has ligase activity, a second assembly facilitator for the second MNAzyme, a second MNAzyme substrate, a first and a second partzyme for a third MNAzyme and at least a third MNAzyme substrate, and wherein said method comprises:

b) associating said first assembly facilitator with components for said first MNAzyme under conditions permitting catalytic activity of said first MNAzyme thus facilitating the catalytic activity of said first MNAzyme thereby allowing modification of said first MNAzyme substrate wherein;

the modification of said first MNAzyme substrate results in the production of a fourth MNAzyme substrate; and wherein the second MNAzyme assembly facilitator facilitates assembly of the said components for second MNAzyme with the second and fourth MNAzyme substrates; and wherein catalytic ligase activity of the second MNAzyme produces a third assembly facilitator for the third MNAzyme, and wherein;

association of said first and second partzymes for the third MNAzyme with said third assembly facilitator, under conditions permitting catalytic activity of the third MNAzyme facilitates the catalytic activity of said third MNAzyme thereby allowing modification of at least the third MNAzyme substrate wherein modification of any one of said substrates, or a combination thereof, is indicative of the presence of said first assembly facilitator.

In one embodiment a product of the reaction catalysed by the third MNAzyme may be a component required to permit function of a fourth nucleic acid enzyme. A product of the reaction catalysed by the fourth nucleic acid enzyme may be a component which participates in a reaction catalysed by the second or third MNAzyme or both.

In one embodiment the modification of any one of said substrates, or a combination thereof, provides a detectable effect. The modification of at least one substrate may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

The first assembly facilitator may be a target to be identified, detected or quantitated.

In one embodiment the DNAzyme ligase may be selected from the group comprising DNAzyme ligases 7Z81, 7Z48, 7Q10 and 9 DB1.

In another embodiment a product of the second MNAzyme may be the second DNAzyme ligase substrate, and wherein the DNAzyme ligase facilitates the ligation of the first and the second DNAzyme ligase substrates thereby producing further second partzyme for the second MNAzyme. A product of the second MNAzyme may be the second DNAzyme ligase substrate, and wherein the DNAzyme ligase facilitates the ligation of the first and the second DNAzyme ligase substrates thereby producing further second assembly facilitator for the second MNAzyme. Moreover a product of the third MNAzyme may be the fourth MNAzyme substrate, and wherein the second MNAzyme facilitates the ligation of the second and the fourth MNAzyme substrates thereby producing a further second partzyme for the third MNAzyme.

In a further embodiment a product of the third MNAzyme may be the fourth MNAzyme substrate, and wherein the second MNAzyme facilitates the ligation of the second and the fourth MNAzyme substrates thereby producing a further third assembly facilitator for the third MNAzyme.

In another aspect of the invention there is provided use of a pair of isolated nucleic acids as catalytic core sequences incorporated into a partzyme pair for an MNAzyme ligase wherein said pairs of nucleic acids are selected from the group consisting of TGGAGGTGGGCTC (SEQ ID NO: 47) and ACG (SEQ ID NO: 48), GGAGGTGGGCTC (SEQ ID NO: 49) and ACGT (SEQ ID NO: 50), GGAGGTTAGCTC (SEQ ID NO: 71) and ACGGCGGAGTGATTG (SEQ ID NO: 72), TGGGAGGTTAGCTC (SEQ ID NO: 73) and ACGGCGGAGTGAT (SEQ ID NO: 74), ATTGGGAGGTTAGCTC (SEQ ID NO: 75) and ACGGCGGAGTG (SEQ ID NO: 76), TGATTGGGAGGTTAGCTC (SEQ ID NO: 77) and ACGGCGGAG (SEQ ID NO: 78), AGTGATTGGGAGGTTAGCTC (SEQ ID NO: 79) and ACGGCGG (SEQ ID NO: 80), GGAGTGATTGGGAGGTTAGCTC (SEQ ID NO: 81) and ACGGC (SEQ ID NO: 82).

In another aspect of the invention there is provided an MNAzyme ligase comprising a pair of isolated nucleic acids as catalytic core sequences incorporated into a partzyme pair wherein said pairs of nucleic acids are selected from the group consisting of TGGAGGTGGGCTC (SEQ ID NO: 47) and ACG (SEQ ID NO: 48), GGAGGTGGGCTC (SEQ ID NO: 49) and ACGT (SEQ ID NO: 50), GGAGGTTAGCTC (SEQ ID NO: 71) and ACGGCGGAGTGATTG (SEQ ID NO: 72), TGGGAGGTTAGCTC (SEQ ID NO: 73) and ACGGCGGAGTGAT (SEQ ID NO: 74), ATTGGGAGGTTAGCTC (SEQ ID NO: 75) and ACGGCGGAGTG (SEQ ID NO: 76), TGATTGGGAGGTTAGCTC (SEQ ID NO: 77) and ACGGCGGAG (SEQ ID NO: 78), AGTGATTGGGAGGTTAGCTC (SEQ ID NO: 79) and ACGGCGG (SEQ ID NO: 80), GGAGTGATTGGGAGGTTAGCTC (SEQ ID NO: 81) and ACGGC (SEQ ID NO: 82).

In another aspect of the invention there is provided use of an MNAzyme ligase to ligate two substrates wherein said substrates are ligated by said MNAzyme ligase to form a product following the engagement of said substrates by the substrate arms of said MNAzyme ligase.

In one embodiment the product may associate with the components of at least one nucleic acid complex.

In another embodiment the product may be selected from the group comprising assembly facilitator, partzyme, substrate, DNAzyme, stabiliser arm, activity inhibitor, assembly inhibitor, or component thereof. The product may participate in a cascade.

In another embodiment at least one substrate is the product of a reaction catalysed by a nucleic acid enzyme.

In another aspect of the invention there is provided a method for the detection of a plurality of targets comprising:

a) providing a plurality of first nucleic acid complexes each comprising components which require association with one of said plurality of targets to facilitate formation of a plurality of first nucleic acid enzymes, wherein each of said plurality of first nucleic acid complexes further comprises at least one substrate, and b) providing at least one component of each of a plurality of second nucleic acid complexes capable of associating with a plurality of products of reactions catalysed by the plurality of first nucleic acid enzymes and forming a plurality of second nucleic acid complexes capable of functioning as a plurality of second nucleic acid enzymes, wherein at least one of said nucleic acid enzymes has ligase activity and at least one of said nucleic acid enzymes is an MNAzyme, and wherein said method comprises:

i) contacting a sample putatively containing said plurality of targets with the plurality of first nucleic acid complexes, wherein said plurality of targets associate with said plurality of first nucleic acid complexes to facilitate formation of said plurality of first nucleic acid enzymes, and ii) contacting a plurality of products of the reactions catalysed by the plurality of first nucleic acid enzymes with at least one component of each of the plurality of second nucleic acid complexes thereby permitting formation of the plurality of said second nucleic acid complexes which function as said plurality of second nucleic acid enzymes, and wherein activity of the first or second or both pluralities of nucleic acid enzymes is indicative of the presence of said plurality of targets.

In one embodiment at least one of the products of the reactions catalysed by any one of the plurality of first or second nucleic acid enzymes may be a component required to permit function of at least one additional nucleic acid enzyme.

In another embodiment at least one of the products of the reactions catalysed by any one of the nucleic acid enzymes associates with the components of any one of the preceding nucleic acid complexes thereby permitting at least one of the nucleic acid complexes to function as further nucleic acid enzyme.

In another aspect of the invention there is provided use of at least two oligonucleotides as multi-component nucleic acid enzyme ligase (MNAzyme ligase) substrates wherein said substrates are modified by an MNAzyme ligase following the engagement of said substrates by the substrate arms of said MNAzyme ligase.

In another aspect of the invention there is provided a method for the detection of at least two targets wherein said method comprises:

a) providing at least two nucleic acid complexes each comprising components which require association with at least one of said targets to facilitate formation of at least two nucleic acid enzyme complexes, and b) contacting a sample putatively containing said at least two targets with said at least two nucleic acid complexes, wherein said targets associate with said nucleic acid complexes to facilitate formation of said nucleic acid enzyme complexes, and wherein at least one product created by the activity of each nucleic acid enzyme complex is required for formation of an additional nucleic acid enzyme complex, and wherein activity of the additional nucleic acid enzyme complex is indicative of the presence of said at least two targets.

In one embodiment at least one of said nucleic acid enzyme complexes may have ligase activity. Further, at least one of said nucleic acid enzyme complexes may be an MNAzyme complex.

According to another aspect of the invention there is provided use of an MNAzyme with ligase activity (MNAzyme ligase) to switch an active MNAzyme to an MNAi complex; wherein said active MNAzyme is formed in the presence of at least a first assembly facilitator component and a second assembly facilitator component and wherein said MNAzyme ligase forms in the presence of at least a third assembly facilitator and wherein said MNAzyme ligase facilitates the ligation of said second assembly facilitator component with an activity inhibitor component to form an activity inhibitor; and wherein said activity inhibitor associates with one or more components of said MNAzyme to form an MNAi complex.

In one embodiment at least one of the assembly facilitators, activity inhibitor component or activity inhibitor may be nucleic acid molecules.

In one embodiment at least one of the assembly facilitators, activity inhibitor component or activity inhibitor may be comprised of DNA or an analogue thereof.

According to another aspect of the invention there is provided a multicomponent nucleic acid enzyme with ligase activity comprising at least two or more oligonucleotide components wherein at least a first oligonucleotide component and a second oligonucleotide component self-assemble in the presence of an MNAzyme ligase assembly facilitator to form a catalytically active multi-component nucleic acid enzyme with ligase activity (MNAzyme ligase), wherein each of said at least first and said second oligonucleotide components comprise a substrate arm portion, a catalytic core portion, and a sensor arm portion;

wherein upon self-assembly, the sensor arm portion of said first and second oligonucleotide components act as sensor arms of the MNAzyme ligase, the substrate arm portion of the first and second oligonucleotide components act as substrate arms of the MNAzyme ligase, and the catalytic core portion of the first and second oligonucleotide components act as a catalytic core of the MNAzyme ligase; and wherein the sensor arms of the MNAzyme ligase interact with said MNAzyme ligase assembly facilitator so as to maintain the first and second oligonucleotide components in proximity for association of their respective catalytic core portions to form the catalytic core of the MNAzyme ligase, said catalytic core capable of ligating at least two substrates, and wherein said substrate arms of said MNAzyme ligase engage first and second substrates so that said catalytic core of said MNAzyme can ligate said substrates.

In one embodiment at least one of said oligonucleotide components, assembly facilitator or substrates of the multi-component nucleic acid enzyme with ligase activity may comprise DNA or an analogue thereof.

In one embodiment ligation of the substrates may provide a detectable effect.

In another aspect of the invention there is provided a composition comprising at least two oligonucleotide partzymes each comprising at least a catalytic core portion, a sensor arm portion, and a reporter arm portion, and at least three further oligonucleotide components comprising an assembly facilitator oligonucleotide and at least two substrate nucleic acids, wherein said composition is capable of forming a multicomponent nucleic acid complex capable of ligating the substrate nucleic acids.

In one embodiment at least one of said oligonucleotide components, assembly facilitator or substrates of the composition may comprise DNA or an analogue thereof.

In another aspect of the invention there is provided a composition comprising at least two or more oligonucleotide components wherein at least a first oligonucleotide component and a second oligonucleotide component self-assemble in the presence of an MNAzyme assembly facilitator to form a catalytically active multi-component nucleic acid enzyme with ligase activity (MNAzyme ligase)

wherein each of said at least first and said second oligonucleotide components comprise a substrate arm portion, a catalytic core portion, and a sensor arm portion;

wherein upon self-assembly, the sensor arm portion of said first and second oligonucleotide components act as sensor arms of the MNAzyme ligase, the substrate arm portion of the first and second oligonucleotide components act as substrate arms of the MNAzyme ligase, and the catalytic core portion of the first and second oligonucleotide components act as a catalytic core of the MNAzyme ligase;

and wherein the sensor arms of the MNAzyme ligase interact with said MNAzyme assembly facilitator so as to maintain the first and second oligonucleotide components in proximity for association of their respective catalytic core portions to form the catalytic core of the MNAzyme ligase, said catalytic core capable of ligating at least one substrate to another, and wherein said substrate arms of said MNAzyme ligase engage first and second substrates so that said catalytic core of said MNAzyme ligase can ligate said substrates.

In one embodiment ligation of the substrates may provide a detectable effect.

In one embodiment at least one of said oligonucleotide components, assembly facilitator or substrates of the composition may comprise DNA or an analogue thereof.

In another aspect of the invention there is provided a multicomponent nucleic acid enzyme with ligase activity wherein at least one oligonucleotide component of said MNAzyme further comprises an aptamer.

In another aspect at least one of the assembly facilitator or substrates further comprises an aptamer.

In one embodiment assembly of the MNAzyme ligase may be directed by the presence or absence of one or more analytes capable of binding the aptamer.

In another aspect of the invention there is provided a method for detecting the presence of at least one assembly facilitator comprising (a) providing at least two or more oligonucleotide components wherein at least a first oligonucleotide component and a second oligonucleotide component self-assemble in the presence of an assembly facilitator to form at least one catalytically active multi-component nucleic acid enzyme with ligase activity (MNAzyme ligase), (b) contacting the two or more oligonucleotide components with a sample putatively containing the assembly facilitator under conditions permitting:

(1) the self-assembly of said at least one catalytically active MNAzyme ligase and (2) the catalytic activity of said at least one MNAzyme ligase; and (c) determining the presence of the catalytic activity of said at least one MNAzyme ligase, wherein the presence of the catalytic activity is indicative of the presence of said at least one assembly facilitator.

In one embodiment at least one of said oligonucleotide components or assembly facilitator may be comprised of DNA or an analogue thereof In one embodiment said assembly facilitator may be a target to be identified, detected or quantitated.

In one embodiment said target may be a nucleic acid.

In a preferred embodiment said nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

In one embodiment the source of the nucleic acid may be selected from the group comprising synthetic, mammalian, human, animal, plant, fungal, bacterial, viral, archaeal sources or any combination thereof.

In one embodiment the method may further comprise a step of amplifying the assembly facilitator.

In one embodiment the step of amplifying may comprise one or more of: polymerase chain reaction (PCR), strand displacement amplification, loop-mediated isothermal amplification, rolling circle amplification, transcription-mediated amplification, self-sustained sequence replication, ligase chain reaction, nucleic acid sequence based amplification, or reverse transcription polymerase chain reaction (RT-PCR).

In one embodiment at least one of said assembly facilitator, said oligonucleotide components or substrates for the reaction or a combination thereof may be comprised of more than one molecule.

In one embodiment the method may further comprise determination of the presence of said catalytic activity during or after said amplification.

In one embodiment the self assembly of the MNAzyme ligase may require contact of the assembly facilitator with one or both of said first and second oligonucleotide components.

In one embodiment the method may further comprise providing at least a third oligonucleotide component that contacts at least a portion of either or both of the first and second oligonucleotide components to self-assemble the MNAzyme ligase.

In one embodiment the method said third oligonucleotide component may be comprised of more than molecule.

In one aspect of the invention there is provided an isolated nucleic acid sequence capable of forming part of a catalytic core of an MNAzyme ligase comprising the sequence selected from the group comprising TGGAGGTGGGCTC (SEQ ID NO: 47), ACG (SEQ ID NO: 48), GGAGGTGGGCTC (SEQ ID NO: 49), ACGT (SEQ ID NO: 50), GGAGGTTAGCTC (SEQ ID NO: 71), ACGGCGGAGTGATTG (SEQ ID NO: 72), TGGGAGGTTAGCTC (SEQ ID NO: 73), ACGGCGGAGTGAT (SEQ ID NO: 74), ATTGGGAGGTTAGCTC (SEQ ID NO: 75), ACGGCGGAGTG (SEQ ID NO: 76), TGATTGGGAGGTTAGCTC (SEQ ID NO: 77), ACGGCGGAG (SEQ ID NO: 78), AGTGATTGGGAGGTTAGCTC (SEQ ID NO: 79), ACGGCGG (SEQ ID NO: 80), GGAGTGATTGGGAGGTTAGCTC (SEQ ID NO: 81), and ACGGC (SEQ ID NO: 82).

According to another aspect of the present invention, there is provided a method for the detection of a first assembly facilitator using a cascade comprising components for a first MNAzyme, a first MNAzyme substrate, components for a second MNAzyme, a second assembly facilitator for the second MNAzyme, a second MNAzyme substrate, a third assembly facilitator for the third MNAzyme, at least a third MNAzyme substrate, and a first partzyme for the third MNAzyme wherein association of said first assembly facilitator with said components for a first MNAzyme under conditions permitting catalytic activity of said first MNAzyme facilitates the catalytic activity of said first MNAzyme thereby cleaving the said first MNAzyme substrate wherein;

the cleavage of the first MNAzyme substrate results in the production of a fourth MNAzyme substrate; and wherein the second MNAzyme assembly facilitator facilitates assembly of the second MNAzyme with the second and fourth MNAzyme substrates; and wherein catalytic ligase activity of the second MNAzyme produces a second partzyme for the third MNAzyme, and wherein;

association of said first and second partzymes for the third MNAzyme with said third assembly facilitator, under conditions permitting catalytic activity of the third MNAzyme facilitates the catalytic activity of said third MNAzyme thereby providing modification of the at least a third MNAzyme substrate.

The modification of the first, second or at least a third MNAzyme substrates or any combination thereof may provide a detectable effect.

The modification of the at least a third MNAzyme substrate may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

In one embodiment of the invention the method further comprises an amplification cascade wherein a product of the third MNAzyme is the fourth MNAzyme substrate, and wherein the second MNAzyme facilitates the ligation of the second and the fourth MNAzyme substrates thereby producing a further second partzyme for the third MNAzyme.

According to another aspect of the present invention, there is provided a method for the detection of a first assembly facilitator using a cascade comprising a components for a first MNAzyme, a first MNAzyme substrate, components for a second MNAzyme, a second MNAzyme assembly facilitator, a second MNAzyme substrate, components for a third MNAzyme and at least a third MNAzyme substrate, wherein association of said first assembly facilitator with said components for a first MNAzyme under conditions permitting catalytic activity of said first MNAzyme facilitates the catalytic activity of said first MNAzyme thereby cleaving the said first MNAzyme substrate wherein;

the cleavage of the first MNAzyme substrate results in the production of the fourth MNAzyme substrate; and wherein the second MNAzyme assembly facilitator facilitates assembly of the second MNAzyme with the second and fourth MNAzyme substrates; and wherein catalytic activity of the second MNAzyme produces a third MNAzyme assembly facilitator for the third MNAzyme, and wherein;

association of said third MNAzyme assembly facilitator with said components for a third MNAzyme under conditions permitting catalytic activity of the third MNAzyme facilitates the catalytic activity of said third MNAzyme thereby providing modification of the at least a third MNAzyme substrate.

The modification of the first, second or at least a third MNAzyme substrate or any combination thereof may provide a detectable effect.

The modification of the at least a third MNAzyme substrate may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

In one embodiment of the invention the method further comprises an amplification cascade wherein a product of the third MNAzyme is the fourth MNAzyme substrate, and wherein the second MNAzyme facilitates the ligation of the second and the fourth MNAzyme substrates thereby producing further third assembly facilitator for the third MNAzyme.

According to another aspect of the present invention, there is provided a method for the detection of a first assembly facilitator using a cascade comprising components for a first MNAzyme with cleavage activity, a first MNAzyme substrate, a first DNAzyme with ligase activity (DNAzyme ligase), a first DNAzyme ligase substrate, a second assembly facilitator, at least a second MNAzyme substrate, and a first partzyme for a second MNAzyme wherein association of said first assembly facilitator with said components for a first MNAzyme under conditions permitting catalytic activity of said first MNAzyme facilitates the catalytic activity of said first MNAzyme thereby providing modification of said first MNAzyme substrate wherein;

the modification of the first MNAzyme substrate results in the production of the second DNAzyme ligase substrate; and wherein the first DNAzyme ligase assembles with the first and second DNAzyme ligase substrates; and wherein catalytic activity of the DNAzyme ligase produces a second partzyme for the second MNAzyme, and wherein;

association of said second partzyme for the second MNAzyme with said second assembly facilitator, and the first partzyme for the second MNAzyme under conditions permitting catalytic activity of the second MNAzyme facilitates the catalytic activity of said second MNAzyme thereby providing modification of the at least second MNAzyme substrate.

At least one of said oligonucleotide components, assembly facilitator or substrates may comprise DNA or an analogue thereof.

The first assembly facilitator may be a target to be identified, detected or quantitated.

The modification of the first or second MNAzyme substrate or ligase substrates or any combination thereof may provide a detectable effect.

The catalytic activity of the second MNAzyme may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

The modification of the second MNAzyme substrate may be cleavage.

The ligation of the substrates may provide a detectable effect.

In one embodiment of the invention the method further comprises an amplification cascade wherein a product of the second MNAzyme is the second DNAzyme ligase substrate, and wherein the DNAzyme ligase facilitates the ligation of the first and second DNAzyme ligase substrates thereby producing a further second partzyme for the second MNAzyme.

The DNAzyme ligase may be selected from the group comprising DNAzyme ligases 7Z81, 7Z48 and 7Q10.

According to another aspect of the present invention, there is provided a method for the detection of a first assembly facilitator using a cascade comprising components for a first MNAzyme with cleavage activity, a first MNAzyme substrate, a first DNAzyme with ligase activity (DNAzyme ligase), a first DNAzyme ligase substrate, components for a second MNAzyme and at least a second MNAzyme substrate, and wherein association of said first assembly facilitator with said components for a first MNAzyme under conditions permitting catalytic activity of said first MNAzyme facilitates the catalytic activity of said first MNAzyme thereby providing modification of said first MNAzyme substrate wherein;

the modification of the first MNAzyme substrate results in the production of a second DNAzyme ligase substrate; and wherein the first DNAzyme ligase assembles with the first and second DNAzyme ligase substrates; and wherein catalytic activity of the DNAzyme ligase produces a second assembly facilitator for the second MNAzyme, and wherein;

association of said second assembly facilitator for the second MNAzyme with said components for a second MNAzyme under conditions permitting catalytic activity of the second MNAzyme facilitates the catalytic activity of said second MNAzyme thereby providing modification of the at least second MNAzyme substrate.

At least one of said oligonucleotide components, assembly facilitator or substrates may comprise DNA or an analogue thereof.

The modification of the first or second MNAzyme substrate or ligase substrates or any combination thereof may provide a detectable effect The first assembly facilitator may be a target to be identified, detected or quantitated.

The catalytic activity of the second MNAzyme may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

The DNAzyme ligase may be selected from the group comprising DNAzyme ligases 7Z81, 7Z48 and 7Q10.

The modification of the second MNAzyme substrate may be cleavage.

The ligation of the substrates may provide a detectable effect.

In one embodiment of the invention the method further comprises an amplification cascade wherein a product of the second MNAzyme is the second DNAzyme ligase substrate, and wherein the DNAzyme ligase facilitates the ligation of the first and second DNAzyme ligase substrates thereby producing further second assembly facilitator for the second MNAzyme.

According to another aspect of the present invention, there is provided a method for the detection of a first assembly facilitator using a cascade comprising components for a first MNAzyme with cleavage activity (a first MNAzyme cleaver), a first cleavable MNAzyme substrate, components for a first MNAzyme with ligase activity (a first MNAzyme ligase), a first MNAzyme ligase assembly facilitator, a first MNAzyme ligase substrate, a second assembly facilitator for a second MNAzyme cleaver, a second cleavable MNAzyme substrate, and a first partzyme for a second MNAzyme cleaver wherein association of said first assembly facilitator with said components for a first MNAzyme cleaver under conditions permitting catalytic activity of said first MNAzyme cleaver facilitates the catalytic activity of said first MNAzyme cleaver thereby providing modification of said first cleavable MNAzyme substrate wherein;

the modification of the first cleavable MNAzyme substrate results in the production of a second MNAzyme ligase substrate; and wherein the MNAzyme ligase assembly facilitator facilitates assembly of the first MNAzyme ligase with the first and second MNAzyme ligase substrates; and wherein catalytic activity of the MNAzyme ligase produces a second partzyme for the second MNAzyme cleaver, and wherein;

association of said first and second partzymes for the second MNAzyme cleaver with said second assembly facilitator, under conditions permitting catalytic activity of the second MNAzyme cleaver facilitates the catalytic activity of said second MNAzyme cleaver thereby providing modification of the second cleavable MNAzyme substrate.

At least one of said oligonucleotide components, assembly facilitators or substrates may comprise DNA or an analogue thereof.

The first assembly facilitator may be a target to be identified, detected or quantitated.

The modification of the first or second cleavable MNAzyme substrate or both may provide a detectable effect.

The ligation of the substrates may provide a detectable effect.

In one embodiment the method further comprises an amplification cascade wherein the product of the second MNAzyme is the second MNAzyme ligase substrate, and wherein the MNAzyme ligase facilitates the ligation of the first and second MNAzyme ligase substrates thereby producing a further second partzyme for the second MNAzyme cleaver.

According to another aspect of the present invention, there is provided a method for the detection of a first assembly facilitator using a cascade comprising components for a first MNAzyme with cleavage activity (a first MNAzyme cleaver), a first cleavable MNAzyme substrate, components for a first MNAzyme with ligase activity (a first MNAzyme ligase), a first MNAzyme ligase assembly facilitator, a first MNAzyme ligase substrate, components for a second MNAzyme cleaver and a second cleavable MNAzyme substrate, wherein association of said first assembly facilitator with said components for a first MNAzyme cleaver under conditions permitting catalytic activity of said first MNAzyme cleaver facilitates the catalytic activity of said first MNAzyme cleaver thereby providing modification of said first cleavable MNAzyme substrate wherein;

the modification of the first cleavable MNAzyme substrate results in the production of the second MNAzyme ligase substrate; and wherein the MNAzyme ligase assembly facilitator facilitates assembly of the first MNAzyme ligase with the first and second MNAzyme ligase substrates; and wherein catalytic activity of the MNAzyme ligase produces a second MNAzyme assembly facilitator for the second MNAzyme cleaver, and wherein;

association of said second MNAzyme assembly facilitator with said components for a second MNAzyme cleaver under conditions permitting catalytic activity of the second MNAzyme cleaver facilitates the catalytic activity of said second MNAzyme cleaver thereby providing modification of the second cleavable MNAzyme substrate.

At least one of said oligonucleotide components, assembly facilitators or substrates may comprise DNA or an analogue thereof.

The modification of the first or second cleavable MNAzyme substrate or both may provide a detectable effect.

The ligation of the substrates may provide a detectable effect.

The first assembly facilitator may be a target to be identified, detected or quantitated.

In one embodiment the method further comprises an amplification cascade wherein the product of the second MNAzyme is the second MNAzyme ligase substrate, and wherein the MNAzyme ligase facilitates the ligation of the first and second MNAzyme ligase substrates thereby producing a further second MNAzyme assembly facilitator for the second MNAzyme cleaver.

In another aspect of the invention there is provided a use of at least one oligonucleotide as a multi-component nucleic acid enzyme (MNAzyme) substrate wherein said substrate is modified by said MNAzyme following the engagement of said substrate by the substrate arms of said MNAzyme.

In another aspect of the invention there is provided a method for making MNAzymes which incorporate partial sequences from a DNAzyme wherein said method comprises the following steps:

a) selecting positions within said DNAzyme sequence for splitting into partial catalytic core sequences b) incorporating said partial catalytic core sequences into partzymes c) detecting catalytic activity of the partzyme pairs to determine which combination of said partial catalytic core sequences in said partzymes is compatible with the formation of active MNAzymes.

In another aspect of the invention there is provided a method for testing partial catalytic core sequences derived from a DNAzyme catalytic core which, upon incorporation into partzymes, generate functionally active MNAzymes, wherein said method comprises a) splitting the catalytic core sequence of said DNAzyme b) incorporating the resulting partial catalytic core sequences into partzymes:

c) detecting MNAzyme activity to determine which combination of said partial catalytic core sequences in said partzymes is compatible with the formation of active MNAzymes.

In another aspect of the invention there is provided a method for identifying which positions within a DNAzyme catalytic core sequence are suitable for splitting into partial catalytic core sequences which, upon incorporation into partzymes, result in functionally active MNAzymes wherein said method comprises the following steps:

a) splitting the catalytic core sequence from said DNAzyme b) incorporating the resulting partial catalytic core sequences into partzymes:

c) detecting MNAzyme activity to determine which combination of said partial catalytic core sequences in said partzymes is compatible with the formation of active MNAzymes.

BRIEF DESCRIPTION OF THE DRAWINGS

Preferred embodiments of the present invention will now be described, by way of example only, with reference to the accompanying drawings wherein.

It would be appreciated by one skilled in the art that the partzyme arm, which is truncated, could be any of the following; the partzyme A sensor arm, the partzyme B sensor arm (as illustrated), the partzyme A substrate arm or the partzyme B substrate arm, or a combination thereof.

Figure 3:
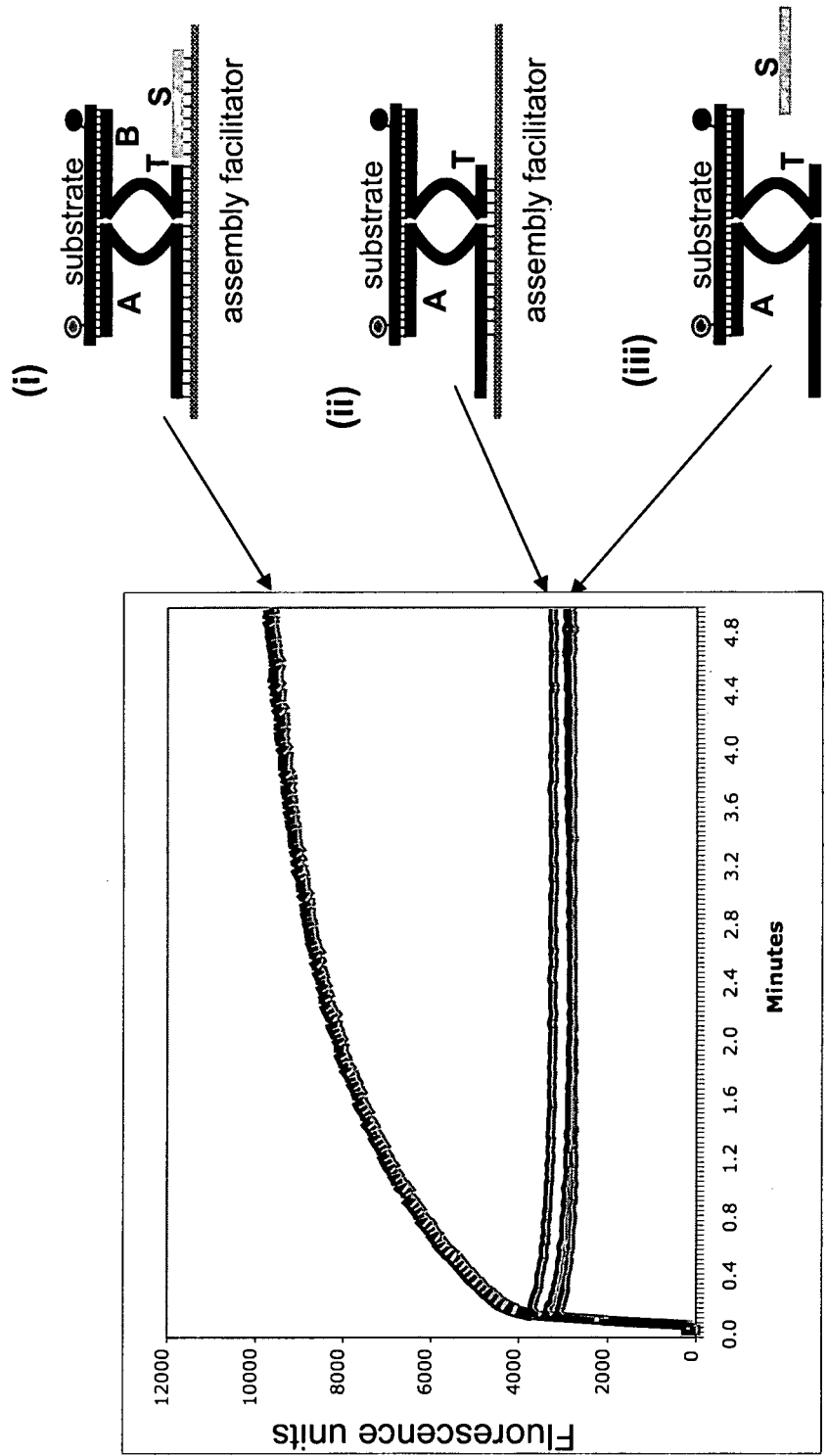

FIG. 3: Changes in output signal (fluorescence) over time in the presence of active and inactive multi-component nucleic acid complexes. In this example, the first partzyme (A) comprises a single component oligonucleotide. The second partzyme (B) has one component containing a substrate arm, a partial catalytic core and a truncated sensor arm (T), and a second component which serves as a stabiliser arm (S).

An increase in fluorescence was observed in reaction (i), which contained all the components of partzymes A and B and an assembly facilitator. This is consistent with the assembly of active MNAzymes and cleavage of the substrate in this reaction. The omission of the stabilizer arm portion of partzyme B (reaction (ii)) resulted in no increase in signal over time indicating that this component is essential for the assembly of active MNAzymes in this system. A control reaction lacking an assembly facilitator (reaction (iii)) also showed no increase in fluorescence over time.

These reactions represent two alternate states for the oligonucleotide complexes. The active MNAzyme (reaction (i)) represents the active complex ("on" state). Those reactions where either a partzyme stabiliser arm component (reaction (ii)), or an assembly facilitator component (reaction (iii)) is omitted, are representative of inactive MNA complexes ("off" states). As such, the MNAzyme catalytic activity can be regulated by the presence or absence of various oligonucleotides and/or by the ability of such oligonucleotide components to be functionally active, for example to be capable of hybridizing with other oligonucleotide components to form stable MNAzymes or MNAzyme complexes. The truncated arm is designed to be insufficient to allow stable MNAzyme assembly under the reaction conditions, unless accompanied by a stabiliser arm component. The stabiliser arm, and the assembly facilitator, can function as "on" switches for MNAzyme activity.

Figure 4:
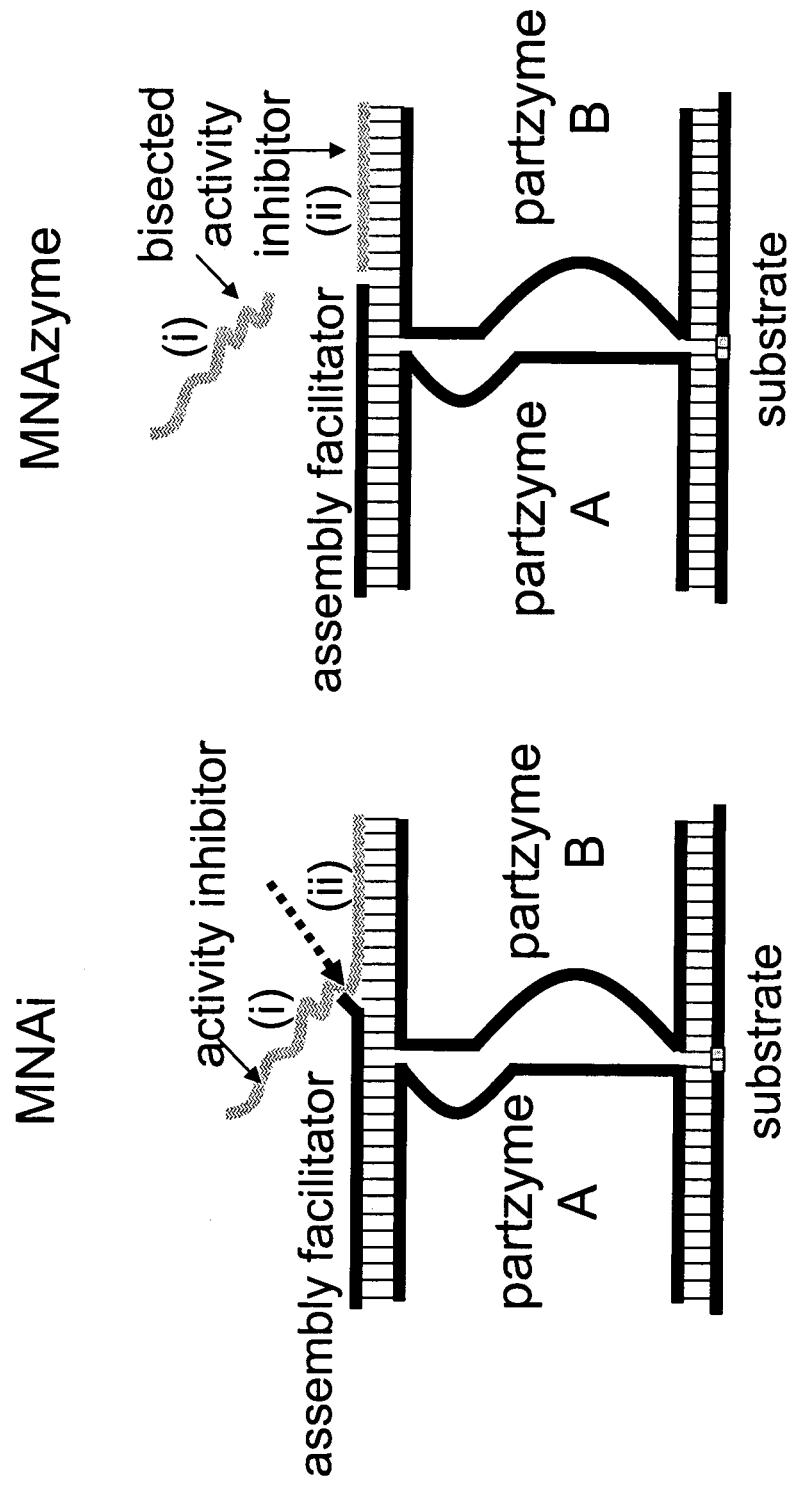

FIG. 4: Depiction of an exemplary design for an inactive multi-component nucleic acid inhibitor (MNAi) complex (left hand side) and an active MNAzyme (right hand side): An MNAi complex is formed when partzymes A and B complex with an assembly facilitator component and an activity inhibitor (left hand side). The inactive MNAi complex is capable of interacting with, but not catalytically modifying, the substrate. In some embodiments, the activity inhibitor may further include a labile or cleavable linker (indicated by the dotted arrow), which may separate two or more domains within the activity inhibitor. Such domains may include, for example, (i) an activity inhibitor portion which is substantially non-complementary to the partzyme components and which exerts an inhibitory effect by disrupting the secondary structure required for formation of a catalytically active MNAzyme and (ii) an activator assembly facilitator portion, which if separated from the activity inhibitor portion, may function as an assembly facilitator component and direct the assembly of an active MNAzyme.

Figure 5:
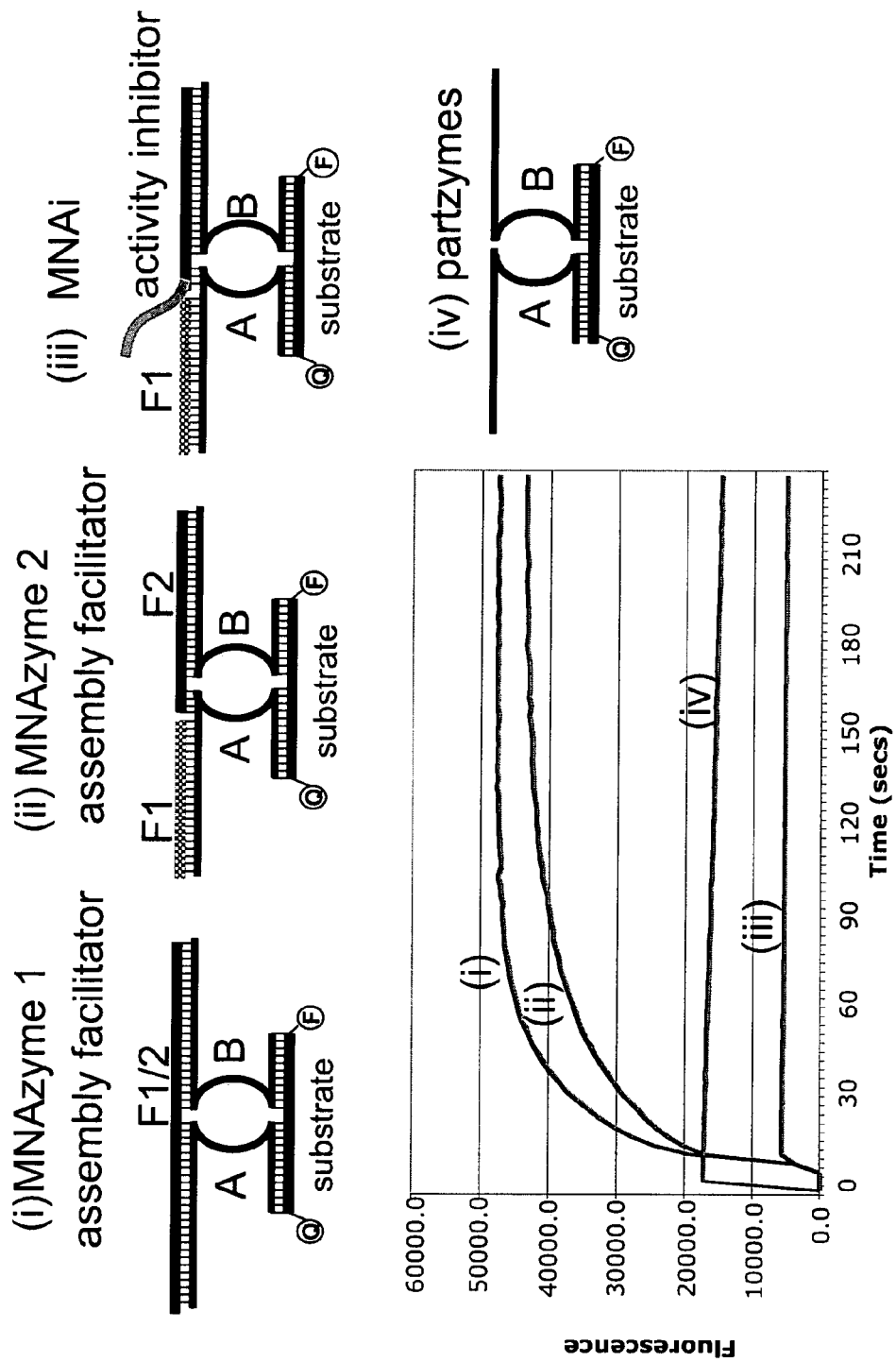

FIG. 5: Demonstration of catalytic activity from various multi-component nucleic acid complexes. All reactions contained partzyme A, partzyme B, and a substrate labelled with a fluorophore quencher dye pair. In addition, reactions contained either (i) an assembly facilitator F1/2, (ii) an assembly facilitator comprising portions F1 and F2 (the sequence of which together correspond to that of assembly facilitator F1/2), (iii) assembly facilitator portion F1 and an activity inhibitor containing two joined domains corresponding to an activity inhibitor portion and portion with the same sequence as F2 or (iv) no assembly facilitator or activity inhibitor.

The change in fluorescence was monitored over time as a measure of catalytic cleavage of the substrate by an active MNAzyme (FIG. 5). The fluorescence increased rapidly in reactions containing either assembly facilitator F1/2 or assembly facilitator components F1 and F2, indicating the formation of active MNAzymes 1 and 2 respectively, both of which are capable of cleaving the substrate. In contrast, the reaction containing F1 and the activity inhibitor showed no increase in fluorescence over time indicating the formation of inactive MNAi complexes. No increase in fluorescence was seen in the absence of assembly facilitator.

Figure 6:
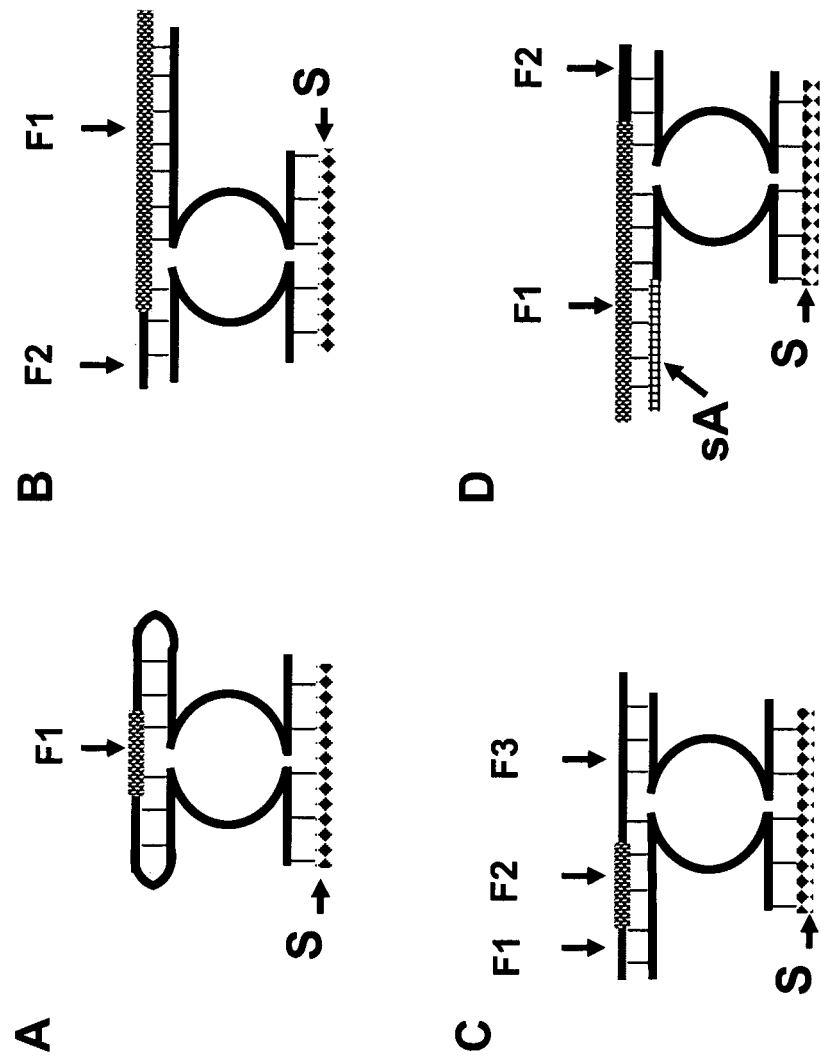

FIG. 6. Exemplary structures for variant MNAzyme designs. Some examples of active MNAzyme complexes are shown in Panels A to D. These structures are all capable of forming catalytically active enzymes, which can modify, for example cleave, a substrate (S). Illustrated are schemes for MNAzyme complexes, which include one assembly facilitator F1 (panel A), two assembly facilitator components F1 and F2 (panels B and D) or three assembly facilitator components F1, F2 and F3 (panel C). Panel A includes sensor arms with self complementary regions within the partzyme sensor arms. MNAzyme complexes may also include one or more stabilising arms (sA) as shown in panel D.

Figure 7:
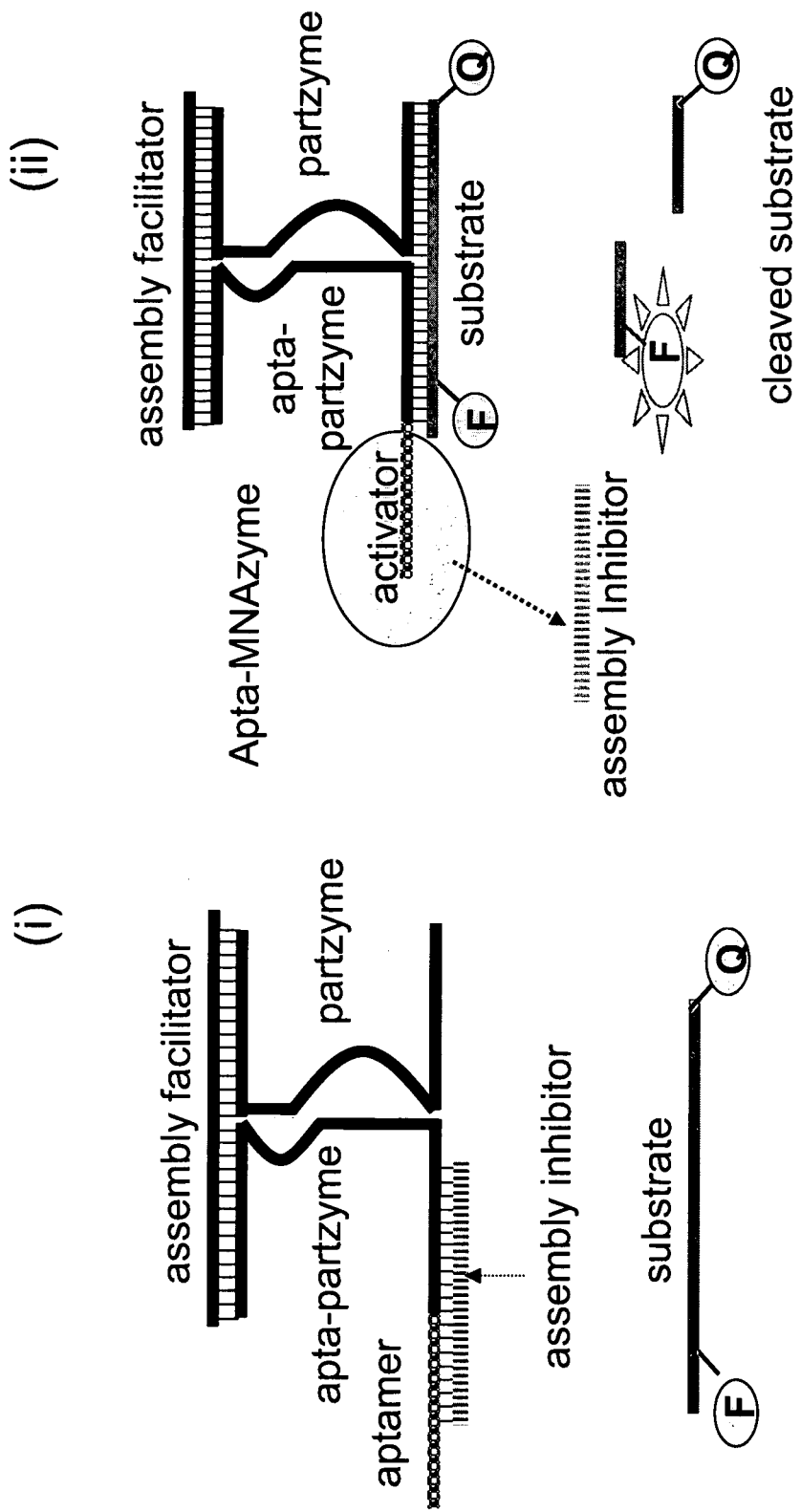

FIG. 7: An exemplary strategy for the modulation of the activity of MNAzymes. The strategy in this system can be used either as (i) a method to control MNAzyme activity using ligands as activator molecules, and/or (ii) a method of detection of nucleic and non-nucleic acid targets using apta-MNAzymes.

The nucleic acid oligonucleotides included in this exemplary apta-MNAzyme detection strategy include;
a) a partzyme;
b) an apta-partzyme which is a partzyme with an aptamer incorporated into one of its ends;
c) an assembly facilitator which is an oligonucleotide which binds to both the apta-partzyme and the partzyme enabling assembly of an active MNAzyme;
d) a substrate e.g. a reporter substrate; and
e) an assembly inhibitor oligonucleotide which hybridises to the apta-partzyme in a region which spans at least part of the aptamer sequence and part of the substrate binding arm of the apta-partzyme sequence.

In the absence of an activator ligand (left hand panel), the assembly inhibitor oligonucleotide binds to the apta-partzyme thus competing with and blocking binding of the reporter substrate. When an activator ligand is present (right hand panel), it binds to the aptamer sequence of the apta-partzyme, blocking the binding of the assembly inhibitor oligonucleotide, and thus allowing assembly of an active apta-MNAzyme complex and subsequent modification, for example cleavage of the substrate (as illustrated) or for example ligation of substrates. As such, an active apta-MNAzyme can only form and cause an increase or decrease in signal, for example, a fluorescent signal, in the presence of a ligand that can bind the aptamer portion of the apta-partzyme.

It would be appreciated that an aptamer sequence could be attached to, for example, one or more of either a substrate arm and/or a sensor arm of either or both of the partzymes. If the aptamer were attached to a sensor arm then the binding of the assembly facilitator could be blocked by an assembly inhibitor oligonucleotide in the absence of a target ligand.

When the apta-MNAzyme has cleavage activity as drawn in this figure then the modification can cause for example an increase in fluorescence by cleavage of a dual labelled reporter substrate thus causing separation of a fluorophore/quencher dye pair.

It would be appreciated that the modification performed by an apta-MNAzyme could be a modification other than cleavage, for example, ligation of two substrates. In this case the signal change could be, for example, a decrease in fluorescence following ligation of two ligatable substrates each labelled with either the fluorophore or the quencher of a fluorophore/quencher dye pair.

This apta-MNAzyme approach could also be used to develop molecular switches that can turn on and off the catalytic activity of an MNA complex. Alternatively it can also be applied to detection of both nucleic acid and non-nucleic acid target ligands.

Figure 8:
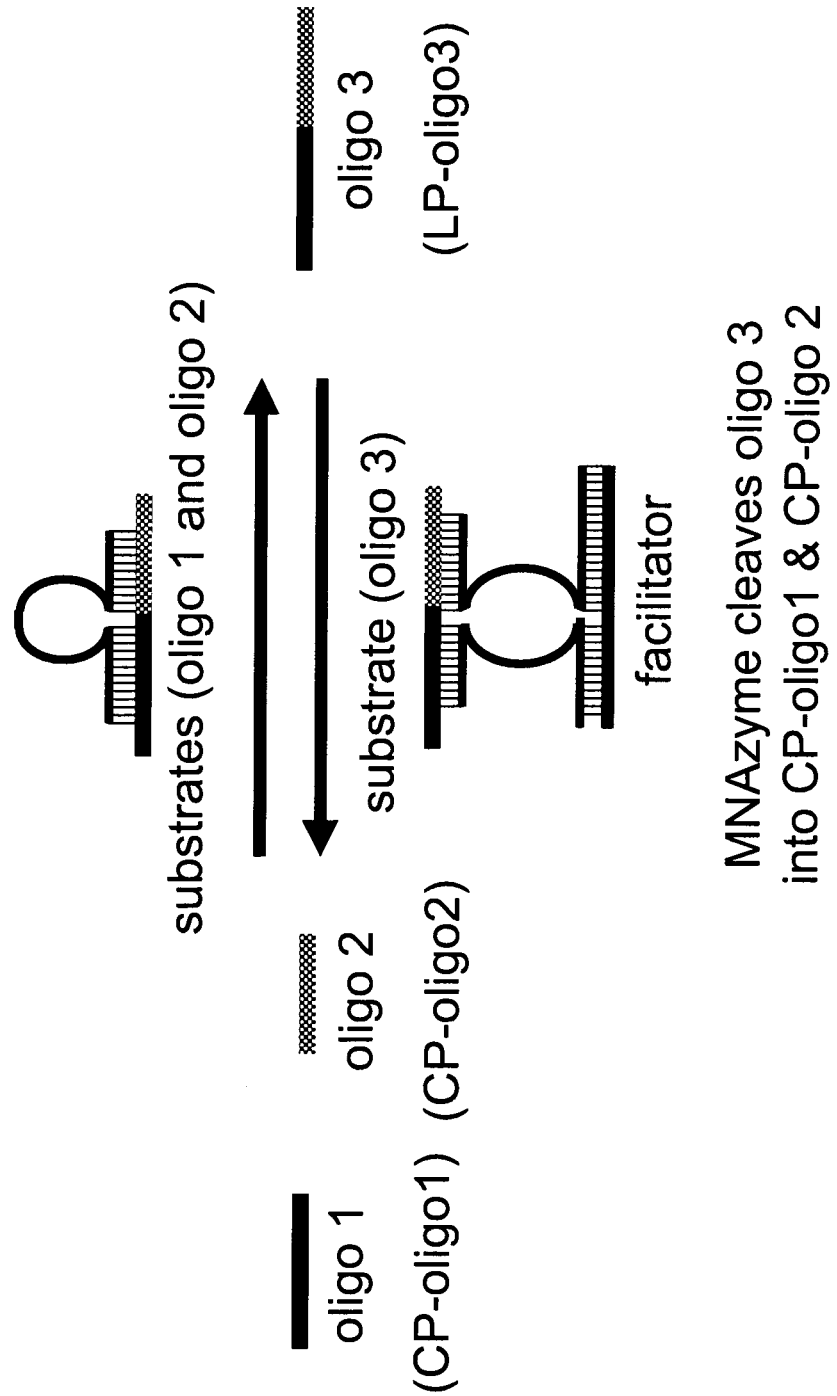

FIG. 8: An example of a cleavage/ligation cascade mediated by a DNAzyme with ligase activity and an MNAzyme with cleavage activity:

A DNAzyme with ligase activity can ligate a first oligonucleotide (oligo 1) to a second oligonucleotide (oligo 2) to create a third ligation product (LP-Oligo 3) with the sequence of oligo 3 and a 2'-5' RNA linkage at the ligation junction, provided oligo 1 and oligo 2 have 2',3'-cyclic phosphate and 5'-hydroxyl termini, for example, as shown. In turn, LP-oligo 3 could be cleaved by an MNAzyme capable of cleaving at a 2'-5' RNA linkage to create cleavage products (CP), CP-oligo 1 and CP-oligo 2, thus regenerating 2',3'-cyclic phosphate and 5'-hydroxyl products, which can participate in further rounds of ligation.

Other DNAzymes with ligase activity may ligate a first oligonucleotide (oligo 1) to a second oligonucleotide (oligo 2) to create a third ligation product (LP-Oligo 3) with the sequence of oligo 3 and a 3'-5' RNA linkage at the ligation junction, provided oligo 1 and oligo 2 have 2',3'-diol and 5'-triphosphate termini, for example. In turn, LP-oligo 3 can be cleaved by an MNAzyme capable of cleaving at a 3'-5' RNA linkage to create cleavage products (CP), CP-oligo 1 and CP-oligo 2 producing products with a 2',3'-cyclic phosphate and 5'-hydroxyl.

Figure 9:
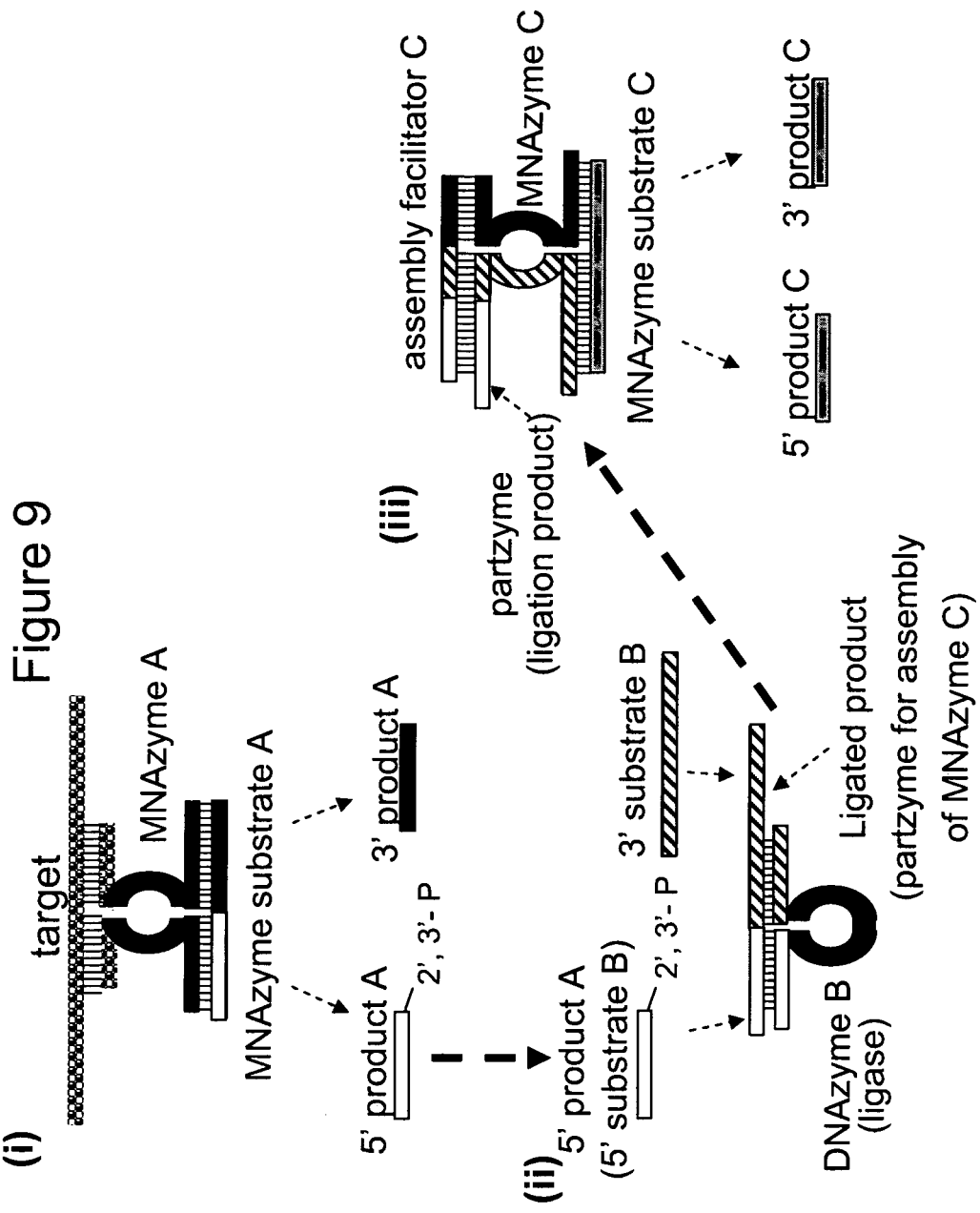

FIG. 9: An example of a cascade reaction which uses two types of nucleic acid enzymes namely MNAzymes, which can cleave substrates, and DNAzyme ligases which can ligate substrates. In step (i) the MNAzyme A forms only in the presence of an assembly facilitator (e.g. a target nucleic acid) and then cleaves MNAzyme substrate A releasing a 5' product A with a 2', 3' cyclic phosphate terminus. In step (ii) the DNAzyme B with ligase activity ligates the 5' product A from step (i) to a 3' ligation substrate B thus creating a ligation product which can serve as a partzyme component of another MNAzyme C. In step (iii) the partzyme/ligation product of step (ii) assembles with a second partzyme and an assembly facilitator C to form MNAzyme C which can cleave substrate C into two products, 5' product C and 3' product C.

In step (i) an assembly facilitator, for example a target nucleic acid, can direct the formation of a first MNAzyme A. MNAzyme A can cleave a substrate A thus generating a 5' cleavage product A which can in turn be used as a substrate for a DNAzyme ligase B. In step (ii) a DNAzyme ligase B can ligate the 5' cleavage product A (also referred to as 5' substrate B) generated in step (i) to another oligonucleotide, 3' ligation substrate B, thus creating a new partzyme for an MNAzyme C. In step (iii) the new partzyme/ligation product generated in step (ii), together with another partzyme, can form a new MNAzyme C in the presence of assembly facilitator C which can cleave a substrate C into two products, 5' product C and 3' product C. A detectable signal can be generated following cleavage of substrate C if this substrate were labelled, for example, with a fluorophore and quencher dye pair.

Further, if the sequence of 5' product C were the same as 5' product A then this product can also serve as a 5' substrate B and a feedback amplification cascade reaction could be initiated. In this reaction MNAzyme C could constantly generate 5' substrate B which in turn could be ligated by DNAzyme ligase B to create more partzymes for formation of more MNAzyme C. This strategy provides a feedback cascade or mechanism for signal amplification following initiation of a reaction by a target analyte which allows assembly of MNAzyme A. The cascade strategy allows detection of target analytes followed by signal amplification using a DNAzyme which can ligate substrates and MNAzymes which can cleave a substrate.

Figure 10:
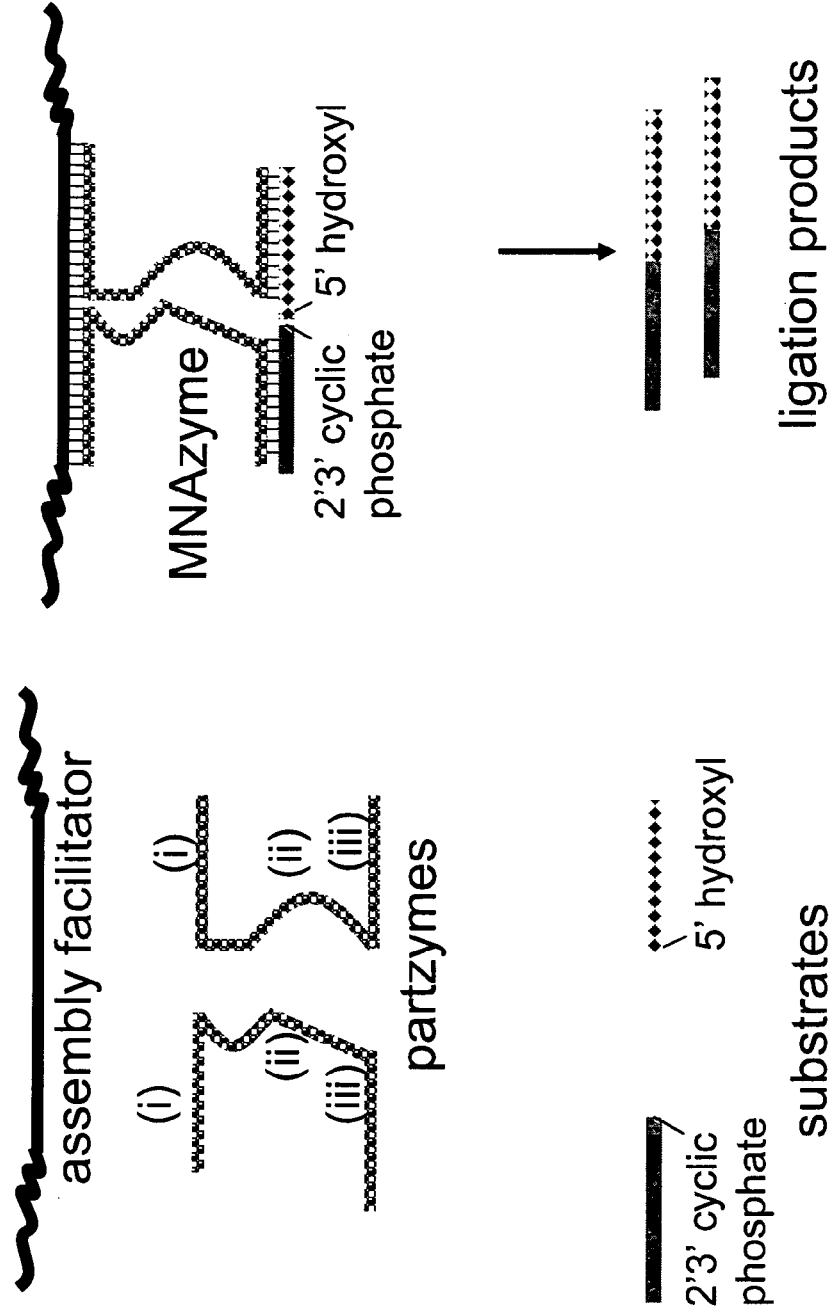

FIG. 10: Example of a structure of an MNAzyme with ligase activity (an MNAzyme ligase). The exemplary MNAzyme ligase is comprised of partzyme sequences which contain three domains including a (i) a sensor arm which hybridizes to an assembly facilitator (e.g. a target nucleic acid), (ii) a domain that constitutes part of a catalytic core and (iii) a substrate binding arm (FIG. 10A). In the presence of assembly facilitator, for example a target nucleic acid, partzymes assemble and form active MNAzyme ligases. These MNAzymes can ligate a 5' substrate with a 2'3' cyclic phosphate and a 3' substrate with 5' hydroxyl (FIG. 10B) to create ligation products that contain non-native 2'-5' linkages.

Alternatively, MNAzymes could ligate two substrates with a 2'3' diol terminus on the 5' substrate with a 5'-triphosphate terminus on the 3' substrate to create ligation products that contain native 3'-5' linkage.

Figure 11:
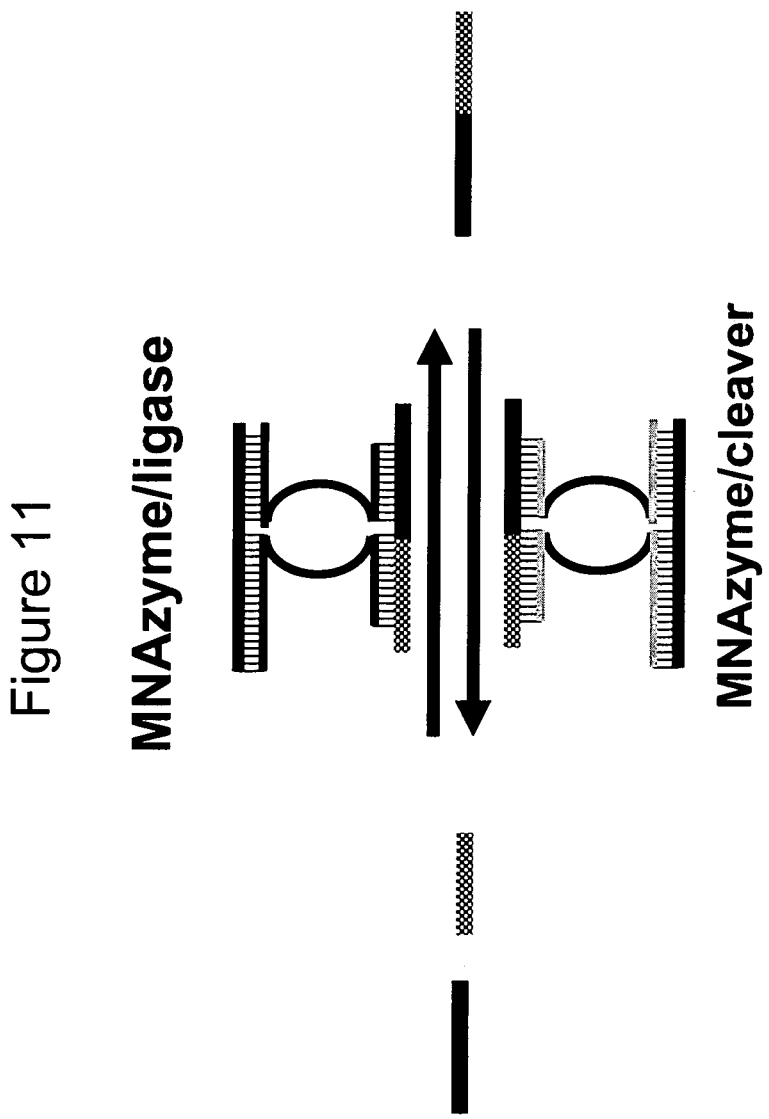

FIG. 11: An exemplary strategy for reactions that use MNAzymes with ligase activity and MNAzymes with cleavage activity.

An MNAzyme with ligase activity could ligate a first oligonucleotide (A) to a second oligonucleotide (B) to create a third ligation product (C) with a 2'-5' RNA linkage at the ligation junction, provided A and B have 2',3'-cyclic phosphate and 5'-hydroxyl termini. In turn, product C could be cleaved by an MNAzyme capable of cleaving at a 2'-5' RNA linkage to create cleavage products A and B, thus regenerating 2',3'-cyclic phosphate and 5'-hydroxyl products, which can participate in further rounds of ligation.

Other MNAzymes with ligase activity could ligate a first oligonucleotide (A) to a second oligonucleotide (B) to create a third ligation product (C) with a 3'-5' RNA linkage at the ligation junction, provided A and B have 2',3'-diol and 5'-triphosphate termini. In turn, product C could be cleaved by an MNAzyme capable of cleaving at a 3'-5' RNA linkage to create cleavage products A and B, producing products with 2',3'-cyclic phosphate and 5'-hydroxyl termini.

Figure 12:
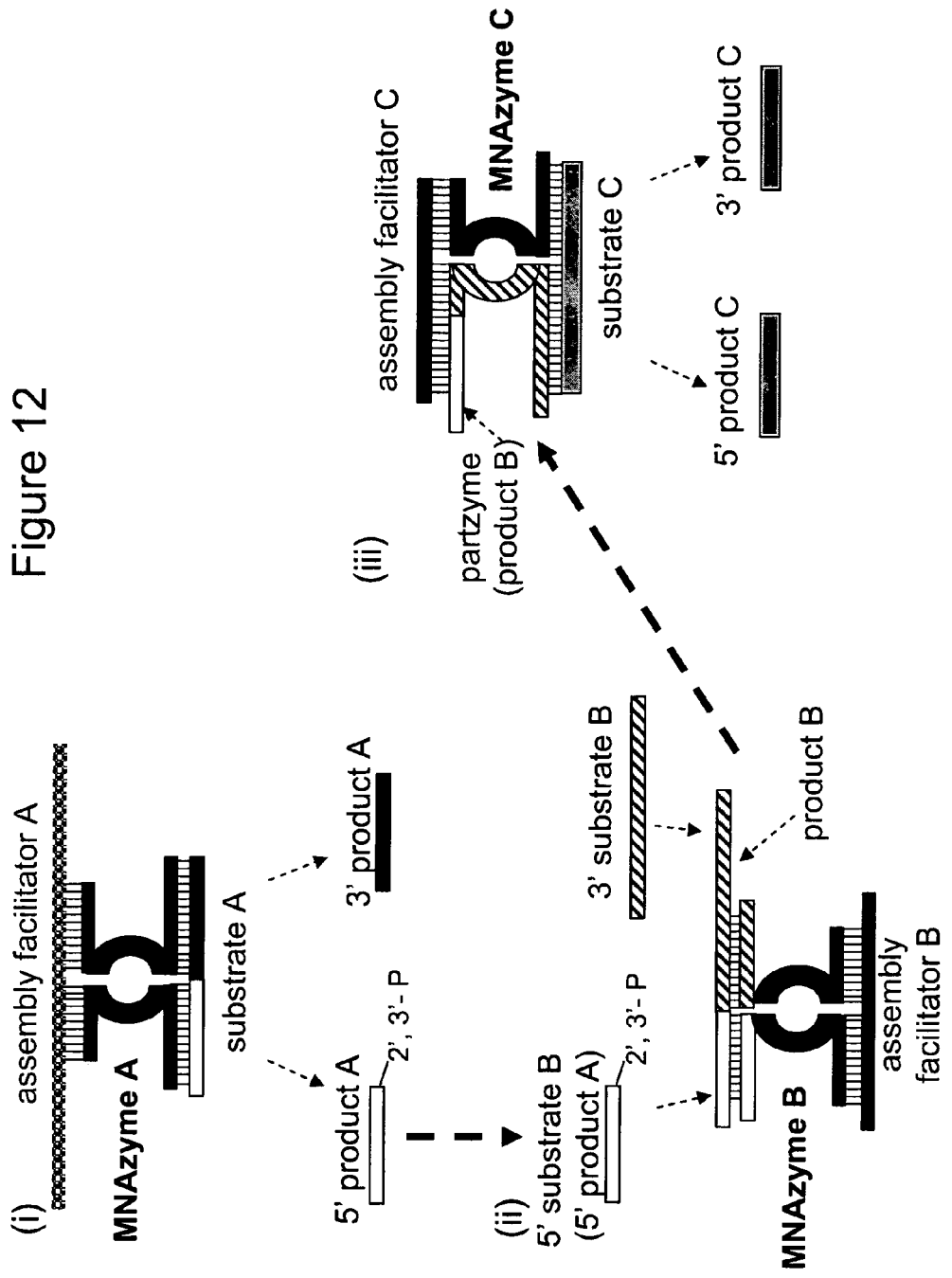

FIG. 12. A strategy for signal detection which uses MNAzymes which cleave and MNAzymes which ligate. In step (i) an assembly facilitator, for example a target nucleic acid, can direct the formation of a first MNAzyme A. MNAzyme A can cleave a substrate A thus generating a 5' cleavage product A which can in turn be used as a substrate for an MNAzyme B which has ligase activity. In step (ii) an MNAzyme ligase B can ligate the 5' cleavage product A (also called the 5' substrate B) generated in step (i) to another oligonucleotide, 3' substrate B, thus creating a new partzyme for an MNAzyme C. In step (iii) the new partzyme/ligation product generated in step (ii), together with another partzyme, can form a new MNAzyme C in the presence of assembly facilitator C which can cleave a substrate C into two products, 5' product C and 3' product C. A detectable signal can be generated following cleavage of substrate C if this substrate were labelled, for example, with a fluorophore and quencher dye pair. The strategy allows detection of target analytes using two types of MNAzymes, namely MNAzymes which can ligate substrates (MNAzyme ligases) and MNAzymes which can cleave a substrate (MNAzyme cleavers).

Further if the sequence of 5' product C were the same as 5' product A then this product could also serve as a 5' substrate B and a feedback cascade reaction could be initiated. In this reaction, MNAzyme C could be constantly generating 5' substrate B which could in turn be ligated by MNAzyme ligase B to create more partzymes for formation of more MNAzyme C. This strategy could provide a mechanism for feedback signal amplification following initiation of a reaction by a target analyte which allows assembly of MNAzyme A.

Figure 13:
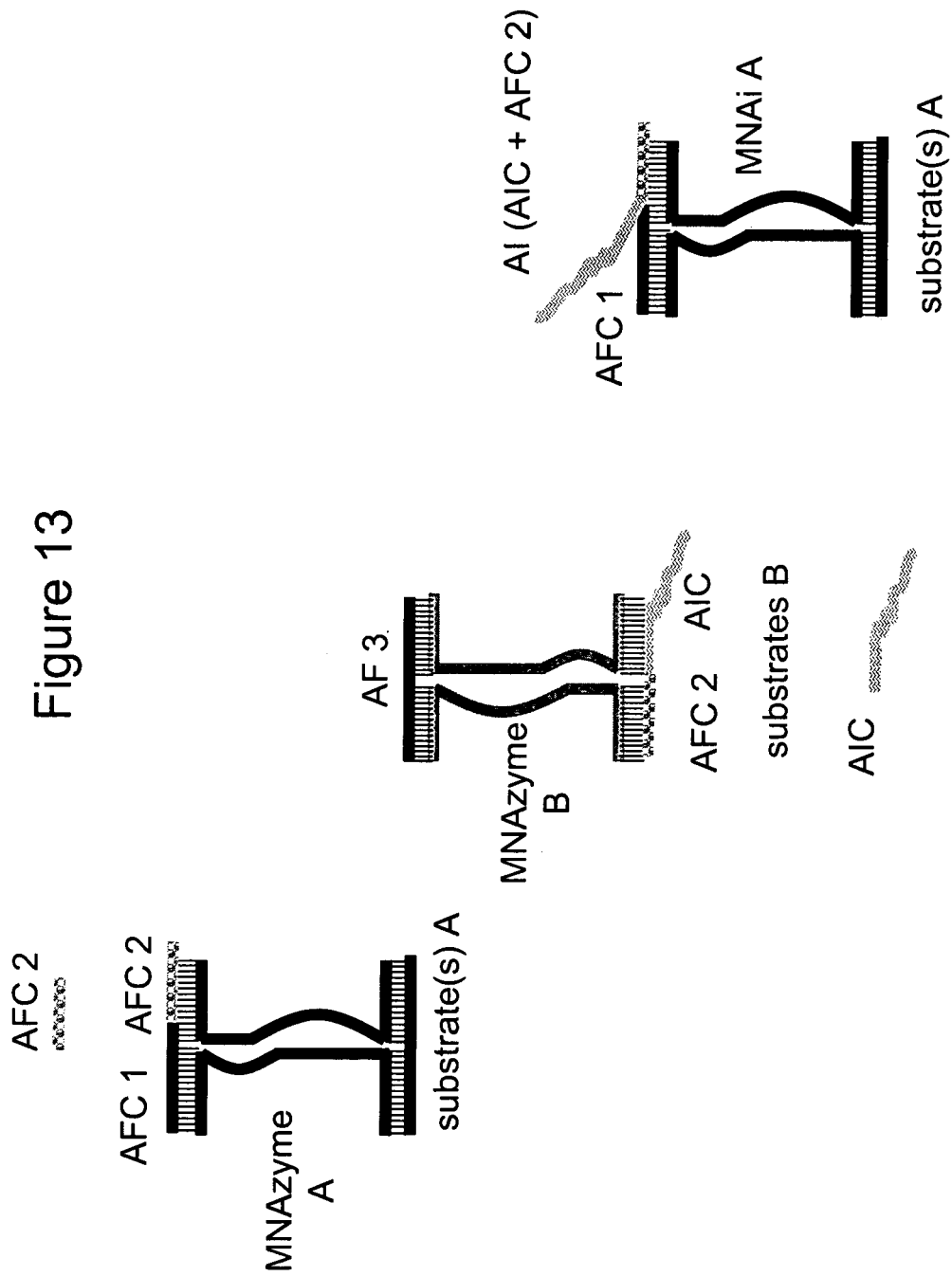

FIG. 13: Depiction of an exemplary strategy for switching an MNA complex between the "on state" of an active MNAzyme to the "off state" of an MNAi complex using a second MNAzyme with ligase activity. An active MNAzyme A, which could be capable of modifying (e.g. cleaving or ligating) a substrate(s) A could be formed in the presence of assembly facilitator component 1 (AFC 1) and assembly facilitator component 2 (AFC 2). A second MNAzyme B, which has ligase activity, could form in the presence of assembly facilitator 3 (AF3) and then could ligate AFC 2 with an activity inhibitor component (AIC) resulting in the formation of an activity inhibitor (AI). This AI could bind to the partzyme components for the MNAzyme A resulting in the formation of an inactive MNAi complex. As such the MNAzyme ligase in this example can operate as an off switch to inactivate an MNAzyme A. The inactive MNAi complex and the catalytically active MNAzyme represent two alternate states for the assembled components, namely an "off" state and the "on" state respectively.

Figure 14:
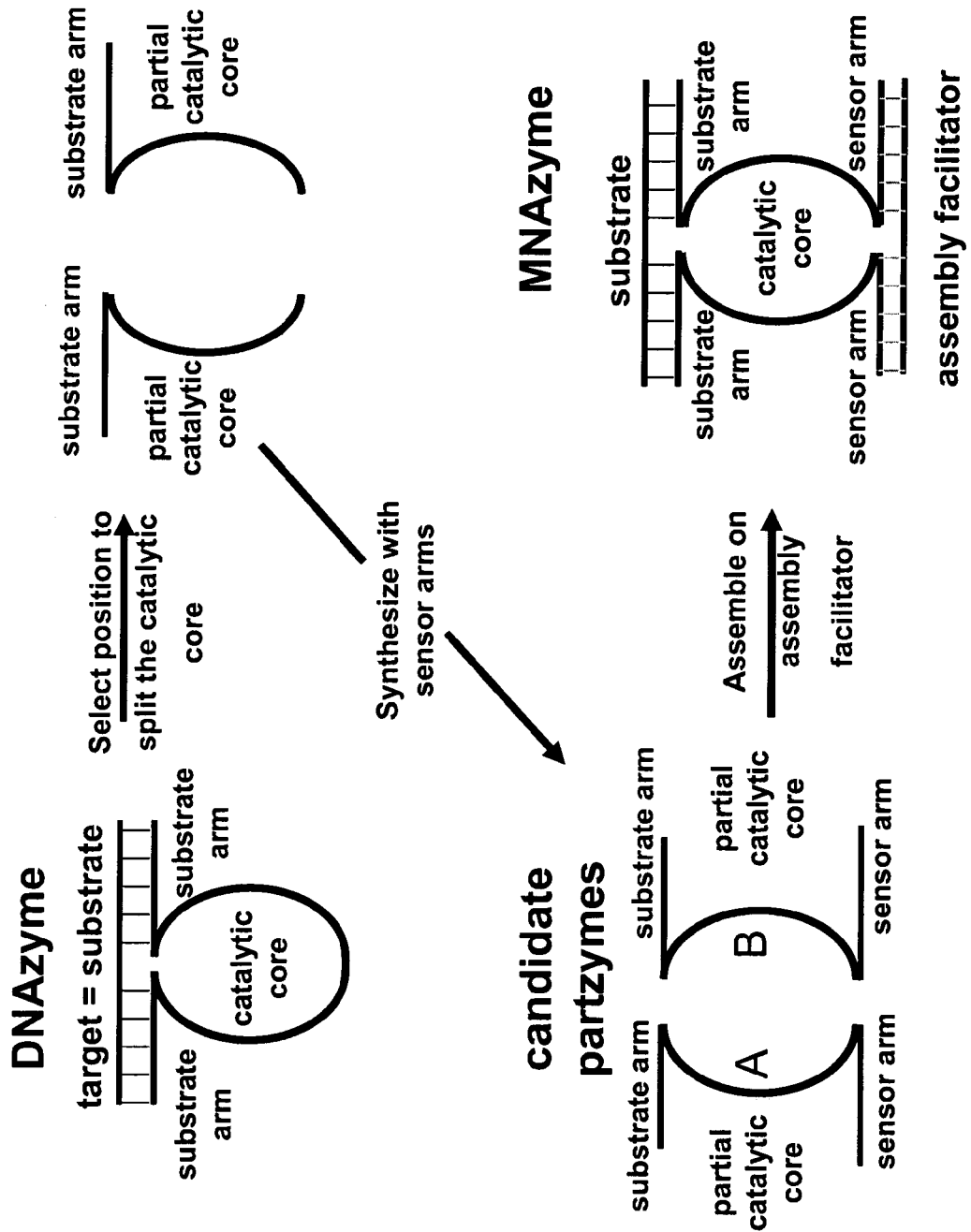

FIG. 14: Depiction of a general method for engineering MNAzymes from uni-molecular DNAzymes.

Many DNAzymes have similar basic structures with multiple domains. These DNAzymes have a conserved catalytic domain (catalytic core) flanked by two non-conserved substrate-binding domains ("substrate arms"), which specifically recognize and hybridise to the substrate (top left hand side structure). The substrate binding domains can be tailored to any substrate provided the substrate contains a site which can be modified by the DNAzyme.

In the first step, positions are identified within the DNAzyme catalytic core at which it can be split, such that each partial portion of the catalytic core can be distributed between two partial sequences such that the two partial cores together constitute an entire catalytic core (top right hand side structure). Two oligonucleotides A and B (candidate partzymes) can then be synthesised (bottom left hand side structure). An oligonucleotide A can be synthesised to contain (i) one substrate binding arm portion capable of binding to a substrate, (ii) one partial catalytic core portion, and (iii) one sensor arm portion capable of binding to an assembly facilitator molecule. A second oligonucleotide B can be synthesised such that it contains (i) one substrate binding arm capable of binding to the same substrate as oligonucleotide A, whereby oligonucleotide B binds the substrate in a position adjacent to that of oligonucleotide A, (ii) one partial catalytic core portion which contains those bases from the entire DNAzyme catalytic core which are not incorporated into oligonucleotide A and (iii) one sensor arm sequence capable of binding to the same assembly facilitator as oligonucleotide A, whereby oligonucleotide B binds the assembly facilitator in a position adjacent to that of oligonucleotide A (bottom left hand side structure).

This process can be repeated thus making a series of pairs of oligonucleotides A and B which incorporate the structure and domains of partzymes, but may or may not have catalytic activity in the presence of a substrate and an assembly facilitator. It would be appreciated by one skilled in the art that a similar process can be undertaken for a nucleic acid enzyme which can act on at least two substrates. Candidate partzyme pairs (pairs of oligonucleotides A and B from the series) can be mixed with substrate(s) matching the substrate arms plus assembly facilitator(s) matching the sensor arms (bottom right hand side structure) and then assayed for the presence of the same type of modifying activity as exhibited by the DNAzyme (top left hand side). Pairs of oligonucleotides A and B which can catalyse the same type of modification of the DNAzyme are useful for the assembly of active MNAzymes.

Figure 15:
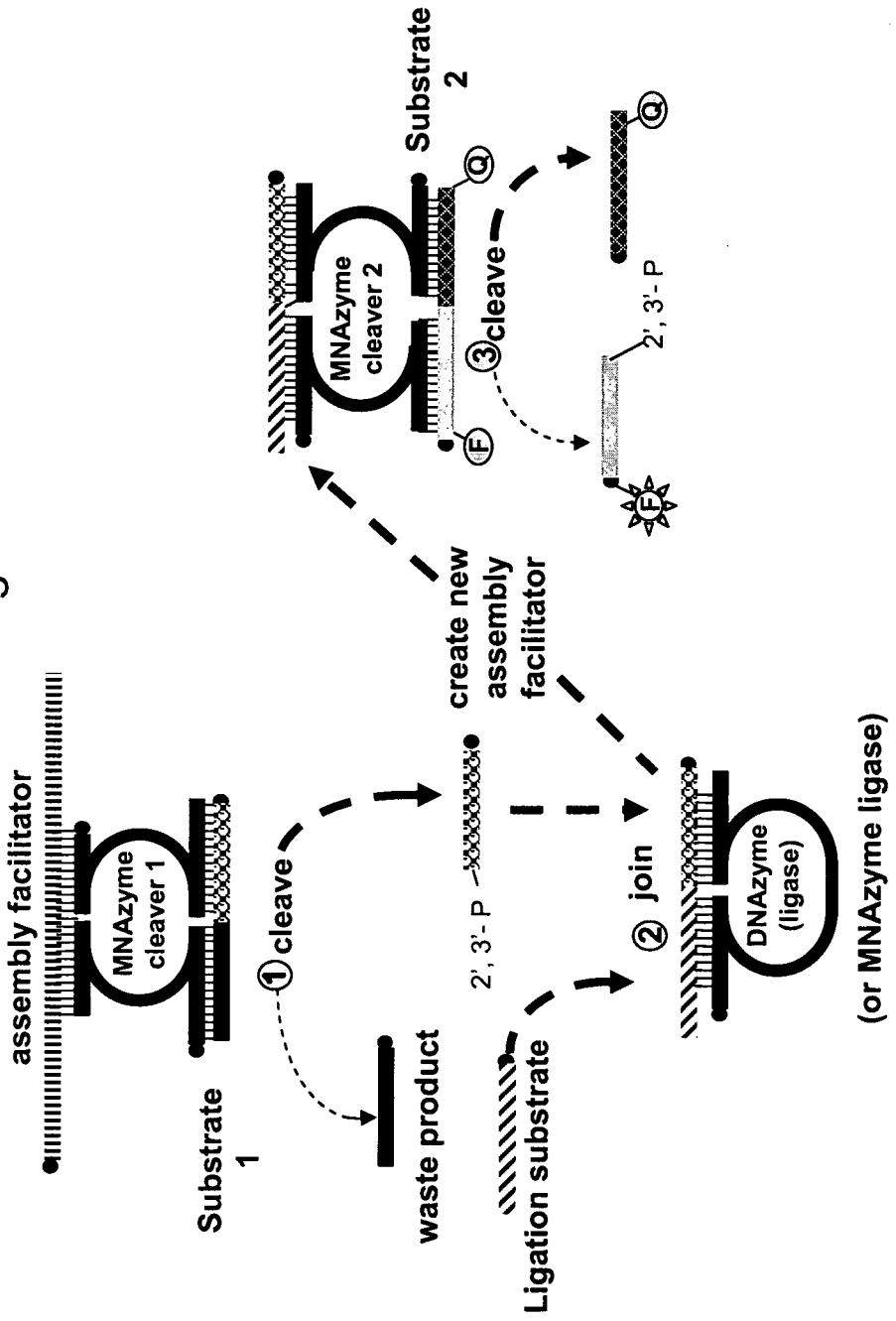

FIG. 15: A cascade reaction using nucleic acid enzymes which cleave substrates, and enzymes which ligate substrates to form a new assembly facilitator. In this illustration the 5' end of the oligonucleotides are indicated by a circle. In step (1) the MNAzyme cleaver assembles in the presence of an assembly facilitator (e.g. a target nucleic acid) and then cleaves MNAzyme substrate 1 releasing a 5' cleavage product with a 2', 3' cyclic phosphate terminus. In step (2) the DNAzyme ligase (or MNAzyme ligase) ligates the 5' cleavage product from step (1) to a 3' ligation substrate thus creating a ligation product which can serve as an assembly facilitator for another MNAzyme cleaver 2. In step (3) the assembly facilitator formed by ligation in step (2) directs the assembly of partzymes which form MNAzyme cleaver 2 which cleaves substrate 2 into two products, a 5' cleavage product with a 2', 3' cyclic phosphate terminus and a 3' cleavage product. A detectable signal can be generated following cleavage of substrate 2 when this substrate is labelled, for example, with a fluorophore and quencher dye pair. The strategy allows detection of target analytes using multiple types of nucleic acid enzymes, namely enzymes which can ligate substrates and enzymes which can cleave a substrate.

Further if the sequence of the 5' product of MNAzyme cleaver 2 were the same as the 5' product of MNAzyme cleaver 1 then this product could also serve as a substrate for the ligase and a feedback cascade reaction could be initiated. In this reaction, MNAzyme cleaver 2 could be constantly generating 5' substrate for the ligase which could in turn be ligated by the ligase to create more assembly facilitators for formation of more MNAzyme cleaver 2. This strategy could provide a mechanism for feedback signal amplification following initiation of a reaction by an assembly facilitator such as a target nucleic acid which allows assembly of MNAzyme cleaver 1.

Figure 16:
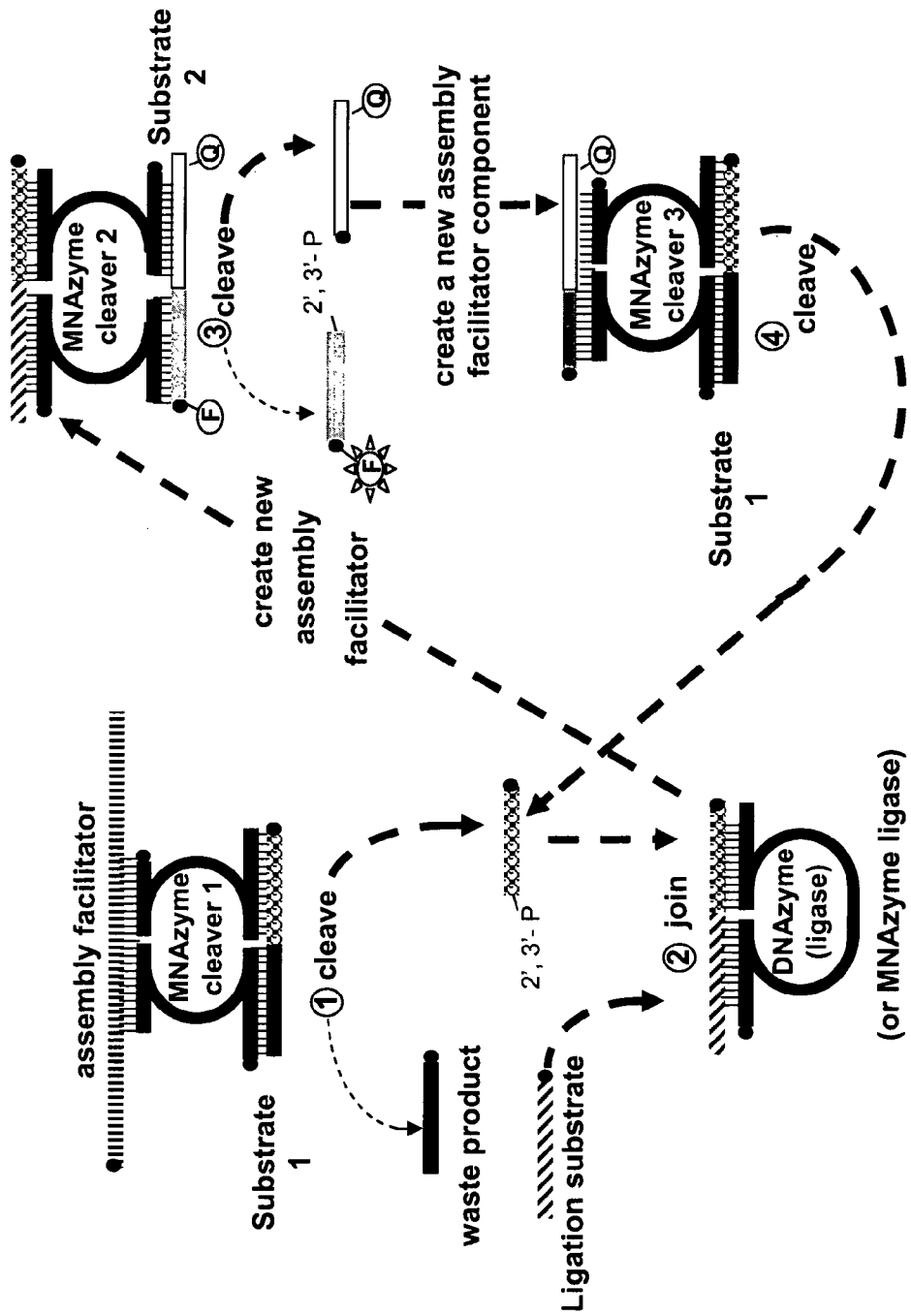

FIG. 16: A possible schema for a feedback cascade reaction which uses two types of nucleic acid enzymes namely enzymes which can cleave substrates, and enzymes which can ligate substrates. In this illustration the 5' end of oligonucleotides are indicated by a circle. In step (1) the MNAzyme cleaver 1 could assemble only in the presence of an assembly facilitator (e.g. a target nucleic acid) and could then cleave MNAzyme substrate 1 releasing a 5' cleavage product with a 2', 3' cyclic phosphate terminus and a 3' waste product. In step (2) the DNAzyme ligase (or MNAzyme ligase) could ligate the 5' cleavage product from step (1) to a 3' ligation substrate thus creating a ligation product which could serve as an assembly facilitator for an MNAzyme cleaver 2. In step (3) the assembly facilitator formed by ligation in step (2) could direct the assembly of partzymes to form MNAzyme cleaver 2 which could cleave substrate 2 into two products, a 5' cleavage product with a 2', 3' cyclic phosphate terminus and 3' cleavage product. A detectable signal could be generated following cleavage of substrate 2 if this substrate were labelled, for example, with a fluorophore and quencher dye pair.

Further, if the sequence of either of the cleavage products of MNAzyme cleaver 2 was useful as an assembly facilitator component for an MNAzyme cleaver 3 then this could initiate a feedback cascade. In this case MNAzyme cleaver 3 could have different sensor arms than MNAzyme cleaver 1 but could have the same substrate arms as MNAzyme cleaver 1. Thus if MNAzyme cleaver 3 were assembled in the presence of an assembly facilitator component generated by cleavage by the MNAzyme cleaver 2, and if MNAzyme cleaver 3 cleaved substrate 1 then the 5' cleavage product of MNAzyme cleaver 3 could also serve as a 5' substrate for the DNAzyme ligase (or the assembled MNAzyme ligase) and a feedback amplification cascade reaction could be initiated.

In this feedback cascade reaction MNAzyme cleaver 3 could constantly generate 5' cleavage product which in turn could serve as a substrate for ligation by the DNAzyme ligase (or the assembled MNAzyme ligase) to create more assembly facilitators that could direct the assembly of more MNAzyme cleaver 2. This strategy could provide a mechanism for feedback signal amplification following initiation of a reaction by an assembly facilitator (eg a target analyte) which allowed assembly of MNAzyme cleaver 1. The strategy could allow detection of one or more assembly facilitators (eg target analytes) followed by signal amplification using a DNAzyme or an MNAzyme which can ligate substrates and MNAzymes which can cleave a substrate.

DEFINITIONS

Certain terms are used herein which shall have the meanings set forth as follows.

The term "comprising" means "including principally, but not necessarily solely". Furthermore, variations of the word "comprising", such as "comprise" and "comprises", have correspondingly varied meanings.

The terms "polynucleotide", "nucleic acid" and "oligonucleotide" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael sources or any combination thereof.

The term "oligonucleotide" typically denotes a segment of DNA or a DNA-containing nucleic acid molecule, or RNA or RNA-containing molecule, or a combination thereof. Examples of oligonucleotides include nucleic acid targets; substrates, for example, those which can be modified by a DNAzyme or an MNAzyme with cleavage, ligase or other enzymatic activity; primers such as those used for in vitro target amplification by methods such as PCR; and components of nucleic acid complexes including but not limited to assembly facilitators and assembly inhibitors, activators, activity inhibitors and/or substrates, which in certain embodiments, may comprise oligonucleotides as defined herein. Partzymes as used herein may also comprise oligonucleotides.

A "displacer" or "displacer oligonucleotide" is an oligonucleotide which can bind to a single stranded region within a first oligonucleotide which comprises at least one region which is single stranded and at least one region which is double stranded by virtue of complementarities of at least one additional oligonucleotide; wherein the displacer oligonucleotide can cause dissociation of the additional oligonucleotide(s) from the first oligonucleotide within at least one double stranded region(s) by a process of branch migration. During branch migration the region(s) of complementarity between the additional oligonucleotide(s) and the first oligonucleotide are separated and replaced by at least one region of complementarity between the displacer oligonucleotide and the first oligonucleotide thus resulting in displacement of the additional oligonucleotide(s). The displacer oligonucleotide is required to comprise at least one region which has the same sequence as one or more regions of the additional oligonucleotide(s) within the double stranded region. The process of branch migration may result in a new double stranded region being formed between the displacer oligonucleotide and the first oligonucleotide and concomitant release of the additional oligonucleotide(s) which renders it single stranded.

The terms "polynucleotide", "nucleic acid" and "oligonucleotide" include reference to any specified sequence as well as to the sequence complementary thereto, unless otherwise indicated. Oligonucleotides may comprise at least one addition or substitution, including but not limited to the group comprising LNA phosphoramidite, 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyl adenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl) carbamoyl)threonine, 2'-O-methyl-5-methyluridine, 2'-O-methyluridine, wybutosine, 3-(3-amino-3-carboxypropyl) uridine, beta D-arabinosyl uridine, and beta D-arabinosyl thymidine.

The term "derivative" when used in relation to a nucleic acid or nucleotide of the present invention includes any functionally equivalent nucleic acids or nucleotides, including any fusion molecules produced integrally (e.g., by recombinant means) or added post-synthesis (e.g., by chemical means). Such fusions may comprise oligonucleotides of the invention with RNA or DNA added thereto or conjugated to a polypeptide (e.g., puromycin or other polypeptide), a small molecule (e.g., psoralen) or an antibody.

The term "analogue" when used in relation to a nucleic acid or nucleotide includes a compound having a physical structure that is related to a DNA or RNA molecule or residue, and may be capable of forming a hydrogen bond with a DNA or RNA residue or an analogue thereof (i.e., it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2' O-methyl cap (Warashina et al., 1999; Cairns et al., 2003; Schubert et al., 2004; Sidorov et al., 2004). Other analogues could also be compatible with catalytic activity of DNAzymes and MNAzymes. Alteration of a nucleic acid with catalytic activity, for example by substitution of one base for another, by substitution of an analogue for a base, or alteration of the sugar component or phosphodiester backbone, can be straight forward for the skilled artisan. For example, alterations can be made during synthesis, or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 1.

TABLE 1

Examples of nucleotide analogues useful herein

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methylguanosine |
| Ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| Mo5u | 5-methoxyuridine |
| Ms2i6a | 2-methylthio-N6-isopentenyladenosine |
| Ms2t6a | N-((9-beta-ribofuranosyl-2-methylthiopurine-6-yl)carbamoyl)threonine |
| Mt6a | N-((9-beta-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta D-arabinosyluridine |
| AraT | beta D-arabinosylthymidine |

The terms "nucleic acid enzyme", "catalytic nucleic acid", "nucleic acid with catalytic activity", and "catalytic nucleic acid enzyme" are used herein interchangeably and shall mean a DNA or DNA-containing molecule or complex or an RNA or RNA-containing molecule or complex or a combination thereof, being a DNA-RNA hybrid molecule or complex, which may recognize at least one substrate and catalyse a modification (such as ligation or cleavage) of the at least one substrate. The nucleotide residues in the catalytic nucleic acids may include the bases A, C, G, T, and U, as well as derivatives and analogues thereof. The terms above include uni-molecular nucleic acid enzymes which may comprise a single DNA or DNA-containing molecule (also known in the art as a "DNA enzyme", "deoxyribozyme" or "DNAzyme") or an RNA or RNA-containing molecule (also known in the art as a "RNA enzyme" or "ribozyme") or a combination thereof, being a DNA-RNA hybrid molecule which may recognize at least one substrate and catalyse a modification (such as ligation or cleavage) of the at least one substrate. The terms above include nucleic acid enzymes which comprise a DNA or DNA-containing complex or an RNA or RNA-containing complex or a combination thereof, being a DNA-RNA hybrid complex which may recognize at least one substrate and catalyse a modification (such as ligation or cleavage) of the at least one substrate. The terms "nucleic acid enzyme", "catalytic nucleic acid", "nucleic acid with catalytic activity", and "catalytic nucleic acid enzyme" include within their meaning MNAzymes.

Figure 1:
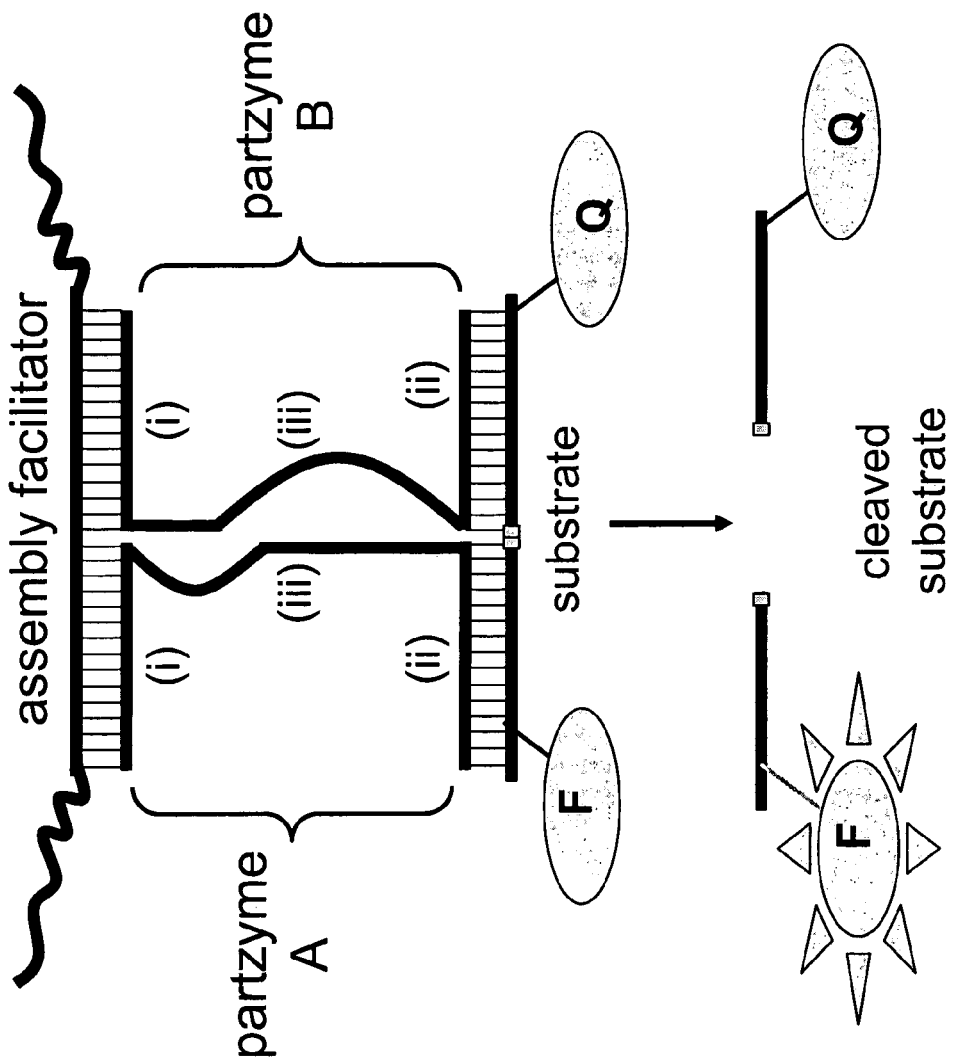
FIG. 1: Depiction of one exemplary design of a Multi-component nucleic acid (MNAzyme): By way of exemplary disclosure, an MNAzyme is comprised of two oligonucleotide components (partzyme A and partzyme B), which self assemble in the presence of an assembly facilitator. When the two partzymes assemble in the presence of the assembly facilitator, a catalytically active MNAzyme forms which is capable of modifying, for example cleaving, a substrate. The two component partzymes have (i) sensor arms, which bind to the assembly facilitator, (ii) substrate arms, which bind the substrate, and (iii) partial catalytic core sequences. The presence of an assembly facilitator molecule provides the "input" signal which directs the assembly of partzyme components in a highly specific fashion which is amenable to modulation. In some embodiments, the assembly facilitator may be, for example, a target nucleic acid sequence present in a test sample. In other embodiments, the assembly facilitator may be, for example a synthetic oligonucleotide included in the milieu to direct the self-assembly of the partzyme components in the presence of a detectable entity or event. Modification of the substrate by the assembled MNAzyme can provide an "output" signal which may be detected and/or quantified. For example, when the substrate is dual labelled with a fluorophore (F) and a quencher (Q), cleavage of the substrate by an active MNAzyme separates the fluorophore and the quencher resulting in a concomitant increase in fluorescence.

The term "MNAzyme" or "multi-component nucleic acid enzyme" as used herein, refers to two or more oligonucleotide sequences (e.g. partzymes) which, only in the presence of an MNAzyme assembly facilitator (for example, a target), form an active nucleic acid enzyme that is capable of catalytically modifying a substrate. MNAzymes can catalyse a range of reactions including cleavage of a substrate, ligation of substrates and other enzymatic modifications of a substrate or substrates. An exemplary MNAzyme comprising partzyme A and partzyme B which has cleavage activity is depicted in FIG. 1. MNAzymes with endonuclease or cleavage activity are also known as "MNAzyme cleavers". With reference to FIG. 1, partzymes A and B each bind to an assembly facilitator (e.g. through Watson-Crick base pairing). The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. Cleavage of a DNA/RNA chimeric reporter substrate is exemplified in the drawing. The MNAzyme cleaves the substrate between a fluorophore and a quencher dye pair, thus generating signal. The terms "multi-component nucleic acid enzyme" and "MNAzyme" are used herein interchangeably and comprise bipartite structures, composed of two molecules, or tripartite structures, composed of three nucleic acid molecules, or other multipartite structures, for example those formed by four or more nucleic acid molecules. The term "MNAzyme complex" refers to a complex formed by an assembled MNAzyme with at least one of its substrates. The MNAzyme or MNAzyme complex may comprise an aptamer and be referred to as an apta-MNAzyme or apta-MNAzyme complex, respectively.

The term "MNAzyme ligase" as used herein, refer to MNAzymes with ligase activity that comprise two or more oligonucleotide sequences (e.g. partzymes) which, only in the presence of an MNAzyme assembly facilitator which may also be referred to herein as a ligase assembly facilitator or assembly facilitator (for example, a target), form an active nucleic acid enzyme that is capable of ligating two substrates.

An exemplary MNAzyme with ligase activity is illustrated in FIG. 10. The MNAzyme ligase ligates the two substrates. The term "MNAzyme ligase" as used herein comprises bipartite structures, composed of two molecules, or tripartite structures, composed of three nucleic acid molecules, or other multipartite structures, for example those formed by four or more nucleic acid molecules.

The term "ligate" as used herein means to join two or more molecules. For example, a "ligase" is an enzyme that catalyses the formation (ligation) of a bond between two or more substrate molecules to make a new molecule. The term "ligation" or "ligase activity" refer to the joining of two or more substrate molecules.

As used herein, the terms "partzyme", "component partzyme" "partzyme component" and "component oligonucleotide" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a modification; a "sensor arm" domain, which may associate with and/or bind to an assembly facilitator; and a "substrate arm" domain, which may associate with and/or bind to a substrate. Illustrations of these regions or domains are shown in FIG. 1 and FIG. 10. Partzymes may comprise at least one additional component including but not limited to an aptamer, referred to herein as an "apta-partzyme."

Figure 2:
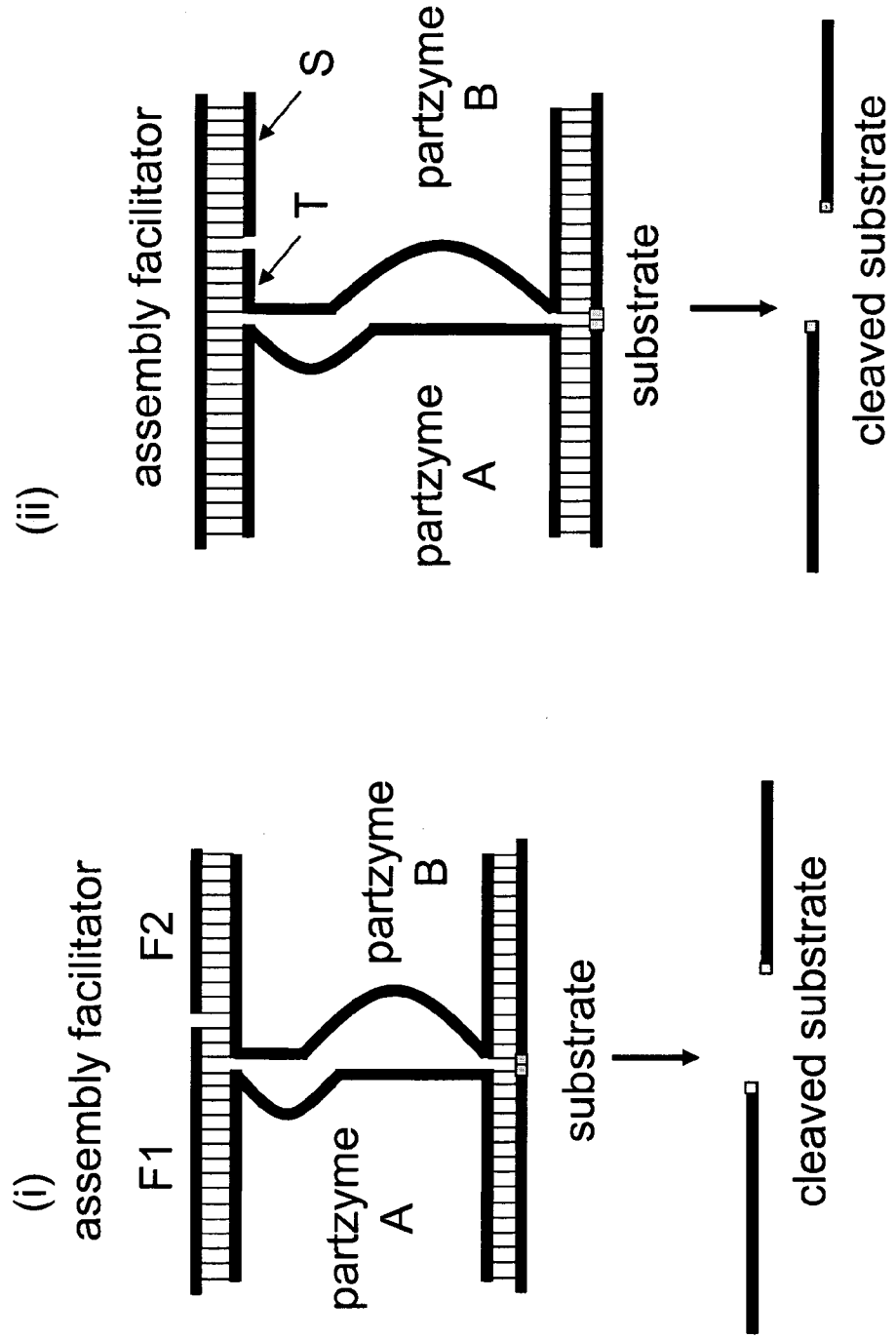
FIG. 2: Additional exemplary designs for active MNAzymes. Panel (i): Depiction of an exemplary design for MNAzymes where multiple assembly facilitator components are required for MNAzyme formation. In this design, one assembly facilitator component (F1) is complementary to regions of the sensor arms of both partzyme A and B, whereas a second assembly facilitator component (F2) is complementary to either partzyme B only (as per this illustration), or partzyme A only. The two assembly facilitator components together direct the assembly of an active MNAzyme which can modify (eg cleave) a substrate. Panel (ii): Depiction of an exemplary design where one partzyme A component and bi-partite partzyme B components assemble in the presence of assembly facilitator to produce an active MNAzyme capable of modifying (eg cleaving) a substrate. In this diagram, partzyme B has a truncated sensor arm (T), which is insufficient to allow stable MNAzyme assembly in the absence of a second component, referred to as a stabiliser arm component (S). Hybridization of the stabiliser arm to the assembly facilitator in a location adjacent to the truncated sensor arm of the partzyme, allows assembly of an active MNAzyme.

An example of an MNAzyme which is composed of more than two molecules is illustrated in FIG. 2 (ii). A partzyme may comprise multiple components, including but not limited to, a partzyme component with a truncated sensor arm and a stabilizing arm component which stabilises the MNAzyme structure by interacting with either an assembly facilitator (as depicted in FIG. 2 (ii)) or with a substrate.

The term "nucleic acid complex" refers to catalytically active or inactive complexes which comprise two or more components selected from the group comprising but not limited to, DNAzymes, partzymes, assembly facilitators, substrates, and other MNA components including stabiliser arms, activity inhibitors, assembly inhibitors, and components or parts thereof.

As used herein the term "nucleic acid complex" includes multicomponent nucleic acid complexes (MNA complexes). Additionally, the term "nucleic acid complex" includes unimolecular nucleic acid enzymes complexed with at least one substrate, for example, a DNAzyme with cleavage activity bound to a substrate or a DNAzyme ligase bound to at least one of its two required substrates. The term "nucleic acid enzyme complex" refers to a DNAzyme complex or an MNAzyme complex. The term "DNAzyme complex" includes DNAzymes with at least one substrate, for example, a DNAzyme with cleavage activity bound to a substrate or a DNAzyme ligase bound to at least one of its two required substrates.

The terms "multi-component nucleic acid complex" or "MNA complex" refer to complexes which comprise two or more components selected from the group comprising but not limited to, partzymes, assembly facilitators, substrates, and other components including stabiliser arms, activity inhibitors, assembly inhibitors, and components or parts thereof. In some embodiments the MNA complex comprises an active MNAzyme. In other embodiments the MNA complex is an inactive complex such as an MNAi complex which may also be referred to herein as a multi-component nucleic acid inhibitor (MNAi) complex or MNAi complex. In yet other embodiments the MNA complex is an inactive MNA complex which may lack one or more of the components required for assembly and/or catalysis by an MNAzyme including, but not limited to the assembly facilitator, and the partzymes, or components thereof. In yet another embodiment the MNA complex comprises components for an apta-MNAzyme in the presence or absence of an assembly inhibitor.

References to "forming a nucleic acid complex capable of functioning as a nucleic acid enzyme" as used herein refer to providing a component necessary for formation of a nucleic acid enzyme complexed with its substrate(s) such that the enzyme can modify the substrate(s). "Permitting formation of a nucleic acid complex which functions as a nucleic acid enzyme" and "allowing a nucleic acid complex to function as a nucleic acid enzyme" as used herein refers to the process that occurs when a component allows formation of a nucleic acid enzyme complexed with its substrate(s) such that the enzyme can modify the substrate(s).

The term "modulator" as used herein is an entity which can increase or decrease the catalytic activity of an MNA complex. Modulators may be "activators", which activate or switch on the activity of an MNAzyme. In some embodiments modulators are "inhibitors" which can switch off or inhibit the activity of the MNAzyme or MNAzyme complex, including but not limited to, "assembly inhibitors" or "activity inhibitors".

The terms "assembly facilitator molecule", "assembly facilitator", "MNAzyme assembly facilitator molecule", "facilitator" and "MNAzyme assembly facilitator" as used herein refer to entities that can facilitate the self-assembly of component partzymes to form a catalytically active MNAzyme by interaction with the sensor arms of the MNAzyme. As used herein, assembly facilitators may facilitate the assembly of MNAzymes which have cleavage, ligase or other enzymatic activities. The term "ligase assembly facilitator" refers to an assembly facilitator that facilitates the assembly of an MNAzyme with ligase activity. An assembly facilitator for MNAzymes with ligase activity may also be referred to by any of the other terms above. In preferred embodiments an assembly facilitator is required for the self-assembly of an MNAzyme. An assembly facilitator may be comprised of one molecule, or may be comprised of two or more "assembly facilitator components" that may pair with, or bind to, the sensor arms of one or more oligonucleotide "partzymes". Assembly facilitator portions may be contained within other components, for example within an activity inhibitor molecule, where they are present in a state whereby they can not contribute to active MNAzyme assembly until liberated from the component by, for example, cleavage. Assembly facilitators may be comprised of one (e.g. FIG. 1, FIG. 2(ii)) or more molecules (e.g. FIG. 2(i), FIG. 4-6).

The assembly facilitator may be a target. The target may be a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The nucleic acid may be amplified. The amplification may comprise one or more of: polymerase chain reaction (PCR), strand displacement amplification, loop-mediated isothermal amplification, rolling circle amplification, transcription-mediated amplification, self-sustained sequence replication, ligase chain reaction, nucleic acid sequence based amplification, or reverse transcription polymerase chain reaction (RT-PCR).

An "activator" as used herein is any MNA structural or modulator oligonucleotide component, any "ligand", "target", or "event" that results in activation of MNAzymes. Activator oligonucleotides include, but are not limited to, an assembly facilitator or assembly facilitator component; a displacer oligonucleotide; a partzyme or component thereof, for example those with truncations of the sensor or substrate arm, and partzyme stabiliser arm components.

In other embodiments activators may activate MNAzymes by removing oligonucleotides that exert an inhibitory effect. Examples of oligonucleotides which can activate through such a mechanism include modulator oligonucleotides which can displace (remove) inhibitory components, or parts thereof, including but not limited to, an "activity inhibitor" or an "assembly inhibitor".

The term "target" as used herein includes any natural or synthetic entity, constituent or analyte which is sought to be detected, identified or quantitated by a method which uses a particular nucleic acid enzyme such as an MNAzyme(s), with or without an additional amplification step and/or cascade. Targets therefore encompass the broadest range of detectable entities, constituents or analytes for which methods of sensitive detection, identification and/or quantification are desirable. Some exemplary targets include, but are not limited to, nucleic acid, protein, polypeptide, peptide, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein. It will be understood that the target may also be an assembly facilitator or activator.

As used herein the term "detectable event" includes a change in the microenvironment of an MNAzyme or MNAzyme complex and/or inactive MNA complex, for example, an MNAi complex or a complex comprising components for an apta-MNAzyme in the presence of an assembly inhibitor. The change may be, for example, physical manipulation, a change in temperature, a change in pH, salt concentration, electric charge, magnetic charge, a change in the concentration of one or more analytes, anions, cations, chelators, or a change in concentration of MNA or modulator components, or any combination thereof. It will also be understood that reference to a "change in the concentration of" includes an increase or a decrease in concentration and also includes the appearance of an entity, including any component(s) for one or more MNA complexes, for example an assembly facilitator or assembly facilitator component, that was previously absent or at undetectable concentration in the microenvironment of the MNA complex, including one or more component(s) for one or more MNA complexes including MNAzymes and apta-MNAzymes, MNAzyme complexes and apta-MNAzyme complexes and/or inactive MNA complexes.

Entities which represent detectable events may also be used as "activators" or "inhibitors" of the catalytic activity of MNAzymes since changes in the microenvironment can be used to manipulate catalytic activity of MNA complexes. As such, these entities allow the catalytic activity of MNAzymes to be switched "on" or "off", for example by promoting transition from an inactive MNA complex to an active MNAzyme, or vice versa. In some embodiments the event or entity promotes assembly and activation of MNAzymes. In some embodiments the event or entity promotes disassembly and inactivation of MNAzymes. In other embodiments the event or entity may direct the assembly or disassembly of inactive MNA complexes. In preferred embodiments the process of activation and inactivation of MNAzyme catalytic activity is reversible.

Alternatively, multi-component nucleic acid complexes may be inactive due to the composition of the microenvironment, which may promote either disassembly of MNA complex components or assembly of only a subset of those molecules required for formation of catalytically active MNAzymes. In some embodiments the activator assembly facilitator component is the product of a reaction occurring in the microenvironment of the inactive MNA complex and/or MNAzyme.

A "detectable effect" or "output" signal is an effect that can be detected or quantified as an indication that modification of a substrate(s) has occurred. The magnitude of the effect may be indicative of the quantity of an input such as an assembly facilitator (e.g. a target). The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

An "activator" assembly facilitator or assembly facilitator portion is a molecule which can be used to control the assembly of active MNAzymes or facilitate the transition from inactive multi-component nucleic acid complexes to active MNAzymes. The said multi-component nucleic acid complexes may be catalytically inactive due to the presence of an activity inhibitor, such as in MNAi complexes.

The term "activity inhibitor" refers to any entity that can bind to one or more components of an MNA complex and direct assembly of catalytically inactive "MNAi" complex (e.g. FIG. 4, FIG. 5(iii), FIG. 13). The inhibition of catalytic activity by the activity inhibitor is mediated by an "activity inhibitor portion", also called an "activity inhibitor component" or an "activity inhibitor domain" which is substantially non-complementary to the partzymes. In preferred embodiments, an activity inhibitor may comprise several distinct functional domains, for example, including but not limited to, functional domains in any combination selected from an activity inhibitor domain, an assembly facilitator domain, a substrate domain, and/or a reporter domain. Such distinct functional domains may or may not coincide with several distinct structural domains in an activity inhibitor. Accordingly, in some embodiments, an activity inhibitor may comprise an activity inhibitor domain which is substantially non-complementary to the partzyme components and which exerts an inhibitory effect by disrupting the secondary structure required for formation of a catalytically active MNAzyme. The presence of an activity inhibitor drives the assembly of inactive MNAi complexes that are capable of interacting with, but not catalytically modifying, a substrate. In some embodiments, an activity inhibitor may comprise an assembly facilitator domain.

In some embodiments, the activity inhibitor may further include a labile or cleavable linker or substrate, which may be located between two or more domains within the activity inhibitor, for example an activity inhibitor domain and an activator assembly facilitator domain. Cleavage at the substrate or linker site may allow separation of an activity inhibitor portion from an activator assembly facilitator portion, which may then function as an assembly facilitator component and direct the assembly of an active MNAzyme.

In some embodiments an MNA component such as an activity inhibitor may be conjugated to other entities. In some embodiments the component (e.g. activity inhibitor) could be conjugated to a gold nanoparticle coupled to a radio-frequency magnetic field to allow remote electronic control of hybridisation. In this approach radio-frequency magnetic fields function as antennas enabling reversible thermal denaturation of specific oligonucleotides, while leaving the surrounding molecules relatively unaffected. In some embodiments the component (e.g. the activity inhibitor) could be labelled with biotin to facilitate capture and physical isolation of the component.

As used herein, an "assembly inhibitor" is a component which inhibits the assembly of an MNAzyme or MNAzyme complex by complementary binding to an essential component of an active MNAzyme or MNAzyme complex, for example by binding to a partzyme component or an assembly facilitator or a substrate. The binding of the assembly inhibitor sequence to at least a first MNAzyme or MNAzyme complex component leads to competition between the assembly inhibitor and the said first component for binding to a second MNAzyme or MNAzyme complex component. For example, the assembly inhibitor may bind to either a partzyme substrate arm (that binds the substrate) or a partzyme sensor arm (that binds the assembly facilitator). When the assembly inhibitor is complementary to (and bound to) the substrate arm, it competes (and blocks) binding of the substrate to the partzyme (FIG. 7) and hence blocks formation of MNAzyme complexes. When the assembly inhibitor is complementary to (and bound to) the sensor arm, it competes (and blocks) binding of the assembly facilitator to the partzyme and hence blocks formation of active MNAzymes. In this manner an assembly inhibitor blocks the assembly of MNAzymes and/or MNAzyme complexes. The assembly inhibitor molecule can be used to control the assembly of MNAzymes and MNAzyme complexes, and further allow the development of strategies for the detection of both non-nucleic acid and nucleic acid analytes.

The terms "substrate" and "substrate molecule" as used herein include any molecule which is capable of being recognized, acted upon or modified by an enzyme including a nucleic acid enzyme. The modification of the substrate(s) provides the "output" signal for monitoring the activity of the MNA system. In particular embodiments, one or more substrate(s) may be recognized and modified by an enzyme. In other embodiments, one or more substrate(s) may be recognized and modified by a nucleic acid with catalytic activity. In preferred embodiments, a substrate or substrates may be recognized and modified by an MNAzyme. The modification of a substrate or substrates can be measured by the appearance of, or increase in, a product(s) of the modification reaction, or by the disappearance of, or decrease in, a substrate(s) modified in the reaction(s). It will be understood that reference to a substrate may refer to at least one of two or more substrates when used in the context of a reaction requiring two or more substrates such as a ligation reaction.

A substrate or substrates may be modified by various enzymatic activities including but not limited to cleavage or ligation. As used herein a substrate may include a "cleavable substrate" which is amenable to enzymatic cleavage, or a "ligatable substrate" or "ligase substrate" which is amenable to enzymatic ligation.

A "reporter substrate" as used herein is a substrate (or substrates) that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

As used herein, "generic substrates" are substrates, for example reporter substrates, that are recognized by and acted on catalytically by a plurality of MNAzymes, each of which can recognize a different assembly facilitator. The use of such substrates facilitates development of separate assays for detection, identification or quantification of a wide variety of assembly facilitators using structurally related MNAzymes all of which recognize a universal generic substrate. These generic substrates can each be independently labelled with one or more labels. In preferred embodiments, independently detectable labels are used to label one or more generic substrates to allow the creation of a convenient system for independently or simultaneously detecting a variety of assembly facilitators using MNAzymes. In some embodiments, substrates cleaved by MNAzymes could be reconstituted, and hence recycled, using an MNAzyme or DNAzyme ligase. In some embodiments, substrate(s) cleaved or ligated by MNAzymes can be further used as components or modulators of additional MNAzyme(s) or DNAzyme(s).

The term "product" refers to the new molecule or molecules that are produced as a result of enzymatic modification of a substrate. As used herein the term "cleavage product" refers to a new molecule produced as a result of cleavage or endonuclease activity by an enzyme. The term "ligation product" refers to a new molecule produced as a result of the ligation of substrates by an enzyme.

The term "MNAi" complex as used herein refers to an MNA complex that is in a catalytically inactive state, wherein catalytic activity is inhibited by an "activity inhibitor" as herein defined. In preferred embodiments, the MNAi complex may be catalytically inactive due to binding of an activity inhibitor oligonucleotide, for example, as depicted in FIG. 4, which shows an exemplary design for an MNAi complex. An MNAi complex can be formed when partzyme A, partzyme B, an assembly facilitator and an activity inhibitor associate to form an inactive complex which can bind a substrate but not modify it.

As used herein an "aptamer" may comprise a structure that has the ability to recognize one or more ligands. For example, the recognition may have a high degree of specificity due to higher level structure of the aptamer, such as, a 3-dimensional binding domain or pocket. Aptamers may therefore bind protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity. Preferred aptamers herein may comprise short single-stranded DNA or RNA oligomers that can be isolated from complex libraries of synthetic nucleic acid by an iterative process of adsorption, recovery, and reamplification. Other preferred aptamers herein may comprise protein, polypeptide, peptide or phylomers or a combination thereof that has the ability to recognize one or more ligands. Aptamers may therefore be generated against almost any target, ranging from small molecules such as amino acids, or antibiotics to protein and nucleic acid structures. An aptamer may be used to build molecular switches into MNA complexes containing assembly inhibitors. The presence of an activator ligand can switch the MNAzyme activity on and the removal of an activator ligand can switch off the activity of an MNAzyme. Further, aptamers can be used to facilitate detection of nucleic acid and non-nucleic acid ligands. Detection of a ligand can further be used to trigger an amplification cascade.

As used herein, the term "cascade" refers to any succession of processes or operations that occur in successive stages, wherein the occurrence of each stage is typically dependent on the occurrence of a preceding stage. As used herein a cascade may be a "linear cascade" wherein stages (or reaction steps) occur in one direction and the occurrence of each stage (or step) is dependent on the occurrence of a preceding stage or step. As used herein, the term "feedback cascade" or "feedback amplification cascade" refers to any succession of processes or operations that occur in successive stages, wherein the occurrence of each stage is typically dependent on the occurrence of a preceding stage and whereby the occurrence of a preceding stage typically depends on processes or operations that occur in subsequent stages. In feedback cascades, the product of any preceding stage could serve as a component or substrate for any subsequent stage and the product of any subsequent stage could serve as a component or substrate for any preceding stage. The cascade may involve activation of an MNAi complex via removal of the influence of an activity inhibitor or component thereof.

A cascade may therefore include, but is not limited to, an enzymatic cascade or any other signal transduction cascade. In some embodiments, a cascade may comprise amplification of a signal resulting from catalytic activity of an MNAzyme. In some embodiments, a cascade may comprise amplification of a signal resulting from catalytic activity of an MNAzyme with cleavage activity. In some embodiments, a cascade may comprise amplification of a signal resulting from catalytic activity of an MNAzyme with ligase activity. In some embodiments, a cascade may comprise amplification of a signal resulting from catalytic activity of DNAzymes or MNAzymes with ligase activity and DNAzymes or MNAzymes with cleavage activity. In preferred embodiments, such an amplification cascade may involve repeated and therefore cyclic amplification of a signal, wherein catalytic activity of a first nucleic acid enzyme creates a molecule required for modification of a substrate(s) by a second nucleic acid enzyme, which can in turn create a molecule required for modification of a substrate(s) by one or more additional nucleic acid enzymes. In some embodiments, the required molecule which is created may include but is not limited to a partzyme, a nucleic acid enzyme, for example a DNAzyme, an assembly facilitator, an assembly facilitator component, a substrate, a stabiliser arm, a component or portion thereof or a combination thereof. In some embodiments, a cascade may therefore involve production of a cumulative effect, and thus detect a target of low abundance by generating a signal to a level at which it may be detected. In other embodiments, more than two catalytic stages may be employed. The cascade may be linear. In a preferred embodiment, the cascade may be exponential. In preferred embodiments, the cascade may be a feedback amplification cascade.

The following abbreviations are used herein and throughout the specification:
 MNA: multi-component nucleic acid;
 MNA complex: multi-component nucleic acid complex;
 MNAzyme: multi-component nucleic acid enzyme;
 MNAi: multi-component nucleic acid inhibitor;
 DNAzyme: deoxyribonucleic acid enzyme;
 PCR: polymerase chain reaction;
 RT-PCR: reverse transcriptase polymerase chain reaction;
 LNA: locked nucleic acid;
 PNA: peptide nucleic acid;
 An: analyte or target;
 F: fluorophore;
 Q: quencher;
 FAM or 6-FAM: 6-Carboxyfluorescein.
 BHQ1: Black Hole Quencher 1
 BHQ2: Black Hole Quencher 2
 shRNA: short hairpin RNA
 siRNA: short interfering RNA
 mRNA: messenger RNA
 tRNA: transfer RNA
 snoRNA: small nucleolar RNA
 stRNA: small temporal RNA
 smRNA: small modulatory RNA
 pre-microRNA: precursor microRNA
 pri-microRNA: primary microRNA
 GTP: guanosine 5'-triphosphate
 CTP: cytosine 5'-triphosphate
 dA TP: deoxyadenosine 5'-triphosphate
 ATP: adenosine 5'-triphosphate
 LP: ligation product
 CP: cleavage product
 oligo: oligonucleotide

DETAILED DESCRIPTION OF ILLUSTRATIVE EMBODIMENTS

It is to be understood at the outset, that the figures and examples provided herein are to exemplify, and not to limit the invention and its various embodiments.

In accordance with the present invention, there is provided methods that utilise multi-component nucleic acid (MNA) complexes. The MNA complexes may be active enzymes (MNAzymes) with modifying activity such as ligase or cleavage activity. Further, the invention relates to cascades which may also include one or more DNAzymes. The invention also relates to methods which use these cascades for the identification, detection and quantification of assembly facilitators such as targets.

1. MNA Complexes Including MNAzymes and Inactive MNA Complexes

The Multi-component Nucleic Acid enzymes (also referred to herein as "MNAzymes") and inhibitors thereof are described in detail in co-pending U.S. application Ser. No. 11/544,926 filed Oct. 6, 2006 and Ser. No. 11/697,021 filed Apr. 5, 2007 and in co-pending international applications PCT/AU2006/001473 and PCT/AU2007/001517, the contents of which are all incorporated herein by reference. MNAzymes are capable of self-assembling from two or more oligonucleotide components, also referred to herein as partzymes. The partzyme oligonucleotides self-assemble in the presence of an MNAzyme assembly facilitator to form an MNAzyme. MNAzymes are therefore catalytically active nucleic acid enzymes. In some embodiments, the presence of an MNAzyme can be detected, and is indicative of the presence of a target, because the MNAzyme forms only in the presence of the target, wherein the target comprises the assembly facilitator. A wide variety of assays based on the basic principles outlined above are provided herein. Compositions comprising oligonucleotides capable of forming MNAzymes, and MNAzymes of various sequences are also provided herein. In some embodiments at least one of the oligonucleotide components, assembly facilitator, activity inhibitor or substrate may comprise an aptamer which is capable of binding to an activator or target.

The present invention describes new methods, and applications for nucleic acid enzymes and complexes. The invention provides oligonucleotide components that can be used to form an MNAzyme with ligase activity which can be useful in detection of analytes, in one step formats or in nucleic acid enzyme cascade reactions.

Further MNAzymes with ligase activity or other catalytic modifying activities can be used to manipulate the activity of other MNAzymes by creating new components which could direct the formation of a new active MNAzyme or MNAzyme complex or promote assembly of an alternative structure which lacks catalytic activity.

MNAzymes with ligase activity or other catalytic activity can create new components for nucleic acid enzymes or nucleic acid enzyme complexes such as new MNAzyme or MNAzyme complex components (e.g. assembly facilitators, partzymes, substrates, stabiliser arms) or DNAzyme complex components (e.g. active DNAzymes or DNAzyme substrates).

Alternatively MNAzymes can be used to direct formation of inactive MNA complexes, including MNAi complexes. MNAi complexes comprise oligonucleotide components, which would be capable of being assembled into active MNAzymes under appropriate conditions, but which when assembled with an "activity inhibitor" result in the formation of complexes which are catalytically inactive. Such inactive MNA complexes are defined herein as "MNAi" complex, and such inactivity may result from the exertion of an inhibitory influence by an activity inhibitor. MNAi complexes can interact with the substrate via the substrate arms of the partzyme components, but cannot catalytically modify the substrate. The activity inhibitor may incorporate additional entities to facilitate removal by physical means which may include, but are not limited to, entities such as attached nucleic acids, nanoparticles, microparticles, proteins, antibodies, RNA, DNA, nucleic acid analogues, biotin groups, glycoproteins, lipoproteins, peptide nucleic acids, locked nucleic acids, peptide-nucleic acid chimeras, radio-frequency moiety, or any combination thereof. The MNAi complex represents an "off" state, whereas the transition to an MNAzyme represents an "on" state.

The present invention describes MNAzyme ligases and their use as a mechanism for switching from an active MNAzyme to an inactive MNAi complex (FIG. 13). The MNAzyme ligase could be used to ligate an activity inhibitor component to an assembly facilitator component to create an activity inhibitor. When an activity inhibitor binds and replaces an assembly facilitator component in an active MNAzyme the complex is switched to an inactive MNAi complex.

Other MNA complexes may contain some or all of the components of an MNAzyme but are not catalytically active either because some required component(s) have not associated to form an active MNAzyme or the microenvironment is incompatible with catalytic activity of an MNAzyme. The catalytic activity may be activated upon the occurrence of a particular event, for example, including but not limited to the presence of an activator component, for example an assembly facilitator, or a change in parameter including but not limited to a change in temperature, wavelength, pressure, concentration of salt, detergent, cations or any other parameter. In some embodiments the catalytic activity of one nucleic acid enzyme, such as an MNAzyme which is present in the microenvironment, can create a new activator for a new nucleic acid enzyme or nucleic acid enzyme complex which may include, but is not limited to, an assembly facilitator or a partzyme.

In preferred embodiments, the MNAzymes are based on one or more DNAzymes and/or ribozymes. DNAzymes and/or ribozymes are known which can perform catalytic modification of at least one substrate wherein the modification may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

More preferred partzyme components for MNAzymes are based on a particular DNAzyme structure. Presently preferred structures for MNAzymes with cleavage activity are based on DNAzymes which cleave, including the 10:23 and 8:17 DNAzymes. Presently preferred structures for MNAzymes with ligase activity are based on DNAzyme ligases which ligate substrates and create 2' 5' linkages, such as the "7Z81" and "7Z48" and 7Q10 DNAzymes, as well as DNAzyme ligases which ligate substrates and create 3'-5' linkages such as the 9 DB1 ligase. In various embodiments the MNAzymes and inactive MNA complexes comprise either or both ribonucleotide bases and deoxyribonucleotide bases. In more preferred embodiments, an MNAzyme and inactive MNA complex is based at least in part on the structure of a DNAzyme. In other preferred embodiments, MNAzymes and inactive MNA complexes comprise at least some deoxyribonucleotide bases or analogues thereof. In more preferred embodiments, the catalytic core portions of partzymes assembled into an MNAzyme comprise one or more deoxyribonucleotide bases or analogues thereof. In still more preferred embodiments, one or more deoxyribonucleotide bases or analogues thereof are involved in the catalysis of a substrate by an MNAzyme. In other embodiments, at least one deoxyribonucleotide base, or its analogue, in the catalytic core improves catalytic activity of an MNAzyme. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

The present invention discloses MNAzyme ligases which are capable of self-assembling from two or more oligonucleotide components, also referred to herein as partzymes. The partzyme oligonucleotides self-assemble in the presence of at least one MNAzyme ligase assembly facilitator to form an MNAzyme ligase. MNAzyme ligases are therefore catalytically active nucleic acid ligases.

An exemplary MNAzyme with ligase activity comprising a first partzyme and a second partzyme is depicted in FIG. 10. With reference to FIG. 10, the first partzyme and the second partzyme each bind to an assembly facilitator (e.g. through Watson-Crick base pairing). The MNAzyme ligase only forms when the sensor arms (i) of the first partzyme and the second partzyme hybridize adjacent to each other on the assembly facilitator. The substrate arms (iii) of the MNAzyme engage the substrates, the modification (ligation) of which is catalyzed by the catalytic core of the MNAzyme ligase, formed by the interaction of the catalytic domains (ii) of the first partzyme and the second partzyme. Ligation of two nucleic acid substrates is exemplified in the drawing.

In some embodiments, the presence of an MNAzyme with ligase activity can be detected, and is indicative of the presence of a target, because the MNAzyme ligase forms only in the presence of the target, wherein the target comprises the assembly facilitator. A wide variety of assays based on the basic principles outlined above are provided herein. Compositions comprising oligonucleotides capable of forming MNAzyme ligases, and MNAzyme ligases of various sequences are also provided herein.

For example, the MNAzyme ligase structures are based on one or more DNAzyme ligases. More preferred are those MNAzyme ligase structures which are based on a particular DNAzyme ligase structure. Presently preferred structures are based on DNAzyme ligases including the 7Q10, 7Z81, 7Z48 and 9 DB1 DNAzyme ligases.

An assembly facilitator such as a target nucleic acid may be detected using an MNAzyme with ligase activity. In one scenario, the provision of target nucleic acid is the initiating step which results in the formation of an MNAzyme with ligase activity. With reference to FIG. 12, the initiating target nucleic acid would be the assembly facilitator B and the assembly facilitator A would be a synthetic molecule included to drive the assembly of MNAzyme A. MNAzyme A would then have the sole purpose of generating a 5' ligatable substrate B with a 2'3' cyclic phosphate terminus in a reaction which could then be added to the reaction which detects the target assembly facilitator B using an MNAzyme B with ligase activity. This approach could provide a practical method for producing substrates with specific termini such as 2'3' cyclic phosphates which may be expensive to synthesise and may be relatively unstable. Further, with reference to FIG. 12, the MNAzyme A partzymes and the assembly facilitator A could be replaced by a DNAzyme with cleavage activity present either in a separate preliminary reaction for ligatable substrate generation or the DNAzyme could be present in the same reaction mix as the MNAzyme with ligase activity. Example 11 demonstrates that cleavage and ligation using a combination of an MNAzyme and a DNAzyme can be performed in a single reaction mix.

As provided herein, MNAzymes and inactive MNA complexes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions, such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates. Analysis of multiple substrates (e.g generic substrates) allows the simultaneous monitoring of multiple "detectable effects" or "output" signals as an indication of the presence of the assembly of multiple active MNAzymes in response to an input event/s or entity/ies (e.g. provision of assembly facilitator/s) which are then able to modify multiple substrates In certain preferred embodiments, the invention envisages MNAzymes with catalytic activity that are comprised of deoxyribonucleotides or which are derived from such molecules by certain modifications/substitutions etc. As a general rule, replacement of the whole molecule with, for example, ribonucleotides, will render the molecule inactive because it relies for its activity on certain key deoxyribonucleotides. In a corresponding fashion, some ribonucleotides in a ribozyme may be substituted with deoxyribonucleotides but replacement of the whole molecule with, for example, deoxyribonucleotides, will render the molecule inactive.

The skilled artisan will appreciate that MNAzymes with cleavage, ligation or other enzymatic activities, and inactive MNA complexes comprise either deoxyribonucleotides or ribonucleotides, or even both. Those MNAzymes and inactive MNA complexes comprising at least one and more preferably, all, deoxyribonucleotide component oligonucleotides are presently preferred. Also preferred are those MNAzymes and inactive MNA complexes comprising at least one deoxyribonucleotide base, or its analogue, within at least one of the partial catalytic cores of the partzymes. Even more preferred are those embodiments where such a base is required for catalytic activity of an MNAzyme with cleavage, ligase or other enzymatic activity.

In certain embodiments at least one component of an MNA complex may comprise a region of self complementarity that may under some conditions form a hairpin structure. In one embodiment, a region of self complementarity may be located in one or both of the partzyme sensor arms. In another embodiment the region of self complementarity may be located in one or both of the partzyme substrate arms. In another embodiment a region or regions of self complementarity may be present in an assembly facilitator, an assembly inhibitor or an activity inhibitor component, or any combination thereof. In other embodiments MNA complexes may bind substrates which may contain regions of self complementarity.

In any of the preceding aspects the catalytic modification of at least one substrate is selected from the group consisting of cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage The skilled artisan will also appreciate that MNAzymes comprised of DNA have advantages over uni-molecular or multipartite ribozymes, for example with respect to stability and ease of use. It is also to be appreciated that in some embodiments, MNAzymes offer advantages over uni-molecular nucleic acid enzymes, for example DNAzymes, which can only recognize one molecule which functions as both the target and the substrate. Further, catalytic modification, for example cleavage, can destroy the DNAzyme's target/substrate and as such the target is not available for another round of recognition. In contrast a single MNAzyme, for example an MNAzyme with cleavage activity, can recognize at least two molecules, namely at least one assembly facilitator and at least one substrate. As such, an assembly facilitator, for example a target nucleic acid present in a sample, is not catalytically modified in the reaction and remains available for further rounds of substrate modification by the MNAzyme. Further, a single MNAzyme which can act on two substrates (e.g. an MNAzyme with ligase activity) can recognize at least three molecules, namely at least one assembly facilitator and at least two substrates. These properties of MNAzymes make them adaptable for systems or processes that require the components to be able to "read" an "input" signal, for example detect the presence of an assembly facilitator, and "write" an "output" signal, for example producing a detectable signal indicative of enzymatic modification of a substrate, or by the creation of a new product (e.g. a new assembly facilitator or component) which can be useful as a new input signal. Such processes include cascade reactions, logic gates and other processes. MNAzymes therefore could provide a mechanism for transduction of information, for example, to receive an input signal and respond with an appropriate output response.

2. Methods for Regulating the Assembly and Disassembly of MNA Complexes and Applications for their Use.

MNAzyme assembly and disassembly may be controlled by changing the microenvironment. Examples of such changes include, but are not limited to, temperature, divalent cation type and concentration, salt concentration, pH, additives, and the presence or absence of critical components essential for assembly and/or activity of an active MNAzyme.

The assembly of catalytically active MNAzymes may be regulated in a temperature-dependent manner. In one embodiment the assembly of catalytically active MNAzymes may be regulated in a pH-dependent manner. In one embodiment the assembly of catalytically active MNAzymes may be regulated in a manner dependent on the presence or absence of divalent cations or chelators. In one embodiment the assembly of catalytically active MNAzymes may be regulated in a salt-dependent manner. In one embodiment the assembly of catalytically active MNAzymes may be regulated in a manner dependent on ionic concentration.

The assembled MNAzyme represents an "on" state, whereas the disassembled MNA complex components represent an "off" state. The assembly and disassembly of MNA complexes can be controlled by temperature. The "on" state can be induced by switching the temperature to one within the range that is compatible with both assembly and catalytic activity of an MNAzyme or MNAzyme complex. Conversely, the "off" states can be induced by switching the temperature to outside the range that is compatible with either assembly and/or catalytic activity of an MNAzyme or MNAzyme complex. The melting temperatures of the components of MNA complexes can be adjusted to only allow assembly within a restricted temperature range. Oligonucleotides which are particularly useful in this aspect of the invention, include but are not limited to, stabilizer arm components, partzyme components with truncated sensor arms and components of assembly facilitator and/or modulator oligonucleotides. Great flexibility is afforded by MNA complexes in which the components of the basic design (FIG. 1) have been further split into smaller component subunits or portions (FIG. 2), the sequence of which can be tailored with respect to the melting temperature, the sequence composition and complementarity, or lack thereof, with other component oligonucleotides. With reference to FIG. 2 it would be appreciated by one skilled in the art that the partzyme arm which is truncated could be any of the following: the partzyme A sensor arm, the partzyme B sensor arm, the partzyme A substrate arm, the partzyme B substrate arm, or any combination thereof.

With reference to FIG. 6, additional exemplary designs for active MNAzyme complexes are shown. MNAzyme complexes with the structures as exemplified in FIG. 6 could also be used to modify substrates in ways other than cleavage, for example, the MNAzyme structures could also ligate substrates.

The sensitivity of an MNAzyme to temperature can be exploited to build thermo-sensors and rheostats. If the temperature were either too high, or too low, for the assembly (hybridization) of the component oligonucleotides, and/or for catalytic activity, then the MNAzyme substrate would not be modified (eg cleaved or ligated). If the temperature were permissive for MNAzyme activity then the substrate would be modified and a signal would be generated. A rise or fall in temperature from one that is incompatible with MNAzyme activity, to another which is compatible with MNAzyme activity, would be detected by a signal generated following substrate modification by the MNAzyme. MNAzymes can thus provide a device capable of detecting temperature changes. One skilled in the art would appreciate that the invention of simple devices using MNAzymes for temperature sensing could be applied in many industries including, for example, the pharmaceutical, food and agricultural industries In other embodiments, a magnetic force can regulate cation concentration and hence provide a switch for modulating MNAzyme activity on and off. Positively charged cations are required for the catalytic activity of some MNAzymes. A magnetic force could alternatively switch the MNAzyme activity off by physically separating the negatively charged MNA oligonucleotides, for example the partzymes, assembly facilitators and substrates or components thereof, from the positively charged cations, for example $Mg^{2+}$. The MNAzyme could then be switched back on by allowing the MNA oligonucleotides and cations to come back in contact.

In some embodiments the active "on" states (MNAzyme) can be induced using a pH within the range that is compatible with activity. Conversely, an "off" state can be induced using a pH outside the range that is compatible with activity. pH may further be used to control activity of MNA complexes by inducing hydrolysis of labile sequences, and thus either creating or destroying a new component for an MNAzyme and/or inactive MNA complex.

The presence or absence of any component of the MNA complexes can provide either an "on" or "off" switch. Changing, for example, the oligonucleotide sequence, the melting temperature and or concentration can achieve finer regulation. The broad scope for designs of components which can assemble into MNA complexes, for example two-part assembly facilitators and/or two-part partzyme components (e.g. with truncated sensor domains and stabilizer arms), introduces flexibility into systems which can allow tailoring (fine tuning) of conditions compatible with hybridization and hence MNA complex assembly. Further, the hybridization strength and stringency of binding of specific oligonucleotides within an MNA complex is affected by many factors, including but not limited to, salt concentration, cation concentration, temperature and the presence or absence of additives (e.g. DMSO). As such, entities that affect hybridization can provide a tool for controlling the assembly and disassembly of MNAzyme and/or inactive MNA complexes.

Physical manipulation of components can be achieved, for example, by exploiting either physical properties of attached moieties as molecular "hooks", and/or by exploiting inherent properties of the oligonucleotides, for example, negative charge, or sequence complementarity. In another embodiment, the attached moiety allows oligonucleotides to be selectively captured, for example using a biotin group. In another embodiment the moiety contains a radio-frequency magnetic field radio to facilitate remote electronic control of hybridisation. This approach could be designed to allow the selective removal of component molecules by targeted thermal denaturation of specific oligonucleotides within an MNA complex, thus allowing activation, or inhibition, of enzymatic activity depending on whether the component molecule is itself an activator or an inhibitor sequence. For example, the activity inhibitor can be selectively denatured from an MNAi complex, allowing transition to the active MNAzyme state.

Other strategies could be used to remove the influence of an activator or inhibitor molecule and thus promote assembly or disassembly of active MNAzymes and inactive MNA complexes such as MNAi complexes. For example, hybridization between two oligonucleotides at single stranded termini can cause DNA branch migration and unzipping of regions of double stranded nucleic acid. The process of unzipping a double stranded region of nucleic acid by branch migration can also be initiated at single stranded region which is not at the termini of a nucleic acid duplex. For example branch migration may be initiated at a single stranded region which lies between two double stranded regions. In one embodiment, an activity inhibitor could be removed from an MNAi complex by a modulator oligonucleotide such as a displacer oligonucleotide which functions by branch migration. In another embodiment, a ligase substrate could be removed from an MNAzyme complex with ligase activity by a modulator oligonucleotide such as a displacer oligonucleotide which functions by branch migration.

In other embodiments, complementary oligonucleotides can be used to out-compete and hence switch "off" or shut down oligonucleotide components, which in themselves may comprise either active MNAzymes or MNAzyme complexes or inactive MNA complexes. The components which are inhibited by this approach may comprise activator or inhibitor components of either MNAzymes or inactive MNA complexes.

DNAzyme with ligase activity). With reference to FIG. 13, an active MNAzyme A, which could be capable of modifying (eg cleaving or ligating) a substrate(s) A could be formed in the presence of assembly facilitator component 1 (AFC 1) and assembly facilitator component 2 (AFC 2). A second MNAzyme B, which has ligase activity, could form in the presence of assembly facilitator 3 (AF3) and could then ligate AFC 2 with an activity inhibitor component (AIC) causing the formation of an activity inhibitor (AI). This AI could bind to the partzyme components for the MNAzyme A and result in the formation of an MNAi A complex which is inactive. As such the MNAzyme ligase in this example could operate as an off switch to inactivate the MNAzyme A. Alternatively, a DNAzyme ligase could replace the MNAzyme B (MNAzyme ligase) and could operate as an off switch to inactivate the MNAzyme A. The inactive MNAi complex and the catalytically active MNAzyme would represent two alternate states for the assembled components, namely an "off" state and the "on" state respectively. The skilled artisan will recognize that the various methods provided herein can generally be used to modulate the assembly or activity of single MNA complexes or of multiple MNA complexes in a single reaction or assay.

3. Use of the Compositions as Molecular Switches

Persons skilled in the art will recognize and understand that the present invention may be equated with a biological "switch", the applications of which are herein contemplated. Exemplary examples of mechanisms for switching on and off MNAzyme activity are listed in Table 2 below.

TABLE 2

Active and inactive MNA states and mechanisms for switching between the two states.

| Type | "On" active state | "Off" inactive state | Example of a mechanism, which can induce transition between active and inactive states. |
|---|---|---|---|
| MNAzyme or MNAzyme complex assembly and disassembly | Fully assembled MNAzyme or MNAzyme complex | Fully or partially disassembled components for an MNAzyme complex | Temperature may be compatible or incompatible with assembly of MNAzymes or MNAzyme complexes<br>An essential MNAzyme or MNAzyme complex component may be provided or removed. |
| Activation or inactivation of MNA complexes containing components for an apta-MNAzyme and an assembly inhibitor | Activator ligand present<br>Assembly inhibitor removed | Activator ligand absent<br>Assembly inhibitor provided | Activator ligand provides a switch by removing assembly inhibitor<br>Removal, displacement or modification of the assembly inhibitor e.g. by branch migration |
| Alternate MNA complex structures | MNAzyme | MNAi complex | Removal, displacement or modification of the activity inhibitor e.g. by branch migration or using a second MNAzyme with ligase activity to create an activity inhibitor |
| Catalysis Inhibition | MNAzyme plus cation e.g. $Mg^{2+}$ | MNAzyme minus cations e.g. $Mg^{2+}$ | Separation of positive cations from negative charged DNA (e.g. the MNA components) using, for example, magnetic force |

An alternate exemplary strategy is designed to facilitate switching an MNA complex between the "on state" of an active MNAzyme to the "off state" of an MNAi complex using a second MNAzyme with ligase activity (or a In this regard, the presence or absence of any component of the multi-component nucleic acid complexes can provide either an "activator" or "on" switch or it may provide an inhibitor or "off" switch.

In some embodiments, the presence or addition of a stabilizer arm can provide an "on" switch. In one embodiment, new stabilizer arms can be generated in the system during a reaction, for example by cleavage of a substrate, which may comprise, for example another MNA complex component. In other embodiments the absence, modification or removal of a stabilizer arm can provide an "off" switch.

In some embodiments, the presence of an assembly facilitator, or a component thereof, can provide an "on" switch. In some embodiments, new assembly facilitators can be generated by MNAzyme cleavage of MNA complex components, for example, by cleavage of a substrate including, but not limited to, those substrates which can serve as another MNA complex component such as an activity inhibitor prior to modification by cleavage. In some embodiments, the assembly facilitators can provide specific "input" signal systems, encoded within the sequence. In some embodiments the assembly facilitator can be recognized or "read". In some embodiments, the partzyme sensor arm can "read" assembly facilitator sequences including those differing by one or more single bases. In other embodiments, the absence or removal of an assembly facilitator, or a component thereof, can provide an "off" switch.

In some embodiments components of MNA complexes may be generated by ligation of components present in the reaction milieu. In some embodiments a partzyme is created by ligation of oligonucleotides thereby generating a new partzyme component which can associate to form, for example, an active MNAzyme. In some embodiments an assembly facilitator is created by ligation of oligonucleotides thereby generating a new assembly facilitator component which can facilitate assembly of an MNA complex. In some embodiments a substrate or other nucleic acid enzyme or component thereof may be generated by ligation of components.

Transition between states of activation and inactivation can provide a mechanism for creating a molecular switch, which can be regulated by alternating between the active and inactive conformations. Such molecular switches may, for example, be applied to the control of nucleic acid replication cascades, or to the regulation of autonomous therapeutic, diagnostic and computational molecular scale devices.

The present invention provides compositions comprising the components for self-assembling MNAi complexes that self-assemble in the presence of one or more MNAzyme assembly facilitator molecules and one or more assembly inhibitor molecules to form catalytically inactive MNAi complexes.

Aspects of the invention may be better understood by reference to the figures. FIG. 1 depicts an example of a basic method for assembling an MNAzyme using an assembly facilitator. More specifically, partzyme A and partzyme B are shown in FIG. 1, each comprising a (i) sensor arm portion, (ii) a substrate arm portion, and (iii) a catalytic core portion. In the presence of an assembly facilitator, the sensor arm portions of partzyme A and partzyme B can hybridize to, and base pair with complementary portions of the assembly facilitator, for example a DNA or RNA target sequence. Upon contacting the assembly facilitator in this fashion, the MNAzyme self-assembles forming a catalytic core which can modify a substrate which is bound by the substrate arms. Preferably the presence of the MNAzyme is detected through the detection or measurement of its catalytic activity. The substrate arms of the assembled MNAzyme can engage a substrate, for example the reporter substrate shown in FIG. 1, through the interaction of the complementary sequences on the substrate arms and the substrate. Once the substrate is so engaged with the substrate arms, the catalytic core can promote the modification (eg. cleavage) of the substrate, which can in turn be measured or detected, directly or indirectly. The MNAzyme can be alternatively assembled (switched on) and dissembled (switched off) using various methods.

One or more of the partzyme sensor arms, the partzyme substrate arms, the assembly facilitator and the substrate may comprise at least two molecules. In one embodiment one or more components for an MNA complex including for example the partzyme sensor arms, the partzyme substrate arms, the assembly facilitator, the activity inhibitor and the substrate may further comprise at least one aptamer.

The assembly facilitator may comprise synthetic oligonucleotides which are added to the mix to drive the assembly of MNA complexes.

With reference to FIG. 2, additional exemplary designs for active MNAzyme complexes are shown. The exemplary structure for one MNAzyme complex is depicted in panel (i) where multiple assembly facilitator components are required for formation of an MNAzyme. In this design, one component (F1) of the assembly facilitator is complementary to regions of the sensor arms of both partzyme A and B, whereas a second assembly facilitator component (F2) has complementarity with either partzyme B only (as per FIG. 2(i)), or partzyme A only. The two assembly facilitator components together direct the assembly of an active MNAzyme which can modify (eg cleave) a substrate. Panel (ii) depicts an exemplary design of an MNAzyme complex where the assembly of partzyme A with a bi-partite partzyme B component in the presence of assembly facilitator produces an active MNAzyme capable of modifying (eg cleaving) a substrate. In this design, partzyme B has a truncated sensor arm (T), which is insufficient to allow stable MNAzyme assembly in the absence of a second component, referred to herein as a stabiliser arm component (S). However, when a stabiliser arm component hybridises to the assembly facilitator in a location adjacent to that where the truncated sensor arm of the partzyme binds, this allows assembly into an active MNAzyme.

The active MNAzyme formed by the assembly of a partzyme A, a partzyme B component with a truncated sensor arm, and stabiliser arm component in the presence of an assembly facilitator represents an "on" state. Omission, removal or modification of either of the partzymes, the partzyme stabiliser arm component, or an assembly facilitator component, may result in a catalytically active "off" state. As such, the MNAzyme catalytic activity can be regulated by the presence or absence of various oligonucleotides and/or by the ability of such oligonucleotide components to be functionally active, for example to be capable of hybridizing with other oligonucleotide components to form stable MNA complexes. The truncated arm is designed to be insufficient to allow stable MNAzyme assembly under the reaction conditions, unless accompanied by a stabiliser arm component. The partzymes, stabiliser arm component, and the assembly facilitator, can thus function as "on" switches for MNAzyme activity.

The reactions illustrated in FIG. 3 represent two alternative states for the MNA complexes. The active MNAzyme (reaction (i)) represents the "on" state. Those reactions where either a partzyme stabiliser arm component (reaction (ii)), or an assembly facilitator component (reaction (iii)) is omitted are inactive MNA complexes representative of "off" states. As such, the MNAzyme catalytic activity can be regulated by the presence or absence of various oligonucleotides and/or by the ability of such oligonucleotide components to be functionally active, for example, to be capable of hybridising with other oligonucleotide components to form stable MNAzymes. The truncated arm is designed to be insufficient to allow stable MNAzyme assembly under the reaction conditions, unless accompanied by a stabiliser arm component. The stabiliser arm and the assembly facilitator can function as "on" switches for MNAzyme activity.

It would be appreciated by one skilled in the art that the partzyme arm which is truncated could be any of the following: the partzyme A sensor arm, the partzyme B sensor arm (as illustrated in FIG. 2 (ii) and FIG. 3 (i)), the partzyme A substrate arm, or the partzyme B substrate, or any combination thereof.

One skilled in the art would recognise that MNAzymes can be used in strategies for creating molecular sensors, molecular switches, and/or modulators or propagators of autocatalytic self-replicating cascades and other iterative processes. Areas of use include, but are not limited to, medical, veterinary, agricultural, food technology, imaging and anti-bioterrorism applications.

With reference to FIG. 4, an MNAi complex is formed when partzymes A and B complex with an assembly facilitator and an activity inhibitor (left hand side). The inactive MNAi complex is capable of interacting with, but not catalytically modifying, the substrate. In some embodiments, the activity inhibitor may further include a labile or cleavable linker, which may separate two or more domains within the activity inhibitor. Such domains may include, for example, (i) an inhibitor portion which is substantially non-complementary to the partzyme components and which exerts an inhibitory effect by disrupting the secondary structure required for formation of a catalytically active MNAzyme and (ii) an activator portion which, if separated from the inhibitor portion, may function as an additional assembly facilitator component and direct the assembly of an active MNAzyme.

With reference to FIG. 4, an active MNAzyme complex (right hand side) can be derived from the components of the MNAi complex, following modification of the activity inhibitor such as to cleave or bisect the molecule and separate the (i) activity inhibitor portion and the (ii) activator assembly facilitator portion. The released activator assembly facilitator portion is then able to function as a second assembly facilitator component, which in concert with a first assembly facilitator component, can direct the assembly of partzyme components A and B into an active MNAzyme capable of catalytically modifying a substrate.

Conversely an active MNAzyme complex (right hand side of FIG. 4) can be converted to an inactive MNAi complex (left hand side of FIG. 4), by ligation or joining of an activity inhibitor portion (i) to the activator assembly facilitator portion (ii) thus creating an activity inhibitor.

The inactive MNAi complex and the catalytically active MNAzyme represent two alternate states for the assembled components, namely an "off" state and the "on" state respectively.

With reference to FIG. 13 an exemplary strategy for switching an MNA complex from the "on state" of an active MNAzyme to the "off state" of an MNAi complex using a second MNAzyme with ligase activity is described. An active MNAzyme A, which could be capable of modifying (eg cleaving or ligating) a substrate(s) A could be formed in the presence of assembly facilitator component 1 (AFC 1) and assembly facilitator component 2 (AFC 2). A second MNAzyme B, which has ligase activity, could form in the presence of assembly facilitator 3 (AF3) and could then ligate AFC 2 with an activity inhibitor component (AIC) resulting in the formation of an activity inhibitor (AI). This AI can bind to the partzyme components for MNAzyme A resulting in the formation of an MNAi A complex which is inactive. As such the MNAzyme ligase in this example can operate as an off switch to inactivate an MNAzyme A. The inactive MNAi complex and the catalytically active MNAzyme represent two alternate states for the assembled components, namely an "off" state and the "on" state respectively.

4. Methods Using Insoluble and Solid Supports

It is also to be understood that generally the methods, whether multiplexed or not, are applicable in solution, or combined with an insoluble support or solid support on which one or more of any MNA complex component(s), including the substrate or portion thereof, may be attached. Further, additional enzymes or components thereof present in an MNAzyme cascade, including DNAzymes with for example, either cleavage and/or ligase activity may be attached to an insoluble support or solid support. Accordingly, at least one of a DNAzyme, a partzyme component, a substrate, an assembly inhibitor, an assembly facilitator or assembly facilitator component, a stabilizer arm and/or an inhibitor such as an activity inhibitor or assembly inhibitor may be bound, attached or tethered. Further, a portion of at least one of a partzyme component, a substrate or substrates, an assembly inhibitor, an assembly facilitator or assembly facilitator component, a stabilizer arm and/or an inhibitor such as an activity inhibitor or an assembly inhibitor may be bound, attached or tethered.

Embodiments of the present invention encompass an insoluble support. By way of example the insoluble support could be in the form of a "chip", otherwise known as an array or microarray, which typically comprise a plurality of oligonucleotides coupled, tethered or otherwise attached to the chip. In particular embodiments, the oligonucleotides comprise nucleic acid.

In particular embodiments, the plurality of oligonucleotides could comprise a plurality of components, or portions thereof, for MNA complexes which include but are not limited to, substrates, and/or partzymes, and/or assembly facilitators, and/or assembly inhibitors and/or activity inhibitors and/or any combination thereof. In particular embodiments, the plurality of oligonucleotides could comprise a plurality of oligonucleotides which are complementary to a domain contained within, and/or appended to, any of the components comprising the plurality of components, or portions thereof, for MNA complexes. In particular embodiments, the plurality of components, or portions thereof, for MNA complexes could comprise oligonucleotides with more than one functional domain which may comprise a substrate, and/or a partzyme, and/or an assembly facilitator, and/or an assembly inhibitor and/or an activity inhibitor and/or any combination thereof.

A plurality of oligonucleotides may be positioned upon a solid support, for example a chip, bead, plate or array by any suitable method known in the art, for example, by pipette, ink-jet printing, contact printing or photolithography. The solid support may be comprised of at least one element, with each element comprising at least one nucleic acid oligonucleotide. The at least one element may be comprised of a plurality of oligonucleotides of the same sequence. The number of elements comprising the solid support may be any number, and where a plurality of elements is positioned on a solid support, the elements may be spaced apart at a uniform or a variable distance, or a combination thereof. In some embodiments, the elements may be positioned randomly, with the respective location of each element then determined. The size and shape of the elements will depend upon the particular application of the present invention, and different sized and shaped elements may be combined into a single solid support. The surface of the solid support may be substantially planar or may have features such as depressions or protuberances, and the elements may be positioned either into the depressions or onto the protuberances. Such depressions may provide a reservoir for solutions into which the elements are immersed, or such protuberances may facilitate drying of the elements. For example, elements may be placed in each well of a 96 well plate. In some embodiments, the solid support may include unique identifiers such as indicia, radio frequency tags, integrated devices such as microprocessors, barcodes or other markings in order to identify each of the elements. The unique identifiers may additionally or alternatively comprise the depressions or protuberances on the surface of the array. Furthermore, the unique identifiers can provide for correct orientation or identification of the chip. The unique identifiers may be read directly by a data capture device or by an optical scanner or detector.

5. Substrate Systems

Also provided in accordance with the present invention are generic reporter substrate systems, which allow rapid system development by allowing facile design changes to create new MNAzymes and inactive MNA complexes which recognize different assembly facilitators. As discussed herein, the substrate arm portion and the catalytic core portion of the partzymes may remain unchanged, with changes only to the sensor arm portion of one or more partzymes required for new assembly facilitators. A generic substrate sequence or sequences is provided and the same substrate or substrates can therefore be incorporated in systems for various diverse applications. Further, the same substrate(s) can be incorporated into the methods in various embodiments herein, including assays where the substrate(s) is free in solution or is tethered or attached to a support. A series of generic substrates can be used in a multiplex reaction allowing simultaneous detection of multiple assembly facilitators.

In some cases, substrates which have been cleaved by an MNAzyme or DNAzyme with endonuclease or cleavage activity can be reconstituted and hence recycled using a DNAzyme ligase or a MNAzyme ligase. Substrates which have been ligated by a DNAzyme or MNAzyme with ligase activity can be recycled as substrates for a DNAzyme or MNAzyme with cleavage activity provided the DNAzyme or MNAzyme cleaver can cleave the link created by ligation by the DNAzyme or MNAzyme ligase. Alternatively, an MNAzyme with cleavage activity may cleave at a site within a ligation product which is not at the junction of the two ligatable substrates provided the cleavage site requirements are met at this site.

As described in more detail below, MNA complexes have an advantageous property in certain embodiments of being able to utilize a universal or generic substrate or substrates. Such a substrate is shown in FIG. 1 in a presently preferred configuration wherein the substrate for an MNAzyme with cleavage activity comprises both a detectable portion and a quencher portion. The quencher portion is adapted to diminish or eliminate a detectable signal from the detectable portion of the substrate until the substrate is cleaved by an MNAzyme. For example, the quencher portion may comprise "Black Hole Quencher 1" (BHQ1) or "Black Hole Quencher 2" (BHQ2).

Thus, the MNAzyme cleaves the substrate between the detectable portion and the quencher portion allowing the two portions to separate in solution, thereby allowing the detectable signal to appear or increase as the quencher portion is distanced from, or effectively removed from the local environment of the detectable portion.

Further, substrate(s) for an MNAzyme with ligase activity, as shown in FIG. 10, can be designed such that one substrate comprises a detectable portion and one substrate comprises a quencher portion. The quencher portion is adapted to diminish or eliminate a detectable signal from the detectable portion when the substrates are ligated into a ligation product thus bringing the detectable and quencher portions into close proximity. For example, the quencher portion may comprise "Black Hole Quencher 1" (BHQ1) or "Black Hole Quencher 2" (BHQ2). Further, either an MNAzyme with ligase activity or a DNAzyme with ligase activity could ligate substrates bringing the detectable portion of one substrate in close proximity with the quencher portion of the second substrate, thereby allowing the detectable signal to decrease.

In another example, if the 5' ligation substrate and the 3' ligation substrate were each labelled with either a fluorophore or quencher dye respectively (or vice versa) then ligation would result in a decrease in fluorescence, which could serve as an indicator of the presence of the target analyte.

In an alternative format, if the 5' ligation substrate, for example, were labelled with a detectable moiety, for example a fluorophore, and the 3' ligation substrate were attached to a discrete location, for example on a solid support such as a chip or a bead, then ligation would result in the appearance of a signal at the discrete location in the presence of target analyte.

The use of the generic or universal substrate(s) is enabled through the design of the MNAzyme's component partzymes. By altering only the sensor arms of the partzymes, but by leaving the substrate arms unchanged, a large variety of MNAzymes or inactive MNA complexes specific for each of a plurality of assembly facilitators can be designed all of which utilize a universal generic substrate(s) to produce an output signal. The skilled artisan will appreciate the advantages that this offers in terms of eliminating the need for customized or unique substrates to respond to each input event or entity. Detection of each new assembly facilitator requires only one or more changes in one or more of the sensor arm portions; while the substrate arm portion and the catalytic core portion may remain constant. Thus, a single substrate (e.g. reporter substrate) for an MNAzyme cleaver, or a single pair of ligatable substrates for an MNAzyme ligase, can be used for detection of a single assembly facilitator or other input event using an MNAzyme, and/or detection of multiple assembly facilitators in a series of systems using altered MNAzymes. A plurality of generic cleavable reporter substrates, or generic ligatable substrate pairs, allows multiplexed monitoring of multiple MNAzymes within one system.

In some instances it may be useful to have different MNAzymes in a mix which have different sensor arms and at least one substrate arm in common. For example, with reference to the feedback cascade illustrated in FIG. 16, the MNAzyme cleaver 3 could have different sensor arms than MNAzyme cleaver 1 but it may have one substrate arm (on one of the partzymes) that is the same as the sequence of one substrate arm of the partzyme of MNAzyme cleaver 1 which interacts with that portion of the sequence on substrate 1 (here, the 5' portion of the substrate) which is subsequently ligated by the ligase. Therefore instead of cleaving substrate 1, MNAzyme cleaver 3 would cleave another substrate (referred to as substrate 3) which has the same sequence at the 5' portion but which has a different portion at the 3' end (or vice versa) with respect to cleavable substrate 1. The cleavage site of substrate 3 would lie at the junction of those sequences which are shared between the cleavable substrates 1 and 3 and those which differ. In this case, when MNAzyme cleaver 3 was assembled in the presence of an assembly facilitator component generated by cleavage by the MNAzyme cleaver 2, and if MNAzyme cleaver 3 cleaved substrate 3 then the 5' cleavage product of MNAzyme cleaver 3 could also serve as a 5' substrate for the DNAzyme ligase (or the assembled MNAzyme ligase) and a feedback amplification cascade reaction could be initiated.

Further, the substrates may incorporate additional entities such as labelled nucleic acids, nanoparticles, microparticles, proteins, antibodies, RNA, DNA, nucleic acid analogues, biotin group, glycoproteins, lipoproteins, peptide nucleic acids, locked nucleic acids, peptide-nucleic acid chimeras, moiety for radio-frequency magnetic field, or any combination thereof.

Substrates can be modified by an MNAzyme thereby providing a "detectable effect" or "output" signal. In the detection process, the substrate modification by an MNAzyme may involve, for example, cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion or phosphoramidate cleavage.

As a consequence of substrate modification by an MNAzyme, a detectable effect may be generated and the magnitude of the effect may therefore be indicative of the quantity of the input signal. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination UV, visible light or infra red spectroscopy, enzymatic methods or any combination thereof.

The method may further comprise quantifying the magnitude of the output signal or detectable effect. In one embodiment the method may further comprise determining the magnitude of the input event from the quantified output signal.

The determination of catalytic activity, for example by determination of the presence of detectable effect or output signal, may be performed in a manner permitting the catalytic activity to be quantified. In one embodiment the magnitude of the detectable event may be determined from the quantified catalytic activity.

Several groups have reported detection of nucleic acid targets, and other analytes with colourimetric readouts (Elghanian et al., 1997, Mirkin et. al, 1996, and Liu and Lu, 2004). The strategy involves preparation of batches of gold nanoparticles, each of which has a distinct DNA oligonucleotide sequence attached to its surface. Gold particles can then be aggregated by the addition of a "bridging oligonucleotide", which has complementarity with the sequences that are attached to the gold particles. Particle aggregation results in a concomitant change in colour from red to blue (Mirkin et al, 1996). Inclusion of a DNAzyme substrate sequence within the bridging oligonucleotide can provide a mechanism for reversing the aggregation of the gold particles (Liu and Lu, 2004). Activation of the lead-dependent DNAzyme by the addition of lead, caused cleavage of the bridging oligonucleotide, dissociation of the gold particles and a change in colour from blue to red.

Simple detectors for monitoring changes could be developed using this principle and an MNAzyme with endonuclease or ligase activity. Changes in temperature or other entities or events could activate MNAzymes which could modify bridging oligonucleotides causing the dissociation (in the case of a cleaver) or association (in the case of a ligase) of nanoparticles and a change in colour.

6. Optimization of the Methods

The skilled artisan will readily understand that the methods described herein may be optimized using a variety of experimental parameters. The particular experimental parameters that are optimized, and the level of such optimization, will depend upon the particular method being employed and/or the particular event to be detected. Such parameters include, but are not limited to, time, temperature, concentration of salts, detergents, cations and other reagents including but not limited to dimethylsulfoxide (DMSO), and length, complementarity, GC content and melting point (Tm) of nucleic acids. The temperature at which such methods may be performed may be in the range of about 20° C. to about 96° C., about 20° C. to about 75° C., about 20° C. to about 60° C. or about 20° C. to about 55° C. The temperature may be constant or may be cycled between one temperature which is compatible with assembly of an MNA complex and/or catalytic activity of an MNAzyme and one temperature which is incompatible with assembly of an MNA complex and/or catalytic activity of an MNAzyme.

Additionally or alternatively, a variation in a parameter, and/or the microenvironment, may be used to trigger activation of the MNA complex from an inactive to an active state. Thus, a parameter in the microenvironment may comprise an "activator" as herein defined, including but not limited to events such as change in temperature, wavelength, concentration of salts, detergents, cations, and concentration of structural and modulator components which include but are not limited to assembly facilitators or assembly facilitator components, partzymes or partzyme components, substrates, assembly inhibitors, activity inhibitors and activator oligonucleotide components. Accordingly, such optimization of parameters and/or microenvironment may be undertaken in order to achieve use of the MNA complexes as elements of cascade reactions or molecular switches.

In one preferred embodiment, optimized reactions for practicing the methods of using MNA complexes are provided herein. In such optimized reactions, activation of catalytic activity, which in some cases may be by one or more nucleic acid enzymes in a cascade, is increased by up to 10, 20, or 30% above unoptimized reactions. More preferred reaction conditions improve catalytic activity by at least 35%, or 40%, and preferably up to 50% or more. In still more preferred embodiments, optimized reactions have an increase in activation of catalytic activity of more than 50%, and up to 66%, 75% or even 100%. In yet more preferred embodiments, a fully optimized reaction method will offer 100, 200 or even 300% or more increase in activation of catalytic activity. Other preferred reaction conditions can improve the activation of catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes may be influenced in a concentration-dependent fashion by the concentration of divalent cations. Preferred optimized reactions are optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

7. Methods Using Aptamers

With reference to FIG. 7, a method is illustrated whereby an activator ligand can be used to switch "on" or "off" the activity of the apta-MNAzyme. The method uses an assembly inhibitor to block activity of apta-MNAzymes in the absence of an activator as illustrated. These methods use aptamers which may comprise a nucleic acid, protein, polypeptide, phylomer, peptide or combination thereof that has the ability to recognize one or more ligands. Aptamers may bind, for example, proteins, polypeptides, peptides or nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof, or any other entity (Lee et al., 2004).

Preferred aptamers herein may comprise short single-stranded DNA or RNA oligomers that can be isolated from complex libraries of synthetic nucleic acids by an iterative process of adsorption, recovery, and reamplification. Other preferred aptamers may comprise protein, polypeptide, peptide or phylomers or a combination thereof that has the ability to recognize one or more ligands. Aptamers may be generated which may recognize and bind almost any target, ranging from small molecules such as amino acids or antibiotics, to protein and nucleic acid structures. In preferred embodiments, aptamers include, for example, nucleic acid binding molecules which are preferably generated by evolution and selection techniques. Preferably, aptamers may comprise DNA or RNA molecules, or a combination of both, including but not limited to the nucleotide analogues as per, for example, Table 1 above.

At least one component of the MNA complex may contain at least one aptamer or portion thereof wherein said aptamer or portion thereof binds a ligand selected from the group comprising nucleic acids, polypeptide, peptide, entire organisms, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof, or any other entity.

An apta-MNAzyme, for example, with either cleavage or ligase activity may incorporate one or more aptamers. The assembly of the apta-MNAzyme may therefore be directed by the presence or absence of one or more analytes which bind the aptamer and cause dissociation of an assembly inhibitor.

One skilled in the art will appreciate that one or more aptamers may be incorporated into either end of the assembly facilitator molecule or molecules, and or the activity inhibitor. Further it will be appreciated that multiple aptamers could be incorporated into one or more of the partzyme oligonucleotide components. Still further it will be appreciated that aptamers could also be incorporated into at least one of the partzyme oligonucleotide components. The assembly facilitator in the strategies illustrated in FIG. 7 can comprise DNA, RNA, LNA, PNA or a sequence containing one or more nucleotide base analogues. One skilled in the art would appreciate that it could be possible to recognise two molecules, for example, one target nucleic acid acting as the assembly facilitator, and one ligand which binds the aptamer.

In the strategy shown in FIG. 7, an aptamer sequence is incorporated at the end of a partzyme (apta-partzyme) in a configuration whereby an active apta-MNAzyme is only formed in the presence of the activator.

It will also be appreciated by one skilled in the art that one or more aptamers could be incorporated into any of the oligonucleotide components, including the partzymes, the assembly facilitator, activity inhibitor or the substrate. Further the aptamer could be incorporated into either end of any one of these oligonucleotides.

The strategy illustrated in FIG. 7 can be used either (i) to provide a method to control apta-MNAzyme activity using ligands as activator molecules, and/or (ii) to provide a method for detection of non-nucleic acid, and nucleic acid targets using apta-MNAzymes. Further, the apta-MNAzyme could be the first nucleic acid enzyme in a cascade reaction designed to detect a range of ligand targets. The nucleic acid oligonucleotides required for one schema for apta-MNAzyme detection strategy include;

a) a partzyme;
b) an apta-partzyme which is a partzyme with an aptamer incorporated into one of its ends;
c) an assembly facilitator which is an oligonucleotide which binds to both the apta-partzyme and the partzyme enabling assembly of an active MNAzyme;
d) a substrate e.g. a reporter substrate; and
e) an assembly inhibitor oligonucleotide which hybridises to the apta-partzyme in a region which spans at least part of the aptamer sequence and part of the substrate binding arm of the apta-partzyme sequence.

In the absence of an activator ligand (FIG. 7; left hand panel), the assembly inhibitor oligonucleotide binds to the apta-partzyme thus competing with and blocking binding of the reporter substrate. When an activator ligand is present (FIG. 7; right hand panel), it binds to the aptamer sequence of the apta-partzyme, blocking the binding of the assembly inhibitor oligonucleotide, and thus allowing assembly of an active apta-MNAzyme complex and subsequent modification, for example cleavage of the substrate (as illustrated in FIG. 7) or ligation of substrates. As such, an active apta-MNAzyme complex can only form and cause fluorescent signal generation in the presence of activators or ligands that can bind an aptamer portion of an apta-partzyme.

In a further embodiment of the apta-MNAzyme schema illustrated in FIG. 7 the system could be used to simultaneously detect a combination of nucleic acid and non-nucleic acid molecules. By way of example, the apta-MNAzyme may be used to detect the presence of (i) a nucleic acid target, which functions as an assembly facilitator and directs the formation of the apta-MNA complex, and (ii) a target activator ligand (e.g. a protein or small molecule) which could displace the assembly inhibitor oligonucleotide and allow assembly of an active apta-MNAzyme complex and subsequent substrate modification.

In another strategy using an apta-MNAzyme with ligase activity, at least two ligatable substrates could be present in the reaction, one of which could be labelled with a fluorophore and the other of which could be labelled with a quencher. When an activator ligand is present, it would bind to the aptamer sequence of the apta-partzyme, blocking the binding of the assembly inhibitor oligonucleotide, and thus allowing binding and ligation of the substrates. As such, apta-MNAzyme complexes could only form and cause a decrease in fluorescent signal in the presence of activators that can bind aptamers.

In some embodiments, modulation of MNAzyme activity can be achieved using either a nucleic acid or a non-nucleic acid target activator ligand as a switch mechanism. In other embodiments, the assembly inhibitor molecule is manipulated by other means so as to modulate activity. For example, the assembly inhibitor could be removed by several strategies including selective thermal denaturation or methods that use oligonucleotides to compete for binding and/or displacer olignucleotides that use branch migration to displace oligonucleotide components of MNA complexes.

It would be appreciated by one skilled in the art that the aptamer sequences for an apta-MNAzyme with modifying activity, for example cleavage or ligation activity, could be appended to either partzyme A or partzyme B or both. In the schema above, the assembly inhibitor oligonucleotide bound to portions of the aptamer and the substrate arm of at least one of the partzymes.

It would also be appreciated by one skilled in the art that the aptamer sequences for an apta-MNAzyme could be appended to the sensor arms of at least one of either partzyme A or partzyme B or both. In this embodiment the assembly inhibitor oligonucleotide would bind to portions of the aptamer and the sensor arm. In the absence of an activator ligand, the assembly inhibitor oligonucleotide binds to the apta-partzyme thus competing with and blocking binding of an assembly facilitator, or assembly facilitator component. When an activator ligand was present, it would bind to the aptamer sequence of the apta-partzyme, blocking the binding of the assembly inhibitor oligonucleotide, and thus allowing binding of the assembly facilitator or assembly facilitator component and directing assembly of an active apta-MNAzyme capable of modifying, for example cleaving or ligating, the substrate or substrates. As such, apta-MNAzymes could only form and cause a change in fluorescent signal, for example an increase or decrease in fluorescence, in the presence of activators that can bind aptamers.

When the apta-MNAzyme has cleavage activity as illustrated in FIG. 7 then the modification can cause for example an increase in fluorescence by cleavage of a dual labelled reporter substrate which results in separation of a fluorophore/quencher dye pair.

It would be appreciated that the modification performed by an apta-MNAzyme could be a modification other than cleavage, for example, ligation of two substrates. In this case the signal change could be, for example, a decrease in fluorescence following ligation of two ligatable substrates each labelled with either the fluorophore or the quencher of a fluorophore/quencher dye pair.

This apta-MNAzyme approach could also be used to develop target detection methods or molecular switches that can turn on and off the catalytic activity of the MNA complex. Further, the apta-MNAzyme approach may comprise the first step in a linear nucleic acid enzyme cascade or a feedback nucleic acid enzyme amplification cascade. The apta-MNAzyme could also be applied to simultaneous detection of both nucleic acid targets such as assembly facilitator and non-nucleic acid target ligands such as those which can bind to aptamers.

8. Cascades

Cascades are any succession of processes or operations that occur in successive stages, wherein the occurrence of each stage is typically dependent on the occurrence of a preceding stage. In a linear cascade, stages (or reaction steps) occur in one direction and the occurrence of each stage (or step) is dependent on the occurrence of a preceding stage or step. In feedback cascades or feedback amplification cascades there may be a succession of processes or operations that occur in successive stages, wherein the occurrence of each stage is typically dependent on the occurrence of a preceding stage and whereby the occurrence of a preceding stage further depends on processes or operations that occur in subsequent stages. In feedback cascades, the product of any preceding stage could serve as a component or substrate for any subsequent stage and the product of any subsequent stage could serve as a component or substrate for any preceding stage.

A cascade may therefore include, but is not limited to, an enzymatic cascade or any other signal transduction cascade. In some embodiments, a cascade may comprise amplification of a signal resulting from catalytic activity of an MNAzyme. In some embodiments, a cascade may comprise amplification of a signal resulting from catalytic activity of an MNAzyme with cleavage activity. In some embodiments, a cascade may comprise amplification of a signal resulting from catalytic activity of an MNAzyme with ligase activity. In some embodiments, a cascade may comprise amplification of a signal resulting from catalytic activity of DNAzymes or MNAzymes with ligase activity and DNAzymes or MNAzymes with cleavage activity. In preferred embodiments, such an amplification cascade may involve repeated and therefore cyclic amplification of a signal, wherein catalytic activity of a first nucleic acid enzyme creates a molecule required for modification of a substrate(s) by a second nucleic acid enzyme, which can in turn create a molecule required for modification of a substrate(s) by one or more additional nucleic acid enzymes. In some embodiments, the required molecule may include but is not limited to a partzyme, a nucleic acid enzyme, for example a DNAzyme, an assembly facilitator, an assembly facilitator component, a substrate, a stabiliser arm, a portion or component thereof or a combination thereof. In some embodiments, a cascade may therefore involve production of a cumulative effect, and thus detect a target of low abundance by generating a signal to a level at which it may be detected. Cascades may be employed to amplify a signal, for example, in applications where an input event is of low intensity, for example when a target is in low abundance, and may not otherwise provide for a output signal that is detectable. In other embodiments, more than two catalytic stages may be employed. The cascade may be linear. In a preferred embodiment, the cascade may be exponential.

In linear cascades (e.g. as illustrated in FIG. 9, 12, 15), each step in the cascade employs a nucleic acid enzyme, some or all of which may be undergoing multiple turnover whereby a single nucleic acid enzyme (e.g. a DNAzyme or MNAzyme) may perform multiple cleavages or ligations or other modifications at one or more steps in the cascade. Multiple turnover may facilitate amplification at one or more steps in the cascade resulting in amplification of the signal detected during the detection step(s).

Further, an extension of the linear cascade could result in a feedback amplification cascade. If, for example, the sequence of a product of a third nucleic acid enzyme was the same as a product of a first nucleic acid enzyme then the said product of the third nucleic acid enzyme could also serve as a molecule permitting a second nucleic acid complex to function as a second nucleic acid enzyme and a feedback amplification cascade could be initiated. In this reaction the third nucleic acid enzyme would constantly generate a product which could in turn serve as a molecule permitting a second nucleic acid complex to function as a second nucleic acid enzyme thus allowing the creation of more product by the second nucleic acid enzyme that could permit the third nucleic acid complex to function as a third nucleic acid enzyme. It is envisaged this strategy could provide a mechanism for feedback signal amplification following initiation of a reaction by an assembly facilitator (eg a target analyte) which could allow assembly of a first nucleic acid enzyme. The strategy could allow detection of assembly facilitators (eg target analytes) followed by signal amplification using for example, a DNAzyme (or MNAzyme) which could ligate substrates and MNAzymes which could cleave a substrate. One possible feedback cascade is illustrated in FIG. 16. Other variations of this schema are described throughout the specification.

Persons skilled in the art will appreciate that the methods described herein may be used to perform a cascade as herein defined. It will be also be appreciated by one skilled in the art that other strategies based on FIGS. 9, 12, 15 and 16 could involve modification of at least one substrate by at least one MNAzyme by a variety of means including, for example cleavage or ligation. Unlike target amplification techniques such as the polymerase chain reaction, or the ligase chain reaction, linear and feedback nucleic acid enzyme (DNAzyme and MNAzyme) cascades allow amplification in formats that require no protein enzymes to facilitate the process. This provides a major advantage over these commonly used target amplification protocols. Further, the ability to control and regulate the catalytic activity of MNAzymes using several oligonucleotide components, such as stabiliser arm components or assembly facilitator components allows the assembly of MNAzymes to be tightly regulated by conditions and components in the microenvironment. Persons skilled in the art will appreciate that the cascades described herein may be initiated by formation of an active MNAzyme or apta-MNAzyme as herein defined.

An additional tool useful in MNAzyme cascade reactions is the use of displacer oligonucleotides. Displacer oligonucleotides can bind to single stranded regions within a DNA complex which has both single stranded and double stranded regions. When the displacer binds the single stranded region of an oligonucleotide (e.g. Oligo 1) it can displace the strand or strands complementary to Oligo 1 (e.g. cOligo 1) within the double stranded regions provided the displacer has the same sequence as the cOligo 1 within the double stranded regions. This can result in a new double stranded structure being formed between the displacer oligonucleotide and Oligo 1 and can cause the release of cOligo 1 as a single stranded oligonucleotide.

This strategy could be useful in MNAzyme cascade reactions. For example, a ligated product bound to an MNAzyme ligase has several non paired bases (a single stranded region) between the double stranded regions formed by complementarity between the substrate arms of the partzymes and the substrates. If a displacer oligonucleotide with complementarity to the substrate (Oligo 1) binds to the single stranded region of the substrate it could displace the complementary partzyme sensor arms (e.g. cOligo 1a and cOligo 1b) by branch migration and separate the partzymes from the ligated product. As such, this could increase the turnover of the ligase enzyme. The process would result in a double stranded molecule comprising the displacer and the ligated product. However if the ligated product were required for a subsequent step in the reaction, for example, if it were to act as an assembly facilitator for a subsequent MNAzyme, then it would be necessary to separate the ligated product from the displacer. If the displacer oligonucleotide was shorter than the ligated product then this would result in single stranded regions at the termini of the duplex formed by the displacer oligonucleotide and the ligation product. In the next step, the partzyme sensor arm could bind to these single stranded regions and remove the displacer oligonucleotide by branch migration thus resulting in a new MNAzyme assembled with partzymes (which themselves would have functioned as displacer oligonucleotides in this instance) and ligated product (now functioning as an assembly facilitator).

Many variations on the strategy are useful in cascades. For example, with reference to FIG. 4 (left hand panel) a displacer could be used to remove the activity inhibitor by binding to the activity inhibitor domain of the activity inhibitor and displace it by branch migration such that the partzyme sensor arm would be rendered single stranded and thus available for binding of an assembly facilitator component.

MNAzyme cascade reactions could be applied to a range of biotechnological applications, especially in diagnostics, but also in other areas such as medical, veterinary, agricultural, food technology, imaging and anti-bioterrorism applications. They could allow detection of proteins and nucleic acids for disease diagnosis, especially so if they facilitate signal amplification. Catalytic nucleic acids and/or cascade reactions can be used for applications other than diagnostics, for example, within the field of computation analysis and biomolecular engineering of nano-scale devices and molecular switches which may be used in therapeutics.

MNAzymes offer advantages over DNAzymes for use in various cascades. DNAzymes can only recognize one molecule which is both its target and the substrate. While the DNAzyme target/substrate(s) can be considered to provide the "input" and the enzyme product (modified target/substrate(s)) can be considered the "output" the DNAzyme is limited in its ability to transduce more complex processes in cascades since both the input and output are merely alternate (modified and unmodified) forms of the same target substrate(s) molecule(s). Further, catalytic modification, for example cleavage, can destroy the DNAzyme's target/substrate and as such the target is not available for another round of recognition. In contrast a single MNAzyme, for example an MNAzyme with cleavage activity, can recognize at least two molecules, namely at least one assembly facilitator and at least one substrate. An assembly facilitator, for example a target nucleic acid present in a sample, would not be catalytically modified in the reaction and would remain available for further rounds of substrate modification by the MNAzyme. Further, a single MNAzyme which can act on two substrates (e.g. an MNAzyme with ligase activity) can recognize at least three molecules, namely at least one assembly facilitator and at least two substrates. These properties of MNAzyme complexes make them useful in processes such as in cascade reactions which may involve input (e.g. a molecule which permits a nucleic acid complex to function as a nucleic acid enzyme) and output (e.g. a molecule which is produced and permits a subsequent nucleic acid complex to function as a nucleic acid enzyme). Further, these properties of MNAzyme complexes make them highly suited to use in processes that require the multiple components to be able to "read" (recognise) an "input" signal (e.g. a molecule which may be a target assembly facilitator or an MNA complex component) and "write" an "output" signal (e.g. to recognise an input and act on a molecule to provide an output; e.g. to recognise an input and modify a substrate to create a new reaction product useful in a subsequent step). The properties of MNAzymes and MNAzyme complexes are useful in one step processes (e.g. detection of a target) and also in, for example, systems employing cascades, logic gates and other processes. MNAzyme complexes provide a mechanism for transduction of complex information, for example, to receive an input signal and respond with an appropriate output response. As highlighted throughout this specification, DNAzymes may still be useful in cascades. Some examples include production of a DNAzyme or a substrate for a DNAzyme complex by a preceding nucleic acid enzyme such as an MNAzyme. MNAzyme ligases are particularly useful in making, for example, new DNAzymes. As such the "output" information of one nucleic acid enzyme generated by, for example ligation or cleavage by an MNAzyme can provide an "input" for the next nucleic acid enzyme complex for example by creating a new DNAzyme or substrate, which can participate in the formation of a DNAzyme complex useful in a following, and/or preceding reaction stage.

An exemplary mechanism for generating a linear cascade using an MNAzyme and a nucleic acid enzyme with ligase activity in a format designed for target detection is depicted in FIG. 9. This figure also describes a general method for target detection. This method relies on a DNAzyme with ligase activity (DNAzyme ligase) to control the assembly of a partzyme for one MNAzyme from at least one of the products of the catalytic activity of one other MNAzyme.

The strategy of FIG. 9 uses a combination of MNAzymes with cleavage activity and a DNAzyme with ligase activity. In step (i) an assembly facilitator, for example a target nucleic acid, can direct the formation of a first MNAzyme A. MNAzyme A can cleave a substrate A thus generating a 5' cleavage product A which can in turn be used as a substrate for a DNAzyme ligase B. In step (ii) a DNAzyme ligase B can ligate the 5' cleavage product A (also referred to as 5' substrate B) generated in step (i) to another oligonucleotide, 3' ligation substrate B, thus creating a new partzyme for an MNAzyme C. In step (iii) the new partzyme/ligation product generated in step (ii) together with another partzyme can form a new MNAzyme C in the presence of assembly facilitator C which can cleave a substrate C into two products, 5' product C and 3' product C. A detectable signal can be generated following cleavage of substrate C if this substrate were labelled, for example, with a fluorophore and quencher dye pair. This cascade provides a mechanism for signal amplification following initiation of a reaction by an assembly facilitator (eg a target analyte) which allows assembly of MNAzyme A. In this linear cascade format, each step employs a nucleic acid enzyme, some or all of which may be undergoing multiple turnover whereby a single nucleic acid enzyme (e.g. a DNAzyme or MNAzyme) may perform multiple cleavages, ligations or other modifications at one or more steps in the cascade. Multiple turnover may facilitate amplification at one or more steps in the cascade resulting in amplification of the signal detected during one or more steps.

Another mechanism for generating an MNAzyme cascade in a format designed for target detection is depicted in FIG. 12. This figure also describes a general method for target detection. This method relies on a combination of MNAzymes with ligase and cleavage activity. The MNAzyme ligase controls the assembly of a partzyme for one MNAzyme cleaver from at least one of the products of the catalytic activity of one other MNAzyme cleaver.

In step (i) an assembly facilitator A, for example a target nucleic acid, can direct the formation of a first MNAzyme A. MNAzyme A can cleave a substrate A thus generating a 5' cleavage product A which can in turn be used as a substrate for a MNAzyme B which has ligase activity. In step (ii) an MNAzyme ligase B (formed by the partzyme components of MNAzyme B in the presence of assembly facilitator B) can ligate the 5' cleavage product A (also referred to as 5' substrate B) generated in step (i) to another oligonucleotide, 3' substrate B, thus creating a new partzyme for an MNAzyme C. In step (iii) the new partzyme/ligation product generated in step (ii) together with another partzyme can form a new MNAzyme C in the presence of assembly facilitator C which can cleave a substrate C into two products, 5' product C and 3' product C. A detectable signal can be generated following cleavage of substrate C if this substrate were labelled, for example, with a fluorophore and quencher dye pair.

Further in the context of FIGS. 9 and 12 if the sequence of 5' product C were the same as 5' product A then this product could also serve as a 5' substrate B and a feedback amplification cascade could be initiated. In this reaction, MNAzyme C would constantly generate a 5' substrate B which could in turn be ligated by the nucleic acid enzyme ligase (DNAzyme B in FIG. 9 or MNAzyme B in FIG. 12) to create more partzymes for formation of more MNAzyme C. This strategy could provide a mechanism for feedback signal amplification following initiation of a reaction by an assembly facilitator (eg a target analyte) which allows assembly of MNAzyme A. These feedback cascade strategies could allow detection of assembly facilitators followed by signal amplification using multiple types of nucleic acid enzymes, for example, DNAzyme ligases or MNAzyme ligases in combination with MNAzymes which can cleave a substrate (MNAzyme cleavers). It will be recognised that this kind of feedback cascade could be used in combination with other strategies described throughout the specification. It would be appreciated that there are many variations that could be applied to cascades which follow a strategy similar to those demonstrated in FIGS. 9 and 12. For example, the ligase could be used to create ligation products which serve as for example, assembly facilitators for another MNAzyme with cleavage, ligase or other enzymatic activity.

An example of one possible cascade following a strategy similar to FIGS. 9 and 12 would be where two or more MNAzymes are responsive to different assembly facilitators (e.g. targets) and could be used in a reaction, with each modification reaction catalysed by each MNAzyme providing a different modification product (e.g. a cleavage or ligation product) which could be used to participate in a following reaction. By way of example, with reference to the cascades of FIGS. 9 and 12, two or more initial MNAzymes responsive to different assembly facilitators (e.g. targets) could be used to provide different modified products which could participate in forming a corresponding number of MNA ligase complexes that can function as nucleic acid enzymes with ligase activity in the next step of the reaction. The nucleic acid ligases could then make various elements for the MNAzyme C reaction, such as an assembly facilitator C, a partzyme A, B, or components thereof. So, for example, one ligase reaction driven by the product of one initial MNAzyme could make an assembly facilitator C for MNAzyme C and another ligase reaction driven by the product of another initial MNAzyme could make a partzyme for MNAzyme C. In such an example, the assay could be arranged such that only when both targets are present to drive both of the ligase reactions and hence make both the assembly facilitator and the partzyme, then MNAzyme C is assembled and catalytically active. This would be a mechanism for detection of multiple targets. Only in the presence of the required number of targets would all the required elements of MNAzyme C be available to modify the substrate C. In this example, the added elements of the reaction mix would be tailored according to how many MNAzyme C elements are made by virtue of recognition of the original targets. So, for example, if two targets were monitored and this in turn drives reactions which result in creation of an assembly facilitator C and partzyme A for MNAzyme C, then only the component partzyme B for MNAzyme C and the substrate C would need to be present to allow the formation of MNAzyme C complexes and the third step in the reaction to proceed.

Similarly, one or more assembly facilitators (e.g. targets) could be detected and feed a number of different elements into one subsequent (e.g. ligation) step. For example, with reference to FIG. 9, one initial reaction could provide the 5' ligase substrate and another initial reaction could produce the 3' ligase substrate. Alternatively, in another example similar to FIG. 12, one initial MNAzyme cleaver could produce the 5' ligase substrate for MNAzyme B and one initial MNAzyme ligase could create a partzyme for MNAzyme ligase B. Only when both products are available to participate in the formation of a MNAzyme complex will the ligase substrates be modified and the cascade reaction continue. It will be understood that the different assembly facilitators (e.g. targets) used in such strategies may comprise different molecules or different sequences within one molecule, or a combination. For example, three different SNPs within one molecule could be detected by three different MNAzymes.

It will be recognised that there are many other variations to this strategy. The general concept of using multiple targets to provide a number of different elements to a reaction which are all required for the reaction to proceed is applicable in many reactions and cascades. The number of targets that are detected can vary e.g. two or more targets may be detected. It could be applied to one or many steps of a cascade. It could also be applied "directly" by providing a component or components for the next step in the cascade, or "indirectly" by allowing a reaction later in the cascade to occur, or various combinations thereof. So, for example, one MNAzyme directed by one target could provide a molecule required for the next reaction and another MNAzyme directed by another target could provide a product required for the next or other following reaction. It would be obvious that other variations may also apply. It would be obvious that this strategy can also be applied to enzymes which effect different modifications (e.g cleavage or ligation) as described above. In addition various combinations of products made by a varying number of nucleic acid enzymes responding to various numbers of targets are possible, which include but are not limited to, partzymes, assembly facilitators and other MNA complex components. A number of nucleic acid enzymes responding to a number of targets may produce one or more components of an additional nucleic acid enzyme or nucleic acid enzyme complex or may produce all the components of an additional nucleic acid enzyme or nucleic acid enzyme complex.

Another example of a cascade reaction which uses nucleic acid enzymes which can cleave substrates, together with nucleic acid enzymes which can ligate substrates is illustrated in FIG. 15. In this example the process of ligation results in the generation of a new assembly facilitator. In step (1) the MNAzyme cleaver 1 assembles only in the presence of an assembly facilitator (e.g. a target nucleic acid) and then cleaves MNAzyme substrate 1 releasing a 5' cleavage product with a 2', 3' cyclic phosphate terminus. In step (2) a DNAzyme ligase (or an MNAzyme ligase) ligates the 5' cleavage product from step (1) to a 3' ligation substrate thus creating a ligation product which can serve as an assembly facilitator for another MNAzyme cleaver 2. In step (3) the assembly facilitator formed by ligation in step (2) directs the assembly of partzymes which form MNAzyme cleaver 2 which can cleave substrate 2 into two products, a 5' cleavage product with a 2', 3' cyclic phosphate terminus and 3' cleavage product. A detectable signal can be generated following cleavage of substrate 2 if this substrate were labelled, for example, with a fluorophore and quencher dye pair. Similar to the linear versions of the cascades illustrated in FIGS. 9 and 12, each step in the cascade in FIG. 15 employs a nucleic acid enzyme, some or all of which may be undergoing multiple turnover whereby a single nucleic acid enzyme (e.g. a DNAzyme or MNAzyme) may perform multiple cleavage or ligation or other modifications at one or more steps in the cascade. Multiple turnover may facilitate amplification at one or more steps in the cascade resulting in amplification of the signal detected during one or more step(s).

Further, an extension of the linear cascade illustrated in FIG. 15 could result in a feedback amplification cascade. If the sequence of the 5' cleavage product of MNAzyme cleaver 2 were the same as the 5' cleavage product of MNAzyme cleaver 1 then the 5' cleavage product of MNAzyme cleaver 2 could also serve as a 5' substrate for the DNAzyme ligase (or MNAzyme ligase) and a feedback amplification cascade reaction could be initiated. In this reaction MNAzyme cleaver 2 would constantly generate 5' cleavage products which could in turn serve as a substrate for ligation by the DNAzyme ligase (or MNAzyme ligase) thus allowing the creation of more assembly facilitators that could direct the assembly of more MNAzyme cleaver 2. It is envisaged this strategy could provide a mechanism for feedback signal amplification following initiation of a reaction by an assembly facilitator (eg a target analyte) which could allow assembly of MNAzyme cleaver 1. The strategy could allow detection of assembly facilitators (eg target analytes) followed by signal amplification using a DNAzyme (or MNAzyme) which can ligate substrates and MNAzymes which can cleave a substrate. Other variations of this schema are described throughout the specifications.

Another exemplary method for generating a feedback cascade reaction using two types of nucleic acid enzymes namely nucleic acid enzymes which can cleave substrates, and nucleic acid enzymes which can ligate substrates is proposed in FIG. 16. FIG. 16 is but one of a number of variations of this general strategy. In step (1) the MNAzyme cleaver 1 assembles only in the presence of an assembly facilitator (e.g. a target nucleic acid) and then cleaves MNAzyme substrate 1 releasing a 5' cleavage product with a 2', 3' cyclic phosphate terminus and a 3' waste product. In step (2) the DNAzyme ligase (or MNAzyme ligase) ligates the 5' cleavage product from step (1) to a 3' ligation substrate thus creating a ligation product which can serve as an assembly facilitator for an MNAzyme cleaver 2. In step (3) the assembly facilitator formed by ligation in step (2) directs the assembly of partzymes to form MNAzyme cleaver 2 which can cleave substrate 2 into two products, a 5' cleavage product with a 2', 3' cyclic phosphate terminus and 3' cleavage product. A detectable signal can be generated following cleavage of substrate 2 if this substrate were labelled, for example, with a fluorophore and quencher dye pair. Further, if the sequence of one of the cleavage products of MNAzyme cleaver 2 were useful as an assembly facilitator component for an MNAzyme cleaver 3 this could facilitate a feedback cascade. In this case, MNAzyme cleaver 3 may have different sensor arms than MNAzyme cleaver 1 but would require at least one substrate arm in common with MNAzyme cleaver 1 in order to provide at least the same 5' ligation substrate to participate in the ligase reaction of step (ii). (In FIG. 16, given it is the same substrate as MNAzyme cleaver 1 (substrate 1), the substrate arms will be the same for MNAzyme cleavers 1 and 3.) In step 4 an MNAzyme cleaver 3 could assemble in the presence of an assembly facilitator component generated by cleavage by the MNAzyme cleaver 2. Further, MNAzyme cleaver 3 could cleave a substrate and generate a 5' cleavage product which could be the same as the 5' cleavage product produced by cleavage of substrate 1 by MNAzyme cleaver 1. In turn, this product could also serve as a 5' substrate for the DNAzyme (or MNAzyme) ligase and a feedback amplification cascade reaction could be initiated. In this reaction MNAzyme cleaver 3 would be constantly generating 5' cleavage product which in turn could serve as a substrate for ligation by the DNAzyme (or MNAzyme) ligase to create more assembly facilitators that could direct the assembly of more MNAzyme cleaver 2. MNAzyme cleaver 2 could then produce more assembly facilitator components for more MNAzyme cleaver 3 and a feedback cascade would be created. This strategy could provide a mechanism for feedback signal amplification following initiation of a reaction by an assembly facilitator (eg a target analyte) which directs assembly of MNAzyme cleaver 1. The strategy would allow detection of assembly facilitators (eg target analytes) followed by signal amplification using a DNAzyme (or MNAzyme) which could ligate substrates and MNAzymes which could cleave substrates.

It will be understood that while a number of the above examples refer to use of a 5' cleavage product as a ligation substrate in a subsequent reaction, that it would also be possible to use a 3' cleavage product as a ligation substrate in a subsequent reaction, or both. Additionally, either a 5' or 3' cleavage product, or both, could be used as a component of a subsequent or preceding nucleic acid enzyme complex. It would also be understood that ligatable substrates may have different termini depending on the ligase used. For example, in addition to 2'3' cyclic phosphate and 5' hydroxyl termini, they may have, for example, 2'3' diol termini and 5' triphosphate termini (see Table 4). MNAzymes with cleavage activity can be selected based on the linkage to be cleaved.

In further variations of this and other examples in the specification, the DNAzyme (or MNAzyme) with ligase activity could ligate fragments and form a DNAzyme capable of cleaving substrate 2 to create an assembly facilitator or other component for another MNAzyme (labelled as MNAzyme cleaver 3 in FIG. 16). As such, in this variation MNAzyme cleaver 2 could be replaced with a DNAzyme cleaver. In another exemplary strategy the DNAzyme (or MNAzyme) ligase could ligate fragments and create a new partzyme capable of associating with another partzyme and an assembly facilitator present in the reaction thus forming an MNAzyme cleaver 2 which could cleave substrate 2 to create an assembly facilitator component for an MNAzyme 3. Other variations on this scheme are possible and are described elsewhere in the specification.

The skilled addressee will appreciate that a number of alternative MNAzyme complexes are possible and may be used in cascades. Several of these designs are illustrated in FIG. 6 where some examples of active MNAzyme complexes are shown in Panels A to D. These structures are all capable of forming catalytically active enzymes, which can modify (e.g. cleave) substrate (S). The illustration contains schemes for MNAzymes, which include one assembly facilitator F1 (panel A), two assembly facilitator components F1 and F2 (panels B and D) or three assembly facilitator components F1, F2 and F3 (panel C). The example shown in panel A includes sensor arms with self complementary regions within the partzyme sensor arms. MNAzymes may also include one or more stabilising arms (sA) as shown in panel D. Variations in one panel could be used in combination with a variation in another panel.

The skilled addressee will appreciate that a number of cascades are demonstrated throughout the specification. It will also be appreciated that the cascades are modular in nature and thus numerous variations to the cascades are possible. Table 3, below provides a non-exhaustive list of possible variations. The skilled addressee will realise that other variations are possible and are included within the scope of the invention.

TABLE 3

Some possible cascades using combinations of MNAzymes or MNAzymes and DNAzymes.

| | *Step | Enzyme | Function |
|---|---|---|---|
| Assay set up variation 1 (e.g. Example 6, FIG. 9; Example 7 and 9, FIG. 12) | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new partzyme for an MNAzyme cleaver 2 required for step 3. |
| | 3 | MNAzyme cleaver 2 | Use the partzyme/ligation product from step 2 as a component for an MNAzyme cleaver 2 which can cleave a substrate. |
| Assay set up variation 2 (e.g. Example 12, FIG. 15) | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new assembly facilitator for an MNAzyme cleaver 2 required for step 3. |
| | 3 | MNAzyme cleaver 2 | Use the assembly facilitator/ligation product from step 2 to facilitate assembly of an MNAzyme cleaver 2 which can cleave a substrate. |
| Assay set up variation 3 | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new DNAzyme required for step 3. |
| | 3 | DNAzyme | Use the DNAzyme/ligation product from step 2 to modify a substrate, for example by cleavage, ligation or other enzymatic activity. |

TABLE 3-continued

Some possible cascades using combinations
of MNAzymes or MNAzymes and DNAzymes.

| | *Step | Enzyme | Function |
|---|---|---|---|
| Assay set up variation 4 (e.g. Example 13, FIG. 16) | 1 | MNAzyme cleaver | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new partzyme for an MNAzyme required for step 3. |
| | 3 | MNAzyme (e.g. a cleaver or ligase) | Use the partzyme/ligation product from step 2 as a component for another MNAzyme which can modify (e.g. cleave or ligate) a substrate to create a product useful as an assembly facilitator or assembly facilitator component in step 4. |
| | 4 | MNAzyme | Use the assembly facilitator or assembly facilitator component generated in step 3 to form an MNAzyme, which can modify a substrate, for example by cleavage, ligation or other enzymatic activity. |
| Assay set up variation 5 (e.g. Example 13, FIG. 16) | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new assembly facilitator for an MNAzyme cleaver 2 required for step 3. |
| | 3 | MNAzyme cleaver 2 | Use the assembly facilitator/ligation product from step 2 to facilitate assembly of an MNAzyme cleaver 2, which can cleave a substrate to create a product useful as an assembly facilitator component in step 4. |
| | 4 | MNAzyme | Use the assembly facilitator component generated in step 3 to form an MNAzyme 3, which can modify a substrate, for example by cleavage, ligation or other enzymatic activity. |
| Assay set up variation 6 | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new DNAzyme required for step 3. |
| | 3 | DNAzyme | Use the DNAzyme/ligation product from step 2 to modify a substrate to create a product useful as an assembly facilitator or assembly facilitator component in step 4 |
| | 4 | MNAzyme | Use the assembly facilitator or assembly facilitator component generated in step 3 to form an MNAzyme, which can modify a substrate, for example by cleavage, ligation or other enzymatic activity. |
| Assay set up variation 7 | 1 | MNAzyme cleaver 1 | Detect assembly facilitator (eg target) and cleave a substrate to create a product useful as a substrate in step 2. |
| | 2 | MNAzyme or DNAzyme ligase | Use the product from step 1 as a substrate, which can be ligated to a second ligation substrate to create a new substrate required for step 3. |
| | 3 | MNAzyme or DNAzyme cleaver | Use the substrate/ligation product from step 2 as a substrate for an MNAzyme or DNAzyme cleaver, which can cleave the substrate to create a product useful as an assembly facilitator component in step 4. |
| | 4 | MNAzyme | Use the assembly facilitator component generated in step 3 to direct assembly of a further MNAzyme, which can modify a substrate, for example by cleavage, ligation or other enzymatic activity |
| Assay set up variation 8 | 1 | MNAzyme cleaver 1 | Detect assembly facilitator (eg target) and cleave a substrate to create a product useful as a substrate in step 2. |

TABLE 3-continued

Some possible cascades using combinations
of MNAzymes or MNAzymes and DNAzymes.

|  | *Step | Enzyme | Function |
|---|---|---|---|
|  | 2 | MNAzyme or DNAzyme ligase 1 | Use the product from step 1 as a substrate, which can be ligated to a second ligation substrate to create a new component (eg a partzyme or assembly facilitator) for an MNAzyme cleaver 2 required for step 3. |
|  | 3 | MNAzyme cleaver 2 | Use the component/ligation product from step 2 as a component for an MNAzyme cleaver 2, which can cleave a substrate to create a product useful as an ligation substrate in step 4. |
|  | 4 | MNAzyme or DNAzyme ligase 2 | Use the product from step 3 as a substrate, which can be ligated to a second ligation substrate to create a new DNAzyme cleaver required for step 5. |
|  | 5 | DNAzyme cleaver | Use the DNAzyme/ligation product from step 4 to cleave the substrate used in step 1. |
| Assay set up variation 9 | 1 | MNAzyme cleaver 1 | Detect assembly facilitator (eg target) and cleave a substrate to create a product useful as a substrate in step 2. |
|  | 2 | MNAzyme or DNAzyme ligase 1 | Use the product from step 1 as a substrate, which can be ligated to a second ligation substrate to create a new component (eg a partzyme or assembly facilitator) for an MNAzyme cleaver 2 required for step 3. |
|  | 3 | MNAzyme cleaver 2 | Use the component/ligation product from step 2 as a component for an MNAzyme cleaver 2, which can cleave a substrate to create a product to use as an ligation substrate in step 4. |
|  | 4 | MNAzyme or DNAzyme ligase 2 | Use the product from step 3 as a substrate, which can be ligated to a second ligation substrate to create a new component (eg assembly facilitator or partzyme) for a further MNAzyme cleaver required for step 5. |
|  | 5 | MNAzyme cleaver | Use the ligation product from step 4 as a component to assemble a further MNAzyme which can cleave the substrate used in step 1. |
| Assay set up variation 10 (e.g. Example 6, FIG. 9; Examples 7 and 9, Figure 12; Example 12, FIG. 15) | 1 | MNAzyme cleaver 1 | Detect assembly facilitator (eg target) and cleave a substrate to create a product useful as a substrate in step 2. |
|  | 2 | MNAzyme or DNAzyme ligase | Use the product from step 1 as a substrate, which can be ligated to a second ligation substrate to create a new component (eg a partzyme or assembly facilitator) for an MNAzyme required for step 3. |
|  | 3 | MNAzyme | Use the component/ligation product from step 2 as a component for an MNAzyme, which can modify a substrate, for example by cleavage, ligation or other enzymatic activity. |
| Assay set up variation 11 | 1 | MNAzyme cleaver 1 | Detect assembly facilitator (eg target) and cleave a substrate to create a product useful as a substrate in step 2. |
|  | 2 | MNAzyme or DNAzyme ligase | Use the product from step 1 as a substrate, which can be ligated to a second ligation substrate to create a new substrate required for step 3. |
|  | 3 | MNAzyme or DNAzyme | Use the substrate/ligation product from step 2 as a substrate for an MNAzyme, which can modify a substrate, for example by cleavage, ligation or other enzymatic activity. |

*Steps can be performed sequentially in individual reaction vessels, various steps can be combined or all steps could be performed in a single reaction vessel with one or more chambers. Each variation could comprise additional steps, including steps which feedback into other parts of the cascade.

A flow chart of a selection of component elements, steps or stages of cascade reactions as used in reactions in examples described herein and illustrated in the figures is shown in Scheme 1. The non-limiting flow chart demonstrates the modularity of various component elements useful in cascade reactions.

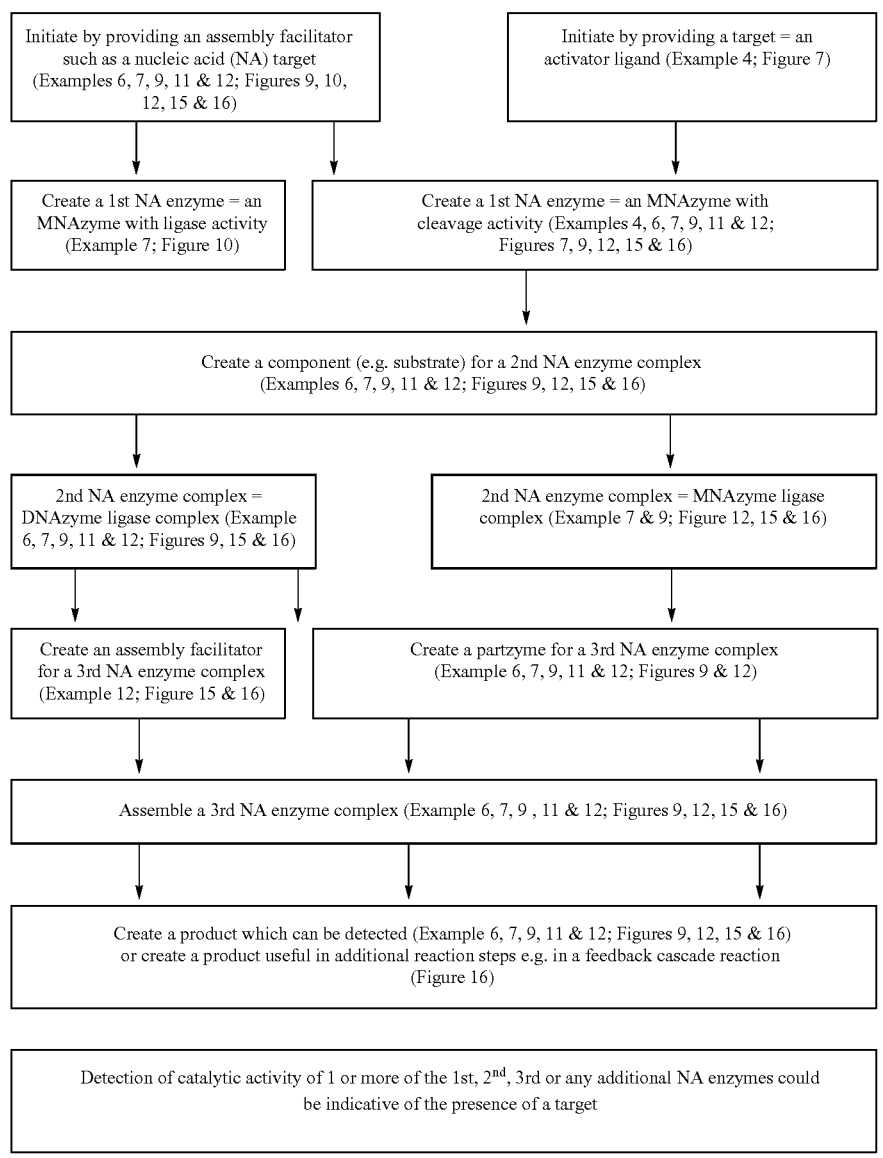

All reactions can use a combination of nucleic acid enzymes, namely multiple MNAzymes or a mix of MNAzymes and DNAzyme(s). The modifications by these enzymes involve a combination of various numbers of cleavage and/or ligation steps. In each case, the product of one step serves as a substrate, an enzyme or an enzyme component for the subsequent step. Nucleic acid enzymes which cleave can be used to create, for example, a new substrate for ligation or a new assembly facilitator component for a new MNAzyme. Nucleic acid enzymes which ligate can be used to create, for example, a new substrate for cleavage in a next step by either a DNAzyme or an MNAzyme enzyme. Further, nucleic acid enzymes which ligate can be used to create, for example, a new DNAzyme or a new component for an MNAzyme, such as an assembly facilitator, a new partzyme or a new stabiliser arm. One skilled in the art will realise that there are a large number of variations on assays which use combinations of nucleic acid enzymes and resultant products which can be used in nucleic acid enzyme cascades. For example, in some of the variations listed in Table 3 where a nucleic acid enzyme is indicated as a cleaver it could be possible to replace this with a ligase (or vice versa). Numerous individual steps useful in a number of such cascade reactions have been demonstrated in the examples and summarised in Scheme 1.

It will be obvious to one skilled in the art that multiple products produced by a single nucleic acid enzyme could be used to permit one or more nucleic acid complex(es) to function as one or more nucleic acid enzyme(s) in one or more subsequent steps.

In some of the steps in Table 3 where the product of one reaction is indicated as being useful as a particular component of a nucleic acid enzyme complex in a subsequent reaction, it could be possible to replace the component with another type of component. For example, in step 1 of Table 3 an MNAzyme could create a product that is useful as an assembly facilitator, rather than as a substrate, for assembly of a nucleic acid enzyme complex.

It will be obvious to one skilled in the art that a signal, for example a fluorescent signal can be generated at a step where a catalytic modification occurs. For example, a fluorescent signal could be generated at any step where there is cleavage by a DNAzyme or MNAzyme one could separate a fluorophore quencher dye pair and cause an increase in fluorescence. Further, a fluorescent signal could be generated at any step where there is, for example, ligation by a DNAzyme or MNAzyme one could bring a fluorophore quencher dye pair into close proximity and cause a decrease in fluorescence. Further, a fluorescent signal could be generated at multiple steps within a cascade reaction.

In all these examples of cascade reactions there is a succession of processes or operations that occur in successive stages, wherein the occurrence of each stage is typically dependent on the occurrence of a preceding stage. Further in examples whereby feedback cascades are described there would be a succession of processes or operations that occur in successive stages, whereby the occurrence of each stage is typically dependent on the occurrence of a preceding stage and whereby the occurrence of at least one preceding stage typically depends on processes or operations that occur in subsequent stages. In feedback cascades, the product of any preceding stage could serve as a component or substrate for any subsequent stage and the product of any subsequent stage could serve as a component or substrate for any preceding stage.

A cascade could be initiated by nucleic acid targets (DNA/RNA) in the presence of components for one or more MNAzyme(s), or a cascade could be initiated by other target analytes (proteins, small molecules etc) in the presence of components for one or more apta-MNAzyme(s)s. Since the reaction would only be initiated in the presence of target analytes, it could provide a technique for detection and/or identification of target analytes. The method is based on the transition between states of inactivation and activation of nucleic acid complexes. Unlike target amplification techniques such as the PCR, or the ligase chain reaction, cascades involving amplification using MNAzyme(s) require no protein enzymes to facilitate the process. Further, the ability to control and regulate the catalytic activity of MNAzyme(s) using several oligonucleotide components, such as stabiliser arm components or assembly facilitator components allows the assembly of MNAzymes to be tightly regulated by conditions and components in the microenvironment.

In relation to cascades initiated by non-nucleic acid target analytes aptamers are useful. Aptamers are DNA, RNA or peptide sequences that have the ability to recognize one or more ligands with great affinity and specificity due to their high level structure, for example, a 3-D binding domain or pocket. Many aptamers have been evolved in vitro for their capacity to bind to ligands, including for example, nucleic acids, proteins, prions, small organic compounds, and/or entire organisms. "Aptazymes" are sequences which have been previously described which have sequences comprised of both aptamer and nucleic acid enzyme sequences, for example an aptamer appended to a DNAzyme or ribozyme. Apta-MNAzymes are MNAzymes which have an aptamer appended to one of the components in an apta-MNA complex. For example an aptamer may be appended to a partzyme, an assembly facilitator, an MNAzyme substrate or any other component of an MNA complex. Association of a non-nucleic acid target analyte with the aptamer may facilitate activity of the nucleic acid enzyme. Thus a cascade may be initiated by a non-nucleic acid target analyte associating with an apta-MNAzyme, for example, as the first step in a cascade. Furthermore, in a cascade, the product of a reaction catalysed by a nucleic acid enzyme in that cascade may associate with an aptamer present on a component of a nucleic acid enzyme other than the initiating MNAzyme or apta-MNAzyme, thereby facilitating activity of that nucleic acid enzyme.

MNAzyme and/or apta-MNAzyme mediated amplification cascades could be applied to a range of biotechnology applications, especially in diagnostics, but also in other medical, veterinary, agricultural, food technology, imaging and anti-bioterrorism applications. They could allow detection of proteins, nucleic acids or other molecules for disease diagnosis by facilitating signal amplification. Catalytic nucleic acids and/or cascade reactions can be used for applications other than diagnostics, for example, within the field of computational analysis and biomolecular engineering of nanoscale devices and switches which may be used in therapeutics.

9. Method which Allows Switching Between Active and Inactive States of MNA Complexes by Removal or Creation of Components Such as the Activity Inhibitor or the Assembly Facilitator.

A transition between active MNAzymes and inactive MNA complexes, or vice versa, can be achieved by the provision or removal of MNA complex components, including but not limited to, one or more activity inhibitors, assembly facilitators, assembly inhibitors, partzymes or stabiliser arms, or parts thereof. In some embodiments, the activity inhibitor may further include a labile or cleavable linker or substrate, which may be located between two or more domains within the activity inhibitor, for example an activity inhibitor domain and an activator assembly facilitator domain. Cleavage at the linker site may allow separation of an activity inhibitor domain from an activator assembly inhibitor domain, which may then function as an assembly facilitator component and direct the assembly of an active MNAzyme. Cleavage of the linker could be achieved by several methods, including but not limited to, MNAzyme cleavage, protein enzyme cleavage, or hydrolysis induced by changes in the pH and or temperature.

Alternatively the assembly inhibitor and/or assembly facilitator could be selectively removed using a process involving branch migration and/or complementarity to component oligonucleotides. Modulator oligonucleotides which function through complementarity may do so by altering the secondary structure of oligonucleotides to which they bind. In some embodiments this may result in an alternate conformation where an activator sequence is now able to assemble with other components to form active MNAzymes. By way of example, such a modulator oligonucleotide may cause the disruption of intramolecular structures such as hairpins which constrain activator molecules in non-functional conformations.

An alternate exemplary strategy is designed to facilitate switching an MNA complex between the "on state" of an active MNAzyme to the "off state" of an MNAi complex using a second MNAzyme with ligase activity (or a DNAzyme with ligase activity). With reference to FIG. 13, an active MNAzyme A, which could be capable of modifying (eg cleaving or ligating) a substrate(s) A could be formed in the presence of assembly facilitator component 1 (AFC 1) and assembly facilitator component 2 (AFC 2). A second MNAzyme B, which has ligase activity, could form in the presence of assembly facilitator 3 (AF3) and could then ligate AFC 2 with an activity inhibitor component (AIC) causing the formation of an activity inhibitor (AI). This AI could bind to the partzyme components for MNAzyme A and result in the formation of an MNAi A complex which is inactive. As such the MNAzyme ligase in this example could operate as an off switch to inactivate an MNAzyme A. Alternatively a DNAzyme ligase could replace the MNAzyme ligase and be used to operate as an off switch to inactivate an MNAzyme A.

The inactive MNAi complex and the catalytically active MNAzyme would represent two alternate states for the assembled components, namely an "off" state and the "on" state respectively.

10. Kits

The present invention also provides kits for practicing the methods disclosed herein. Typically, kits for carrying out the methods of the present invention contain all the necessary reagents to carry out the method. Typically, kits may comprise at least a first container containing a first nucleic acid complex (e.g. an MNA complex), wherein formation of a first nucleic acid enzyme requires the addition of a sample putatively containing a target to be detected, identified and/or quantitated. Formation of the enzyme may lead to the production of a component, for example a substrate, suitable for participation in a subsequent reaction. In the subsequent reaction the component allows a further nucleic acid complex to function as a nucleic acid enzyme. Reagents to allow formation of further nucleic acid complexes which form nucleic acid enzyme complexes when contacted by a component produced by a nucleic acid enzyme of a previous reaction may also be provided.

In certain embodiments components for each of the nucleic acid complexes which can allow formation of active nucleic acid enzyme complexes may be present in the same or separate containers. In other embodiments components for each of the nucleic acid complexes which can allow formation of active nucleic acid enzyme complexes may be present in separate containers. For example, in one embodiment a kit may comprise one or more required components for each of the nucleic acid complexes in separate containers.

It will be understood that not all components for all nucleic acid complexes are required to be in the kit as they may be generated as part of a cascade reaction. Components which allow multiplex reactions are also envisaged.

In other embodiments components for additional nucleic acid enzyme complexes with, for example, either cleavage or ligase activity may also form part of the kits of the present invention. In yet other embodiments the kits of the present invention may include DNAzymes or parts thereof.

Typically, the kits of the present invention will also comprise one or more other containers, containing for example, wash reagents, and/or other reagents as required in the performance of the methods of the invention.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods. Kits and methods of the invention may be used in conjunction with automated analysis equipment and systems, for example, including but not limited to, real time PCR machines.

For application to detection, identification or quantitation of different targets or events, a single kit of the invention may be applicable, or alternatively different kits, for example containing reagents specific for each target, may be required.

Methods and kits of the present invention find application in any circumstance in which it is desirable to detect, identify or quantitate any entity or event.

11. Methods of Making MNAzymes

The present invention also provides methods for engineering MNAzymes from uni-molecular DNAzymes.

DNAzymes and/or ribozymes are known which are capable of catalytic modification of at least one substrate wherein the modification may be selected from the group comprising cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage The methods of making MNAzymes described herein are applicable to a plurality of nucleic acid enzymes such as those above and including but not limited to those described in Hobartner and Silverman (2007) and those listed in the table below.

TABLE 4

Some uni-molecular nucleic acids enzymes which may be used to form an MNAzyme.

| Reaction catalysed | Specific nucleic acid enzyme (& primary composition) | Substrate requirements | Product |
| --- | --- | --- | --- |
| Cleavage | hammerhead ribozyme (RNA) | NU*X<br>3'-5' RNA linkage | 2'3' cyclic phosphate and 5' hydroxyl |
|  | 10:23 DNAzyme (DNA) | R*Y<br>3'-5' RNA linkage | 2'3' cyclic phosphate and 5' hydroxyl |
|  | 8:17 DNAzyme (DNA) | A*G<br>3'-5' RNA linkage | 2'3' cyclic phosphate and 5' hydroxyl |
|  | 7Q10 DNAzyme (DNA) | UA*GR<br>2'-5' RNA linkage | 2'3' cyclic phosphate and 5' hydroxyl |
|  | 7Z81 DNAzyme (DNA) | UA*GR<br>2'-5' RNA linkage | 2'3' cyclic phosphate and 5' hydroxyl |
| Ligation | 7Q10 DNAzyme (DNA) | UA*GR<br>2'3' cyclic phosphate and 5' hydroxyl | 2'-5' RNA linkage |
|  | 7Z81 DNAzyme (DNA) | UA*GR<br>2'3' cyclic phosphate and 5' hydroxyl | 2'-5' RNA linkage |
|  | 9DB1 DNAzyme (DNA) | D*RA<br>2'3' diol and 5'-triphosphate | 3'-5' RNA linkage |

The skilled addressee will recognise that many DNAzymes have similar basic structures with multiple domains. These DNAzymes have a conserved catalytic domain (catalytic core) flanked by two non-conserved substrate-binding domains ("substrate arms"), which specifically recognize and hybridise to the substrate. The substrate binding domain can be tailored to any substrate provided the substrate contains a site which can be modified by the DNAzyme. Several catalytic nucleic acids, including the hammerhead ribozyme, the 10:23 and 8:17 DNAzymes, the "7Z81", "7Z48" and "7Q10"

ligases, the "UV1C" thymine dimer photoreversion DNAzyme and the "DAB22" carbon-carbon bond forming DNAzyme, have similar basic structures with multiple domains.

With reference to FIG. 14, a method for engineering an MNAzyme from a uni-molecular DNAzyme (top left hand side structure) is illustrated whereby in the first step, positions are identified within the DNAzyme catalytic core at which it can be split, such that each partial portion of the catalytic core can be distributed between two partial sequences such that the two partial cores together constitute an entire catalytic core (top right hand side structure). Two oligonucleotides A and B (candidate partzymes) can then be synthesised (bottom left hand side structure). An oligonucleotide A can be synthesised to contain (i) one substrate binding arm portion capable of binding to a substrate, (ii) one partial catalytic core portion, and (iii) one sensor arm portion capable of binding to an assembly facilitator molecule. A second oligonucleotide B can be synthesised such that it contains (i) one substrate binding arm capable of binding to the same substrate as oligonucleotide A, whereby oligonucleotide B binds the substrate in a position adjacent to that of oligonucleotide A, (ii) one partial catalytic core portion which contains those bases from the entire DNAzyme catalytic core which are not incorporated into oligonucleotide A and (iii) one sensor arm sequence capable of binding to the same assembly facilitator as oligonucleotide A, whereby oligonucleotide B binds the assembly facilitator in a position adjacent to that of oligonucleotide A. This process can be repeated thus making a series of pairs of oligonucleotides A and B which incorporate the structure and domains of partzymes, but may or may not have catalytic activity in the presence of a substrate and an assembly facilitator.

Some or all of the candidate partzyme pairs (pairs of oligonucleotides A and B from the series) can then be incubated in the presence of the assembly facilitator complementary to the sensor arm portions of the partzymes and a substrate which is complementary to the substrate arm portions of the partzymes. Incubation is performed under conditions which are compatible with modification of a substrate by the DNAzyme from which the partial catalytic core sequences were derived. Pairs of oligonucleotides A and B, which can perform the same type of modification (e.g. cleavage) to the substrate as the DNAzyme from which partial sequences were derived, are useful as partzymes which can be assembled into MNAzymes and MNAzyme complexes (bottom right hand side structure). The sequences of the partial catalytic cores are suitable for incorporation into other partzymes of new MNAzymes. New partzymes can be synthesised which are tailored to new substrates (by changing the substrate binding domains of each partzyme) and/or to new assembly facilitators (by changing the sensor binding domains of each partzyme).

The method for engineering an MNAzyme that acts on a first and second substrate e.g. a MNAzyme ligase starting from a uni-molecular nucleic acid enzyme (e.g. DNAzyme ligase) requires the similar steps whereby in the first step, positions are identified within the DNAzyme catalytic core at which it can be split, such that each partial portion of the catalytic core can be distributed between two partial sequences such that the two partial cores together constitute an entire catalytic core. Two oligonucleotides A and B (candidate partzymes) can then be synthesised. An oligonucleotide A can be synthesised to contain (i) one substrate binding arm portion capable of binding to a first substrate, (ii) one partial catalytic core portion, and (iii) one sensor arm portion capable of binding to an assembly facilitator molecule. A second oligonucleotide B can be synthesised such that it contains (i) one substrate binding arm capable of binding to a second substrate, (ii) one partial catalytic core portion which contains those bases from the entire DNAzyme catalytic core which are not incorporated into oligonucleotide A and (iii) one sensor arm sequence capable of binding to the same assembly facilitator as oligonucleotide A, whereby oligonucleotide B binds the assembly facilitator in a position adjacent to that of oligonucleotide A. This process can be repeated thus making a series of pairs of oligonucleotides A and B which incorporate the structure and domains of partzymes, but may or may not have catalytic activity in the presence of the substrates and an assembly facilitator.

Some or all of the candidate partzyme pairs (pairs of oligonucleotides A and B from the series) can then be incubated in the presence of the assembly facilitator complementary to the sensor arm portions of the partzymes and the two substrates which are complementary to the substrate arm portions of the partzymes. Incubation is performed under conditions which are compatible with modification (e.g. ligation) of the substrates by the DNAzyme from which the partial catalytic core sequences were derived. Pairs of oligonucleotides A and B which can perform the same type of modification (e.g. ligation) to the substrates as the DNAzyme from which partial sequences were derived are useful as partzymes which can be assembled into MNAzymes and MNAzyme complexes. The sequences of the partial catalytic cores are suitable for incorporation into other partzymes for other MNAzymes. New partzymes can be synthesised which are tailored to new substrates (by changing the substrate binding domains of each partzyme) and/or to new assembly facilitators (by changing the sensor binding domains of each partzyme).

Further, a similar method can be used to examine tolerance to changes in the partial sequence derived from splitting the DNAzyme catalytic core that can be incorporated into component partzymes. For example, modifications to the partial catalytic cores incorporated into partzymes can be made which include, by way of example, insertions, deletions, substitution with alternate DNA bases, or substitution with DNA analogues such as ribonucleotides, inosine or other analogue bases. Candidate partzyme pairs containing one or more modification(s) can then be assayed as above to determine whether or not they contain a pair of partial catalytic core sequences which are suitable for incorporation into partzymes that can assemble into catalytically active MNAzymes.

The present invention will now be further described in greater detail by reference to the following specific examples, which should not be construed as in any way limiting the scope of the invention.

EXAMPLES

Example 1

Example of an MNAzyme where Partzyme B Comprises Two Molecules

Many variations on the basic design of an MNAzyme are contemplated in the present invention. In this example, MNAzymes were assembled in the presence of an assembly facilitator from partzyme A, and partzyme B which contained two components, namely one partzyme component with a truncated sensor arm, and one component that functions as a stabiliser arm. MNAzyme assembly occurs via Watson-Crick base recognition of the partzyme sensor arms and the assembly facilitator sequence. In the following example, the use of a truncated arm and stabiliser arm was demonstrated.

The MNAzyme detection strategy used in this example is illustrated in FIG. 2 (panel (ii)) and in FIG. 3 (*i*).

An example of the oligonucleotides required for this strategy are described below:

a) a partzyme A;

b) a partzyme B comprising a first component which contains a substrate arm, a partial catalytic core and truncated sensor arm; and a second stabiliser arm component, which hybridizes to the assembly facilitator, adjacent to the truncated sensor arm of the partzyme. This stabiliser arm is designed to facilitate MNAzyme assembly when the truncated sensor arm of the partzyme is hybridized to the assembly facilitator; and c) a substrate, for example a reporter substrate.

Alternatively, oligonucleotides useful in this strategy are a partzyme B; a partzyme A comprising a first component which contains a substrate arm, a partial catalytic core and truncated sensor arm; and a second stabiliser arm component, which can hybridize to the assembly facilitator, adjacent to the truncated sensor arm of the partzyme.

Active MNAzyme assembly also requires the presence of an assembly facilitator.

1.1. Partzyme Oligonucleotides and Stabiliser Arm

In this example, the truncated sensor arm of partzyme B was only 5 nucleotides in length. The sequences of partzymes A and the two partzyme B components are shown below (5' to 3'). In the following sequences the bases in bold hybridize with the assembly facilitator, bases underlined form part of the catalytic core of the assembled MNAzyme, and bases in italics hybridize to the substrate. The "-P" indicates 3' phosphorylation of the oligonucleotide.

SEQ ID NO: 1 Partzyme A4 XdA4/2-P:
ACTGGATGTCCATCTGTCTGACAACGAGAGGAAACCTT-P

SEQ ID NO: 2 Partzyme B5 component 1 XdB5/2-P:
*TGCCCAGGG*AGGCTAGCTTATAC-P

SEQ ID NO: 3 Partzyme B stabiliser arm component XdS-P:
CTTCGTGAGGGTGAG-P 1.2. Reporter Substrate The reporter substrate used in this example was SubBi-2 end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

SEQ ID NO: 4 SubBi-2-FB: AAGGTTTCCTCguCCCTGGGCA 1.3. Assembly Facilitator Molecule The sequence of the synthetic oligonucleotide used as the assembly facilitator is below (5' to 3'). This assembly facilitator was fully matched with the partzyme B sensor arm. Nuclease-free water was used in place of target as a "no target" control.

SEQ ID NO: 5 Assembly facilitator Xd-T:
TGCCCCCTCACCCTCACGAAGGTATACAGACAGATGGACATCCAGT
TGGTGA 1.4 Reaction Conditions Detection of the assembly facilitator was measured by an increase in fluorescent signal caused by cleavage of the reporter substrate by the catalytically active MNAzyme. Reactions were initiated by the addition of substrate and the total volume of all reactions was 50 μL. Reactions were conducted at 55° C. on a FLUOstar OPTIMA (BMG Biotech). Fluorescence for each reaction was read every 2 seconds for a total of 5 minutes. All reactions contained 200 nM SubB1-2-FB, 200 nM XdA4/2-P, 200 nM XdB5/2-P, 1×PCR Buffer II (Applied Biosystem) and 25 mM $MgCl_2$. In addition, reactions contained oligonucleotides as listed in Table 5.

TABLE 5

Additional reagents in MNAzyme reactions.

| Reaction | Assembly Facilitator | Stabiliser arm |
|---|---|---|
| (i) | 200 nM of Xd-T | 200 nM of XdS-P |
| (ii) | 200 nM of Xd-T | No stabilizer arm |
| (iii) | No assembly facilitator (water control) | 200 nM of XdS-P |

1.5 Results: Assembly of Active MNAzymes in the Presence of the Partzymes and an Assembly Facilitator.

When both the assembly facilitator, and a partzyme stabiliser arm component were included in the reaction (Reaction (i): FIG. 3), active MNAzymes assembled and cleaved the substrate, resulting in an increase in fluorescence over time. In contrast, there was no increase in fluorescence in the absence of the assembly facilitator (Reaction (iii): FIG. 3). Further, the presence of the stabiliser arm was shown to be essential for formation of active MNAzymes or MNAzyme complexes. A reaction containing all reaction components including the assembly facilitator, but which lacked the stabiliser arm component, gave no increase in fluorescence over time (Reaction (ii): FIG. 3). As such, the 5 bases of the sensor arm of partzyme B were insufficient to form a stable MNAzyme or MNAzyme complex but the presence of a stabiliser arm component was shown to be capable of compensating for the short length (truncation) of the partzyme sensor arm and allowing stable MNAzyme formation under stringent temperature conditions (55° C. in this example). The stabiliser arm component is thus an essential oligonucleotide for assembly of active MNAzymes in this system, which uses a partzyme with a truncated sensor arm.

Further, when an alternative assembly facilitator, which had a single nucleotide mismatch with respect to the partzyme A sensor arm was included in a reaction containing partzyme A and the two components of partzyme B, the fluorescent signal did not increase over time (data not shown).

This example demonstrates that MNAzymes could only form in the presence of a fully matched assembly facilitator under the conditions of the experiment. One skilled in the art will appreciate that transition between an active MNAzyme and an inactive multi-component nucleic acid complex can be regulated by providing fully matched or mismatched assembly facilitators. Further, the example demonstrates the use of two-component partzymes, which comprise a first molecule that contains truncated sensor arms, and a second stabiliser arm molecule. The requirement for the presence of a stabiliser arm molecule in such systems, provides another tool with which one can regulate the assembly of MNAzymes.

Great flexibility is afforded by MNA complexes which contain multiple oligonucleotide components, the sequences of which can be tailored with respect to the melting temperature, the sequence composition and complementarity or lack thereof with other component oligonucleotides. Shorter sequences, including but not limited to, partzyme components with truncated arms, stabilizer arms, and assembly facilitator components are particularly useful in this aspect of the invention. While this example uses an MNAzyme with cleavage activity, it would be appreciated that similar structural designs for MNAzymes or MNAzyme complexes could be used in MNAzymes which cause modifications other than cleavage, for example, MNAzyme which could ligate.

Example 2

Detection of Target Analytes using MNAzymes with Ligase Activity

An example of an MNAzyme which can modify at least two substrates, such as an MNAzyme with ligase activity could be used for detection of a nucleic acid target. An MNAzyme with ligase activity could be assembled from two partzymes which comprise active partial catalytic core pairs derived from, for example, the 7Q10 DNAzyme or the 7Z81 DNAzyme as exemplified in example 7 and 9 respectively. The partzymes could have sensor arms complementary to the target nucleic acid which could act as an assembly facilitator for an active MNAzyme ligase. The substrate arms could be complementary to two substrate molecules which contain ligatable sequences with appropriate termini (e.g. Table 4).

If the 5' ligation substrate and the 3' ligation substrate were each labelled with either a fluorophore and quencher dye respectively (or vice versa) then ligation could result in a decrease in fluorescence which could serve as an indicator of the presence of the target nucleic acid. In an alternative format, if the 5' ligation substrate were labelled with a detectable moiety, for example a fluorophore, and the 3' ligation substrate were attached to a discrete location, for example on a chip, then ligation could result in the appearance of a signal at the discrete location in the presence of target nucleic acid.

The strategy could also be used for detection of other ligands if the MNAzyme were an apta-MNAzyme with ligase activity which contained an aptamer sequence capable of specifically binding the target ligand.

Further, the ligation of two substrates by an MNAzyme in the presence of a target analyte could constitute the first step in a cascade reaction.

Example 3

Mechanisms for Facilitating and Inhibiting the Assembly of Active MNAzymes or MNAi Complexes An MNAzyme is composed of partzymes, which assemble in the presence of one or more assembly facilitators, to form an active enzyme (e.g. FIGS. 1, 2, 4 (right hand panel) and FIG. 5 (i and ii)). The assembly facilitator(s), which binds to partzyme sensor arms, can be a target analyte, or can be a synthetic nucleic acid molecule(s) added to the reaction mix to drive MNAzyme assembly. In addition to their capacity to contribute to active MNAzyme assembly, partzymes can assemble into an inactive, non-catalytic, MNAi complex when they hybridise with an "activity inhibitor" molecule (FIG. 4 (left hand panel) and FIG. 5 (*iii*). Various alternative oligonucleotide sequences were tested for their capacity to regulate the assembly of either active MNAzyme or inactive MNAi complexes.

In this example (depicted in FIGS. 4 and 5), MNAzyme assembly was examined in the presence of (i) a single molecule (assembly facilitator F1/2), or (ii) two molecules (assembly facilitator component F1 and assembly facilitator component F2), whose sequences together comprise that present in facilitator F1/2. Facilitator F2 binds to the whole sensor arm of one partzyme and overlaps to bind 4 base pairs of the sensor arm of the second partzyme. In another reaction, an "activity inhibitor" molecule, which has a sequence that includes that of facilitator F2 plus an additional activity inhibitor domain, was tested for its ability to drive the reaction towards assembly of inactive MNAi complexes.

3.1 Partzyme Oligonucleotides

The sequences of partzymes A and partzyme B are shown below (5' to 3'). In the following sequences the bases in bold hybridize with the assembly facilitator, bases underlined form part of the catalytic core of the assembled MNAzyme, and bases in italics hybridize to the substrate. The "-P" indicates 3' phosphorylation of the oligonucleotide.

SEQ ID NO 6: Partzyme A RO5A4/2-P:
CAAACGAGTCCTGGCCTTGTCTACAACGAGAGGAAACCTT-P SEQ ID NO 7: Partzyme B RO5B5/2-P:
*TGCCCAGGGA*GGCTAGCTGTGGAGACGGATTACACCTTCCCACTTGC-P 3.2 Reporter Substrate The reporter substrate for this example was SubBi-2-FB with the sequence, 5' to 3', as below. SubBi-2-FB was end-labelled with a 6-FAM moiety at the 5' end and a BHQ1 moiety at the 3' end. Cleavage of SubBi-2-FB was monitored at 530 nm (FAM emission wavelength) with excitation at 485 nm (FAM excitation wavelength). The lower case bases represent RNA and the upper case bases represent DNA.

SEQ ID NO: 4 SubBi-2-FB: AAGGTTTCCTCguCCCTGGGCA 3.3 Regulator Oligonucleotides.

Several molecules were tested in this example for their ability to regulate the assembly of MNAzymes and/or MNAi complex. The sequence, which constitutes assembly facilitator F2, was also contained within the sequences of facilitator F1/2 and the activity inhibitor and is in bold and underlined.

SEQ ID NO 8: Assembly Facilitator F1/2:
GCAAGTGGGAAGGTGTAATCCGTCTCCACAGACAAGGCCAGGACTCGTTTG

SEQ ID NO: 9 Assembly Facilitator F1:
GCAAGTGGGAAGGTGTAATCCGTCT

SEQ ID NO: 10 Assembly Facilitator F2:
CCACAGACAAGGCCAGGACTCGTTTG

SEQ ID NO: 11 Activity inhibitor molecule:
AAGGTTTCCTCGTCCCTGGGCACCACAGACAAGGCCAGGACTCGTTTG

3.4 Reaction Components and Monitoring of MNAzyme Activity.

Real time monitoring of MNAzyme activity was performed on a BMG LabTech FluoStar fluorometer in a total reaction volume of 50 µL. Reactions were monitored isothermally at 55° C. for 4 minutes. The reaction was initiated by injection of the fluorescent substrate SubBi-2-FB (10 µl of 1 µM solution) into reaction mixture containing 1×PCR Buffer II (Applied Biosystems), 25 mM MgCl$_2$, 200 nM of Partzyme A RO5A4/2-P, 200 nM of Partzyme B RO5B5/2-P and either (i) 400 nM of Assembly Facilitator F1/2, or (ii) 400 nM of Assembly Facilitator component F1 and 400 nM of Assembly Facilitator component F2, or (iii) 400 nM of Activity inhibitor and 400 nM of Assembly Facilitator component F1, or (iv) no Assembly facilitator.

3.5 Results:

The results using the combinations of various regulatory or structural component oligonucleotides are shown in FIG. 5. A rapid increase in fluorescent signal, indicative of high level of MNAzyme cleavage activity, was seen in reactions containing either assembly facilitator F1/2 (FIG. 5 (*i*)), or assembly facilitator components F1 and F2 (FIG. 5 (*ii*)). No increase in fluorescence over time was observed in the absence of a facilitator (FIG. 5 (*iv*)). This demonstrates that an assembly facilitator need not always be an unbroken oligonucleotide, but rather can be split into multiple shorter facilitator components, which align adjacent to each other on one of the sensor arms of a partzyme.

No increase in fluorescent signal was observed over time in reactions containing the activity inhibitor and facilitator F1 (FIG. 5 (*iii*)). Since the activity inhibitor molecule includes the sequence of facilitator F2, then the additional non-complementary inhibitory sequence adjoined to facilitator F2 is the element driving the assembly of inactive MNAi complexes. The MNAi complex can bind to a substrate but cannot catalytically modify it. As a result, the substrate was not cleaved and fluorescence did not increase over time in the presence of MNAi complexes (FIG. 5 (*iii*)). Comparison between reactions containing the assembly facilitator components F1 and F2 (FIG. 5 (*ii*)), with those containing the assembly facilitator F1 and the activity inhibitor (which incorporates the F2 sequence) (FIG. 5 (*iii*)), demonstrates that the presence of an inhibitory domain within an activity inhibitor can provide a tool with which to regulate enzymatic activity by driving the assembly of inactive MNAi complexes and preventing the formation of active MNAzymes.

Thus an MNAzyme, designed to form in the presence of an assembly facilitator F1/2, generated fluorescence. The example demonstrated that the assembly facilitator F1/2 could be split into two parts (assembly facilitator components F1 and F2) and retain the capacity to direct the assembly of catalytic active MNAzymes. Together the two assembly facilitator components can stabilise active MNAzyme formation and cause fluorescence, provided they bind adjacent to each other on the partzyme sensor arm. Subsequent experiments, performed under identical reaction conditions, demonstrated that no increase in fluorescence over time was observed in the presence of assembly facilitator component F2 only (data not shown). As such, this example demonstrates the assembly of partzymes into active MNAzymes can require the presence of multiple component assembly facilitators. When multi-component assembly facilitators are required, the presence or absence of one or more of these components can be used to control the assembly of active MNAzymes and as such switch them on and off.

It was further discovered that an activity inhibitory molecule could prevent MNAzyme assembly by hybridising to a partzyme and disrupting the secondary structure at the junction of the two assembly facilitator component on a partzyme sensor arm which is required for enzymatic activity (see FIGS. 4 and 5 as examples). It would be appreciated by one skilled in the art, that an inhibitory molecule could be designed to hybridise to either partzyme A or B, and to either the sensor or substrate arm of partzyme.

Molecules including activity inhibitors, partzyme stabilizer arm components and assembly facilitators or components thereof, can be used to regulate the assembly of active MNAzymes and inactive MNAi complex. Transition between states of activation (MNAzyme) and inactivation (MNAi complex) can provide a mechanism for creating a molecular switch, which can be regulated by alternating between the active and inactive conformations. Such molecular switches could be applied to the control of nucleic acid replication cascades or to the regulation of autonomous therapeutic, diagnostic and computational molecular scale devices. Various protocols which can be employed to induce the dissociation of a specific oligonucleotide component are discussed throughout this document.

Example 4

Application of MNAzymes to Detect Non-Nucleic Acid Analytes Including Small Molecules Such as Adenosine 5'-Triphosphate Aptamers are single-stranded DNA or RNA molecules evolved in vitro from large pools of random-sequence oligonucleotides for their capacity to bind target analytes with high affinity and specificity. Aptamers have been selected for their ability to bind specifically to many types of analytes including proteins, carbohydrates, lipids, nucleotides, whole cells and viruses. In this example, an aptamer sequence was incorporated at the end of a partzyme (apta-partzyme) in a configuration whereby an active apta-MNAzyme was only formed in the presence of the activator ligand. There are several ways of achieving this goal, including the strategy used in the following example, which is illustrated in FIG. 7.

The nucleic acid oligonucleotides included in this exemplary apta-MNAzyme detection strategy are illustrated in FIG. 7 and include;

a) a partzyme;

b) an apta-partzyme which is a partzyme with an aptamer incorporated into one of its ends;

c) an assembly facilitator which binds to both the apta-partzyme and the partzyme enabling assembly of an active MNAzyme;

d) a substrate e.g. a reporter substrate; and e) an assembly inhibitor oligonucleotide which hybridises to the apta-partzyme in a region which spans at least part of the aptamer sequence and part of the substrate binding arm of the partzyme sequence.

In the absence of an activator ligand (FIG. 7, panel (i)), the assembly inhibitor oligonucleotide binds to the apta-partzyme thus preventing it from binding to the substrate. In the presence of an activator ligand (FIG. 7, panel (ii)), the activator ligand can interact with the aptamer sequence of the apta-partzyme, thus preventing binding of the assembly inhibitor and allowing an active apta-MNAzyme to assemble, then bind to and cleave the substrate. As such, apta-MNAzymes can only form and cause fluorescent signal generation in the presence of an activator ligand.

The strategy was demonstrated using detection of a small molecule, ATP. The 27 nucleotide long aptamer sequence used in this example has been previously reported as being highly specific for binding of ATP and dATP (Achenbach, et al 2005, Huizenga and Szostak, 1995).

4.1 Partzyme Oligonucleotides, Assembly Facilitator and Inhibitory Oligonucleotides In this example the ATP aptamer sequence was adjoined to the substrate arm of a partzyme, to produce an apta-partzyme molecule (FIG. 7). The sensor arms of the apta-partzyme and another partzyme were designed to bind to a synthetic assembly facilitator, included in the reaction to drive the assembly of MNAzymes when targets or regulatory analytes are present. The sequences of apta-partzyme AtpA2/1 and partzyme AtpB3/1 are shown below (5' to 3'). In the following sequences the bases in bold hybridize with the assembly facilitator, bases underlined form part of the catalytic core of the assembled MNAzyme, and bases in italics hybridize to the substrate. In addition, bases in plain text in partzyme AtpA2/1 indicate a DNA aptamer sequence that can bind to ATP or dATP.

SEQ ID NO: 12 Apta-Partzyme A2 AtpA2/1:
AACGTACACTGCACGCGGTCGAAATAGTGAGTACCTGGGGGAGTATTGC
GGAGGAAGGT SEQ ID NO: 13 Partzyme B3 AtpB3/1:
*CATCTCTTCT*CCGAGCGTCTGTACCGTGTAC

The sequence of the assembly facilitator is shown below (5' to 3')

```
        Assembly facilitator AtpC/1:
                                  SEQ ID NO: 14
        GTACACGGTACAGACCGTGCAGTGTACGTT
```

The sequence of the "assembly inhibitor" oligonucleotide is shown below (5' to 3').

```
        Assembly Inhibitor AtpR/1:
                                  SEQ ID NO: 15
        CCAGGTACTCACTATTT
```

4.2 Reporter Substrate

Apta-MNAzyme activity was monitored by cleavage of a dual-labelled nucleic acid reporter substrate. The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Changes in fluorescence due to cleavage of SubBi-1-FB at the ribonucleotide between the FAM and BHQ1 were monitored at 520 nm (FAM emission wavelength) with excitation at 490 nm (FAM excitation wavelength).

```
                                  SEQ ID NO: 16
        SubBi-1-FB: ACTCACTATaGGAAGAGATG
```

4.3 Target or Regulatory Analytes and Control Molecules

The activator ligands used for this example were adenosine 5'-triphosphate (ATP) and deoxyadenosine 5'-triphosphate (dATP). Guanosine 5'-triphosphate (GTP) and cytosine 5'-triphosphate (CTP) were used as negative control molecules. All molecules were purchased from Bioline. Nuclease-free water was used as a no analyte control.

4.4 Reaction Conditions

The presence of the activator ligand was measured by an increase in fluorescent signal caused by cleavage of the reporter substrate by the catalytically active apta-MNAzyme. Reactions were initiated by the addition of substrate and the total volume of all reactions was 50 μL. Prior to substrate injection, all reactions were pre-incubated at 60° C. for 5 minutes (to reduce secondary structure). Reactions were conducted at 47° C. on a FLUOstar OPTIMA (BMG Biotech). Fluorescence for each reaction was read every 3 seconds for a total of 10 minutes. Each reaction contained a final concentration of 200 nM AtpA2/1, 200 nM AtpB3/1, 200 nM AtpC/1, 200 nM AtpR/1, 200 nM SubBi-1-FB, 25 mM $MgCl_2$, 50 mM Tris HCl pH 7.5 and 2 mM of either ATP, or dATP, or GTP, or CTP or no analyte (water control).

4.5 Results: Detection and Cleavage of SubBi-1-FB Reporter Substrate

In the absence of ATP or dATP a low level of fluorescence was seen which did not increase over time, demonstrating that in the absence of ATP, the assembly inhibitor prevented the assembly of active apta-MNAzyme complexes. In the presence of ATP or dATP, the fluorescent signal was higher and it increased over time. This indicates that the inhibitor oligonucleotide was displaced by dATP and ATP and an active apta-MNAzyme was formed. Assembly of the apta-MNAzyme was ligand-dependent. In the presence of GTP or CTP a low level of fluorescence was seen which did not increase over time. The fluorescence observed in the presence of GTP or CTP was similar to that observed in the absence of ATP or dATP i.e. in the no ligand water control. This example demonstrates that MNAzymes can be coupled to aptamers for the detection of analytes in an approach that is highly specific for the target analyte. This example further demonstrates that an assembly inhibitor molecule can be used to control the assembly of apta-MNAzymes, and that a molecule e.g. ATP can serve as a activator ligand or molecular regulator in this system.

One skilled in the art will recognise that the design of this strategy can be flexible. The aptamer can be incorporated, for example, into either end (5' or 3') of either of the two partzymes containing partial catalytic core sequences. As such, the assembly inhibitor can bind to the aptamer region and to either the substrate arm (that binds the substrate) or the sensor arm (that binds the assembly facilitator). In the former design (FIG. 7 and this example), the inhibitor blocks binding of the substrate. In the latter design, the inhibitor would prevent binding of the assembly facilitator with the apta-partzyme and therefore would prevent assembly of active MNAzymes.

The literature contains sequences for a large number of aptamers capable of detecting many types of analytes. These include proteins, carbohydrates, lipids, prions, nucleotides, whole cells and viruses. Aptamers to all these types of analytes could be linked to partzymes to detect a very diverse range of molecules. Reaction conditions (buffer, temperature, divalent cation concentration etc), which are compatible with both binding of analytes to aptamers (or apta-partzymes) and cleavage of a reporter substrate by an MNAzyme, can be determined by empirical testing.

MNAzyme activity can be modulated by the removal or addition of the assembly inhibitor. Changing the oligonucleotide sequence, the melting temperature and or concentration can achieve finer regulation. The hybridization of the assembly inhibitor within an MNA is affected by many factors, including but not limited to, salt concentration, cation concentration, temperature and the presence or absence of additives (e.g. DMSO). As such, entities that affect hybridization can provide a tool for controlling the assembly and disassembly of MNAzymes, The assembly facilitator can be removed by physical manipulation of components and can be achieved, for example, by exploiting either physical properties of attached moieties as molecular "hooks", and/or by exploiting inherent properties of the oligonucleotides, for example, negative charge, or sequence complementarity.

MNAzymes and apta-MNAzymes can be used for detection of target analytes including nucleic acid targets and/or non-nucleic acid ligands. Further they can be used to detect analytes in a direct detection format (as demonstrated in this example) or they can be used in nucleic acid enzyme cascade reactions. In one embodiment an MNAzyme and/or an apta-MNAzyme could facilitate the first step in the cascade. In one embodiment the nucleic acid cascade could use a combination of MNAzymes, or a combination of MNAzyme(s) and DNAzyme(s) which could modify one or more substrate(s) by, for example, cleavage and/or ligation.

Example 5

A Cascade Reaction which Uses a Nucleic Acid Enzyme with Ligase Activity and a Nucleic Acid Enzyme with Cleavage Activity A reaction useful for inclusion in cascade reactions and/or molecular switches exploiting the catalytic activities of two nucleic acid enzymes is outlined in FIG. 8. One reaction could be mediated by a DNAzyme ligase, which can ligate a 5' substrate with a 2',3'-cyclic phosphate and a 3' substrate with a 5' hydroxyl to form a ligation product with a non-native 2'-5' linkage at the junction of the two substrates. Examples of such DNAzyme ligases are known in the art (see summary Table 4). The other reaction could be mediated by an MNAzyme cleaver which could use the ligation product as a substrate and could cleave it at the non-native 2'-5' linkage created by ligation. Cleavage could produce two cleavage products, a 5' product which would have a 2',3'-cyclic phosphate terminus and a 3' product which would have a 5'-hydroxyl terminus. In turn, one or both of the cleavage products could serve as a substrate or substrates for the DNAzyme ligase.

Alternatively a reaction could be mediated by a DNAzyme ligase, which can ligate a 5' substrate with a 2',3'-diol and a 3' substrate with a 5'-triphosphate terminus to form a ligation product with a native 3'-5' linkage at the junction of the two substrates. Examples of such DNAzyme ligases are known in the art (see summary Table 4). The other reaction could be mediated by an MNAzyme cleaver which could use the ligation product as a substrate and could cleave it at the native 3'-5' linkage created by ligation. Cleavage could produce two cleavage products, a 5' product which would have a 2',3'-cyclic phosphate terminus and a 3' product which would have a 5'-hydroxyl terminus. In turn, one or both of the cleavage products could serve as a substrate or substrates for a DNAzyme ligase that can ligate such termini.

Alternatively, an MNAzyme with cleavage activity may cleave at a site within a ligation product which is not at the junction of the two ligatable substrates provided the cleavage site requirement are met at this site.

In a preferred format (FIG. 8), a DNAzyme ligase could ligate a first oligonucleotide (oligo 1) to a second oligonucleotide (oligo 2) to create a third ligation product (LP) oligonucleotide (oligo 3), provided oligo 1 and oligo 2 have 2',3'-cyclic phosphate and 5'-hydroxyl termini. In turn, LP-oligo 3 could be cleaved by an MNAzyme into cleavage products (CP), CP-oligo 1 and CP-oligo 2, thus regenerating oligonucleotides with 2',3'-cyclic phosphate and 5'-hydroxyl termini, which could participate in further rounds of ligation.

In a multiplex format, several oligonucleotides, for example four oligonucleotide, each with 2',3'-cyclic phosphate and a 5'-hydroxyl termini, could be ligated by a series of DNAzyme ligases into 16 new unique LP sequences (i.e. each combination of oligonucleotides 1, 2, 3 and 4). A series of MNAzymes could then cleave LP-oligo 1 through to LP-oligo 16 back into component oligonucleotides, now called CP-oligo 1, CP-oligo 2, CP-oligo 3 and CP-oligo 4. Alternatively, an MNAzyme with cleavage activity may cleave at a site within a LP which is not at the junction of the two ligatable substrates provided the cleavage site requirements are met at this site. In this scenario complex mixtures of oligonucleotide sequences could be created, shuffled and/or rearranged.

A set of MNAzymes could use a constant assembly facilitator (as illustrated) in FIG. 8, and/or the MNAzyme could use the LP sequences from previous ligation rounds as its assembly facilitator. As such, new information (input) data produced by the ligation of oligonucleotides, could be recognized "read" by the MNAzyme. The MNAzyme could then cleave "write" to produce new output products, and/or information. Systems where MNAzymes could read the input LP, and then cleave them into CP-oligos, other than those originally in the pool of starting molecules, could be used to rewrite or recode new output sequences.

In some embodiments, ligation by a DNAzyme could "write" input data, for example, by making new assembly facilitators, or components thereof. An MNAzyme could "read" the data, by interrogating the information encoded within the assembly facilitator using the partzyme sensor arms. An MNAzyme could then "write" data, for example, a new sequence (e.g. a cleavage product) thus creating new output data which could then be "read" by a DNAzyme ligase (e.g. by ascertaining the suitability of MNAzyme cleavage products to serve as ligation substrates for the DNAzyme ligase).

In other embodiments, cleavage by an MNAzyme could "write" input data, for example, by creating new ligatable substrates. A DNAzyme ligase could "read" the data, by interrogating the information encoded within the substrates using the substrate binding arms. A DNAzyme ligase can then "write" data, for example, by making a new ligation product sequence. The new ligation product could serve as a component necessary for formation of an active MNAzyme cleaver, for example it could serve as a new assembly facilitator or component thereof. The ligation product could thus provide new output data which could then be "read" by an MNAzyme cleaver (by ascertaining the suitability of DNAzyme ligation product to serve as an assembly facilitator or assembly facilitator component for the MNAzyme cleaver).

As such, this MNAzyme/DNAzyme ligase cascade could form an automaton. Such devices are capable of converting information from one form into another, according to a defined procedure. In this case the procedures would be encoded and directed by the substrate arms and/or the sensor arms of the MNAzymes and DNAzyme ligases.

An automaton, which was capable of solving computational problems was developed by Benenson et al, 2001, using DNA and protein enzymes (a restriction endonuclease and a ligase). The restriction endonuclease cleaved the double stranded DNA and the protein ligase ligated the cleavage products in a cascade reaction. The protein enzymes served as the "hardware" and the DNA encoded the "software". The input and automaton were programmed by selection of the appropriate DNA software sequences. The automaton proceeded via a cascade of restriction endonuclease cleavage, hybridization and ligation cycles, producing a detectable output molecule that encoded the automaton's final state and thus the computational result (Benenson et al, 2001).

The DNAzyme ligase/MNAzyme cascade could be used in a similar manner to the cascade used by Benenson et al (2001) and thus provide a device capable of solving computational problems. Unlike Benenson's device, a DNAzyme ligase/MNAzyme cascade, requires no protein enzymes to achieve the same results. While Benenson's device was programmed by double stranded DNA, a DNAzyme ligase/MNAzyme cascade, would be encoded by the various sequences, including for example, the initial input oligonucleotide(s), the substrate arms and/or the sensor arms of the MNAzymes and the substrate arms of DNAzyme ligases.

In another embodiment, the DNAzyme ligase/MNAzyme cascade could also be used to "shuffle" oligonucleotide sequences as a method of constructing, and/or increasing the diversity of, molecular libraries.

In some embodiments, a DNAzyme ligase could be used to create or destroy components of MNAzyme and or inactive MNA. By way of example a DNA ligase could attach an "activity inhibitor" to an "assembly facilitator component" resulting in the assembly of MNAi complex ("off" state). Alternatively a DNAzyme ligase could attach a sensor or substrate arm to a partzyme component to create an "on" switch for MNAzymes by promoting assembly. In another embodiment, the DNAzyme ligase could be attached to a sequence labeled with a moiety that allows oligonucleotides to be selectively captured, for example using a biotin group or the moiety could contain a radio-frequency magnetic field radio to facilitate remote electronic control of hybridisation. This approach could allow selective removal of component molecules allowing activation or inhibition of enzymatic activity. For example, the activity inhibitor could be selectively denatured from an MNAi complex resulting in transition to the active MNAzyme state.

It would be appreciated that the DNAzyme ligase used in this example (as illustrated in FIG. 8) could be replaced by an MNAzyme ligase (as illustrated in FIG. 11).

Example 6

Demonstration of a Reaction which Exploits the Activity of Multiple Nucleic Acid Enzymes, in this Example Specifically MNAzymes which Cleave Nucleic Acid Substrates and DNAzymes which Ligate Nucleic Acid Substrates, Whereby the Cleavage or Ligation Products Created by One Type of Nucleic Acid Enzyme Forms a New Substrate or Enzyme Component which Participates in the Next Nucleic Acid Enzyme Reaction The strategy used in this example is illustrated in FIG. 9. This example demonstrates (i) using target nucleic acid to direct the formation of an MNAzyme (MNAzyme A) which can cleave a substrate (MNAzyme substrate A) thus generating a 5' cleavage product A which can in turn be used as a substrate for a DNAzyme B with ligase activity; (ii) using a DNAzyme ligase B to ligate the 5' cleavage product A generated in step (i) to another oligonucleotide ligation substrate thus creating a new partzyme; and (iii) using the new partzyme/ligation product generated in step (ii) to form a new MNAzyme (MNAzyme C) which can cleave a substrate (MNAzyme substrate C). In this example the labelling of MNAzyme substrate C with a fluorophore and quencher dye pair allowed fluorescent monitoring of the reaction.

The DNAzyme ligase B used in this example has previously been reported to ligate RNA through the formation of a 2'-5' phosphodiester linkage from a 2',3'-cyclic phosphate and a 5'-hydroxyl group (Prior et al, 2004). Apart from the requirement of a 5' substrate with a 2',3'-cyclic phosphate end, the DNAzyme ligase used in this example also requires a specific sequence motif at the ligation junction, being ua*g (A or G) (where lower case denotes RNA bases and uppercase notes an RNA or DNA base and * denotes the ligation site).

In the first step, MNAzyme A forms in the presence of target nucleic acid and is used to cleave MNAzyme substrate A (preSub5) thus generating a cleavage fragment which has a 2',3'-cyclic phosphate end. In the second step the DNAzyme ligase was then used to ligate the 5' product A (preSub5 cleavage fragment) with another oligonucleotide ligation substrate (preSub3). In the third step the ligated product functions as a new partzyme, which together with a second partzyme and an assembly facilitator can form MNAzyme C and cleave a fluorescently labelled substrate C (SubBi-2-FB).

6.1 DNAzyme Ligase B

The DNA oligonucleotide sequence which acts as a DNAzyme ligase is listed below.

```
DNAzyme ligase 7Z81-10/10:
                                       SEQ ID NO: 17
CCTCTCGTTGACGGCGGAGTGATTGGGAGGTTAGCTCTAGTGAGTGC
```

6.2 Partzyme Oligonucleotides

In the following sequences the bases in bold hybridize with the target nucleic acid sequence, bases underlined form part of the catalytic core of the assembled MNAzyme, and bases in italics hybridize to the substrate.

The following are sequences of the partzymes which form components of MNAzyme A:

```
Partzyme A2/MNAzyme A miR20A2/1:
                                       SEQ ID NO: 18
TACCTGCACTACGGTCGAAATAGTGAGT Partzyme B3/MNAzyme A miR20B3/1:
                                       SEQ ID NO: 19
CATCTCTTCTCCGAGCTAAGCACTTTA
```

The following sequence corresponds to the partzyme which associates with the ligation product/partzyme to form a component of MNAzyme C.

```
Partzyme B5/MNAzyme C STB5/2(21):
                                       SEQ ID NO: 20
TGCCCAGGGAGGCTAGCTCTGTCGTCGGAGTGGTCGTCG
```

6.3 MNAzyme Substrate A (Substrate for MNAzyme A)

In the following sequence, the lower case bases represent RNA and the uppercase bases represent DNA.

```
                                       SEQ ID NO: 21
preSub5: CTGTAGCACTCACTAuaGGAAGAGATG
```

6.4 DNAzyme Ligase Substrate

In the following sequence, the lower case base represents RNA and the uppercase bases represent DNA. The 3' DNAzyme ligase substrate was synthesised to have the sequence below and a 5' hydroxyl group:

```
                                       SEQ ID NO: 22
preSub3: gGAACAACGAGAGGAAACCTT
```

6.5 MNAzyme Substrate C (Fluorescent Reporter Substrate for MNAzyme C)

The reporter substrate used in this example was SubBi-2. In the current example, SubBi-2 was end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

```
                                       SEQ ID NO: 4
SubBi-2-FB: AAGGTTTCCTCguCCCTGGGCA
```

6.6 Target Sequence for MNAzyme A

The target sequence recognised by MNAzyme A was a synthetic DNA oligonucleotide homologous to the human microRNA miR-20 RNA sequence. It had the following sequence:

```
D-20 target (MNAzyme A target):
                                       SEQ ID NO: 23
TAAAGTGCTTATAGTGCAGGTA
```

6.7 Assembly Facilitator for MNAzyme C

The assembly facilitator required for MNAzyme C formation was a synthetic DNA oligonucleotide with the following sequence:

```
Assembly Facilitator for MNAzyme C:
                                       SEQ ID NO: 24
CGACGACCACTCCGACGACAGTCCTATAGTGAGTGCTACAG
```

6.8 Reaction Conditions

The reaction was performed in three sequential steps (i), (ii) and (iii) in three separate tubes as described below.

(i) Cleavage of preSub5 by MNAzyme A to generate the 5' cleavage product/ligase substrate with the required 2',3'-cyclic phosphate end was performed at 40° C. for 1 hour in a total reaction volume of 100 µl. The reactions contained 500 nM preSub5, 50 mM Tris HCl (pH 9.0 at 25° C.), 25 mM MgCl$_2$ and:
a) Partzymes for MNAzyme A (100 nM miR20A2/1 and 100 nM miR20B3/1) and 100 nM of D-20 target; or
b) no additional oligonucleotides (no cleavage control)

(ii) Ligation was performed at 40° C. for 2 hours in a total reaction volume of 25 µl. Reactions contained 10 µl of previous cleavage reaction mix (i-a) or (i-b), 200 nM preSub3, 150 mM NaCl, 2 mM KCl, 50 mM Tris HCl (pH 9.0 at 25° C.) and 40 mM MgCl$_2$ and:
a) 200 nM of DNAzyme ligase 7Z81-10/10, or
b) no additional oligonucleotide (no ligation control)

(iii) End-point fluorescent detection due to MNAzyme cleavage mediated by a partzyme formed by ligation was performed isothermally at 55° C. for 45 minutes on the Cepheid Smartcycler. Reactions were initiated by the addition of the fluorescently labelled substrate SubBi-2-FB. Reactions contained 10 µl of previous ligation reaction mix, 200 nM of partzyme STB5/2(21), 200 nM of the assembly facilitator for MNAzyme C, 50 mM Tris HCl (pH 9.0 at 25° C.), 25 mM MgCl$_2$ and 200 nM of the substrate SubBi-2-FB in a total reaction volume of 25 µl.

The increase in fluorescence due to cleavage of MNAzyme substrate C (SubBi-2-FB) was monitored over time for reactions that had contained the following oligonucleotide reagents (Table 6).

TABLE 6

Increase in fluorescence due to cleavage of MNAzyme substrate C (SubBi-2-FB) monitored over time.

|  | Step (i) | Step (ii) | Step (iii) | Result |
| --- | --- | --- | --- | --- |
| Reaction 1 (Test i-a, ii-a) | Substrate A MNAzyme A partzymes Target | 10 µl from step (i) Ligase substrate DNAzyme ligase | 10 µl from step (ii) MNAzyme C partzyme B Substrate C Assembly facilitator C | An increase in fluorescence was observed over time |
| Reaction 2 (Control (i-b, ii-a - no MNAzyme A) | Substrate A | 10 µl from step (i) Ligase substrate DNAzyme ligase | 10 µl from step (ii) MNAzyme C partzyme B Substrate C Assembly facilitator C | No increase in fluorescence was observed over time |
| Reaction 3 (Control (i-a, ii-b) - no DNAzyme ligase) | Substrate A MNAzyme A partzymes Target | 10 µl from step (i) Ligase substrate | 10 µl from step (ii) MNAzyme C partzyme B Substrate C Assembly facilitator C | No increase in fluorescence was observed over time |

The increase in fluorescence over time was measured for step (iii) of reactions 1, 2 and 3 (Table 6). Reaction 1, which had contained all oligonucleotide reaction components for steps (i), (ii) and (iii), showed an increase in fluorescence over time. In contrast Reaction 2, which lacked both the MNAzyme A oligonucleotide partzyme components and the target sequence for MNAzyme A for step (i) showed no increase in fluorescence over time. Similarly, Reaction 3, which lacked the DNAzyme ligase oligonucleotide required for step (ii), showed no increase in fluorescence over time. Together these reactions indicate that the following events have occurred in Reaction 1.

Firstly, MNAzyme A cleaved MNAzyme substrate A in the presence of specific target (D-20) producing two fragments, one of which is the 5' fragment with the sequence CTGTAG-CACTCACTAua (SEQ ID NO: 40) that had a 2',3'-cyclic phosphate terminus. Secondly, this 5' fragment was ligated to a second oligonucleotide ligase substrate present in the reaction mix of step (ii) and this resulted in the formation of a new oligonucleotide (ligation product) with the sequence of CTG-TAGCACTCACTAuagGAACAACGAGAGGAAACCTT (SEQ ID NO: 51) (where upper case represent DNA bases and lower case represent RNA bases). This ligation product in turn functioned as a partzyme component for MNAzyme C. This newly created partzyme associated with a second partzyme in the presence of an assembly facilitator and created MNAzyme C. MNAzyme C cleaved MNAzyme substrate C (SubBi-2-FB) resulting in separation of a fluorophore/quencher dye pair thus causing an increase in fluorescence.

The "no MNAzyme A cleavage" control (Reaction 2) demonstrated that cleavage and generation of the 5' fragment with the 2',3'-cyclic phosphate terminus was essential for subsequent ligation and formation of one of the partzymes required for MNAzyme C. The "no ligation" control (Reaction 3) demonstrated that the ligation of the 5' cleavage product A with 2',3'-cyclic phosphate terminus to a second 3' ligase substrate was essential for the formation of one of the components of MNAzyme C.

The strategy demonstrated in this example allows detection of target analytes in a cascade reaction which used two types of nucleic acid enzymes, namely DNAzymes which can ligate substrates (DNAzyme ligases) and MNAzymes which can cleave substrates (MNAzyme cleavers). Multiple turnover at each enzymatic step in the cascade could allow signal amplification.

The cascade strategy demonstrated in this example and illustrated in FIG. 9 could be extended and used to create a feedback amplification cascade. If the sequence of 5' cleavage product C was the same as 5' cleavage product A then this product could also serve as a 5' substrate B and a feedback cascade reaction could be initiated. In this reaction, MNAzyme cleaver C would be constantly generating 5' substrate B which in turn would be ligated by DNAzyme ligase B to create more partzymes for formation of more MNAzyme cleaver C. This strategy could provide a mechanism for feedback amplification following initiation of a reaction by an assembly facilitator e.g. a target analyte which could direct the assembly of MNAzyme cleaver A. The strategy would allow detection of target analytes followed by signal amplification by feedback cascade using two types of nucleic acid enzymes, namely DNAzymes which can ligate substrates (DNAzyme ligases) and MNAzymes which can cleave a substrate (MNAzyme cleavers).

One skilled in the art would appreciate that there are many variants on this basic cascade strategy. By way of example, the DNAzyme B could be used to create ligation products which serve as assembly facilitators for another MNAzyme which could have, for example, cleavage, ligase or other enzymatic activity. Further variations are included throughout the specification.

Example 7

Sequences and Conditions which Allow the Formation of MNAzymes with Ligase Activity and Testing of these MNAzymes with Ligase Activity in a Format Useful in Cascade Reactions DNAzyme ligase 7Q10 was used as a basis for generating candidate MNAzyme ligase partzyme sequences in this example. As illustrated in FIG. 10 each ligase partzyme was comprised of three sequence domains, including (i) a sensor arm which hybridizes to the assembly facilitator (eg a target nucleic acid), (ii) a domain that constitutes part of a catalytic core and (iii) a substrate binding arm. The partial core sequences were designed to incorporate portions of the catalytic region of the 7Q10 DNAzyme ligase which has previously been reported to ligate RNA through the formation of a 2'-5' phosphodiester linkage from a 2',3'-cyclic phosphate and a 5'-hydroxyl group (Flynn-Charlebois et al, 2003).

A multi-step assay was used to assess the enzymatic activity of combinations of candidate partzyme sequences. The general strategy is outlined in FIG. 12 and can also form the basis of a signal amplification technique. In the first step, MNAzyme A forms in the presence of assembly facilitator A and is used to cleave MNAzyme substrate A thus generating a 5' cleavage product A which has a 2',3'-cyclic phosphate end. In the second step active MNAzyme B with ligase activity, assembles in the presence of assembly facilitator B and then ligates the 5' product A (5' substrate B) to a 3' substrate B. In the third step, the ligated product B functions as a new partzyme, which together with another partzyme and an assembly facilitator C can form MNAzyme C and then cleave a substrate C which may be, for example, fluorescently labelled. The catalytic activity of several ligase partzyme pairs was assayed.

7.1 Partzyme Oligonucleotides which Incorporate Domains that Correspond to Incomplete Catalytic Core Sequences of a DNAzyme with Ligase Activity (7Q10).

In this experiment the series of partzyme pairs, for the second step, were all synthesized with sensor arms designed to hybridize to an assembly facilitator (AFMzLB), and with substrate arms designed to hybridize to two substrate sequences, 5LSubB and 3LSubB. The sequences of the partzyme pairs used in this experiment are listed below (5' to 3'). The bases underlined form part of the catalytic core of the assembled candidate MNAzymes, bases in bold (sensor domain) hybridize with the assembly facilitator and bases in italics (substrate domain) hybridize to the substrates.

```
Split 1 Partzyme A-RO5LS1A:
                              SEQ ID NO: 25
AACGAGTCCTGGCCTTGTCTGGCTCTAGTGAGTGC Split 1 Partzyme B-RO5LS1B:
                              SEQ ID NO: 26
TCTCGTTGTTACGTGGAGGTGGTGGAGACGGATTACACCTT Split 2 Partzyme A-RO5LS2A:
                              SEQ ID NO: 27
AACGAGTCCTGGCCTTGTCTGGGCTCTAGTGAGTGC Split 2 Partzyme B-RO5LS2B:
                              SEQ ID NO: 28
TCTCGTTGTTACGTGGAGGTGTGGAGACGGATTACACCTT Split 3 Partzyme A-RO5LS3A:
                              SEQ ID NO: 29
AACGAGTCCTGGCCTTGTCTTGGGCTCTAGTGAGTGC Split 3 Partzyme B-RO5LS3B:
                              SEQ ID NO: 30
TCTCGTTGTTACGTGGAGGGTGGAGACGGATTACACCTT Split 4 Partzyme A-RO5LS4A:
                              SEQ ID NO: 31
AACGAGTCCTGGCCTTGTCTTGGAGGTGGGCTCTAGTGAGTGC Split 4 Partzyme B-RO5LS4B:
                              SEQ ID NO: 32
TCTCGTTGTTACGGTGGAGACGGATTACACCTT Split 5 Partzyme A-RO5LS5A:
                              SEQ ID NO: 33
AACGAGTCCTGGCCTTGTCTGGAGGTGGGCTCTAGTGAGTGC Split 5 Partzyme B-RO5LS5B:
                              SEQ ID NO: 34
TCTCGTTGTTACGTGTGGAGACGGATTACACCTT Split 6 Partzyme A-RO5LS6A:
                              SEQ ID NO: 35
AACGAGTCCTGGCCTTGTCTGTGGAGGTGGGCTCTAGTGAGTGC Split 6 Partzyme B-RO5LS6B:
                              SEQ ID NO: 36
TCTCGTTGTTACGTGGAGACGGATTACACCTT Split 7 Partzyme A-RO5LS7A:
                              SEQ ID NO: 37
AACGAGTCCTGGCCTTGTCTGAGGTGGGCTCTAGTGAGTGC Split 7 Partzyme B-RO5LS7B:
                              SEQ ID NO: 38
TCTCGTTGTTACGTGGTGGAGACGGATTACACCTT
```

7.2 Control DNAzyme with Ligase Activity.

A DNAzyme ligase 7Q10 with substrate arms designed to hybridize to the substrate sequences 5LSubB and 3LSubB was used in this experiment and the sequence is listed below (5' to 3'). The bases underlined form the catalytic core and bases in italics hybridize to the substrates.

```
        DNAzyme ligase-7Q10-10/10:
                              SEQ ID NO: 39
        TCTCGTTGTTACGTGGAGGTGGGCTCTAGTGAGTGC
```

7.3 MNAzyme Substrate A (Substrate for MNAzyme A)

In the following sequence, the lower case bases represent RNA and the uppercase bases represent DNA.

```
                              SEQ ID NO: 21
SubA/Pre5LSubB: CTGTAGCACTCACTAuaGGAAGAGATG
```

7.4 The 3' Substrate B for Ligation

The sequence of the 3' substrate for ligation used in this experiment is listed below (5' to 3'). The oligonucleotide has a 5' hydroxyl group. The lower case bases represent RNA and the upper case represent DNA.

```
        Ligase 3' Substrate B-3LSubB:
                              SEQ ID NO: 22
        gGAACAACGAGAGGAAACCTT
```

7.5 Substrate for MNAzyme C (Fluorescent Reporter Substrate C for Detection)

The reporter substrate used in this example was SubBi-2. In the current example, SubBi-2 was end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

```
        SubBi-2-FB:
                              SEQ ID NO: 4
        AAGGTTTCCTCguCCCTGGGCA
```

7.6 Assembly Facilitators

The assembly facilitator A recognized by MNAzyme A sensor domains was a synthetic DNA oligonucleotide with the following sequence:

```
        AF-MzCA:
                              SEQ ID NO: 42
        CGTCGTGAGATGAGGAAGAGATGGATGGGCAC
```

The assembly facilitator B recognized by MNAzyme B sensor domains was a synthetic DNA oligonucleotide with the following sequence:

```
        AF-MzLB:
                              SEQ ID NO: 43
        AAGGTGTAATCCGTCTCCACAGACAAGGCCAGGACTCGTTTG
```

The assembly facilitator C recognized by MNAzyme C sensor domains was a synthetic DNA oligonucleotide with the following sequence:

```
        AF-MzCC:
                              SEQ ID NO: 24
        CGACGACCACTCCGACGACAGTCCTATAGTGAGTGCTACAG
```

7.7 Partzymes for MNAzymes with Cleavage Activity.

Partzymes for MNAzyme A were synthesized with the following sequence:

```
        Partzyme A/MNAzyme A - 4SyntA2/1(16):
                              SEQ ID NO: 45
        GTGCCCATCCATCTCCGGTCGAAATAGTGAGT Partzyme B/MNAzyme A - 4SyntB3/1(16):
                              SEQ ID NO: 46
        CATCTCTTCTCCGAGCTTCCTCATCTCACGACG
```

One partzyme for MNAzyme C was synthesized with the following sequence:

```
Partzyme B/MNAzyme C - STB5/2(21)
                               SEQ ID NO: 20
TGCCCAGGGAGGCTAGCTCTGTCGTCGGAGTGGTCGTCG
```

7.8 Detection of Ligase Activity.
7.8.1 Reaction Conditions

The reaction was performed in three sequential steps (i), (ii) and (iii) in three separate tubes as described below.
(i) Cleavage of SubA/pre5LSubB by MNAzyme A to generate the 5' ligase substrate (5LSubB) with the required 2',3'-cyclic phosphate end was performed at 40° C. for 1 hour. The reactions contained 100 nM of partzyme 4SyntA2/1(16), 100 nM of partzyme 4SyntB3/1(16), 100 nM of the assembly facilitator AF-MzCA, 500 nM SubA/Pre5LSubB, 50 mM Tris HCl (pH 9.0 at 25° C.) and 50 mM $MgCl_2$.
(ii) Ligations were performed at 40° C. for 2 hours in a total reaction volume of 25 µl. Reactions contained 10 µl of the cleavage reaction mix from step (i), 200 nM 3LSubB, 200 nM AF-MzLB, 150 mM NaCl, 2 mM KCl, 50 mM Tris HCl (pH 9.0 at 25° C.) and 40 mM $MgCl_2$ and:
a) 200 nM of control DNAzyme ligase 7Q10-10/10, or
b) 200 nM of each of Split 1 partzymes A and B (RO5LS 1A and RO5LS1B), or
c) 200 nM of each of Split 2 partzymes A and B (RO5LS2A and RO5LS2B), or
d) 200 nM of each of Split 3 partzymes A and B (RO5LS3A and RO5LS3B), or
e) 200 nM of each of Split 4 partzymes A and B (RO5LS4A and RO5LS4B), or 200 nM of each of Split 5 partzymes A and B (RO5LS5A and RO5LS5B), or
g) 200 nM of each of Split 6 partzymes A and B (RO5LS6A and RO5LS6B), or
h) 200 nM of each of Split 7 partzymes A and B (RO5LS7A and RO5LS7B), or
i) 200 nM of each of Split 2 partzyme A (RO5LS2A) and Split 4 partzyme B (RO5LS4B).

An additional "no 5' ligation substrate" control reaction lacked 10 µl from the cleavage reaction mix from step (i). This reaction mix contained 200 nM 3LSubB, 200 nM of each of Split 4 partzymes A and B (RO5LS4A and RO5LS4B), 150 mM NaCl, 2 mM KCl, 50 mM Tris HCl (pH 9.0 at 25° C.), 40 mM $MgCl_2$, 200 nM AF-MzLB and 200 nM of SubA/Pre5LsubB
(iii) Fluorescent detection due to MNAzyme C cleavage mediated by a partzyme formed by ligation in step (ii) was performed isothermally at 55° C. for up to 3.5 hours on the Cepheid Smartcycler with data collection points at 5 minute intervals. Reactions were initiated by the addition of the fluorescently labelled substrate SubBi-2-FB. Reactions contained 10 µl of previous ligation reaction mix (ii-a or ii-b or ii-c or ii-d or ii-e or ii-f or ii-g or ii-h or ii-i or "no-ligation substrate" control), 200 nM of partzyme B for MNAzyme C (STB5/2(21)), 200 nM of the assembly facilitator for MNAzyme C (AF-MzCC), 50 mM Tris HCl (pH 9.0 at 25° C.), 25 mM $MgCl_2$ and 200 nM of the substrate SubBi-2-FB in a total reaction volume of 25 µl. The increase in fluorescence due to cleavage of MNAzyme substrate C (SubBi-2-FB) was monitored over time for reactions.
7.8.2 Results
a) Control Reactions.

The positive control DNAzyme ligase reaction (steps i, ii-a and iii) showed an increase in fluorescence over time. This reaction confirms that MNAzyme A can form and cleave SubA/Pre5LSubB to generate a product (5LSubB) which has a 2',3'-cyclic phosphate which makes it suitable for use as a substrate by the DNAzyme ligase. The sequence of 5LSubB is CTGTAGCACTCACTAua (SEQ ID NO: 40) where upper case represents DNA bases and lower case represents RNA bases. This control reaction demonstrated the uni-molecular DNAzyme ligase 7Q10-10/10 ligated 5LSubB and 3LSubB and formed a new oligonucleotide (ligation product) with the sequence of CTGTAGCACTCACTAuagGAACAAC-GAGAGGAAACCTT (SEQ ID NO: 51) (where upper case represents DNA bases and lower case represents RNA bases). This ligation product in turn functioned as a partzyme component of MNAzyme C which cleaved substrate C (SubBi-2-FB) resulting in an increase in fluorescence. This increase in fluorescence acted as a surrogate marker of ligase activity.

The "no 5' ligation substrate" control reaction (steps ii and iii only) did not show an increase in fluorescence over time. This demonstrates that if SubA/Pre5LSubB is not cleaved by MNAzyme A to generate 5LSubB then no appropriate 5' ligation substrate is available for ligation to 3LSubB. As a result no partzyme for MNAzyme C is generated and no increase in fluorescence is observed.

b) Reactions Designed to Test for the Presence of Ligase Activity when Using Candidate Partzyme Pairs which May or May not have Capacity to Form Functional MNAzyme Ligases.

Reactions that incorporated steps i and iii along with either step ii-e (Split 4) or ii-f (Split 5) showed an increase in fluorescence over time. Splitting the catalytic core of the DNAzyme ligase 7Q10 at these positions and then reassembling the partial cores in the partzymes in the presence of an assembly facilitator produced active MNAzyme ligases under these reaction conditions.

Reactions which incorporated steps i and iii along with either step ii-b (Split 1) or ii-c (Split 2) or ii-d (Split 3) or ii-g (Split 6) or ii-h (Split 7) or ii-i (Split 2/4) showed no increase in fluorescence after 35 min of monitoring by MNAzyme C cleavage. This demonstrates that splitting the catalytic core of the DNAzyme ligase 7Q10 at these positions and then reassembling the partial cores with an assembly facilitator does not produce detectable MNAzyme ligase activity under these reaction conditions.

The example has generated a number of partzyme sequences that can be used to assemble MNA complexes, which are inactive or have various levels of enzymatic activity depending on the specific sequences and combinations thereof. The general design for candidate partzyme sequences tested are summarized in Table 7.

TABLE 7

General design for partzymes sequences tested. Sequences of the partzyme sequence pairs (based on the 7Q10 DNAzyme ligase) that were tested for potential MNAzyme ligase activity where N is any nucleotide, (N)x is any number of nucleotides which bind to a substrate sequence (substrate domain) and (N)y is any number of nucleotides which bind to an assembly facilitator (sensor domain).

| Split # | Partzyme A | Partzyme B |
|---|---|---|
| Split 1 | (N)yGGCTC (N)x (SEQ ID NOS 101 and 107) | (N)xACGTGGAGGTG (N)y (SEQ ID NOS 41 and 108) |

TABLE 7-continued

General design for partzymes sequences tested.
Sequences of the partzyme sequence pairs
(based on the 7Q10 DNAzyme ligase) that were
tested for potential MNAzyme ligase activity where
N is any nucleotide, (N)x is any number of
nucleotides which bind to a substrate sequence
(substrate domain) and (N)y is any number of
nucleotides which bind to an assembly facilitator
(sensor domain).

| Split # | Partzyme A | Partzyme B |
|---|---|---|
| Split 2 | (N)y GGGCTC(N)x (SEQ ID NOS 102 and 109) | (N)x ACGTGGAGGT (N)y (SEQ ID NOS 44 and 110) |
| Split 3 | (N)y TGGGCTC(N)x (SEQ ID NOS 103 and 111) | (N)xACGTGGAGG(N)y (SEQ ID NOS 104 and 112) |
| Split 4 | (N)y TGGAGGTGGGCTC (N)x (SEQ ID NOS 47 and 113) | (N)xACG(N)y (SEQ ID NOS 48 and 114) |
| Split 5 | (N)y GGAGGTGGGCTC (N)x (SEQ ID NOS 49 and 115) | (N)xACGT(N)y (SEQ ID NOS 50 and 116) |
| Split 6 | (N)y GTGGAGGTGGGCTC (N)x (SEQ ID NOS 53 and 117) | (N)xAC(N)y (SEQ ID NOS 105 and 118) |
| Split 7 | (N)y GAGGTGGGCTC (N)x (SEQ ID NOS 54 and 119) | (N)xACGTG(N)y (SEQ ID NOS 106 and 120) |
| Split 2/4 | (N)yGGGCTC (N)x (SEQ ID NOS 102 and 121) | (N)xACG (N)y (SEQ ID NOS 48 and 114) |

Sequence of the DNAzyme ligase7Q10 where N is any nucleotide and (N)x is any number of nucleotides which bind to a substrate sequence.
(N)x ACGTGGAGGTGGGCTC(N)x (SEQ ID NOS 52 and 122)
The first SEQ ID NO identifier for each sequence refers only to the core sequences.
The second SEQ ID NO identifier refers to the full sequence.

Active MNAzymes, including examples as demonstrated above with splits equivalent to Split 4 or Split 5 would have a wide number of applications. By way of example, the MNAzyme ligases could be used to detect target analytes. MNAzyme ligases can be designed to assemble only in the presence of an analyte such as an RNA or DNA target sequence (the assembly facilitator). If the 5' ligation substrate and the 3' ligation substrate were each labelled with either a fluorophore and quencher dye respectively (or vice versa) then ligation would result in a decrease in fluorescence which could serve as an indicator of the presence of the target analyte. In an alternative format, if the 5' ligation substrate were labelled with a detectable moiety, for example a fluorophore, and the 3' ligation substrate were attached to a discrete location, for example on a chip or bead, then ligation would result in the appearance of a signal at the discrete location in the presence of target analyte.

The strategy used to assay for ligase activity in this example is illustrated in FIG. 12. Once active partzymes have been identified the same cascade reaction can then be used to detect the presence of an assembly facilitator, for example a target analyte. The cascade reaction allowing detection uses two types of nucleic acid enzymes, namely MNAzymes which can ligate substrates and MNAzymes which can cleave substrates. Multiple turnover at each enzymatic step in the cascade could allow signal amplification.

The cascade demonstrated in this example and illustrated in FIG. 12 could be extended and used to create a feedback amplification cascade. If the sequence of 5' cleavage product C was the same as 5' cleavage product A then this product could also serve as a 5' substrate B and a feedback cascade reaction could be initiated. In this reaction, MNAzyme cleaver C could be constantly generating 5' substrate B which could in turn be ligated by the MNAzyme ligase B to create more partzymes for formation of more MNAzyme cleaver C. This strategy could provide a mechanism for feedback amplification following initiation of a reaction by a target analyte which could direct the assembly of MNAzyme cleaver A. The strategy would allow detection of target analytes followed by signal amplification by a feedback cascade using two types of MNAzyme, namely MNAzyme ligases and MNAzyme cleavers.

Further, this example can also be considered as an example of a reaction where the initiating step results in the formation of an MNAzyme with ligase activity. In this scenario, with reference to FIG. 12, the initiating target nucleic acid would be the assembly facilitator B (AF-MzLB) and the assembly facilitator A (AF-MzCA) would be a synthetic molecule included to drive the assembly of MNAzyme A. MNAzyme A would then have the sole purpose of generating a 5' ligatable substrate B with 2'3' cyclic phosphate termini in a reaction which could then be added to the reaction which detects the target assembly facilitator B using an MNAzyme B with ligase activity. This could provide a practical method for producing substrates with a 2'3' cyclic phosphate terminus which are expensive to synthesise and relatively unstable. Further the MNAzyme A partzymes and the assembly facilitator A could be replaced by a DNAzyme with cleavage activity present either in a separate preliminary reaction for ligatable substrate generation or the DNAzyme could be present in the same reaction mix as the MNAzyme with ligase activity. Example 11 demonstrates that cleavage and ligation using a combination of an MNAzyme and a DNAzyme can be performed in a single reaction mix.

One skilled in the art would appreciate that there are many variants on this basic cascade strategy. By way of example, the MNAzyme B could be used to create ligation products which serve as assembly facilitators for another MNAzyme with cleavage, ligase or other enzymatic activity. In another example, MNAzyme C could modify a substrate by means other than cleavage. Further embodiments are included throughout the specification.

Example 8

An Exemplary Strategy for Switching an MNA Complex Between the "on State" of an Active MNAzyme to the "Off State" of an MNAi Complex Using a Second MNAzyme with Ligase Activity FIG. 13 illustrates an exemplary strategy for switching an MNA complex between the "on state" of an active MNAzyme to the "off state" of an MNAi complex using a second MNAzyme with ligase activity. In this strategy, an active MNAzyme A, which could be capable of modifying (e.g. cleaving or ligating) a substrate(s) A could be formed in the presence of assembly facilitator component 1 (AFC 1) and assembly facilitator component 2 (AFC 2). A second MNAzyme B, which has ligase activity, could form in the presence of, for example, an assembly facilitator 3 (AF3)

which could comprise one or more components, and could then ligate AFC 2 with an activity inhibitor component (AIC) causing the formation of an activity inhibitor (AI). This AI could bind to the partzyme components for the MNAzyme A and result in the formation of an MNAi A complex which is inactive. As such the MNAzyme ligase in this example could operate as an off switch to inactivate an MNAzyme A. The inactive MNAi complex and the catalytically active MNAzyme would represent two alternate states for the assembled components, namely an "off" state and the "on" state respectively.

Example 9

Sequences and Conditions which Allow the Formation of MNAzymes with Ligase Activity and Testing of these MNAzymes with Ligase Activity in a Format Useful in a Signal Amplification Cascade DNAzyme ligase 7Z81 was used as a basis for generating candidate MNAzyme ligase partzyme sequences in this example. As illustrated in FIG. 10 each ligase partzyme was comprised of three sequence domains, including (i) a sensor arm which hybridizes to the assembly facilitator (e.g. a target nucleic acid), (ii) a domain that constitutes part of a catalytic core and (iii) a substrate binding arm. The partial core sequences were designed to incorporate portions of the catalytic region of the 7Z81 DNAzyme ligase which has previously been reported to ligate RNA through the formation of a 2'-5' phosphodiester linkage from a 2',3'-cyclic phosphate and a 5'-hydroxyl group (Prior et al, 2004).

A multi-step assay was used to assess the enzymatic activity of combinations of candidate partzyme sequences. The general strategy is outlined in FIG. 12 and can also form the basis of a signal amplification technique. In the first step, MNAzyme A forms in the presence of assembly facilitator A and is used to cleave MNAzyme substrate A thus generating a 5' cleavage product A which has a 2',3'-cyclic phosphate end. In the second step active MNAzyme B with ligase activity, assembles in the presence of assembly facilitator B and then ligates the 5' product A (5' substrate B) to a 3' substrate B. In the third step, the ligated product B functions as a new partzyme, which together with another partzyme and an assembly facilitator C can form MNAzyme C and then cleave substrate C, which may be, for example, fluorescently labelled. The catalytic activity of several candidate ligase partzyme pairs was assayed.

9.1 Partzyme Oligonucleotides which Incorporate Domains that Correspond to Incomplete Catalytic Core Sequences of a DNAzyme with Ligase Activity (7Z81).

In this experiment the series of partzyme pairs, for the second step, were all synthesized with sensor arms designed to hybridize to an assembly facilitator (AFMzLB), and with substrate arms designed to hybridize to two substrate sequences, 5LSubB and 3LSubB. The sequences of the partzyme pairs used in this experiment are listed below (5' to 3'). The bases underlined form part of the catalytic core of the assembled candidate MNAzymes, bases in bold (sensor domain) hybridize with the assembly facilitator and bases in italics (substrate domain) hybridize to the substrates.

Split 1 Partzyme A - R05S1A:
SEQ ID NO: 55
CAAACGAGTCCTGGCCTTGTCT<u>GGAGGTTAGCTC</u>*TAGTGAGTGC*

Split 1 Partzyme B - R05S1B:
SEQ ID NO: 56
*CCTCTCGTTG*<u>ACGGCGGAGTGATT</u>GGTGGAGACGGATTACACCTT

Split 2 Partzyme A - R05S2A:
SEQ ID NO: 57
CAAACGAGTCCTGGCCTTGTCT<u>TGGGAGGTTAGCTC</u>*TAGTGAGTGC*

Split 2 Partzyme B - R05S2B:
SEQ ID NO: 58
*CCTCTCGTTG*<u>ACGGCGGAGTGAT</u>GTGGAGACGGATTACACCTT

Split 3 Partzyme A - R05S3A:
SEQ ID NO: 59
CAAACGAGTCCTGGCCTTGTCT<u>ATTGGGAGGTTAGCTC</u>*TAGTGAGTGC*

Split 3 Partzyme B - R05S3B:
SEQ ID NO: 60
*CCTCTCGTTG*<u>ACGGCGGAGTG</u>GTGGAGACGGATTACACCTT

Split 4 Partzyme A - R05S4A:
SEQ ID NO: 61
CAAACGAGTCCTGGCCTTGTCT<u>TGATTGGGAGGTTAGCTC</u>*TAGTGAGTGC*

Split 4 Partzyme B - R05S4B:
SEQ ID NO: 62
*CCTCTCGTTG*<u>ACGGCGGAG</u>GTGGAGACGGATTACACCTT

Split 5 Partzyme A - R05S5A:
SEQ ID NO: 63
CAAACGAGTCCTGGCCTTGTCT<u>AGTGATTGGGAGGTTAGCTC</u>*TAGTGAGTGC*

Split 5 Partzyme B - R05S5B:
SEQ ID NO: 64
*CCTCTCGTTG*<u>ACGGCGG</u>GTGGAGACGGATTACACCTT

Split 6 Partzyme A - R05S6A:
SEQ ID NO: 65
CAAACGAGTCCTGGCCTTGTCT<u>GGAGTGATTGGGAGGTTAGCTC</u>*TAGTGAGTGC*

Split 6 Partzyme B - R05S6B:
SEQ ID NO: 66
*CCTCTCGTTG*<u>ACGGC</u>GTGGAGACGGATTACACCTT

9.2 Control DNAzyme with Ligase Activity.

The DNAzyme ligase used in this example has previously been reported to ligate RNA and form a 2'-5' phosphodiester linkage using a 5' ligation substrate with a 2',3'-cyclic phosphate and a 3' ligation substrate with a 5'-hydroxyl group (Prior et al, 2004). Apart from the requirement for specific termini on the substrates, the DNAzyme ligase used in this example also requires a specific sequence motif at the ligation junction.

A DNAzyme ligase 7Z81 with substrate arms designed to hybridize to the substrate sequences 5LSubB and 3LSubB was used in this experiment and the sequence is listed below (5' to 3'). The bases underlined form the catalytic core and bases in italics hybridize to the substrates.

DNAzyme ligase - 7Z81-10/10:
SEQ ID NO: 17
*CCTCTCGTTG*<u>ACGGCGGAGTGATTGGGAGGTTAGCTC</u>*TAGTGAGTGC*

9.3 MNAzyme Substrate A (Substrate for MNAzyme A)

The sequence of Substrate A (Pre5LSubB2-FB) is below. It is internally labelled 5' of the ribases with a 6-FAM moiety and labelled 3' of the ribases with BHQ1 moiety (underlined bases). The lower case bases represent RNA and the upper case bases represent DNA.

```
       Substrate A - Pre5LSubB2-FB:
                                SEQ ID NO: 67
       CTGTAGCACTCACTAuaGGAAGAGATGAG
```

9.4 The 3' Substrate B for Ligation

The sequence of the 3' substrate for ligation used in this experiment is listed below (5' to 3'). The oligonucleotide has a 5' hydroxyl group. The lower case bases represent RNA and the upper case bases represent DNA.

```
       Ligase 3' Substrate B - 3LSubB:
                                SEQ ID NO: 22
       gGAACAACGAGAGGAAACCTT
```

9.5 Substrate for MNAzyme C (Fluorescent Reporter Substrate C for Detection)

The reporter substrate used in this example was SubBi-2. In the current example, SubBi-2 was end-labelled with a Quasar 670 moiety at the 5' end, a BHQ2 moiety at the 3' end and designated SubBi-2-Q6B2. Cleavage of SubBi-2-Q6B2 was monitored at 665 nm with excitation at 635 nm. The sequence of SubBi-2-Q6B2 is listed below (5' to 3'); the lower case bases represent RNA and the upper case bases represent DNA.

```
       SubBi-2-Q6B2:
                                SEQ ID NO: 4
       AAGGTTTCCTCguCCCTGGGCA
```

9.6 Assembly Facilitators

The assembly facilitator A recognized by MNAzyme A sensor domains was a synthetic DNA oligonucleotide with the following sequence:

```
       AF-MzCA2:
                                SEQ ID NO: 68
       GCCATTGTCGAACACCTGCTGGATGACCAGC
```

The assembly facilitator B recognized by MNAzyme B sensor domains was a synthetic DNA oligonucleotide with the following sequence:

```
       AF-MzLB:
                                SEQ ID NO: 43
       AAGGTGTAATCCGTCTCCACAGACAAGGCCAGGACTCGTTTG
```

The assembly facilitator C recognized by MNAzyme C sensor domains was a synthetic DNA oligonucleotide with the following sequence:

```
       AF-MzCC:
                                SEQ ID NO: 24
       CGACGACCACTCCGACGACAGTCCTATAGTGAGTGCTACAG
```

9.7 Partzymes for MNAzymes with Cleavage Activity.

Partzymes for MNAzyme A were synthesized with the following sequence:

```
Partzyme A/MNAzyme 1 - RO4A2/1(11);
GCTGGTCATCCAGCAGCGGTCGAAATAGTGAGTGC  SEQ ID NO: 69

Partzyme B/MNAzyme 1 - RO4B3/1(12):
CTCATCTCTTCTCCGAGCGTGTTCGACAATGGC    SEQ ID NO: 70
```

One partzyme for MNAzyme C was synthesized with the following sequence:

```
       Partzyme B/MNAzyme C - STB5/2(21)
                                SEQ ID NO: 20
       TGCCCAGGGAGGCTAGCTCTGTCGTCGGAGTGGTCGTCG
```

9.8 Detection of Ligase Activity.

9.8.1 Reaction Conditions

The reaction was performed in three sequential steps (i), (ii) and (iii) in three separate tubes as described below.

(i) Cleavage of Pre5LSubB2-FB by MNAzyme A to generate the 5' ligase substrate (5LSubB) with the required 2',3'-cyclic phosphate end was performed at 40° C. for 1 hour. The reactions contained 50 nM of partzyme RO4A2/1(11), 50 nM of partzyme RO4B3/1(12), 100 nM of the assembly facilitator AF-MzCA2, 1000 nM Pre5LSubB2-FB, 50 mM Tris HCl (pH 9.0 at 25° C.) and 40 mM $MgCl_2$.

(ii) Ligations were performed at 40° C. for 2 hours in a total reaction volume of 25 μl. Reactions contained 10 μl of the cleavage reaction mix from step (i), 1000 nM 3LSubB, 500 nM AF-MzLB, 150 mM NaCl, 2 mM KCl, 50 mM Tris HCl (pH 9.0 at 25° C.) and 40 mM $MgCl_2$ and either:

a) 500 nM of control DNAzyme ligase 7Z81-10/10, or b) 500 nM of each of Split 1 partzymes A and B (RO5S1A and RO5S1B), or c) 500 nM of each of Split 2 partzymes A and B (RO5S2A and RO5S2B), or d) 500 nM of each of Split 3 partzymes A and B (RO5S3A and RO5S3B), or e) 500 nM of each of Split 4 partzymes A and B (RO5S4A and RO5S4B), or f) 500 nM of each of Split 5 partzymes A and B (RO5S5A and RO5S5B), or g) 500 nM of each of Split 6 partzymes A and B (RO5S6A and RO5S6B), or h) no DNAzyme or partzymes (no ligase control)

(iii) Fluorescent detection due to MNAzyme C cleavage mediated by a partzyme formed by ligation in step (ii) was performed isothermally at 55° C. for 2 hours on the Cepheid Smartcycler with data collection points at 72 second intervals. Reactions were initiated by the addition of the fluorescently labelled substrate SubBi-2-Q6B2. Reactions contained 10 μl of previous ligation reaction mix (ii-a or ii-b or ii-c or ii-d or ii-e or ii-f or ii-g or ii-h, 500 nM of partzyme B for MNAzyme C (STB5/2(21)), 100 nM of the assembly facilitator for MNAzyme C (AF-MzCC), PCRII Buffer (Applied Biosystems), 50 mM $MgCl_2$ and 1000 nM of the substrate SubBi-2-Q6B2 in a total reaction volume of 25 μl. The increase in fluorescence due to cleavage of MNAzyme substrate C (SubBi-2-Q6B2) was monitored over time for each reaction.

9.8.2 Results a) Control Reactions.

The positive control DNAzyme ligase reaction (steps i, ii-a and iii) showed an increase in fluorescence over time. The signal produced by the ligase dependent formation of MNAzyme C was measured in arbitrary fluorescent units. The overall change in fluorescence (final fluorescence minus initial fluorescence) and the time at which the reaction came to completion (plateau in fluorescence signal) is shown in Table 8. This change in fluorescence observed in the control DNAzyme reaction confirmed that the steps in the cascade reaction have been successfully achieved. In this reaction MNAzyme A formed and cleaved Pre5LSubB2-FB to generate a product (5LSubB) which has a 2',3'-cyclic phosphate which makes it suitable for use as a substrate by the DNAzyme ligase. The sequence of the cleavage product 5LSubB is CTGTAGCACTCACTAua (SEQ ID NO: 40) where upper case represents DNA bases and lower case represents RNA bases. This control reaction demonstrated the uni-molecular DNAzyme ligase 7Z81-10/10 ligated 5LSubB and 3LSubB and formed a new oligonucleotide (ligation product) with the sequence of CTGTAGCACTCACTAuag-GAACAACGAGAGGAAACCTT (SEQ ID NO: 51) (where upper case represents DNA bases and lower case represents RNA bases). This ligation product in turn functioned as a partzyme component of MNAzyme C, which cleaved substrate C (SubBi-2-Q6B2) resulting in an increase in fluorescence. This increase in fluorescence acted as a surrogate marker of ligase activity.

The no ligase control reaction (steps i, ii-h and iii) showed an insignificant increase in fluorescence over time (Table 8). This demonstrates that if no ligase is present 5LSubB cannot be ligated to 3LSubB. As a result no partzyme for MNAzyme C is generated and no increase in fluorescence is observed.

b) Reactions Designed to Test for the Presence of Ligase Activity when Using Candidate Partzyme Pairs, which May or May not have the Capacity to Form Functional MNAzyme Ligases.

TABLE 8

Change in fluorescence over time for various partzymes.

| | Change in fluorescence (fluorescent units) | Time to reaction completion |
|---|---|---|
| 7Z81 control DNAzyme | 1545 | 25 minutes |
| Partzymes with Split 1 | 479 | >2 hours |
| Partzymes with Split 2 | 1294 | >2 hours |
| Partzymes with Split 3 | 1337 | >2 hours |
| Partzymes with Split 4 | 1284 | 84 minutes |
| Partzymes with Split 5 | 1755 | 35 minutes |
| Partzymes with Split 6 | 1123 | 83 minutes |
| Control - no ligase (no DNAzyme or candidate partzymes) | 34 | N/A |

The example has generated a number of partzyme sequences that can be used to assemble MNAzymes, which have various levels of activity depending on the specific sequences and combinations thereof. The general design for the candidate partzymes sequences which were tested are summarized in Table 9.

TABLE 9

General design for partzymes sequences tested.
Sequences of the partzyme sequence pairs (based on the 7Z81 DNAzyme ligase) that were tested for potential MNAzyme ligase activity where N is any nucleotide, (N)x is any number of nucleotides which bind to a substrate sequence (substrate domain) and (N)y is any number of nucleotides which bind to an assembly facilitator (sensor domain).

| Split # | Partzyme A | Partzyme B |
|---|---|---|
| Split 1 | (N)y GGAGGTTAGCTC (N)x (SEQ ID NOS 71 and 123) | (N)x ACGGCGGAGTGATTG (N)y (SEQ ID NOS 72 and 124) |
| Split 2 | (N)y TGGGAGGTTAGCTC (N)x (SEQ ID NOS 73 and 125) | (N)x ACGGCGGAGTGAT (N)y (SEQ ID NOS 74 and 126) |
| Split 3 | (N)y ATTGGGAGGTTAGCTC (N)x (SEQ ID NOS 75 and 127) | (N)x ACGGCGGAGTG (N)y (SEQ ID NOS 76 and 128) |
| Split 4 | (N)y TGATTGGGAGGTTAGCTC (N)x (SEQ ID NOS 77 and 129) | (N)x ACGGCGGAG (N)y (SEQ ID NOS 78 and 130) |
| Split 5 | (N)y AGTGATTGGGAGGTTAGCTC (N)x (SEQ ID NOS 79 and 131) | (N)x ACGGCGG (N)y (SEQ ID NOS 80 and 132) |
| Split 6 | (N)yGGAGTGATTGGGAGGTTAGCTC (N)x (SEQ ID NOS 81 and 133) | (N)x ACGGC (N)y (SEQ ID NOS 82 and 134) |

Sequence of the DNAzyme ligase 7Z81 where N is any nucleotide and (N)x is any number of nucleotides which bind to a substrate sequence.
(N)x ACGGCGGAGTGATTGGGAGGTTAGCTC (N)x (SEQ ID NOS 83 and 135)
The first SEQ ID NO identifier for each sequence refers only to the core sequences.
The second SEQ ID NO identifier refers to the full sequence.

Reactions that incorporated steps i and iii along with step ii-b (Split 1), ii-c (Split 2), ii-d (Split 3), ii-e (Split 4), ii-f (Split 5) and ii-g (Split 6) showed an increase in fluorescence over time. The capacity of each candidate partzyme pair to ligate substrates was measured by a change in arbitrary fluorescent units. The overall change in fluorescence (final fluorescence minus initial fluorescence) and the time at which the reaction came to completion (plateau in fluorescence signal) is shown in Table 8. Splitting the catalytic core of the DNAzyme ligase 7Z81 at those positions (Table 9) and then reassembling the partial cores in the partzymes in the presence of an assembly facilitator produced active MNAzyme ligases under these reaction conditions.

Active MNAzymes, including examples as demonstrated above, and particularly the MNAzyme with the division equivalent to Split 5, would have a wide number of applications. By way of example, the MNAzyme ligases could be used to detect target analytes. MNAzyme ligases can be designed to assemble only in the presence of an analyte such as an RNA or DNA target sequence (the assembly facilitator). As an example, if the 5' ligation substrate and the 3' ligation substrate were each labelled with either a fluorophore or quencher dye respectively (or vice versa) then ligation would result in a decrease in fluorescence, which could serve as an indicator of the presence of the target analyte. In an alternative format, if the 5' ligation substrate were labelled with a detectable moiety, for example a fluorophore, and the 3' ligation substrate were attached to a discrete location, for example on a chip or bead, then ligation would result in the appearance of a signal at the discrete location in the presence of target analyte.

The strategy used to assay for ligase activity in this example, as illustrated in FIG. 12, constitutes a linear cascade which could be used to create a feedback signal amplification cascade. If the sequence of 5' product C were the same as that of 5' product A then this product could also serve as a 5' substrate B and a feedback cascade reaction could be initiated. In this reaction, MNAzyme C could constantly be generating a 5' substrate B which could in turn be ligated by MNAzyme ligase B to create more partzymes for formation of more MNAzyme C. This strategy could provide a mechanism for feedback amplification following initiation of a reaction by an assembly facilitator (e.g. target analyte) which could direct assembly of MNAzyme A. The strategy could allow detection of assembly facilitators (e.g. target analytes) followed by signal amplification using two types of MNAzymes, namely MNAzymes which could ligate substrates (MNAzyme ligases) and MNAzymes which could cleave a substrate (MNAzyme cleavers).

One skilled in the art would appreciate that there are many variants on this basic strategy. By way of example, the MNAzyme B could be used to create ligation products, which serve as assembly facilitators for another MNAzyme with cleavage, ligase or other enzymatic activity. In another example, MNAzyme C could modify a substrate by means other than cleavage. Further embodiments are included throughout the specification.

Example 10

General Method for Engineering MNAzymes from DNAzymes

In vitro evolution techniques have facilitated the discovery and development of many DNAzymes (reviewed Emilsson and Breaker, 2002). In vitro evolved DNAzymes have been discovered which have the capacity to catalyse a broad range of reactions including cleavage of nucleic acids, ligation of nucleic acids, porphyrin metallation, formation of carbon-carbon bonds, DNA phosphorylation, ester bonds, amide bonds, DNA deglycosylation, thymine dimer photoreversion and phosphoramidate cleavage (reviewed Silverman, 2007).

Many DNAzymes have similar basic structures with multiple domains. These DNAzymes comprise a conserved catalytic domain (catalytic core) flanked by two non-conserved substrate-binding domains ("arms"), which specifically recognize and hybridise to the substrate (for example, for DNAzyme cleavers or those that act on one substrate) or at least two substrates (for example, for DNAzyme ligases or those that act on at least two substrates). The substrate binding domains can be tailored to any substrate provided the substrate or substrates contains a site(s) which can be modified by the DNAzyme. This example describes a general strategy for engineering new MNAzymes based on any known DNAzyme. This general strategy is illustrated schematically in FIG. 14.

The method is described firstly for deriving MNAzymes from DNAzymes with modifying activity, for example cleavage activity. In the first step, positions within the DNAzyme catalytic core at which it can be split are identified, in order that each partial portion of the catalytic core can be distributed between two sequences such that the two partial cores together constitute an entire catalytic core. An oligonucleotide A can then be synthesised to contain (i) one substrate binding arm portion capable of binding to a substrate, (ii) one partial catalytic core portion, and (iii) one sensor arm portion capable of binding to an assembly facilitator molecule. A second oligonucleotide B is synthesised such that it contains (i) one substrate binding arm portion capable of binding to the same substrate as oligonucleotide A, whereby oligonucleotide B binds the substrate in a position adjacent to that of oligonucleotide A, (ii) one partial catalytic core portion which contains those bases from the entire DNAzyme catalytic core which are not incorporated into oligonucleotide A and (iii) one sensor arm portion capable of binding to the same assembly facilitator as oligonucleotide A, whereby oligonucleotide B binds the assembly facilitator in a position adjacent to that of oligonucleotide A. This process can be repeated thus making a series of pairs of oligonucleotides A and B which incorporate the structure and domains of partzymes, but may or may not have catalytic activity in the presence of a substrate and an assembly facilitator.

Some or all of the candidate partzyme pairs (pairs of oligonucleotides A and B from the series) can then be incubated in the presence of the assembly facilitator complementary to the sensor arm portions of the partzymes and a substrate which is complementary to the substrate arm portions of the partzymes. Incubation is performed under conditions which are compatible with modification of a substrate by the DNAzyme from which the partial catalytic core sequences were derived. Pairs of oligonucleotides A and B which can perform the same type of modification to the substrate as the DNAzyme from which partial sequences were derived are useful as partzymes which can be assembled into MNAzymes. The sequences of the partial catalytic cores are suitable for incorporation into other partzymes. New partzymes can be synthesised which are tailored to new substrates (by changing the substrate binding domains of each partzyme) and/or to new assembly facilitators (by changing the sensor binding domains of each partzyme).

The method for engineering an MNAzyme that acts on two substrates (e.g. an MNAzyme ligase) from a uni-molecular nucleic acid enzyme (e.g. a DNAzyme ligase) requires similar steps whereby in the first step, positions are identified within the DNAzyme catalytic core at which it can be split, such that each partial portion of the catalytic core can be distributed between two partial sequences such that the two partial cores together constitute an entire catalytic core. Two oligonucleotides A and B (candidate partzymes) can then be synthesised. An oligonucleotide A can be synthesised to contain (i) one substrate binding arm portion capable of binding to a first substrate (e.g. ligatable substrate), (ii) one partial catalytic core portion, and (iii) one sensor arm portion capable of binding to an assembly facilitator molecule. A second oligonucleotide B can be synthesised such that it contains (i) one substrate binding arm capable of binding to a second substrate (e.g. ligatable substrate), (ii) one partial catalytic core portion which contains those bases from the entire DNAzyme catalytic core which are not incorporated into oligonucleotide A and (iii) one sensor arm sequence capable of binding to the same assembly facilitator as oligonucleotide A, whereby oligonucleotide B binds the assembly facilitator in a position adjacent to that of oligonucleotide A. This process can be repeated thus making a series of pairs of oligonucleotides A and B which incorporate the structure and domains of partzymes, but may or may not have catalytic activity in the presence of the substrates and an assembly facilitator.

Some or all of the candidate partzyme pairs (pairs of oligonucleotides A and B from the series) can then be incubated in the presence of the assembly facilitator complementary to the sensor arm portions of the partzymes and substrates (e.g.

ligatable substrates) which are complementary to the substrate arm portions of the partzymes. Incubation is performed under conditions which are compatible with modification of the substrates (e.g. by ligation) by the DNAzyme from which the partial catalytic core sequences were derived. Pairs of oligonucleotides A and B which can perform the same modification (e.g. ligation) to the substrates as the DNAzyme from which partial sequences were derived are useful as partzymes which can be assembled into MNAzymes. The sequences of the partial catalytic cores are suitable for incorporation into other partzymes. New partzymes can be synthesised which are tailored to new substrates (by changing the substrate binding domains of each partzyme) and/or to new assembly facilitators (by changing the sensor binding domains of each partzyme).

Specific examples of the use of this approach to identify partial catalytic cores suitable for incorporation into partzymes capable of forming active MNAzymes are demonstrated for two DNAzymes with ligase activity (examples 7 and 9 and one DNAzyme, with cleavage activity (example 14).

Further, a similar method can be used to examine tolerance to changes in the partial sequence derived from splitting the DNAzyme catalytic core that can be incorporated into component partzymes. For example, modifications to the partial catalytic cores incorporated into partzymes can be made which include, by way of example, insertions, deletions, substitution with alternate DNA bases, or substitution with DNA base analogues such as ribonucleotides, inosine bases or other analogues. Candidate partzyme pairs containing one or more modification(s) can then be assayed as above to determine whether or not they are suitable as partzymes that can assemble into catalytically active MNAzymes.

Example 11

A Cascade Reaction which Exploits the Activity of Multiple Nucleic Acid Enzymes

The general strategy used in this example is outlined in FIG. 9 and can also form the basis of a signal amplification technique. In this specific example the reaction was performed in two steps. In the first step (FIG. 9 (*i*) and (ii)), an MNAzyme A formed in the presence of assembly facilitator (e.g. a target nucleic acid) and was used to cleave a substrate (MNAzyme substrate A) thus generating a 5' cleavage product which had a 2',3'-cyclic phosphate end. Simultaneously a DNAzyme ligase was used to ligate the 5' cleavage product to another oligonucleotide ligation substrate B thus creating a ligation product that functioned as a new MNAzyme component (e.g. a partzyme). In the second step (FIG. 9 (*iii*)), the partzyme ligation product generated in the first step participates in the formation of a new MNAzyme (MNAzyme C), which can cleave a substrate (MNAzyme substrate C). In this example the labelling of MNAzyme substrate C with a fluorophore and quencher dye pair allowed fluorescent monitoring of the reaction.

11.1 Partzymes for MNAzyme A

In the first step, MNAzyme A formed in the presence of an assembly facilitator (AF-MzCA2) and was used to cleave MNAzyme substrate A (Pre5LSubB2-FB). The sequences of the MNAzyme A partzymes (RO4A2/1(11) and RO4B3/1 (12)) are listed below. The bases underlined form part of the catalytic core, bases in bold hybridize with the assembly facilitator and bases in italics hybridize to the substrates.

```
Partzyme A/MNAzyme A - RO4A2/1(11);
GCTGGTCATCCAGCAGCGGTCGAAATAGTGAGTGC    SEQ ID NO: 69

Partzyme B/MNAzyme A - RO4B3/1(12):
CTCATCTCTTCTCCGAGCGTGTTCGACAATGGC      SEQ ID NO: 70
```

11.2 DNAzyme with Ligase Activity

The DNAzyme ligase used in this example has previously been reported to ligate RNA through the formation of a 2'-5' phosphodiester linkage from a 2',3'-cyclic phosphate and a 5'-hydroxyl group (Prior et al, 2004). Apart from the requirement of a 5' substrate with a 2',3'-cyclic phosphate end, the DNAzyme ligase used in this example also requires a specific sequence motif at the ligation junction.

In the first step, the DNAzyme ligase 7Z81 (7Z81-10/10) with substrate arms designed to hybridize to the substrate sequences 5LSubB and 3LSubB was used in this experiment and the sequence is listed below (5' to 3'). The bases underlined form the catalytic core and bases in italics hybridize to the substrates.

```
DNAzyme ligase - 7Z81-10/10:
                                       SEQ ID NO: 17
CCTCTCGTTGACGGCGGAGTGATTGGGAGGTTAGCTCTAGTGAGTGC
```

11.3 Partzymes for MNAzyme C

In the second step the ligated product functioned as a new partzyme, which together with a partzyme B (STB5/2(21)) and assembly facilitator (AF-MzCC), formed MNAzyme C and cleaved a fluorescently labelled substrate C (SubBi-2-Q6B2). The control partzyme A (LS817A4/2), which was the same sequence as the ligated product also formed MNAzyme C with partzyme B (STB5/2(21)). The following sequences correspond to the partzymes, which form part of MNAzyme C. The bases underlined form part of the catalytic core, bases in bold hybridize with the assembly facilitator and bases in italics hybridize to the substrates.

```
Partzyme B/MNAzyme C - STB5/2(21)
                                       SEQ ID NO: 20
TGCCCAGGGAGGCTAGCTCTGTCGTCGGAGTGGTCGTCG Partzyme A/MNAzyme C - LS817A4/2
                                       SEQ ID NO: 84
CTGTAGCACTCACTATAGGAACAACGAGAGGAAACCTT
```

11.4 MNAzyme Substrate A (Substrate for MNAzyme Cleaver A)

MNAzyme substrate A was cleaved by the MNAzyme cleaver A. The resultant 5' fragment denoted 5LSubB was then ligated to 3LSubB by the DNAzyme ligase. The sequence of substrate A (Pre5LSubB2-FB) is below. It is internally labelled 5' of the ribobases with a 6-FAM moiety and labelled 3' of the ribobases with BHQ1 moiety (underlined bases). The lower case bases represent RNA and the upper case bases represent DNA.

```
Substrate A - Pre5LSubB2-FB:
CTGTAGCACTCACTAuaGGAAGAGATGAG      SEQ ID NO: 67
```

11.5 DNAzyme Ligase Substrate B

The sequence of the 3' substrate for ligation used in this experiment is listed below (5' to 3'). The oligonucleotide has a 5' hydroxyl group. The lower case bases represent RNA and the upper case bases represent DNA.

```
Ligase 3' Substrate B - 3LSubB:
gGAACAACGAGAGGAAACCTT         SEQ ID NO: 22
```

11.6 Substrate for MNAzyme C (Fluorescent Reporter Substrate C for Detection)

The reporter substrate used in this example was SubBi-2. In the current example, SubBi-2 was end-labelled with a Quasar 670 moiety at the 5' end, a BHQ2 moiety at the 3' end and designated SubBi-2-Q6B2. Cleavage of SubBi-2-Q6B2 was monitored at 665 nm with excitation at 635 nm. The sequence of SubBi-2-Q6B2 is listed below (5' to 3'); the lower case bases represent RNA and the upper case bases represent DNA.

```
                                   SEQ ID NO: 4
SubBi-2-Q6B2: AAGGTTTCCTCguCCCTGGGCA
```

11.7 Assembly Facilitators

The assembly facilitator A recognized by MNAzyme A sensor domains was a synthetic DNA oligonucleotide with the following sequence:

```
AF-MzCA2:
GCCATTGTCGAACACCTGCTGGATGACCAGC  SEQ ID NO: 68
```

The assembly facilitator C recognized by MNAzyme C sensor domains was a synthetic DNA oligonucleotide with the following sequence:

```
AF-MzCC:
                                  SEQ ID NO: 24
CGACGACCACTCCGACGACAGTCCTATAGTGAGTGCTACAG
```

11.8 Reaction Conditions

The reaction was performed in two sequential steps, 1 and 2, in two separate tubes as described below.

(1) Cleavage of Pre5LSubB2-FB by MNAzyme A to generate the 5' cleavage product/ligase substrate (5LSubB) with the required 2',3'-cyclic phosphate end, and ligation of this fragment with 3LSubB by the DNAzyme ligase, was performed at 45° C. for 2 hours in a total reaction volume of 50 μl. The reactions contained, 70 mM Tris HCl (pH 9.0 at 25° C.), 50 mM $MgCl_2$, 150 mM NaCl, 2 mM KCl, 40 nM RO4B3/1(12), 40 nM RO4A2/1(11), 200 nM Pre5LSubB2-FB and either:

a) 40 nM AF-MzCA2, 200 nM DNA Ligase 7Z81-10/10 and 100 nM 3LSubB; or b) 40 nM AF-MzCA2 and 100 nM 3LSubB; or c) 40 nM AF-MzCA2 and 200 nM DNA Ligase 7Z81-10/10; or d) 200 nM DNA Ligase 7Z81-10/10 and 100 nM 3LSubB; or e) 100 nM 3LSubB only; or 200 nM DNA Ligase 7Z81-10/10 only (2) Fluorescent detection resulting from cleavage by MNAzyme C was performed isothermally at 55° C. for 1 hour on the Cepheid Smartcycler. Reactions were initiated by the addition of the fluorescently labelled substrate SubBi-2-Q6B2. Reactions contained 10 μl of one of the previous ligation reaction mixes (1-a or 1-b or 1-c or 1-d or 1-e or 1-f) and 200 nM of partzyme B (STB5/2(21)) and 200 nM assembly facilitator (AF-MzCC) for MNAzyme C, and 200 nM of the substrate SubBi-2-Q6B2 in a total reaction volume of 25 μl. A positive control reaction (1-g) was also included where 200 nM of the control partzyme A for MNAzyme C (LS817A4/2) was also added to 10 μl of reaction (1-f).

11.9 Results

The increase in fluorescence due to cleavage of MNAzyme substrate C (SubBi-2-Q6B2) was monitored over time for reactions that had contained the following oligonucleotide reagents (Table 10).

TABLE 10

Increase in fluorescence due to cleavage of MNAzyme substrate C (SubBi-2-Q6B2) monitored over time.

| | Step 1 | Step 2 | Result |
|---|---|---|---|
| Reaction 1 (test 1-a) | MNAzyme A partzymes Substrate A Assembly facilitator A (target) DNAzyme ligase Ligase substrate B | 10 μl from step 1 MNAzyme C partzyme B Assembly Facilitator C Substrate C | An increase in fluorescence was observed over time and the reaction came to completion in 15 minutes. |
| Reaction 2 (1-b control - no DNAzyme ligase) | MNAzyme A partzymes Substrate A Assembly facilitator A (target) Ligase substrate B | 10 μl from step 1 MNAzyme C partzyme B Assembly Facilitator C Substrate C | No increase in fluorescence was observed over |
| Reaction 3 (1-c control - no 3'ligase substrate B) | MNAzyme A partzymes Substrate A Assembly facilitator A (target) DNAzyme ligase | 10 μl from step 1 MNAzyme C partzyme B Assembly Facilitator C Substrate C | No increase in fluorescence was observed over time |
| Reaction 4 (1-d control - no assembly facilitator A) | MNAzyme A partzymes Substrate A DNAzyme ligase Ligase substrate B | 10 μl from step 1 MNAzyme C partzyme B Assembly Facilitator C Substrate C | A minimal increase in fluorescence was observed over time |

TABLE 10-continued

Increase in fluorescence due to cleavage of MNAzyme substrate C (SubBi-2-Q6B2) monitored over time.

| | Step 1 | Step 2 | Result |
|---|---|---|---|
| Reaction 5 (1-e control - no DNAzyme ligase and no assembly facilitator A) | MNAzyme A partzymes Substrate A Ligase substrate B | 10 μl from step 1 MNAzyme C partzyme B Assembly Facilitator C Substrate C | No increase in fluorescence was observed over time |
| Reaction 6 (1-f control - no ligase substrate B and no assembly facilitator A) | MNAzyme A partzymes Substrate A DNAzyme ligase | 10 μl from step 1 MNAzyme C partzyme B Assembly Facilitator C Substrate C | No increase in fluorescence was observed over time |
| Reaction 7 (1-g positive control with MNAzyme C partzyme A LS817A4/2) | MNAzyme A partzymes Substrate A DNAzyme ligase | 10 μl from step 1 MNAzyme C partzyme B Assembly Facilitator C Substrate C MNAzyme C partzyme A LS817A4/2 | An increase in fluorescence was observed over time and the reaction came to completion in less than 1 minute |

The fluorescence level was measured over time for step (2) of reactions 1 to 7 (Table 10). Reaction 1 (1-a), which had contained all oligonucleotide reaction components for steps (1) and (2), showed an increase in fluorescence over time. The change in fluorescence observed was greater than 484 arbitrary units in this reaction resulting in an increase from approximately 46 at time 0 to over 530 after 1 hour of monitoring fluorescence.

In contrast Reaction 2 (1-b), which lacked the DNAzyme ligase (7Z81-10/10) oligonucleotide for step (1) showed no increase in fluorescence over time. Reaction 3 (1-c), which lacked ligase substrate B (3LSubB) but contained the DNAzyme ligase from step (1) showed no increase in fluorescence over time. Reaction 4 (1-d) which lacked assembly facilitator A (AF-MzCA2) from step (1) showed a minimal increase in fluorescence over time above the background drift observed of approximately 40 arbitrary units over the course of 1 hour of fluorescence monitoring. Reaction 5 (1-e) which lacked both the assembly facilitator A and the DNAzyme ligase from step (1) showed no increase in fluorescence over time. Reaction 6 (1-f) which lacked both the ligase substrate B and the assembly facilitator A showed no increase in fluorescence over time. Reaction 7 (1-g) was the positive control that contained the control MNAzyme C partzyme A (LS817A4/2), and showed an increase in fluorescence over time whereby the reaction was completed in less than 1 minute. Together these reactions indicate that the following events have occurred in Reaction 1 (1-a).

Firstly, MNAzyme A cleaves Substrate A (Pre5LSubB2-FB) in the presence of specific target assembly facilitator A (AF-MzCA2) producing two fragments, one of which was the 5' fragment 5LSubB (CTGTAGCACTCACTAua) (SEQ ID NO: 40) that has a 2',3'-cyclic phosphate terminus. Secondly, 5LSubB was ligated to a second DNAzyme oligonucleotide ligase substrate B (3LSubB) present in the reaction mix of step (1) and this resulted in the formation of a new oligonucleotide (ligation product) with the sequence of CTGTAG-CACTCACTAuagGAACAACGAGAGGAAACCTT (SEQ ID NO: 51) (where upper case represent DNA bases and lower case represent RNA bases). This ligation product in turn functioned as a partzyme for MNAzyme C. This newly ligated partzyme A associated with MNAzyme C partzyme B and assembly facilitator C to create MNAzyme C. MNAzyme C cleaved MNAzyme substrate C (SubBi-2-Q6B2) resulting in separation of a fluorophore/quencher dye pair thus causing an increase in fluorescence.

The "no ligation" controls (Reaction 2 (1-b) and 3 (1-c)) demonstrated that the ligation of the 5' cleavage (5LSubB) fragment with 2',3'-cyclic phosphate terminus to a second ligase substrate B (3LSubB) is essential for the formation of the partzyme component of MNAzyme C.

The "no assembly facilitator A (AF-MzCA2)" controls (Reactions 4 (1-d), 5 (1-e) and 6 (1-0)) demonstrated that cleavage of MNAzyme substrate A (Pre5LSubB2-FB) by MNAzyme A and generation of a 5' fragment with the 2',3'-cyclic phosphate terminus was essential for subsequent ligation and formation of the partzyme required for assembly and activity of MNAzyme C.

The cascade reaction in this example allowed the detection of the presence of an assembly facilitator, in this example a target nucleic acid sequence. The cascade reaction allowing detection uses two types of nucleic acid enzymes, namely DNAzymes which can ligate substrates and MNAzymes which can cleave substrates. Multiple turnover at each enzymatic step in the cascade could allow signal amplification.

The cascade demonstrated in this example and illustrated in FIG. 9 could be extended and used to create a feedback amplification cascade. If the sequence of 5' cleavage product C were the same as 5' cleavage product A then this product could also serve as a 5' substrate B and a feedback cascade reaction could be initiated. In this reaction, MNAzyme cleaver C could be constantly generating 5' substrate B which could in turn be ligated by the DNAzyme ligase B to create more partzymes for formation of more MNAzyme cleaver C. This strategy could provide a mechanism for feedback amplification following initiation of a reaction by a target analyte which could direct the assembly of MNAzyme cleaver A. The strategy could allow detection of target analytes followed by signal amplification by a feedback cascade using two types of nucleic acid enzymes namely DNAzyme ligases and MNAzyme cleavers.

Further, it would be obvious to one skilled in the art that the DNAzyme ligase could ligate two fragments and create several possible enzymes, enzyme components or substrates useful in this cascade which include but are not limited to, a) a partzyme for a second MNAzyme (e.g. an MNAzyme cleaver as shown in this example and labelled as MNAzyme C in FIG. 9); or b) a new assembly facilitator for a second MNAzyme as described in example 12, and labelled as MNAzyme Cleaver 2 in FIG. 15; or c) a new DNAzyme capable of modifying a substrate or substrates (e.g. by cleavage, ligation etc) or a substrate suitable for modification by an MNAzyme or DNAzyme. Further it would be obvious to one skilled in the art that the DNAzyme with ligase activity could be substituted with an MNAzyme with ligase activity as demonstrated in example 7 and 9. The strategy is versatile and could be performed as either a sequential cascade of the first and second steps or as a feedback cascade reaction where step 2 (FIG. 9 (*iii*)) creates a component for step 1 (FIG. 9 (*i*) and (ii)). Additionally, step 2 (FIG. 9 (*iii*)) could create a component for a further subsequent reaction.

Example 12

An Example of a Cascade Reaction which Exploits the Activity of Multiple Nucleic Acid Enzymes The general strategy used in this example is outlined in FIG. 15 and can also form the basis of a signal amplification technique. In the first step, an MNAzyme (MNAzyme cleaver 1) forms in the presence of assembly facilitator (e.g. a target nucleic acid) and is used to cleave a substrate (MNAzyme substrate 1) thus generating a 5' cleavage product which has a 2',3'-cyclic phosphate end. In the second step a DNAzyme ligase is used to ligate the cleavage product generated in step one to another oligonucleotide ligation substrate thus creating a ligation product that functions as an assembly facilitator. In the third step, the assembly facilitator ligation product generated in step two participates in the formation of a new MNAzyme (MNAzyme cleaver 2), which can cleave a substrate (MNAzyme substrate 2). In this example the labelling of MNAzyme substrate 2 with a fluorophore and quencher dye pair allowed fluorescent monitoring of the reaction.

12.1 Partzymes for MNAzyme Cleaver 1

In the first step, MNAzyme cleaver 1 formed in the presence of an assembly facilitator (AF-MzCA2) and was used to cleave MNAzyme substrate 1 (Pre5LSubB2-FB). The sequences of the MNAzyme cleaver 1 partzymes (RO4A2/1 (11) and RO4B3/1(12)) are listed below. The bases underlined form part of the catalytic core, bases in bold hybridize with the assembly facilitator and bases in italics hybridize to the substrates.

Partzyme A/MNAzyme 1-RO4A2/1(11);
SEQ ID NO: 69
GCTGGTCATCCAGCAGCGGTCGAA*ATAGTGAGTGC*

Partzyme B/MNAzyme 1-RO4B3/1(12):
SEQ ID NO: 70
*CTCATCTCTTCT*CCGAGCGTGTTCGACAATGGC

12.2 DNAzyme with Ligase Activity

The DNAzyme ligase used in this example has previously been reported to ligate RNA through the formation of a 2'-5' phosphodiester linkage from a 2',3'-cyclic phosphate and a 5'-hydroxyl group (Prior et al, 2004). Apart from the requirement of a 5' substrate with a 2',3'-cyclic phosphate end, the DNAzyme ligase used in this example also requires a specific sequence motif at the ligation junction.

In the second step, the DNAzyme ligase 7Z81 (7Z81-10/10) with substrate arms designed to hybridize to the substrate sequences 5LSubB and 3LSubB was used in this experiment and the sequence is listed below (5' to 3'). The bases underlined form the catalytic core and bases in italics hybridize to the substrates.

DNAzyme ligase-7Z81-10/10:
SEQ ID NO: 17
*CCTCTCGTT*GACGGCGGAGTGATTGGGAGGTTAGCTC*TAGTGAGTGC*

12.3 Partzymes for MNAzyme Cleaver 2

In the third step the ligated product functions as a new assembly facilitator, which together with a pair of partzymes can form MNAzyme cleaver 3 and cleave a fluorescently labelled substrate 3 (SubBi-3-TxB2). The following sequences correspond to the partzymes, which form components of MNAzyme cleaver 2. The bases underlined form part of the catalytic core, bases in bold hybridize with the assembly facilitator and bases in italics hybridize to the substrates.

Partzyme A/MNAzyme 2-LIGFACA5/3:
SEQ ID NO: 85
AAGGTTTCCTCTCGTTGTTCCTACAACGA*GGTTGTGCTG*

Partzyme B/MNAzyme 2-LIGFACB6/3:
SEQ ID NO: 86
*CGGTTGGTGA*GGCTAGCTATAGTGAGTGCTACAG

12.4 MNAzyme Substrate 1 (Substrate for MNAzyme Cleaver 1)

MNAzyme substrate 1 was cleaved by the MNAzyme cleaver 1. The resultant 5' fragment denoted 5LSubB was then ligated to 3LSubB by the DNAzyme ligase. The sequence of substrate 1 (Pre5LSubB2-FB) is below. It is internally labelled 5' of the ribobases with a 6-FAM moiety and labelled 3' of the ribobases with BHQ1 moiety (underlined bases). The lower case bases represent RNA and the upper case bases represent DNA.

Substrate 1-Pre5LSubB2-FB:
SEQ ID NO: 67
CTGTAGCAC<u>T</u>CACTAuaGGAAGAGATGA<u>G</u>

12.5 DNAzyme Ligase Substrate

The sequence of the 3' substrate for ligation used in this experiment is listed below (5' to 3'). The oligonucleotide has a 5' hydroxyl group. The lower case bases represent RNA and the upper case bases represent DNA.

Ligase 3' Substrate-3LSubB:
SEQ ID NO: 22
gGAACAACGAGAGGAAACCTT 12.6 MNAzyme Substrate 2 (Fluorescent Reporter Substrate for MNAzyme Cleaver 2)

The reporter substrate used in this example was SubBi-3. In the current example, SubBi-3 was end-labelled with a Texas Red moiety at the 5' end, a BHQ2 moiety at the 3' end and designated SubBi-3-TxB2. Cleavage of SubBi-3-TxB2 was monitored at 610 nm (TxB2 emission wavelength) with excitation at 585 nm (TxB2 excitation wavelength). The sequence of SubBi-3-TxB2 is listed below (5' to 3'); the lower case bases represent RNA and the upper case bases represent DNA.

SEQ ID NO: 87
SubBi-3-TxB2: CAGCACAACCguCACCAACCG 12.7 Assembly Facilitator Sequence for MNAzyme Cleaver 1

The assembly facilitator recognized by MNAzyme cleaver 1 sensor domains was a synthetic DNA oligonucleotide with the following sequence:

SEQ ID NO: 68
AF-MzCA2: GCCATTGTCGAACACCTGCTGGATGACCAGC 12.8 Reaction Conditions The reaction was performed in three sequential steps (i), (ii) and (iii) in three separate tubes as described below.

(i) Cleavage of Pre5LSubB2-FB by MNAzyme cleaver 1 to generate the 5' cleavage product/ligase substrate (5LSubB) with the required 2',3'-cyclic phosphate end was performed at 40° C. for 66 minutes in a total reaction volume of 100 µl. The reactions contained 50 mM Tris HCl (pH 9.0 at 25° C.), 50 mM MgCl$_2$, 150 mM NaCl, 2 mM KCl, 50 nM RO4B3/1(12), 50 nM RO4A2/1(11) and either:
a) 1000 nM Pre5LSubB2-FB, 50 nM AF-MzCA2; or
b) 1000 nM Pre5LSubB2-FB; or
c) 50 nM AF-MzCA2.

(ii) Ligation was performed at 40° C. for 2 hours in a total reaction volume of 50 µl. Reactions contained 25 µl of previous cleavage reaction mix (i-a) or (i-b), or (i-c), 500 nM 3LSubB, in a reaction with a final concentration of 150 mM NaCl, 2 mM KCl, 50 mM Tris HCl (pH 9.0 at 25° C.) and 50 mM MgCl$_2$ and:
a) 500 nM of DNAzyme ligase 7Z81-10/10, or
b) no DNAzyme ligase (no ligation control)

(iii) Fluorescent detection due to MNAzyme cleavage resulting from assembly of partzymes for MNAzyme cleaver 2 in the presence of the assembly facilitator formed by ligation of the cleavage product of Pre5LSubB2-FB (5LSubB) and the ligation substrate (3LSubB) was performed isothermally at 50° C. for 2 hours on the Cepheid Smartcycler. Reactions were initiated by the addition of the fluorescently labelled substrate SubBi-3-TxB2. Duplicate reactions contained 10 µl of one of previous ligation reaction mixes ((i-a/ii-a) or (i-a/ii-b) or (i-b/ii-a) or (i-b/ii-b) or (i-c/ii-a) or (i-c/ii-b)) and 200 nM of partzyme A (LIGFACA5/3) and 200 nM partzyme B (LIGFACB6/3) for MNAzyme cleaver 2, and 400 nM of the substrate SubBi-3-TxB2 in a total reaction volume of 25 µl.

12.9 Results

The increase in fluorescence due to cleavage of MNAzyme substrate 2 (SubBi-3-TxB2) was monitored over time for reactions that had contained the following oligonucleotide reagents (Table 11).

TABLE 11

Increase in fluorescence due to cleavage of MNAzyme substrate 2 (SubBi-3-TxB2) monitored over time.

| | Step (i) | Step (ii) | Step (iii) | Result |
|---|---|---|---|---|
| Reaction 1 (Test i-a/ii-a) | MNAzyme 1 partzymes Substrate 1 Assembly facilitator 1 (target) | 25 µl from step (i) Ligase substrate DNAzyme ligase | 10 µl from step (ii) MNAzyme 2 partzymes Substrate 2 | An increase in fluorescence was observed over time |
| Reaction 2 (Control i-a/ii-b - no DNAzyme ligase) | MNAzyme 1 partzymes Substrate 1 Assembly facilitator 1 (target) | 25 µl from step (i) Ligase substrate | 10 µl from step (ii) MNAzyme 2 partzymes Substrate 2 | No increase in fluorescence was observed over time |
| Reaction 3 (Control i-b/ii-a - no Assembly facilitator 1 (target)) | MNAzyme 1 partzymes Substrate 1 | 25 µl from step (i) Ligase substrate DNAzyme ligase | 10 µl from step (ii) MNAzyme 2 partzymes Substrate 2 | No increase in fluorescence was observed over time |
| Reaction 4 (Control i-b/ii-b - no Assembly facilitator 1 (target) and no DNAzyme ligase) | MNAzyme 1 partzymes Substrate 1 | 25 µl from step (i) Ligase substrate | 10 µl from step (ii) MNAzyme 2 partzymes Substrate 2 | No increase in fluorescence was observed over time |
| Reaction 5 (Control i-c/ii-a - no Substrate 1) | MNAzyme 1 partzymes Assembly facilitator 1 (target) | 25 µl from step (i) Ligase substrate DNAzyme ligase | 10 µl from step (ii) MNAzyme 2 partzymes Substrate 2 | No increase in fluorescence was observed over time |
| Reaction 6 (Control i-c/ii-b - no Substrate 1 and no DNAzyme ligase) | MNAzyme 1 partzymes Assembly facilitator 1 (target) | 25 µl from step (i) Ligase substrate | 10 µl from step (ii) MNAzyme 2 partzymes Substrate 2 | No increase in fluorescence was observed over time |

The fluorescence level was measured over time for step (iii) of reactions 1, 2, 3, 4, 5 and 6 (performed in duplicate) (Table 10). Reaction 1 (i-a/ii-a), which had contained all oligonucleotide reaction components for steps (i), (ii) and (iii), showed an increase in fluorescence over time. The change in fluorescence observed was greater than 900 arbitrary units in this reaction resulting in an increase from approximately 180 at time 0 to over 1100 after 2 hours.

In contrast, reactions 2, 3, 4, 5 and 6 showed no increase in fluorescence over time above the background drift observed of approximately 50 arbitrary units over the course of 2 hours of fluorescence monitoring. As such, Reaction 2 (1-a/ii-b), which lacked the ligase DNAzyme oligonucleotide for step (ii) showed no increase in fluorescence over time. Reaction 3 (i-b/ii-a), which lacked the assembly facilitator 1 (AF-MzCA2) but contained the DNAzyme ligase from step (ii) showed no increase in fluorescence over time. Reaction 4 (i-b/ii-b), which lacked both the assembly facilitator 1 (AF-MzCA2) and the DNAzyme ligase from step (ii) showed no increase in fluorescence over time. Reaction 5 (i-c/ii-a), which lacked the Substrate 1 (Pre5LSubB2-FB) but contained the DNAzyme ligase from step (ii) showed no increase in fluorescence over time. Reaction 6 (i-c/ii-b), which lacked both the Substrate 1 (Pre5LSubB2-FB) and the DNAzyme ligase showed no increase in fluorescence over time. Together these reactions indicate that the following events have occurred in reaction 1.

Firstly, MNAzyme cleaver 1 cleaves Substrate 1 (Pre5LSubB2-FB) in the presence of specific assembly facilitator 1 (AF-MzCA2) producing two fragments, one of which was the 5' fragment 5LSubB (CTGTAGCACTCACTAua) (SEQ ID NO: 40) that has a 2',3'-cyclic phosphate terminus. Secondly, 5LSubB was ligated to a second DNAzyme oligonucleotide ligase substrate (3LSubB) present in the reaction mix of step (ii) and this resulted in the formation of a new oligonucleotide (ligation product) with the sequence of CTGTAGCACTCACTAuagGAACAACGAGAGGAAACCTT (SEQ ID NO: 51) (where upper case represent DNA bases and lower case represent RNA bases). This ligation product in turn functioned as an assembly facilitator for MNAzyme cleaver 2. This newly ligated assembly facilitator associated with the partzymes to create MNAzyme cleaver 2. MNAzyme cleaver 2 cleaved MNAzyme substrate 2 (SubBi-3-TxB2) resulting in separation of a fluorophore/quencher dye pair thus causing an increase in fluorescence.

The "no ligation" controls (Reaction 2, 4 and 6) demonstrated that the ligation of the 5' cleavage fragment (5LSubB) with 2',3'-cyclic phosphate terminus to a second ligase substrate (3LSubB) is essential for the formation of the assembly facilitator component of MNAzyme cleaver 2.

The "no assembly facilitator (AF-MzCA2)" controls (Reaction 3 and 4) demonstrated that cleavage of Substrate 1 (Pre5LSubB2-FB) by MNAzyme cleaver 1 and generation of a 5' fragment with the 2',3'-cyclic phosphate terminus (5LSubB) was essential for subsequent ligation and formation of an assembly facilitator required for assembly of MNAzyme cleaver 2.

The strategy demonstrated in this example could be used to create a feedback signal amplification cascade. If cleavage by MNAzyme cleaver 2 generated the same 5' cleavage product as was generated by MNAzyme cleaver 1 then this cleavage product could also be ligated to form a ligation product that could in turn function as another new MNAzyme component (e.g. partzyme, assembly facilitator or substrate) for the assembly of additional MNAzyme cleaver 2 complexes.

Further, it would be obvious to one skilled in the art that the DNAzyme ligase could ligate two fragments and create several possible enzymes or enzyme components useful in this cascade which include but are not limited to, a) a new assembly facilitator for a second MNAzyme cleaver (as shown in this example) or b) a new partzyme for a second MNAzyme as shown in examples 6, 7, 9, and 11, or c) a new DNAzyme capable of modifying a substrate or substrates (e.g. by cleavage, ligation etc). Further it would be obvious to one skilled in the art that the DNAzyme with ligase activity could be substituted with an MNAzyme with ligase activity as demonstrated in example 7 and 9. The strategy is versatile and could be performed as either a sequential cascade of the first, second and third steps or as a feedback cascade reaction where step 3 creates a component for step 2 and step 2 creates components for step 3. Additionally, step 3 could create a component for a further subsequent reaction.

Example 13

A Cascade Reaction with Possible Feedback

A schematic representation of one variation of a feedback amplification cascade is illustrated in FIG. 16. The initial steps of a cascade involving MNAzyme cleavage, DNAzyme ligation and MNAzyme cleavage are illustrated in FIG. 15 and demonstrated in example 6, 7, 9, 11 and 12. The schema described in this example and illustrated in FIG. 16 extends the strategy of the cascade in example 6, 7, 9, 11 and 12 and describes a strategy for a feedback amplification cascade.

As illustrated in FIG. 16, in a first step an MNAzyme cleaver 1 could assemble only in the presence of an assembly facilitator (e.g. a target nucleic acid) and then cleave MNAzyme substrate 1 to release a 5' cleavage product with a 2', 3' cyclic phosphate terminus. In a second step a DNAzyme ligase (or an assembled MNAzyme ligase) could ligate the 5' cleavage product from the first step to a 3' ligation substrate to create a ligation product which could serve as an assembly facilitator for another MNAzyme cleaver 2. In a third step an assembly facilitator formed by ligation in the second step could direct the assembly of partzymes which could form an MNAzyme cleaver 2 which could cleave substrate 2 into two products, a 5' product cleavage with a 2', 3' cyclic phosphate terminus and 3' cleavage product. A detectable signal could be generated following cleavage of substrate 2 if this substrate were labelled, for example, with a fluorophore and quencher dye pair.

Further, if the sequence of either of the cleavage products of MNAzyme cleaver 2 was useful as an assembly facilitator component for an MNAzyme cleaver 3 then this could initiate a feedback cascade. In this case MNAzyme cleaver 3 could have different sensor arms than MNAzyme cleaver 1 but could have the same substrate arms as MNAzyme cleaver 1. Thus if MNAzyme cleaver 3 were assembled in the presence of an assembly facilitator component generated by cleavage by the MNAzyme cleaver 2, and if MNAzyme cleaver 3 cleaved substrate 1 then the 5' cleavage product of MNAzyme cleaver 3 could also serve as a 5' substrate for the DNAzyme ligase (or the assembled MNAzyme ligase) and a feedback amplification cascade reaction could be initiated. In this reaction MNAzyme cleaver 3 would constantly generate 5' cleavage product which in turn could serve as a substrate for ligation by the DNAzyme ligase (or the assembled MNAzyme ligase) to create more assembly facilitators that could direct the assembly of more MNAzyme cleaver 2. This strategy could provide a mechanism for feedback signal amplification following initiation of a reaction by an assembly facilitator (eg a target analyte) which allowed assembly of MNAzyme cleaver 1. The strategy could allow detection of one or more assembly facilitators (eg target analytes) followed by signal amplification using a DNAzyme or an MNAzyme which can ligate substrates and MNAzymes which can cleave a substrate.

In a further variation the DNAzyme (or MNAzyme) with ligase activity could ligate fragments to form a DNAzyme capable of cleaving substrate 2 to create an assembly facilitator component for an MNAzyme 3. As such, in this variation MNAzyme cleaver 2 could be replaced with a DNAzyme cleaver created by ligation from the second step.

It would also be obvious to one skilled in the art that signal could be generated by cleavage of substrate 1 and/or substrate 2 provided the substrates were labelled, for example, with fluorophore quencher dye pairs. In this case, cleavage would result in an increase in fluorescence. Further, it would be possible to measure a change in fluorescence following ligation of the ligation substrate and the 5' product of MNAzyme cleaver 1 and/or MNAzyme cleaver 3 if the fragments were each labelled with either a fluorophore or a quencher. In this scenario ligation would result in a change in fluorescence either in solution or at a specific location in an assay where, for example, one ligatable substrate is attached to a solid support.

The assembly facilitator component generated by cleavage (or ligation) in step 2 or step 3 by an MNAzyme or a DNAzyme could be any one of numerous designs. By way of example, they could resemble any the configurations for assembly facilitator and/or partzyme sensor arms as illustrated in FIG. 6.

In another variation of feedback cascade strategy wherein the products of MNAzyme cleaver 2 could be used as an assembly facilitator component for an MNAzyme cleaver 3, the MNAzyme cleaver 3 could have a modified structure. In this variant, MNAzyme cleaver 3 could have different sensor arms than MNAzyme cleaver 1 but it may have one substrate arm (on one of the partzymes) for MNAzyme 3 that is the same as the sequence of the partzyme of MNAzyme cleaver 1 which interact with that portion of the sequence on substrate 1 (the 5' portion of the substrate) which is subsequently ligated by the ligase. As such MNAzyme cleaver 3 would cleave a substrate (cleavable substrate 3) which has the same sequence at the 5' portion but which has a different portion at the 3' end or vice versa with respect to cleavable substrate 1. The cleavage site of substrate 3 would lie at the junction of those sequences which are shared between the cleavable substrates 1 and 3 and those which differ. In this case, when MNAzyme cleaver 3 was assembled in the presence of an assembly facilitator component generated by cleavage by the MNAzyme cleaver 2, and if MNAzyme cleaver 3 cleaved substrate 3 then the 5' cleavage product of MNAzyme cleaver 3 could also serve as a 5' substrate for the DNAzyme ligase (or the assembled MNAzyme ligase) and a feedback amplification cascade reaction could be initiated. In this reaction MNAzyme cleaver 3 would constantly generate 5' cleavage product which in turn could serve as a substrate for ligation by the DNAzyme ligase (or the assembled MNAzyme ligase) to create more components, for example, an assembly facilitator that could direct the assembly of more MNAzyme cleaver 2. This strategy could provide a mechanism for feedback signal amplification following initiation of a reaction by an assembly facilitator (eg a target analyte) which allowed assembly of MNAzyme cleaver 1. The strategy could allow detection of an assembly facilitator (eg a target analyte) followed by signal amplification using a DNAzyme or an MNAzyme which can ligate substrates and MNAzymes which can cleave a substrate.

It would also be understood by one skilled in the art that nucleic acid enzymes used in the cascade could create different components that could be used in a subsequent reaction such as in a feedback situation. By way of example, with reference to FIG. 16 an MNAzyme cleaver 2 could create a stabiliser arm for MNAzyme cleaver 3, instead of the assembly facilitator component as illustrated. In another variation, MNAzyme cleaver 2 could be replaced by an MNAzyme ligase that could create, for example a partzyme or assembly facilitator for MNAzyme cleaver 3, or a DNAzyme cleaver as opposed to the illustration in FIG. 16 whereby an MNAzyme cleaver 2 creates an assembly facilitator component.

In another variant strategy the DNAzyme (or MNAzyme) ligase could ligate fragments and create a new partzyme capable of associating with another partzyme and an assembly facilitator present in the reaction thus forming an MNAzyme cleaver 2 which could cleave substrate 2 to create an assembly facilitator component for an MNAzyme 3.

Variations described can also be used as appropriate in other cascades throughout the specification. Further variations described elsewhere in the specifications could also be applied here.

The nucleic acid enzyme cascades, including the feedback cascades, allow signal generation following detection of target analytes. The first MNAzyme in the cascade may be an MNAzyme or apta-MNAzyme thus MNAzyme systems can be designed for detection of nucleic acid targets and non-nucleic acid analytes, for example proteins or lipids.

Further, feedback cascades could further amplify the output or detectable signal. Signal amplification cascades using nucleic acid enzymes have advantages over target amplification and detection technologies, for example real time PCR. While target amplification technologies are powerful tools which have been widely used in research and/or in clinical diagnostics, each has inherent disadvantages. They all require the use of protein enzymes (e.g. DNA polymerase, RNA polymerase, reverse transcriptase, and/or ligase). The inclusion of protein enzymes increases the complexity and cost of reagent manufacture and decreases the shelf life of kits containing reagents. Other associated technical challenges include contamination by replicons (target amplicons) from previous reactions leading to false positive signal, and/or background signal caused by replication of primer sequences (primer-dimers) or background caused by target-independent ligation.

Example 14

Testing MNAzyme Activity from a Series of Partzyme Pairs which Contain Variant Partial Catalytic Core Sequences Derived from the 10:23 Catalytic Core Multi-component nucleic acid enzymes (MNAzymes) can be made which incorporate partial sequences from a variety of in vitro evolved DNAzymes. Active MNAzymes, based on partial sequences from the 8:17 and 10:23 DNAzymes, have been demonstrated. Further, several alternative partzyme designs based on the 8:17 and 10:23 DNAzymes have been shown to either have or lack cleavage activity (PCT/AU2006/001473, Johnson & Johnson Research Pty Limited). This example identifies both active and inactive partzyme sequences based on partial catalytic core sequences from the 10:23 DNAzyme which can cleave a substrate. Further, the example provides a general protocol for the steps necessary to identify the optimal place(s) to split a catalytic core sequence such that, when the partial catalytic core sequences are incorporated into partzymes, functional active MNAzymes are generated.

Other DNAzymes, either known or evolved in vitro, could be subjected to a similar analysis to that described in this example and in examples 7 and 9. Therefore these examples provide a method that one skilled in the art could use to identify partial catalytic core sequences for active MNAzymes capable of many functions including cleavage (this example) or ligation (examples 7 and 9), or other in vitro evolved functions, including but not limited to phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

14.1 Partzyme Oligonucleotides

The method in this example was used to investigate which positions within the 10:23 catalytic core sequence are suitable for splitting into partial catalytic core sequences which, upon incorporation into partzymes, result in functionally active MNAzymes. The 10:23 sequence was split at various points and then the two partial sequences were incorporated into a series of partzyme pairs which were designed to cleave a substrate in the presence of target (human RPLPO gene). The partial catalytic cores for each partzyme pair which were tested are shown in Table 12 with reference to the complete catalytic core sequence of the 10:23 DNAzyme (Santoro and Joyce, 1997).

TABLE 12

Bases and position in the 10:23 DNAzyme and in a series of variant partzyme pairs where the bases at positions 1 to 15 of the core have been distributed differently between two partzymes A and B.

| Position # | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 10:23 DNAzyme (Santoro & Joyce, 1997) | | G | G | C | T | A | G | C | T | A | C | A | A | C | G | A |
| Design 6 A4:B5 (T8-A9) | Partzyme A | | | | | | | | | A | C | A | A | C | G | A |
| | Partzyme B | G | G | C | T | A | G | C | T | | | | | | | |
| Design 7 A5:B6 (C7-T8) | Partzyme A | | | | | | | | T | A | C | A | A | C | G | A |
| | Partzyme B | G | G | C | T | A | G | C | | | | | | | | |
| Design 8 A6:B7 (A11-A12) | Partzyme A | | | | | | | | | | | | A | C | G | A |
| | Partzyme B | G | G | C | T | A | G | C | T | A | C | A | | | | |
| Design 9 A7:B8 (A9-C10) | Partzyme A | | | | | | | | | | C | A | A | C | G | A |
| | Partzyme B | G | G | C | T | A | G | C | T | A | | | | | | |
| Design 10 A8:B9 (G6-C7) | Partzyme A | | | | | | | C | T | A | C | A | A | C | G | A |
| | Partzyme B | G | G | C | T | A | G | | | | | | | | | |
| Design 11 A9:B10 (A5-G6) | Partzyme A | | | | | | G | C | T | A | C | A | A | C | G | A |
| | Partzyme B | G | G | C | T | A | | | | | | | | | | |

TABLE 12 discloses SEQ ID NOS 136-138, respectively, in order of appearance.

All sequences are written 5' to 3'. The MNAzyme design and partzyme nomenclature identifies the DNAzyme and the location of the split within the core. For example, Design 6 is a 10:23 derived MNAzyme with partzyme A4 and partzyme B5 design (A4:B5), where the core has been split between T at position 8 and A at position 9 (T8-A9).

In this experiment the series of partzyme pairs were all synthesized with sensor arms designed to hybridise to exon 5 of the human RPLPO gene, and with substrate arms directed against the substrate, SubBi-2. The partzyme pairs used in this experiment were synthesized by Sigma-Proligo and their sequences are listed below (5' to 3'). The bases underlined form part of the catalytic core of the assembled MNAzyme, bases in bold hybridise with the nucleic acid target and bases in italics hybridise to the substrate. The "-P" indicates 3' phosphorylation of the oligonucleotide.

```
RPLPO Partzyme Pair A4:B5
RO5A4/2-P
                                      SEQ ID NO: 6
CAAACGAGTCCTGGCCTTGTCTACAACGAGAGGAAACCTT -P RO5B5(16)/2-P
                                      SEQ ID NO: 88
TGCCCAGGGAGGCTAGCTGTGGAGACGGATTACA -P RPLPO Partzyme Pair A5:B6
RO5A5/2(22)-P
                                      SEQ ID NO: 89
CAAACGAGTCCTGGCCTTGTCTTACAACGAGAGGAAACCTT -P RO5B6(16)/2-P
                                      SEQ ID NO: 90
TGCCCAGGGAGGCTAGCGTGGAGACGGATTACA -P RPLPO Partzyme Pair A6:B7
RO5A6(22)/2-P
                                      SEQ ID NO: 91
CAAACGAGTCCTGGCCTTGTCTACGAGAGGAAACCTT -P RO5B7(16)/2-P
                                      SEQ ID NO: 92
TGCCCAGGGAGGCTAGCTACAGTGGAGACGGATTACA -P RPLPO Partzyme Pair A7:B8
RO5A7(22)/2-P
                                      SEQ ID NO: 93
CAAACGAGTCCTGGCCTTGTCTCAACGAGAGGAAACCTT -P RO5B8(16)/2-P
                                      SEQ ID NO: 94
TGCCCAGGGAGGCTAGCTAGTGGAGACGGATTACA -P RPLPO Partzyme Pair A8:B9
RO5A8(22)/2-P
                                      SEQ ID NO: 95
CAAACGAGTCCTGGCCTTGTCTCTACAACGAGAGGAAACCTT -P RO5B9(16)/2-P
                                      SEQ ID NO: 96
TGCCCAGGGAGGCTAGGTGGAGACGGATTACA -P RPLPO Partzyme Pair A9:B10
RO5A9(22)/2-P
                                      SEQ ID NO: 97
CAAACGAGTCCTGGCCTTGTCTGCTACAACGAGAGGAAACCTT -P RO5B10(16)/2-P
                                      SEQ ID NO: 98
TGCCCAGGGAGGCTAGTGGAGACGGATTACA -P
```

14.2. Reporter Substrate

The reporter substrate for this example is SubBi-2 with the sequence, 5' to 3', as below. In the current example, SubBi-2 was end-labelled with a 6-FAM moiety at the 5' end and a BHQ1 moiety at the 3' end and was designated SubBi-2-FB. Cleavage of SubBi-2-FB was monitored at 530 nm (FAM emission wavelength) with excitation at 485 nm (FAM excitation wavelength). The lower case bases represent RNA and the upper case bases represent DNA.

```
SubBi-2-FB
AAGGTTTCCTCguCCCTGGGCA          SEQ ID NO: 4
```

14.3. PCR Primers for the Amplification of Exon 5 of the Human RPLPO Gene.

The sequences of the primers are shown, 5' to 3', below.

```
5' Primer 5RO5/2
GCTACCCAACTGTTGCATC             SEQ ID NO: 99

3' Primer 3RO5/2
AGCAGCCACAAAGGCAGA              SEQ ID NO: 100
```

14.4. Target Template

Human genomic DNA extracted from K562 cells was used as template in the PCR reaction.

14.5. Reaction Conditions

Real time amplification of the target sequence and detection of catalytic activity of the partzyme pairs was conducted in a 25 μL reaction cycled on an ABI 7700 thermocycler (Applied Biosystems). The cycling parameters were 95° C. for 7 minutes, 10 cycles of 95° C. for 15 seconds and 65° C. for 30 seconds (with a 1° C. decrease in temperature per cycle), and finally 50 cycles of 95° C. for 15 seconds and 50° C. for 30 seconds. Each reaction contained 0.04 μM 5RO5/2 and 0.2 μM of 3RO5/2, 10 mM $MgCl_2$, 50 μM each dNTP (dATP, dCTP, dGTP, dTTP), 1× Immobuffer (Bioline), 0.2 SubBi-2-FB, 1× Rox reference dye (Invitrogen), 10 Units of Rnasin (Progema) and 1 Unit of Immolase Polymerase (Bioline) and 100 ng of genomic DNA. In addition each reaction contained a pair of partzymes 0.2 μM of partzyme A and 0.2 μM of partzyme B (RPLPO Partzyme Pair A4:B5 or A5:B6 or A6:B7 or A7:B8 or A8:B9 or A9:B10).

14.6. Results

Using a real time MNAzyme-PCR method, catalytic activity was detected from three of the six RPLPO partzyme pairs. Partzyme pair A4:B5 and A5:B6 showed high levels of catalytic activity, allowing detection of target after 22 cycles (Table 13). The A7:B8 partzyme pair was also active, although less active than A4:B5 and A5:B6. No catalytic activity was detected from partzyme pairs A6:B7, A8:B9 or A9:B10 under the conditions of this experiment.

TABLE 13

Threshold Cycle (Ct) values obtained using various partzyme pairs

| Core Split (see table above, this example) | Ct | Comment |
|---|---|---|
| A4:B5 (T8-A9) | 19.3 | This combination of partial catalytic core sequences in these partzymes is compatible with formation of active MNAzymes. |

TABLE 13-continued

Threshold Cycle (Ct) values obtained using various partzyme pairs

| Core Split (see table above, this example) | Ct | Comment |
|---|---|---|
| A5:B6 (C7-T8) | 21.6 | This combination of partial catalytic core sequences in these partzymes is compatible with formation of active MNAzymes. |
| A6:B7 (A11-A12) | No signal at 50 cycles | This combination of partial catalytic core sequences in these partzymes is not compatible with formation of active MNAzymes under these experimental conditions. |
| A7:B8 (A9-C10) | 31.7 | This combination of partial catalytic core sequences in these partzymes is compatible with formation of active MNAzymes. |
| A8:B9 (G6-C7) | No signal at 50 cycles | This combination of partial catalytic core sequences in these partzymes is not compatible with formation of active MNAzymes under these experimental conditions. |
| A9:B10 (A5-G6) | No signal at 50 cycles | This combination of partial catalytic core sequences in these partzymes is not compatible with formation of active MNAzymes under these experimental conditions. |

The Ct values are averaged from triplicate reactions, when the threshold fluorescence level was set at 0.2 and the baseline background fluorescence was subtracted between cycles 1 and 14.

This example demonstrates that there are several ways of splitting the catalytic core of the 10:23 DNAzyme such that when the partial core sequences are incorporated into partzymes, they can form catalytically active MNAzymes. The example also demonstrates that not all partial core sequences form active MNAzymes when incorporated into partzymes. The method demonstrated in this example can be used to identify partial core sequences suitable for incorporation into partzymes capable of assembling into active MNAzymes.

PATENTS AND PATENT PUBLICATIONS

PCT International Publication No. WO 99/50452

OTHER REFERENCES

Achenbach, J., Nutiu, R. and Li, Y. (2005) Structure-switching allosteric deoxyribozymes. Analytica Chimica Acta. 534(1): 41-51.
Benenson, Y., Paz-Elizur, T., Adar, R., Keinan, E., Livneh, Z. and Shapiro, E. (2001) Programmable and autonomous computing machine made of biomolecules. Nature. November 22; 414(6862):430-4
Breaker, R. R. and Joyce, G. F. (1994) A DNA enzyme that cleaves RNA. Chem. Biol. December; 1(4): 223-9.
Cairns, M., King, A. and Sun, L. (2000) Nucleic acid mutation analysis using catalytic DNA. Nucl Acids Res. 28(3): e9.
Cairns, M., King, A. and Sun, L. (2003) Optimisation of the 10-23 DNAzyme-substrate pairing interactions enhanced RNA cleavage activity at purine-cytosine target sites. Nucl Acids Res. June 1; 31(11): 2883-9.
Carmi, N., Shultz, L. A. and Breaker, R. R. (1996) In vitro selection of self-cleaving DNAs. Chem. Biol. 3(12): 1039-46.
Coppins, R. L. and Silverman, S. K. (2004) Rational modification of a selection strategy leads to deoxyribozymes that create native 3'-5' RNA linkages
Cruz, R. P., Withers, J. B. and Li, Y. (2004) Dinucleotide junction cleavage versatility of 8-17 deoxyribozyme. Chem. Biol. January; 11(1): 57-67.
Elghanian, R., Storhoff, J., Mucic, R., Letsinger, R. and Mirkin, C. (1997) Selective colorimetric detection of polynucleotides based on the distance-dependent optical properties of gold nanoparticles. Science. 277: 1078-1079.
Emillson, G. M. and Breaker, R. R. (2002) Deoxyribozymes: new activities and new applications. Cell. Mol. Life. Sci. 59, 596-607.
Flynn-Charlebois, A., Prior, T. K., Hoadley, K. A. and Silverman, S. K. (2003) In vitro evolution of an RNA-cleaving DNA enzyme into an RNA ligase switches the selectivity from 3'-5' to 2'-5'. J. Am. Chem. Soc. 125: 5346-50
Haseloff, J. and Gerlach, W. L. (1988) Simple RNA enzymes with new and highly specific endoribonucleases activities. Nature. August 18; 334(6183): 585-91.
Hobartner, C. and Silverman, S. K. (2007) Recent advances in DNA catalysis. Biopolymers. 87 (5-6): 279-291.
Huizenga, D. and Szostak, J. (1995) A DNA aptamer that binds adenosine and ATP. Biochemistry. 34: 656-665
Kurata, H., Miyagishi, M., Kuwabara, T., Warashima M. and Taira, K. (2000) Maxizymes: Allosterically controllable ribozymes with biosensor function. Journal of Biochemistry and Molecular Biology, 33: 5, 359-363
Lee, J. F., Hesselberth, J. R., Meyers, L. A. and Ellington, A. D. (2004) Aptamer Database. Nucl Acids Res. 32(90001): D95-100.
Levy, M. and Ellington, A. (2003) Exponential growth by cross-catalytic cleavage of deoxyribozymogens. Proc Natl Acad Sci USA. 100(11): 6416-21.
Liu, J. and Lu, Y. (2004) Adenosine-dependent assembly of aptazyme-functionalized gold nanoparticles and its application as a colorimetric biosensor. Analytical Chemistry. 76: 1627-1632.
Mirkin, C., Letsinger, R., Mucic, R. and Storhoff, J. (1996) A DNA-based method for rationally assembling nanoparticles into macroscopic materials. Nature. 382: 607-609.
Paul, N. and Joyce, G. (2004) Minimal self-replicating systems. Current Opinion in Chemical Biology. 8(6): 634-639.
Perreault, J., Labuda, D., Usman, N., Yang, J. and Cedergren, R. (1991) Relationship between T-hydroxyls and magnesium binding in the hammerhead RNA domain: a model for ribozyme catalysis. Biochemistry. 30(16): 4020-5.
Perreault, J., Wu, T., Cousineau, B., Ogilvie, K. and Cedergren, R. (1990) Mixed deoxyribo- and ribo-oligonucleotides with catalytic activity. Nature. 344(6266): 565-7.
Prior, T. K., Semlow, D. R. Flynn-Charlebois, Rashid, I. And Silverman, S. K. (2004) Structure-function correlations derived from faster variants of a RNA ligase deoxyribozyme. Nucleic Acids Research, 32, 1075-1082.

Raillard, S. A. and Joyce, G. F. (1996) Targeting sites within HIV-1 cDNA with a DNA-cleaving ribozyme. Biochemistry. 35(36): 11693-701.

Santoro, S. and Joyce, G. (1997) A general purpose RNA cleaving DNA enzyme. Proc Natl Acad Sci USA. 94: 4262-4266.

Santoro, S. W. and Joyce, G. F. (1998) Mechanism and utility of an RNA-cleaving DNA enzyme. Biochem. 37(38): 13330-42.

Schubert, S., Furste, J., Werk, D., Grunert, H., Zeichhardt, H., Erdmann, V. and Kurreck, J. (2004) Gaining target access for deoxyribozymes. J Mol. Biol. May 28; 339(2): 355-63.

Sidorov, A., Grasby, J. and Williams, D. (2004) Sequence-specific cleavage of RNA in the absence of divalent metal ions by a DNAzyme incorporating imidazolyl and amino functionalities. Nucl Acids Res. March 5; 32(4): 1591-601.

Silverman, S. (2004) Breaking up is easy to do (if you're a DNA enzyme that cleaves RNA). Chem. Biol. January; 11(1): 7-8.

Silverman, S. K. (2007) In vitro selection and application of nucleic acid enzymes (Ribozymes and deoxyribozymes). Wiley Encyclopedia of Chemical Biology. In Press.

Tabor, J. J., Levy, M. and Ellington, A. D. (2006) Deoxyribozymes that recode sequence information. Nucleic Acids Res. 34(8): 2166-2172

Warashina, M., Kuwabara, T., Nakamatsu, Y. and Taira, K. (1999) Extremely high and specific activity of DNA enzymes in cells with a Philadelphia chromosome. Chem. Biol. April; 6(6): 237-50.

Zaborowska, Z., Furste, J., Erdmann, V. and Kurreck, J. (2002) Sequence requirements in the catalytic core of the "10-23" DNA enzyme. J Biol. Chem. 277(43): 240617-22.

The invention claimed is:

1. A method for detecting the presence of a target nucleic acid in a sample, the method comprising
    (a) providing first and second oligonucleotide components and two nucleic acid substrates, wherein the first and second oligonucleotide components are capable of self-assembly in the presence of the target nucleic acid to form a catalytically active multi-component nucleic acid enzyme with a catalytic core having ligase activity (MNAzyme ligase) capable of ligating the two nucleic acid substrates, wherein the first and second oligonucleotide components are first and second partzymes respectively, and each of the first and second partzymes comprises a catalytic core portion, a substrate arm portion, and a sensor arm portion, and the catalytic core portion is between the substrate arm portion and the sensor arm portion; wherein the sensor arm of the first partzyme and the sensor arm of the second partzyme can hybridize adjacent to each other on the target nucleic acid and the substrate arm portion of the first partzyme and the substrate arm portion of the second partzyme can hybridize to the two nucleic acid substrates so that the two nucleic acid substrates are adjacent each other on said catalytically active MNAzyme ligase and thereby capable of ligating each other on said catalytically active MNAzyme ligase and the substrate arm portion of the first partzyme and the substrate arm portion of the second partzyme are adjacent each other on said catalytically active MNAzyme ligase when the target nucleic acid is present in the sample,
    (b) contacting the first and second oligonucleotide components and the two nucleic acid substrates with the sample under conditions permitting self-assembly of the catalytically active MNAzyme ligase when the target nucleic acid is present in the sample, and
    (c) determining the ligase activity of the catalytically active MNAzyme ligase by detecting a ligated nucleic acid product formed by ligation of a 5' end of one substrate of the two nucleic acid substrates to a 3' end of other substrate of the two nucleic acid substrates, wherein the presence of the ligase activity of said catalytically active MNAzyme ligase is indicative of the presence of the target nucleic acid in the sample.

2. The method of 1 wherein the target nucleic acid is a target nucleic acid which can be identified, detected or quantitated.

3. The method of claim 1 wherein the catalytic core portion of the first partzyme and the catalytic core portion of the second partzyme are catalytic core portions of a DNAzyme with a ligase activity selected from the group consisting of 7Z81 DNA enzyme, 7Z48 DNA enzyme, 7Q10 DNA enzyme and 9DB1 DNA enzyme.

4. The method of claim 1, wherein catalytic core portions of the first and second partzymes comprise a pair of oligonucleotides selected from the group consisting of TGGAGGTGGGCTC (SEQ ID NO: 47) and ACG (SEQ ID NO: 48), GGAGGTGGGCTC (SEQ ID NO: 49) and ACGT (SEQ ID NO: 50), GGAGGTTAGCTC (SEQ ID NO: 71) and ACGGCGGAGTGATTG (SEQ ID NO: 72), TGGGAGGTTAGCTC (SEQ ID NO: 73) and ACGGCGGAGTGAT (SEQ ID NO: 74), ATTGGGAGGTTAGCTC (SEQ ID NO: 75) and ACGGCGGAGTG (SEQ ID NO: 76), TGATTGGGAGGTTAGCTC (SEQ ID NO: 77) and ACGGCGGAG (SEQ ID NO: 78), AGTGATTGGGAGGTTAGCTC (SEQ ID NO: 79) and ACGGCGG (SEQ ID NO: 80), GGAGTGATTGGGAGGTTAGCTC (SEQ ID NO: 81) and ACGGC (SEQ ID NO: 82).

* * * * *

SEQUENCE LISTING

```
<160> NUMBER OF SEQ ID NOS: 138

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylation

<400> SEQUENCE: 1
actggatgtc catctgtctg acaacgagag gaaacctt                            38

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: Phosphorylation

<400> SEQUENCE: 2
tgcccaggga ggctagctta tac                                            23

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: Phosphorylation

<400> SEQUENCE: 3
cttcgtgagg gtgag                                                     15

<210> SEQ ID NO 4
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
aaggtttcct cguccctggg ca                                              22

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgccccctca ccctcacgaa ggtatacaga cagatggaca tccagttggt ga             52

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(40)
<223> OTHER INFORMATION: Phosphorylation

<400> SEQUENCE: 6
caaacgagtc ctggccttgt ctacaacgag aggaaacctt                           40

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(47)
<223> OTHER INFORMATION: Phosphorylation

<400> SEQUENCE: 7
tgcccaggga ggctagctgt ggagacggat tacaccttcc cacttgc                   47

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcaagtggga aggtgtaatc cgtctccaca gacaaggcca ggactcgttt g              51

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 9
gcaagtggga aggtgtaatc cgtct                                    25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccacagacaa ggccaggact cgtttg                                   26

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaggtttcct cgtccctggg caccacagac aaggccagga ctcgtttg           48

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aacgtacact gcacgcggtc gaaatagtga gtacctgggg gagtattgcg gaggaaggt    59

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catctcttct ccgagcgtct gtaccgtgta c                             31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtacacggta cagaccgtgc agtgtacgtt                               30

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 15
ccaggtactc actattt                                                  17

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
actcactata ggaagagatg                                               20

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctctcgttg acggcggagt gattgggagg ttagctctag tgagtgc                 47

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tacctgcact acggtcgaaa tagtgagt                                      28

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
catctcttct ccgagctaag cacttta                                       27

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcccaggga ggctagctct gtcgtcggag tggtcgtcg                          39

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 21
ctgtagcact cactauagga agagatg        27

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
ggaacaacga gaggaaacct t        21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taaagtgctt atagtgcagg ta        22

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgacgaccac tccgacgaca gtcctatagt gagtgctaca g        41

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aacgagtcct ggccttgtct ggctctagtg agtgc        35

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tctcgttgtt acgtggaggt ggtggagacg gattacacct t        41

<210> SEQ ID NO 27
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 27
aacgagtcct ggccttgtct gggctctagt gagtgc                                36

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tctcgttgtt acgtggaggt gtggagacgg attacacctt                            40

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aacgagtcct ggccttgtct tgggctctag tgagtgc                               37

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tctcgttgtt acgtggaggg tggagacgga ttacacctt                             39

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aacgagtcct ggccttgtct tggaggtggg ctctagtgag tgc                        43

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tctcgttgtt acggtggaga cggattacac ctt                                   33

<210> SEQ ID NO 33
<211> LENGTH: 42
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 33
aacgagtcct ggccttgtct ggaggtgggc tctagtgagt gc                              42

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tctcgttgtt acgtgtggag acggattaca cctt                                      34

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aacgagtcct ggccttgtct gtggaggtgg gctctagtga gtgc                            44

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tctcgttgtt acgtggagac ggattacacc tt                                        32

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aacgagtcct ggccttgtct gaggtgggct ctagtgagtg c                              41

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tctcgttgtt acgtggtgga gacggattac acctt                                     35

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
tctcgttgtt acgtggaggt gggctctagt gagtgc                36

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
ctgtagcact cactaua                17

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acgtggaggt g                11

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgtcgtgaga tgaggaagag atggatgggc ac                32

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaggtgtaat ccgtctccac agacaaggcc aggactcgtt tg                42

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
acgtggaggt                10

<210> SEQ ID NO 45
<211> LENGTH: 32
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 45
gtgcccatcc atctccggtc gaaatagtga gt                                32

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
catctcttct ccgagcttcc tcatctcacg acg                               33

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tggaggtggg ctc                                                     13

<210> SEQ ID NO 48
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48 acg                                                                 3

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaggtgggc tc                                                      12

<210> SEQ ID NO 50
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 acgt                                                                4

<210> SEQ ID NO 51
<211> LENGTH: 38
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
ctgtagcact cactauagga acaacgagag gaaaccctt                          38

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
acgtggaggt gggctc                                                  16

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtggaggtgg gctc                                                    14

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaggtgggct c                                                       11

<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caaacgagtc ctggccttgt ctggaggtta gctctagtga gtgc                   44

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctctcgttg acggcggagt gattggtgga gacggattac acctt                  45

<210> SEQ ID NO 57
<211> LENGTH: 46
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 57
caaacgagtc ctggccttgt cttgggaggt tagctctagt gagtgc                    46

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cctctcgttg acggcggagt gatgtggaga cggattacac ctt                       43

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
caaacgagtc ctggccttgt ctattgggag gttagctcta gtgagtgc                  48

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctctcgttg acggcggagt ggtggagacg gattacacct t                         41

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
caaacgagtc ctggccttgt cttgattggg aggttagctc tagtgagtgc                50

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cctctcgttg acggcggagg tggagacgga ttacacctt                            39

<210> SEQ ID NO 63
<211> LENGTH: 52
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 63
caaacgagtc ctggccttgt ctagtgattg ggaggttagc tctagtgagt gc              52

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctctcgttg acggcgggtg gagacggatt acacctt                               37

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caaacgagtc ctggccttgt ctggagtgat tgggaggtta gctctagtga gtgc            54

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctctcgttg acggcgtgga gacggattac acctt                                 35

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ctgtagcact cactauagga agagatgag                                        29

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gccattgtcg aacacctgct ggatgaccag c                                     31

<210> SEQ ID NO 69
<211> LENGTH: 35

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gctggtcatc cagcagcggt cgaaatagtg agtgc                               35

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctcatctctt ctccgagcgt gttcgacaat ggc                                 33

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaggttagc tc                                                        12

<210> SEQ ID NO 72
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acggcggagt gattg                                                     15

<210> SEQ ID NO 73
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgggaggtta gctc                                                      14

<210> SEQ ID NO 74
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acggcggagt gat                                                       13

<210> SEQ ID NO 75
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 75
attgggaggt tagctc                                                        16

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acggcggagt g                                                             11

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgattgggag gttagctc                                                      18

<210> SEQ ID NO 78
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 acggcggag                                                                 9

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agtgattggg aggttagctc                                                    20

<210> SEQ ID NO 80
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 acggcgg                                                                   7

<210> SEQ ID NO 81
<211> LENGTH: 22
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 81
ggagtgattg ggaggttagc tc                                         22

<210> SEQ ID NO 82
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 acggc                                                             5

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
acggcggagt gattgggagg ttagctc                                    27

<210> SEQ ID NO 84
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctgtagcact cactatagga acaacgagag gaaacctt                        38

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaggtttcct ctcgttgttc ctacaacgag gttgtgctg                       39

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cggttggtga ggctagctat agtgagtgct acag                            34

<210> SEQ ID NO 87
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
cagcacaacc gucaccaacc g                                              21

<210> SEQ ID NO 88
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: Phosphorylation

<400> SEQUENCE: 88
tgcccaggga ggctagctgt ggagacggat taca                                34

<210> SEQ ID NO 89
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: Phosphorylation

<400> SEQUENCE: 89
caaacgagtc ctggccttgt cttacaacga gaggaaacct t                        41

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylation

<400> SEQUENCE: 90
tgcccaggga ggctagcgtg gagacggatt aca                                 33

<210> SEQ ID NO 91
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylation

<400> SEQUENCE: 91
caaacgagtc ctggccttgt ctacgagagg aaacctt                             37
```

-continued

```
<210> SEQ ID NO 92
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylation

<400> SEQUENCE: 92
tgcccaggga ggctagctac agtggagacg gattaca                              37

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: Phosphorylation

<400> SEQUENCE: 93
caaacgagtc ctggccttgt ctcaacgaga ggaaacctt                            39

<210> SEQ ID NO 94
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(35)
<223> OTHER INFORMATION: Phosphorylation

<400> SEQUENCE: 94
tgcccaggga ggctagctag tggagacgga ttaca                                35

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: Phosphorylation

<400> SEQUENCE: 95
caaacgagtc ctggccttgt ctctacaacg agaggaaacc tt                        42

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: Phosphorylation
```

```
<400> SEQUENCE: 96
tgcccaggga ggctaggtgg agacggatta ca                                      32

<210> SEQ ID NO 97
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(43)
<223> OTHER INFORMATION: Phosphorylation

<400> SEQUENCE: 97
caaacgagtc ctggccttgt ctgctacaac gagaggaaac ctt                          43

<210> SEQ ID NO 98
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Phosphorylation

<400> SEQUENCE: 98
tgcccaggga ggctagtgga gacggattac a                                       31

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gctacccaac tgttgcatc                                                     19

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
agcagccaca aaggcaga                                                      18

<210> SEQ ID NO 101
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 ggctc                                                                     5
```

```
<210> SEQ ID NO 102
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102 gggctc                                                                    6

<210> SEQ ID NO 103
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103 tgggctc                                                                   7

<210> SEQ ID NO 104
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104 acgtggagg                                                                 9

<210> SEQ ID NO 105
<211> LENGTH: 2
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105 ac                                                                        2

<210> SEQ ID NO 106
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 acgtg                                                                     5

<210> SEQ ID NO 107
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
```

-continued

<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 107 nggctcn                                                              7

<210> SEQ ID NO 108
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 108
nacgtggagg tgn                                                       13

<210> SEQ ID NO 109
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 109 ngggctcn                                                             8

<210> SEQ ID NO 110
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 110
nacgtggagg tn                                                                    12

<210> SEQ ID NO 111
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 111 ntgggctcn                                                                         9

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 112
nacgtggagg n                                                                     11

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 113
ntggaggtgg gctcn                                                                 15

<210> SEQ ID NO 114
<211> LENGTH: 5
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 114 nacgn                                                                      5

<210> SEQ ID NO 115
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 115
nggaggtggg ctcn                                                           14

<210> SEQ ID NO 116
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 116 nacgtn                                                                     6

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
```

```
<220> FEATURE:
<221> NAME/KEY: modified_base
<222> LOCATION: (16)..(16)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 117
ngtggaggtg ggctcn                                                        16

<210> SEQ ID NO 118
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 118 nacn                                                                      4

<210> SEQ ID NO 119
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 119
ngaggtgggc tcn                                                           13

<210> SEQ ID NO 120
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<223> OTHER INFORMATION: see specification as filed for detailed
      description of substitutions and preferred embodiments
```

```
<400> SEQUENCE: 120 nacgtgn                                                                    7

<210> SEQ ID NO 121
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 121 ngggctcn                                                                   8

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 122
nacgtggagg tgggctcn                                                       18

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 123
nggaggttag ctcn                                                           14

<210> SEQ ID NO 124
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 124
nacggcggag tgattgn                                                    17

<210> SEQ ID NO 125
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 125
ntgggaggtt agctcn                                                     16

<210> SEQ ID NO 126
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 126
nacggcggag tgatn                                                      15

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 127
nattgggagg ttagctcn                                                    18

<210> SEQ ID NO 128
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 128
nacggcggag tgn                                                         13

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 129
ntgattggga ggttagctcn                                                  20

<210> SEQ ID NO 130
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
```

-continued

```
<220> FEATURE:
<223> OTHER INFORMATION: see specification as filed for detailed
      description of substitutions and preferred embodiments

<400> SEQUENCE: 130
nacggcggag n                                                              11

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 131
nagtgattgg gaggttagct cn                                                  22

<210> SEQ ID NO 132
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 132 nacggcggn                                                                  9

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 133
nggagtgatt gggaggttag ctcn                                                24
```

```
<210> SEQ ID NO 134
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 134 nacggcn                                                                  7

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<223> OTHER INFORMATION: see specification as filed for detailed
      description of substitutions and preferred embodiments

<400> SEQUENCE: 135
nacggcggag tgattgggag gttagctcn                                         29

<210> SEQ ID NO 136
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggctagctac aacga                                                        15

<210> SEQ ID NO 137
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggctagctac a                                                            11

<210> SEQ ID NO 138
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 138
gctacaacga                                                            10
```